US009434724B2

(12) United States Patent
Bilcer et al.

(10) Patent No.: US 9,434,724 B2
(45) Date of Patent: Sep. 6, 2016

(54) QUINUCLIDINES FOR MODULATING ALPHA 7 ACTIVITY

(71) Applicant: Alpharmagen, LLC, South San Francisco, CA (US)

(72) Inventors: Geoffrey M. Bilcer, Shorewood, MN (US); Raymond Ng, San Ramon, CA (US)

(73) Assignee: ALPHARMAGEN, LLC, South San Francisco, CA (US)

(*) Notice: Subject to any disclaimer, the term of this patent is extended or adjusted under 35 U.S.C. 154(b) by 0 days.

(21) Appl. No.: 14/794,497

(22) Filed: Jul. 8, 2015

(65) Prior Publication Data

US 2016/0009706 A1 Jan. 14, 2016

Related U.S. Application Data

(60) Provisional application No. 62/023,580, filed on Jul. 11, 2014.

(51) Int. Cl.
| | | |
|---|---|---|
| C07D 453/00 | (2006.01) | |
| C07D 209/04 | (2006.01) | |
| A61K 31/439 | (2006.01) | |
| C07D 453/02 | (2006.01) | |
| A61K 45/06 | (2006.01) | |

(52) U.S. Cl.
CPC ........... *C07D 453/02* (2013.01); *A61K 31/439* (2013.01); *A61K 45/06* (2013.01)

(58) Field of Classification Search
CPC . C07D 453/00; C07D 209/04; A61K 31/439
USPC .......................................... 546/133; 548/469
See application file for complete search history.

(56) References Cited

U.S. PATENT DOCUMENTS

| | | | |
|---|---|---|---|
| 4,797,406 A | 1/1989 | Richardson et al. | |
| 4,910,193 A | 3/1990 | Buchheit | |
| 4,950,759 A | 8/1990 | van Wijngaarden et al. | |
| 4,985,424 A | 1/1991 | van Wijngaarden et al. | |
| 5,106,851 A | 4/1992 | Turconi et al. | |
| 5,187,166 A | 2/1993 | Kikuchi et al. | |
| 5,190,953 A | 3/1993 | Munson, Jr. et al. | |
| 5,272,154 A | 12/1993 | Dixon et al. | |
| 5,300,512 A | 4/1994 | Flynn et al. | |
| 5,399,562 A | 3/1995 | Becker et al. | |
| 5,512,579 A | 4/1996 | Miyazawa et al. | |
| 5,543,426 A | 8/1996 | Dixon et al. | |
| 5,561,149 A | 10/1996 | Azria et al. | |
| 5,583,140 A | 12/1996 | Bencherif et al. | |
| 5,597,919 A | 1/1997 | Dull et al. | |
| 5,604,231 A | 2/1997 | Smith et al. | |
| 5,658,925 A | 8/1997 | Miyazawa et al. | |
| 5,672,601 A | 9/1997 | Cignarella | |
| 5,677,311 A | 10/1997 | Miyazawa et al. | |
| 5,712,270 A | 1/1998 | Sabb | |
| 5,723,472 A | 3/1998 | Miyazawa et al. | |
| 5,852,041 A | 12/1998 | Cosford et al. | |
| 5,861,418 A | 1/1999 | Miyazawa et al. | |
| 6,638,925 B2 | 10/2003 | Czollner et al. | |
| 6,916,828 B2 | 7/2005 | Farrerons Gallemi et al. | |
| 8,114,891 B2 * | 2/2012 | Pfister .................. C07D 471/08 514/305 | |
| 2005/0250808 A1 | 11/2005 | Xie et al. | |
| 2009/0088418 A1 | 4/2009 | Pfister et al. | |
| 2010/0035136 A1 | 2/2010 | Huang et al. | |

FOREIGN PATENT DOCUMENTS

| | | |
|---|---|---|
| CN | 201523099 U | 7/2010 |
| CN | 202254195 U | 5/2012 |
| DE | 3810552 A1 | 10/1989 |
| EP | 0 094 742 A2 | 11/1983 |
| EP | 0 094 742 A3 | 11/1983 |
| EP | 0 094 742 B1 | 11/1983 |
| EP | 0 297 858 A2 | 1/1989 |
| EP | 0 297 858 A3 | 1/1989 |
| EP | 0309423 A2 | 3/1989 |
| EP | 0 350 130 A2 | 1/1990 |
| EP | 0 350 130 A3 | 1/1990 |
| EP | 0 382 687 A2 | 8/1990 |
| EP | 0 382 687 A3 | 8/1990 |
| EP | 0 382 687 B1 | 8/1990 |
| EP | 0 491 664 A1 | 6/1992 |
| EP | 0 491 664 B1 | 6/1992 |
| GB | 2 295 387 A | 5/1996 |
| JP | 58-188885 A | 11/1983 |
| JP | 4-308590 A | 10/1992 |
| JP | 09-328469 A | 12/1997 |
| JP | 2002-221349 A | 8/2002 |
| JP | 2008-525464 A | 7/2008 |

(Continued)

OTHER PUBLICATIONS

Arneric, S.P. et al. (1995). "Preclinical Pharmacology of ABT-418: A Prototypical Cholinergic Channel Activator for the Potential Treatment of Alzheimer's Disease," *CNS Drug Rev.* 1(1):1-26.
Arneric, S.P. et al. (Jan. 1996). "Cholinergic Channel Modulators as a Novel Therapeutic Strategy for Alzheimer's Disease," *Exp. Opin. Invest. Drugs* 5(1):79-100.
Bannon, A.W. et al. (Jan. 2, 1998). "Broad-Spectrum, Non-Opioid Analgesic Activity by Selective Modulation of Neuronal Nicotinic Acetylcholine Receptors," *Science* 279(2):77-81.
Bencherif, M. et al. (1996). "RJR-2403: A Nicotinic Agonist with CNS Selectively I. In Vitro Characterization," *J. Pharm. and Exp. Therapeutics* 279(3):1413-1421.
Bencherif, M. et al. (Aug. 2002). "Targeting Neuronal Nicotinic Receptors: A Path to New Therapies," *Current Drug Targets: CNS and Neurological Disorders* 1(4):349-357.
Bennett, J.C. et al. Eds. (1996). Cecil Textbook of Medicine, 20th Edition, 2:1992-1996, 1992-1996.
Brioni et al., (1997) "The Pharmacology of (−)-Nicotine and Novel Cholinergic Channel Modulators" Adv. Pharmacol. (37):153-214.
Broadley and Kelly, (2001) "Muscarinic Receptor Agonists and Antagonists" *Molecules*, (6):142-193.
Cancer and Metastasis Reviews (1998). 17(1):91-106. (same as Lala ref).
CECLI Textbook of Medicine, 20th Edition (1996), vol. 2, pp. 1992-1996.
CECLI Textbook of Medicine, 20th Edition (1996), vol. 2, pp. 2050-2057.

(Continued)

*Primary Examiner* — Niloofar Rahmani
(74) *Attorney, Agent, or Firm* — Morrison & Foerster LLP

(57) ABSTRACT

Provided are substituted quinuclidine compounds, pharmaceutical compositions comprising such compounds, and methods of modulating α7 nicotinic acetylcholine receptors and treating neurological disorders using such compounds.

33 Claims, No Drawings

(56) References Cited

FOREIGN PATENT DOCUMENTS

| WO | WO-93/15080 A1 | 8/1993 |
|---|---|---|
| WO | WO-94/08992 A1 | 4/1994 |
| WO | WO-96/31475 A2 | 10/1996 |
| WO | WO-96/31475 A3 | 10/1996 |
| WO | WO-96/40682 A1 | 12/1996 |
| WO | WO-97/30998 A1 | 8/1997 |
| WO | WO-97/40049 A1 | 10/1997 |
| WO | WO-99/03859 A1 | 1/1999 |
| WO | WO-99/21834 A1 | 5/1999 |
| WO | WO-99/62505 A2 | 12/1999 |
| WO | WO-99/62505 A3 | 12/1999 |
| WO | WO-01/36417 A1 | 5/2001 |
| WO | WO-02/00652 A1 | 1/2002 |
| WO | WO-02/15662 A2 | 2/2002 |
| WO | WO-02/15662 A3 | 2/2002 |
| WO | WO-02/16355 A2 | 2/2002 |
| WO | WO-02/16355 A3 | 2/2002 |
| WO | WO-02/16356 A2 | 2/2002 |
| WO | WO-02/16356 A3 | 2/2002 |
| WO | WO-02/16357 A2 | 2/2002 |
| WO | WO-02/16357 A3 | 2/2002 |
| WO | WO-02/16358 A2 | 2/2002 |
| WO | WO-02/16358 A3 | 2/2002 |
| WO | WO-02/17358 A2 | 2/2002 |
| WO | WO-02/17358 A3 | 2/2002 |
| WO | WO-02/051841 A1 | 7/2002 |
| WO | WO-2006/069097 A2 | 6/2006 |
| WO | WO-2006/069097 A3 | 6/2006 |
| WO | WO-2008/118742 A1 | 10/2008 |
| WO | WO-2009/046025 A1 | 4/2009 |

OTHER PUBLICATIONS

Chiari, A. et al. (Nov. 1999). "Sex Differences in Cholinergic Analgesia I," *Anesthesiology* 91(5):1447-1454.

CNN.com (2003). "FDA Mulls Drug to Slow Late-Stage Alzheimer's," Located at <http://www.cnn.com/2003/health/conditions/O9/24/a;zheimers.drug.ap.indexhtml>, Last Visited on Sep. 23, 2003, 2 Pages.

Damaj, M.I. et al. (1999). "Antinociceptive and Pharmacological Effects of Metanicotine, a Selective Nicotinic Agonist," *J. Pharmacol. Exp. Ther.* 291(1):390-398.

Decina et aL, (1990) "Cigarette Smoking and Neuroleptic-Induced Parkinsonism" *Biol. Psychiatry,* 28:502-508.

Dolle, F. et al. (2001, e-pub. Aug. 1, 2001). "Synthesis and Preliminary Evaluation of a Carbon-11-Labelled Agonist of the α7 Nicotinic Acetylcholine Receptor," *J. Labelled Comp. Radiopharm.* 44:785-795.

Freedman et al., (1995) "Evidence in Postmortem Brain Tissue for Decreased Nos. of Hippocampal Nicotinic Receptors in Schizophrenia" *Biological Psychiatry,* 38: 22-33.

Golub, T.R. et al. (1999). *Science* 286:531-537.

Hall et al., (1972) "Effects of Nicotine on the Release of $^3$H-Noradrenaline From the Hypothalamus" *Biochem. Pharmacol.* (21):1829-1838.

Hamon, (1994) "Neuropharmacology of anxiety: Perspectives and Prospects"*Trends in Pharmacol Sci,* (15):36-39.

Harsing et al., (1993) "Dopamine Efflux from Striatum After Chronic Nicotine: Evidence for Autoreceptor Desensitization" *Journal of Neurochemistry,* 59(1): 48-54.

Heeschen et al., (2002) "A Novel Angiogenic Pathway Mediated by Non-Neuronal Nicotinic Acetylcholine Receptors" *The Journal of Clinical Investigation,* (110)4:527-536.

Hery et al., (1977) "Control of the Release of Newly Synthetized $^3$H-5_Hydroxytryptamine by Nicotinic and Muscarinic Receptors in Rat Hypothalamic Slices" *Archive of Pharmacology,* (296):91-97.

Holladay, M.W. et al. (Dec. 19, 1997). "Neuronal Nicotinic Acetylcholine Receptors as Targets for Drug Discovery," *J. Med. Chem.* 40(26):4169-4194.

J. Hughes, (1994) "Nicotine and Neuropsychiatric Disorders" International Symposium on Nicotine: The Effects of Nicotine on Biological Systems II, Proceedings from Intl. Symp. Nie. Session 6:S40.

International Search Report mailed Mar. 2, 2009, for PCT Application No. PCT/US2008/078320, filed Sep. 30, 2008, 1 page.

Jeyarasasingam et al., (2002)"Stimulation of Non-α7 Nicotinic Receptors Partially Protects Dopaminergic Neurons from 1-Methyl-4-Phenylpyridinium-induced Toxicity in Culture" *Neuroscience* (109)2:275-285.

Lala, P.K. et al. (1998). *Cancer and Metastasis Reviews* 17(1):91-106.

Lavand'Homme, P.M. et al. (Nov. 1999). "Sex Differences in Cholinergic Analgesia II: Differing Mechanisms in Two Models of Allodynia," *Anesthesiology* 91(5):1455-1466.

Leonard et al., (1996) "Nicotinic Receptor Function in Schizophrenia" *Schizophrenia Bulletin* (22):431-445.

Levin, E.D. et al. (Aug. 2002). "Nicotinic Treatment for Cognitive Dysfunction," *Current Drug Targets: CNS and Neurological Disorders* 1(4):423-431.

Lippiello, P.M. et al. (1996). "RJR-2403: A Nicotinic Agonist with CNS Selectivity. II. In Vivo Characterization," *J. Pharm. and Exp. Therapeutics* 279(3):1422-1429.

M. P. Caulfield, (1993) "Muscarinic Receptors-Characterization, Coupling and Function" *Pharmacol. Ther.* (58):319-379.

Macor, J.E. et al. (2001). "The 5-HT$_3$ Antagonist Tropisetron (ICS 25-930) is a Potent and Selective α7 Nicotinic Receptor Partial Agonist," *Bioorg. Med. Chem. Lett.* 11:319-321.

Mazurov, A. et al. (2006). "Selective α7 Nicotinic Acetylcholine Receptor Ligands," *Current Medicinal Chemistry* 13:1567-1584, erratum (2007) 12(12):1593.

Medline Plus (Jun. 27, 2007). "Cancer," Located at <http://nlm.nih.gov/medlineplus/cancer.html>, Last Visited on Jul. 6, 2007, 10 Pages.

Onaivti et al., (1994) "Chronic Nicotine Reverses Age-associated Increases in Tail-Flick Latency and Anxiety in Rats" *Life Sciences* (54):193-202.

O'Neill, M.J. et al. (Aug. 2002). "The Role of Neuronal Nicotinic Acetylcholine Receptors in Acute and Chronic Neurodegeneration," *Current Drug Targets: CNS and Neurological Disorders* 1(4):399-411.

Pullan et al., (1994)"Transdermal Nicotine for Active Ulcerative Colitis" *N. Engl. J. Med.* (330)12:811-815.

Pomerleau et al., (1984) "The Effects of cigarette smoking on pain and anxiety" *Addictive Behaviors,* (9);265-271.

Rapier et al., (1988) "Stereo selective Nicotine-Induced Release of Dopamine from Striatal Synaptosomes: Concentration Dependence and Repetitive Stimulation" *Journal of Neurochemistry,* (50)4:1123-1130.

Rowell et al., (1984) "Nicotinic Stimulation of [$^3$H] Acetylcholine Release from Mouse Cerebral Cortical Synaptosomes" *Journal of Neurochemistry,* (43)6:1593-1598.

Sanberg et al., (1993) "Nicotine Potentiation of Haloperidol-Induced Catalepsy: Striatal Mechanisms" *Pharmacol. Biochem. & Behavior* (46):303-307.

Sandor et al., (1991) "Effect of nicotine on dopaminergic-cholinergic interaction in the striatum" *Brain Research,* 567:313-316.

Schmitt, (2000) "Exploring the Nature of Molecular Recognition in Nicotinic Acetylcholine Receptors" *Current Med. Chem,*(7):749-800.

Sjak-shie et al., (1993) "Effects of Chronic nicotine and pilocarpine administration on neocortical neuronal density and [$^3$H]GABA uptake in nucleus basalis lesioned rats" *Brain Research,* 624:295-298.

Stevens, K.E. et al. (1998). "Selective α7-Nicotinic Agonists Normalize Inhibition of Auditory Response in DBA Mice," *Psychopharm.* 136:320-327.

Toth et al., (1992) "Effect of Nicotine on Extracellular Levels of Neurotransmitters Assessed by Microdialysis in Various Brain Regions: Role of Glutamic Acid" *Neurochemical Research,* (17)3:265-271.

Turconi, M. et al., Synthesis of a new class of 2,3-dihydro-2-oxo-1H-benzimidazole-1-carboxylic acid derivatives as highly potent 5-HT3 receptor antagonists, Journal of medicinal Chemistry, 1990, vol. 33, No. 8, pp. 2101-2108.

(56) References Cited

OTHER PUBLICATIONS

Tripathi et al., (1982) "Nicotine-Induced Antinociception in Rats and Mice: Correlation with Nicotine Brain Levels" *JPET,* (221)1:91-96.

Utsugisawa et al., (2002) "Over-Expression of α7 Nicotinic Acetylcholine Receptor Induces Sustained ERK Phosphorylation and N-cadherin Expression in PC12 Cells" Molecular Brain Research, (106):88-93.

Vippagunta et al. (2001). *Advanced Drug Delivery Reviews* 48:3-26.

Vizi, (1973) "Acetylcholine Release from Guinea-Pig Ileum by Parasympathetic Ganglion Stimulants and Gastrin-Like Polypeptides" *Br. J. Pharmac.* (47):765-777.

Wagner et al., (1988) "Does Smoking Reduce the Risk of Neuroleptic Parkinsonoids?" Pharmacopsychiatry (21):302-303.

Wikipedia.com (Date Unknown). "Cancer," located at <http://www.nlm.nih.gov/medlineplus/cancer.html>, last visited on Jul. 6, 2007, 2 pages.

Williams, M. et al. (May 1994). "Neuronal Nicotinic Acetylcholine Receptors," *Drug News & Perspectives* 7(4):205-223.

Written Opinion mailed Oct. 1, 2015, for PCT Application No. PCT/US2015/039560, filed Jul. 8, 2015, 5 pages.

Xiao et al., (2002) "Identification of gene expression profile of dorsal root ganglion in the rat peripheral axotomy model of neuropathic pain" *Proc. Nat. Acad. Sci.,* (99)12:8360-8365.

\* cited by examiner

QUINUCLIDINES FOR MODULATING ALPHA 7 ACTIVITY

CROSS-REFERENCE TO RELATED APPLICATIONS

This application claims priority benefit of U.S. Provisional Application No. 62/023,580, filed Jul. 11, 2014, the disclosure of which is incorporated herein by reference in its entirety.

TECHNICAL FIELD

Provided herein are substituted quinuclidine compounds, pharmaceutical compositions comprising such compounds, and methods of modulating α7 nicotinic acetylcholine receptors and treating neurological disorders using such compounds.

BACKGROUND

Nicotine has been proposed to have a number of pharmacological effects. See, for example, Pullan et al., N. Engl. J. Med. 330, 811 (1994). Certain of those effects may be related to effects upon neurotransmitter release. See, for example, Sjak-shie et al., Brain Res. 624, 295 (1993), where neuroprotective effects of nicotine are proposed. Release of acetylcholine and dopamine by neurons, upon administration of nicotine, has been reported by Rowell et al., J. Neurochem. 43, 1593 (1984); Rapier et al., J. Neurochem. 50, 1123 (1988); Sandor et al., Brain Res. 567, 313 (1991) and Vizi, Br. J. Pharmacol. 47, 765 (1973). Release of norepinephrine by neurons, upon administration of nicotine, has been reported by Hall et al., Biochem. Pharmacol. 21, 1829 (1972). Release of serotonin by neurons, upon administration of nicotine, has been reported by Hery et al., Arch. Int. Pharmacodyn. Ther. 296, 91 (1977). Release of glutamate by neurons, upon administration of nicotine, has been reported by Toth et al., Neurochem Res. 17, 265 (1992). Confirmatory reports and additional recent studies have included the modulation, in the central nervous system (CNS), of glutamate, nitric oxide, GABA, tachykinins, cytokines, and peptides (reviewed in Brioni et al., Adv. Pharmacol. 37, 153 (1997)). In addition, nicotine reportedly potentiates the pharmacological behavior of certain formulations used for the treatment of certain disorders. See, for example, Sanberg et al., Pharmacol. Biochem. & Behavior 46, 303 (1993); Harsing et al., J. Neurochem. 59, 48 (1993) and Hughes, Proceedings from Intl. Symp. Nic. S40 (1994). Furthermore, various other beneficial pharmacological effects of nicotine have been proposed. See, for example, Decina et al., Biol. Psychiatry 28, 502 (1990); Wagner et al., Pharmacopsychiatry 21, 301 (1988); Pomerleau et al., Addictive Behaviors 9, 265 (1984); Onaivi et al., Life Sci. 54, 193 (1994); Tripathi et al., JPET 221, 91 (1982) and Hamon, Trends in Pharmacol. Res. 15, 36 (1994).

Various compounds that target nicotinic acetylcholine receptors (NAChRs) have been reported as being useful for treating a wide variety of conditions and disorders. See, for example, Williams et al., DN&P 7, 205 (1994); Arneric et al., CNS Drug Rev. 1, 1 (1995); Arneric et al., Exp. Opin. Invest. Drugs 5, 79 (1996); Bencherif et al., JPET 279, 1413 (1996); Lippiello et al., JPET 279, 1422 (1996); Damaj et al., J. Pharmacol. Exp. Ther. 291, 390 (1999); Chiari et al., Anesthesiology 91, 1447 (1999); Lavand'homme and Eisenbach, Anesthesiology 91, 1455 (1999); Holladay et al., J. Med. Chem. 40, 4169 (1997); Bannon et al., Science 279, 77 (1998); PCT WO 94/08992, PCT WO 96/31475, PCT WO 96/40682, and U.S. Pat. No. 5,583,140 to Bencherif et al., U.S. Pat. No. 5,597,919 to Dull et al., U.S. Pat. No. 5,604,231 to Smith et al., and U.S. Pat. No. 5,852,041 to Cosford et al. Nicotinic compounds are reported as being particularly useful for treating a wide variety of CNS disorders. Indeed, a wide variety of compounds have been reported to have therapeutic properties. See, for example, Bencherif and Schmitt, Current Drug Targets: CNS and Neurological Disorders 1, 349 (2002), Levin and Rezvani, Current Drug Targets: CNS and Neurological Disorders 1, 423 (2002), O'Neill et al., Current Drug Targets: CNS and Neurological Disorders 1, 399 (2002), U.S. Pat. No. 5,187,166 to Kikuchi et al., U.S. Pat. No. 5,672,601 to Cignarella, PCT WO 99/21834, PCT WO 97/40049, UK Patent Application GB 2295387, and European Patent Application 297,858.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin. Relatively common CNS disorders include presenile dementia (early-onset Alzheimer's disease), senile dementia (dementia of the Alzheimer's type), micro-infarct dementia, AIDS-related dementia, Creutzfeld-Jakob disease, Pick's disease, Parkinsonism including Parkinson's disease, Lewy body dementia, progressive supranuclear palsy, Huntington's chorea, tardive dyskinesia, hyperkinesia, mania, attention deficit disorder, anxiety, dyslexia, schizophrenia, depression, obsessive-compulsive disorders and Tourette's syndrome.

The NAChRs characteristic of the CNS have been shown to occur in several subtypes, the most common of which are the α4β2 and α7 subtypes. See, for example, Schmitt, Current Med. Chem. 7, 749 (2000). Ligands that interact with the α7 NAChR subtype have been proposed to be useful in the treatment of schizophrenia. There are a decreased number of hippocampal NAChRs in postmortem brain tissue of schizophrenic individuals. Also, there is improved psychological effect in smoking versus non-smoking schizophrenic individuals. Nicotine improves sensory gating deficits in animals and schizophrenics. Blockade of the α7 NAChR subtype induces a gating deficit similar to that seen in schizophrenia. See, for example, Leonard et al., Schizophrenia Bulletin 22, 431 (1996). Biochemical, molecular, and genetic studies of sensory processing in individuals with the P50 auditory-evoked potential gating deficit suggest that the α7 NAChR subtype may function in an inhibitory neuronal pathway. See, for example, Freedman et al., Biological Psychiatry 38, 22 (1995).

More recently, α7 NAChRs have been proposed to be mediators of angiogenesis, as described by Heeschen et al., J. Clin. Invest. 100, 527 (2002), U.S. Pat. No. 6,417,207, U.S. Pat. No. 7,045,534, WO 01/08683 and WO 01/08684. In these studies, inhibition of the α7 subtype was shown to decrease inflammatory angiogenesis. Also, α7 NAChRs have been proposed as targets for controlling neurogenesis and tumor growth (Utsugisawa et al., Molecular Brain Research 106, 88 (2002) and U.S. Patent Application 2002/0016371). Finally, the role of the α7 subtype in cognition (Levin and Rezvani, Current Drug Targets: CNS and Neurological Disorders 1, 423 (2002)), neuroprotection (O'Neill et al., Current Drug Targets: CNS and Neurological Disorders 1, 399 (2002) and Jeyarasasingam et al., Neuroscience 109, 275 (2002)), and neuropathic pain (Xiao et al., Proc. Nat. Acad. Sci. 99, 8360 (2002)) has recently been recognized.

Various compounds have been reported to interact with α7 NAChRs and have been proposed as therapies on that basis. See, for instance, WO 99/62505, WO 99/03859, WO 97/30998, WO 01/36417, WO 02/15662, WO 02/16355, WO 02/16356, WO 02/16357, WO 02/16358, WO 02/17358, Stevens et al., Psychopharm. 136, 320 (1998), Dolle et al., J. Labelled Comp. Radiopharm. 44, 785 (2001) and Macor et al., Bioorg. Med. Chem. Lett. 11, 319 (2001) and references therein. Among these compounds, a common structural theme is that of a substituted tertiary bicyclic amine (e.g., quinuclidine). Similar quinuclidine compounds have also been reported to bind to muscarinic (U.S. Pat. No. 5,712,270, WO 02/00652 and WO 02/51841) as well as serotonergic receptors (U.S. Pat. No. 5,300,512 and U.S. Pat. No. 5,399,562).

European Patent Publication No. 491664A1 discloses 3,7-disubstituted indole derivatives for treating psychiatric disorders.

PCT Publication No. WO 93/15080 discloses azabicyclo compounds as calcium channel antagonists.

European Patent Publication No. 382687A2 discloses benzofused-N-containing heterocycle derivatives as muscarinic receptor blocking agents.

European Patent Publication No. 350130A2 discloses substituted 1,7-annelated 1H-indazoles as antagonists of "neuronal" 5-HT receptors.

U.S. Pat. No. 5,399,562 discloses indolones useful as 5-HT$_4$ agonists or antagonists and 5-HT$_3$ antagonists.

U.S. Pat. No. 5,300,512 discloses benzimidazole compounds useful in treating 5-HT$_4$ and/or 5-HT$_3$ mediated conditions.

PCT Publication No. WO 2009/046025 discloses substituted quinuclidine compounds useful in modulating α7 NAChR.

It would be desirable to provide useful methods for the prevention and treatment of nicotinic receptor-mediated conditions by administering a compound which mediates such conditions to an individual susceptible to or suffering from such a condition. It would be highly beneficial to provide individuals suffering from certain conditions (e.g., CNS diseases) with interruption of the symptoms of those conditions by the administration of a formulation containing an active ingredient having nicotinic pharmacology which has a beneficial effect (e.g., upon the functioning of the CNS), but does not provide any significant associated side effects. It would be highly desirable to provide a formulation incorporating a compound that interacts with NAChRs, such as those that have the potential to affect the functioning of the CNS. It would be highly desirable that such a compound, when employed in an amount sufficient to affect the functioning of the CNS, would not significantly affect those NAChR subtypes that have the potential to induce undesirable side effects (e.g., appreciable activity at cardiovascular and skeletal muscle receptor sites). In addition, it would be highly desirable to provide a formulation incorporating a compound which interacts with nicotinic receptors but not muscarinic receptors, as the latter are associated with side effects, such as hypersalivation, sweating, tremors, cardiovascular and gastrointestinal disturbances, related to the function of the parasympathetic nervous system (see Caulfield, Pharmacol. Ther. 58, 319 (1993) and Broadley and Kelly, Molecules 6, 142 (2001)). Furthermore, it would be highly desirable to provide formulations, which are selective for the α7 NAChR subtype, for the treatment of certain conditions (e.g., schizophrenia, cognitive disorders, neuropathic pain, and inflammation).

SUMMARY

In one aspect, provided herein is a compound having the Formula (I):

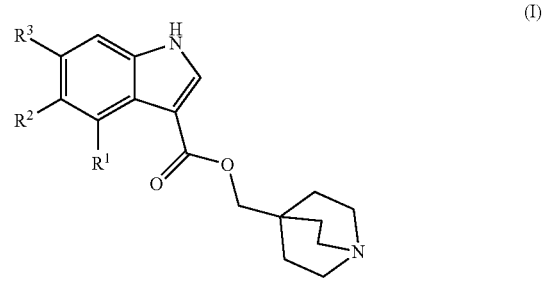

wherein $R^1$ is $C_1$-$C_6$ alkyl, $C_1$-$C_6$ alkoxy, $C_3$-$C_6$ cycloalkyl, or bromo, wherein the $C_1$-$C_6$ alkyl, $C_1$-$C_6$ alkoxy, or $C_3$-$C_6$ cycloalkyl is unsubstituted or substituted with 1 to 5 halo substituents;

$R^2$ and $R^3$ are each independently hydrogen, $C_1$-$C_6$ alkyl, $C_3$-$C_6$ cycloalkyl, halo, cyano, —$NR^aR^b$, —$NHC(O)R^c$, —$OR^d$, or —$OC(O)R^e$;

$R^a$, $R^b$, and $R^c$ are each independently hydrogen, unsubstituted $C_1$-$C_6$ alkyl, or unsubstituted $C_3$-$C_6$ cycloalkyl;

$R^d$ is hydrogen, $C_1$-$C_6$ alkyl, or $C_3$-$C_6$ cycloalkyl, wherein the $C_1$-$C_6$ alkyl or $C_3$-$C_6$ cycloalkyl is unsubstituted or substituted with 1 to 5 substituents independently selected from the group consisting of hydroxyl, $C_1$-$C_6$ alkoxy, and halo; and $R^e$ is unsubstituted $C_1$-$C_6$ alkyl or unsubstituted $C_3$-$C_6$ cycloalkyl;

provided that 1) at least one of $R^2$ and $R^3$ is hydrogen, and 2) when $R^1$ is $C_1$-$C_6$ alkoxy, $R^2$ is other than hydrogen, or a salt thereof.

In some embodiments, $R^1$ is $C_1$-$C_6$ alkyl or $C_3$-$C_6$ cycloalkyl, wherein the $C_1$-$C_6$ alkyl or $C_3$-$C_6$ cycloalkyl is unsubstituted or substituted with 1 to 5 halo substituents. In some embodiments, $R^1$ is unsubstituted $C_1$-$C_6$ alkyl. In some embodiments, $R^1$ is —$CH_3$. In some embodiments, $R^1$ is $C_1$-$C_6$ alkoxy, which is unsubstituted or substituted with 1 to 5 halo substituents. In some embodiments, $R^1$ is —$OCH_3$. In some embodiments, $R^1$ is bromo.

In some embodiments, $R^2$ is hydrogen. In some embodiments, $R^2$ is $C_1$-$C_6$ alkyl or $C_3$-$C_6$ cycloalkyl. In some embodiments, $R^2$ is —$CH_3$. In some embodiments, $R^2$ is halo. In some embodiments, $R^2$ is fluoro or chloro. In some embodiments, $R^2$ is cyano. In some embodiments, $R^2$ is —$OR^d$, and $R^d$ is hydrogen or unsubstituted $C_1$-$C_6$ alkyl. In some embodiments, $R^d$ is —$CH_3$. In some embodiments, $R^2$ is —$OR^d$, and $R^d$ is $C_1$-$C_6$ alkyl substituted with $C_1$-$C_6$ alkoxy. In some embodiments, $R^2$ is —$OR^d$, and $R^d$ is $C_1$-$C_6$ alkyl substituted with hydroxyl. In some embodiments, $R^2$ is —$OR^d$, and $R^d$ is $C_1$-$C_6$ alkyl substituted with —$NR^aR^b$.

In some embodiments, $R^3$ is hydrogen. In some embodiments, $R^3$ is $C_1$-$C_6$ alkyl or $C_3$-$C_6$ cycloalkyl. In some embodiments, $R^3$ is —$CH_3$. In some embodiments, $R^3$ is halo. In some embodiments, $R^3$ is fluoro or chloro. In some embodiments, $R^3$ is cyano. In some embodiments, $R^3$ is —$OR^d$, and $R^d$ is hydrogen or unsubstituted $C_1$-$C_6$ alkyl. In some embodiments, $R^d$ is —$CH_3$.

In some embodiments, $R^1$ is $C_1$-$C_4$ alkyl, $C_1$-$C_4$ alkoxy, $C_3$-$C_4$ cycloalkyl, or bromo, wherein the $C_1$-$C_4$ alkyl is unsubstituted or substituted with 1 to 5 fluoro substituents;

$R^2$ and $R^3$ are each independently hydrogen, $C_1$-$C_6$ alkyl, fluoro, chloro, cyano, —$NHC(O)R^c$, —$OR^d$, or —$OC(O)R^e$;

$R^c$ is hydrogen or unsubstituted $C_1$-$C_6$ alkyl;

$R^d$ is hydrogen or $C_1$-$C_6$ alkyl, wherein the $C_1$-$C_6$ alkyl is unsubstituted or substituted with 1 to 5 substituents independently selected from the group consisting of hydroxyl, $C_1$-$C_6$ alkoxy, and halo; and $R^e$ is unsubstituted $C_1$-$C_6$ alkyl;

provided that 1) at least one of $R^2$ and $R^3$ is hydrogen, and 2) when $R^1$ is $C_1$-$C_4$ alkoxy, $R^2$ is other than hydrogen, or a salt thereof.

In another aspect, provided herein is a pharmaceutical composition comprising a compound described herein, or a pharmaceutically acceptable salt thereof, and a pharmaceutically acceptable carrier.

In another aspect, provided herein is a method for treating or preventing a condition mediated by the α7-nicotinic acetylcholine receptor (α7 NAChR), comprising administering to an individual in need thereof an effective amount of a compound described herein, or a pharmaceutically acceptable salt thereof.

In some embodiments, the condition is selected from the group consisting of schizophrenia, cognitive symptoms of schizophrenia, attention deficit symptoms of schizophrenia, cognitive deficits associated with schizophrenia, Alzheimer's disease, neurodegeneration associated with Alzheimer's disease, pre-senile dementia (mild cognitive impairment), senile dementia, Parkinson's disease, psychosis, cognitive deficits associated with psychosis, attention deficit disorder, attention deficit hyperactivity disorder (ADHD), a mood disorder (e.g., depression, anxiety, and post-traumatic stress disorder), cognitive deficits associated with a mood disorder, an affective disorder, pain, symptoms associated with pain, inflammation, traumatic brain injury, and Huntington's disease. In some embodiments, the condition is selected from the group consisting of schizophrenia, cognitive symptoms of schizophrenia, attention deficit symptoms of schizophrenia, cognitive deficits associated with schizophrenia, Alzheimer's disease, neurodegeneration associated with Alzheimer's disease, and Parkinson's disease.

In some embodiments, the compound is administered once per day.

In some embodiments, the compound is administered orally.

In some embodiments, the method further comprises administering to the individual in need thereof an additional pharmaceutical agent, treatment modality, or combination thereof. In some embodiments, the additional pharmaceutical agent, treatment modality, or combination thereof is selected from the group consisting of an acetylcholinesterase inhibitor, an antipsychotic agent, and an NMDA antagonist.

In another aspect, provided herein is a composition comprising an effective amount of a compound described herein, or a pharmaceutically acceptable salt thereof, for use in treating or preventing a condition mediated by the α7-nicotinic acetylcholine receptor (α7 NAChR). The conditions mediated by the α7-nicotinic acetylcholine receptor (α7 NAChR) include those described herein and as treated according to the various methods described herein.

In another aspect, provided herein is a composition comprising an effective amount of a compound described herein, or a pharmaceutically acceptable salt thereof, for use in the manufacture of a medicament for treating or preventing a condition mediated by the α7-nicotinic acetylcholine receptor (α7 NAChR). The conditions mediated by the α7-nicotinic acetylcholine receptor (α7 NAChR) include those described herein and as treated according to the various methods described herein.

In another aspect, provided herein is the use of a composition comprising an effective amount of a compound described herein, or a pharmaceutically acceptable salt thereof, for treating or preventing a condition mediated by the α7-nicotinic acetylcholine receptor (α7 NAChR). The conditions mediated by the α7-nicotinic acetylcholine receptor (α7 NAChR) include those described herein and as treated according to the various methods described herein.

In another aspect, provided herein is a kit comprising a composition comprising an effective amount of a compound described herein, or a pharmaceutically acceptable salt thereof, and instructions for use.

Preferences and options for a given aspect, feature or parameter of the compositions and methods provided herein should, unless the context indicates otherwise, be regarded as having been disclosed in combination with any and all preferences and options for all other aspects, features and parameters of the compositions and methods provided herein, for example, use of the compounds of Table 1 and/or Table 2 in the treatment of, or a preparation of a medicament for, schizophrenia, cognitive symptoms of schizophrenia, attention deficit symptoms of schizophrenia, cognitive deficits associated with schizophrenia, Alzheimer's disease, neurodegeneration associated with Alzheimer's disease, pre-senile dementia (mild cognitive impairment), senile dementia, Parkinson's disease, psychosis, cognitive deficits associated with psychosis, attention deficit disorder, attention deficit hyperactivity disorder (ADHD), a mood disorder (e.g., depression, anxiety, and post-traumatic stress disorder), cognitive deficits associated with a mood disorder, an affective disorder, pain, symptoms associated with pain, inflammation, traumatic brain injury, and Huntington's disease.

DETAILED DESCRIPTION

Provided herein are compounds and formulations that may be useful in the treatment and prevention of conditions mediated by the α7-nicotinic acetylcholine receptor (α7 NAChR) including methods for administering a therapeutically effective amount of a compound or formulation that mediates such conditions to an individual susceptible to or suffering from such a condition. Individuals suffering from certain conditions (e.g., CNS diseases) may be provided with interruption or amelioration of the symptoms of those conditions, by the administration of a formulation containing an active ingredient (e.g., having nicotinic pharmacology) which has a beneficial effect (e.g., upon the functioning of the CNS), but does not provide any significant associated side effects. The compounds provided herein may have the advantageous property such that administration of the compound in an amount sufficient to affect the functioning of the CNS would not significantly affect those NAChR subtypes that have the potential to induce undesirable side effects (e.g., appreciable activity at cardiovascular and skeletal muscle receptor sites). These compounds may further interact with nicotinic receptors but not muscarinic receptors, as the latter are associated with side effects, such as hypersalivation, sweating, tremors, cardiovascular and gastrointestinal disturbances, related to the function of the parasympathetic nervous system. These compounds may further be selective for the α7 NAChR subtype, for the treatment of certain conditions (e.g., schizophrenia, cognitive symptoms of schizophrenia, attention deficit symptoms of schizophrenia, cognitive deficits associated with schizophrenia, Alzheimer's disease, neurodegeneration associated with Alzheimer's disease, and Parkinson's disease).

The compounds provided herein may bind to α7 NAChR and/or have agonist potential for α7 NAChR. The compounds provided herein may additionally have desirable pharmacokinetic properties including, without limitation, plasma stability.

The term "alkyl" refers to saturated aliphatic groups including straight-chain, branched-chain, and combinations thereof, having the number of carbon atoms specified, or if no number is specified, having up to 12 carbon atoms. Examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, and neopentyl.

The term "cycloalkyl" refers to saturated alicyclic groups having the number of carbon atoms specified, or if no number is specified, having up to 12 carbon atoms. Examples of cycloalkyl groups include, but are not limited to, cyclopropyl, cyclobutyl, cyclopentyl, cyclohexyl, and adamantyl. Cycloalkyl groups can consist of one ring, including, but not limited to, groups such as cycloheptyl, or multiple fused rings, including, but not limited to, groups such as adamantyl or norbornyl.

The term "alkoxy" as used herein refers to an —O-alkyl group having the number of carbon atoms specified, or if no number is specified, having up to 12 carbon atoms. Examples of alkoxy groups include, but are not limited to, groups such as methoxy, ethoxy, propyloxy (propoxy) (either n-propoxy or iso-propoxy), and butoxy (either n-butoxy, iso-butoxy, sec-butoxy, or tert-butoxy). In some embodiments, the alkoxy substituent is methoxy. In some embodiments, the alkoxy substituent is cyclopropoxy.

The term "substituted" refers to the replacement of one or more hydrogen atoms of a moiety with a monovalent or divalent radical. A moiety lacking the term "substituted" is intended to be an unsubstituted moiety (e.g., "alkyl" is intended an unsubstituted alkyl unless indicated as a substituted alkyl).

The terms "halo" and "halogen" as used herein refer to the Group VIIa elements (Group 17 elements in the 1990 IUPAC Periodic Table, IUPAC Nomenclature of Inorganic Chemistry, Recommendations 1990) and include Cl, Br, F and I substituents. In some embodiments, halogen substituents are Cl and F.

As used herein, "isomer" includes all stereoisomers of the compounds referred to in the formulas herein, including enantiomers, diastereomers, as well as all conformers, rotomers, and tautomers. Provided herein are all enantiomers of any chiral compound disclosed, in either substantially pure levorotatory or dextrorotatory form, or in a racemic mixture, or in any ratio of enantiomers. For compounds disclosed as an (R)-enantiomer, also provided is the (S)-enantiomer; for compounds disclosed as the (S)-enantiomer, also provided is the (R)-enantiomer. Provided herein are any diastereomers of the compounds referred to in the above formulas in diastereomerically pure form and in the form of mixtures in all ratios.

Unless stereochemistry is explicitly indicated in a chemical structure or chemical name, the chemical structure or chemical name is intended to embrace all possible stereoisomers, conformers, rotomers, and tautomers of the compound depicted. For example, a compound containing a chiral carbon atom is intended to embrace both the (R) enantiomer and the (S) enantiomer.

Unless particular isotopes are explicitly indicated in a chemical structure or chemical name, the chemical structure or chemical name is intended to embrace all possible isotopomers of the compound depicted. For example, a compound containing a hydrogen atom is intended to embrace proton-, deuterium-, and tritium-containing isotopomers.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) Protective Groups in Organic Synthesis, 3rd Ed. (John Wiley & Sons, Inc., New York), the content of which is incorporated by reference herein. Amino protecting groups include, but are not limited to, mesitylenesulfonyl (Mts), benzyloxycarbonyl (CBz or Z), t-butyloxycarbonyl (Boc), t-butyldimethylsilyl (TBS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, α-,α-dimethyl-dimethoxybenzyloxycarbonyl (DDZ), 5-bromo-7-nitroindolinyl, and the like. Hydroxyl protecting groups include, but are not limited to, Fmoc, TBS, photolabile protecting groups (such as nitroveratryl oxymethyl ether (Nvom)), Mom (methoxy methyl ether), and Mem (methoxy ethoxy methyl ether), NPEOC (4-nitrophenethyloxycarbonyl) and NPEOM (4-nitrophenethyloxymethyloxycarbonyl).

Certain compounds provided herein can exist in unsolvated forms as well as solvated forms (i.e., "solvates"). Compounds provided herein may also include hydrated forms (i.e., "hydrates"). A hydrate form may also be considered a solvate form. In general, the solvated and hydrated forms are equivalent to unsolvated forms and are provided herein. Also provided are all polymorphs, including crystalline and non-crystalline forms. In general, all physical forms are equivalent for the uses contemplated herein.

Provided herein are all salts of the compounds described herein, as well as methods of using such salts of the compounds. Also provided herein are all non-salt forms of any salt of a compound named herein, as well as other salts of any salt of a compound named herein. In one embodiment, the salts of the compounds comprise pharmaceutically acceptable salts. "Pharmaceutically acceptable salts" are those salts which retain the biological activity of the free compounds and which can be administered as drugs or pharmaceuticals to humans and/or animals. The desired salt of a basic functional group of a compound (such as a quinuclidine nitrogen or a heterocyclic nitrogen) may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. The desired salt of an acidic functional group of a compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts.

In all uses of the compounds of the formulas disclosed herein (e.g., a compound of Formula I and/or any compound of Table 1 or Table 2), also provided herein is use of any or all of the stereochemical, enantiomeric, diastereomeric, conformeric, rotomeric, tautomeric, solvate, hydrate, polymorphic, crystalline, non-crystalline, salt, and pharmaceutically acceptable salt forms of the compounds as described.

A substantially pure compound means that the compound is present with no more than 15% or no more than 10% or no more than 5% or no more than 3% or no more than 1% of the total amount of compound as impurity and/or in a different form. For instance, substantially pure S,S compound means that no more than 15% or no more than 10% or no more than 5% or no more than 3% or no more than 1% of the total R,R; S,R; and R,S form is present.

As used herein, "therapeutically effective amount" indicates an amount that results in a desired pharmacological and/or physiological effect for the condition. The effect may be prophylactic in terms of completely or partially preventing a condition or symptom thereof and/or may be therapeutic in terms of a partial or complete cure for the condition and/or adverse effect attributable to the condition. For example, a partial or complete cure of schizophrenia may be indicated by a clinical improvement of schizophrenia, such as improvement in cognitive impairment.

As used herein, the term "pharmaceutically acceptable carrier," and cognates thereof, refers to adjuvants, binders, diluents, etc. known to the skilled artisan that are suitable for administration to an individual (e.g., a mammal or non-mammal). Combinations of two or more carriers are also contemplated. The pharmaceutically acceptable carrier(s) and any additional components, as described herein, should be compatible for use in the intended route of administration (e.g., oral, parenteral) for a particular dosage form, as would be recognized by the skilled artisan.

As used herein, the term "pharmaceutical agent" or "additional pharmaceutical agent," and cognates of these terms, are intended to refer to active agents other than the claimed compounds, for example, drugs, which are administered to elicit a therapeutic effect. The pharmaceutical agent(s) may be directed to a therapeutic effect related to the condition that a claimed compound is intended to treat or prevent (e.g., conditions mediated by α7 NAChR, including, but not limited to those conditions described herein (e.g., Alzheimer's disease, Parkinson's disease, Huntington's disease, schizophrenia, ADHD, etc.)). or, the pharmaceutical agent may be intended to treat or prevent a symptom of the underlying condition (e.g., promote cognition enhancement, attention, working memory, episodic secondary memory, memory recall, sensory gating, reaction time, immediate and delayed word recall, visual tracking, and word recognition) or to further reduce the appearance or severity of side effects of administering a claimed compound.

When used with respect to methods of treatment/prevention and the use of the compounds and formulations thereof described herein, an individual "in need thereof" may be an individual who has been diagnosed with or previously treated for the condition to be treated. With respect to prevention, the individual in need thereof may also be an individual who is at risk for a condition (e.g., a family history of the condition, life-style factors indicative of risk for the condition, etc.).

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children and premature infants. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. Examples of non-mammals include, but are not limited to, birds, and the like. The term "individual" does not denote a particular age or sex.

In some variations, the individual has been identified as having one or more of the conditions described herein. Identification of the conditions as described herein by a skilled physician is routine in the art and may also be suspected by the individual or others, for example, due to loss of memory in the case of Alzheimer's, exhibiting the symptoms of schizophrenia, etc.

In some embodiments, the individual has been identified as susceptible to one or more of the conditions as described herein. The susceptibility of an individual may be based on any one or more of a number of risk factors and/or diagnostic approaches appreciated by the skilled artisan, including, but not limited to, genetic profiling, family history, medical history (e.g., appearance of related conditions), lifestyle or habits.

As used herein, "treatment or prevention of a condition mediated by the α7 NAChR" indicates administering one or more of the compounds discussed herein, with or without additional pharmaceutical agents, in order to reduce, eliminate, and/or prevent either the condition or one or more symptoms of the condition, or to retard the progression of the disease or of one or more symptoms of the condition, or to reduce the severity of the disease or of one or more symptoms of the condition.

As used herein and in the appended claims, the singular forms "a", "an" and "the" include plural forms, unless the context clearly dictates otherwise.

Reference to "about" a value or parameter herein includes (and describes) variations that are directed to that value or parameter per se. For example, a description referring to "about X" includes the description of "X".

Compounds

The nomenclature of certain quinuclidine compounds described herein may be determined using ChemOffice 13, including the ChemOffice 13 plugin for MS Excel (MS Office Professional Plus 2013). The skilled artisan will recognize that a compound may be given more than one chemical name, and different chemical names may be used to describe the same compound (e.g., using more than one nomenclature convention).

In one aspect, provided herein are quinuclidin-4-ylmethyl 1H-indole-3-carboxylate compounds which are substituted at the 4-position of the indole moiety. In some embodiments, the compounds are further substituted at the 5-position of the indole moiety. In some embodiments, the compounds are further substituted at the 6-position of the indole moiety. In some embodiments, the compounds are not substituted at the 7-position of the indole moiety. In some embodiments, the compounds are not substituted at the 5-, 6-, or 7-position of the indole moiety. The positional numbering for the indole moiety is as follows:

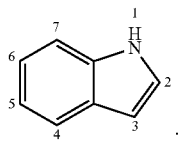

In another aspect, provided are compounds of Formula (I):

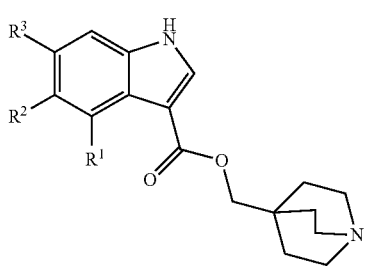

wherein $R^1$ is $C_1$-$C_6$ alkyl, $C_1$-$C_6$ alkoxy, $C_3$-$C_6$ cycloalkyl, or bromo, wherein the $C_1$-$C_6$ alkyl, $C_1$-$C_6$ alkoxy, or $C_3$-$C_6$ cycloalkyl is unsubstituted or substituted with 1 to 5 halo substituents;

$R^2$ and $R^3$ are each independently hydrogen, $C_1$-$C_6$ alkyl, $C_3$-$C_6$ cycloalkyl, halo, cyano, —$NR^aR^b$, —NHC(O)$R^c$, —$OR^d$, or —OC(O)$R^e$;

$R^a$, $R^b$, and $R^c$ are each independently hydrogen, unsubstituted $C_1$-$C_6$ alkyl, or unsubstituted $C_3$-$C_6$ cycloalkyl;

$R^d$ is hydrogen, $C_1$-$C_6$ alkyl, or $C_3$-$C_6$ cycloalkyl, wherein the $C_1$-$C_6$ alkyl or $C_3$-$C_6$ cycloalkyl is unsubstituted or substituted with 1 to 5 substituents independently selected from the group consisting of hydroxyl, $C_1$-$C_6$ alkoxy, and halo; and $R^e$ is unsubstituted $C_1$-$C_6$ alkyl or unsubstituted $C_3$-$C_6$ cycloalkyl;

provided that 1) at least one of $R^2$ and $R^3$ is hydrogen, and 2) when $R^1$ is $C_1$-$C_6$ alkoxy, $R^2$ is other than hydrogen, or a salt thereof.

In some embodiments of Formula (I), $R^1$ is $C_1$-$C_4$ alkyl, $C_1$-$C_4$ alkoxy, $C_3$-$C_4$ cycloalkyl, or bromo, wherein the $C_1$-$C_4$ alkyl is unsubstituted or substituted with 1 to 5 fluoro substituents;

$R^2$ and $R^3$ are each independently hydrogen, $C_1$-$C_6$ alkyl, fluoro, chloro, cyano, —NHC(O)$R^c$, —$OR^d$, or —OC(O)$R^e$;

$R^c$ is hydrogen or unsubstituted $C_1$-$C_6$ alkyl;

$R^d$ is hydrogen or $C_1$-$C_6$ alkyl, wherein the $C_1$-$C_6$ alkyl is unsubstituted or substituted with 1 to 5 substituents independently selected from the group consisting of hydroxyl, $C_1$-$C_6$ alkoxy, and halo; and $R^e$ is unsubstituted $C_1$-$C_6$ alkyl;

provided that 1) at least one of $R^2$ and $R^3$ is hydrogen, and 2) when $R^1$ is $C_1$-$C_4$ alkoxy, $R^2$ is other than hydrogen, or a salt thereof.

In some embodiments of Formula (I), $R^1$ is unsubstituted $C_1$-$C_6$ alkyl. In some embodiments, $R^1$ is unsubstituted $C_1$-$C_4$ alkyl. In some embodiments, $R^1$ is methyl. In other embodiments, $R^1$ is $C_1$-$C_6$ alkyl substituted with 1 to 5 halo substituents. In some embodiments, $R^1$ is $C_1$-$C_4$ alkyl substituted with 1-5 halo substituents. In some embodiments, $R^1$ is trifluoromethyl.

In some embodiments of Formula (I), $R^1$ is unsubstituted $C_3$-$C_6$ alkyl. In some embodiments, $R^1$ is unsubstituted $C_3$-$C_4$ alkyl. In some embodiments, $R^1$ is cyclopropyl. In other embodiments, $R^1$ is $C_3$-$C_6$ alkyl substituted with 1-5 halo substituents. In some embodiments, $R^1$ is $C_3$-$C_4$ alkyl substituted with 1-5 halo substituents.

In some embodiments of Formula (I), $R^1$ is unsubstituted $C_1$-$C_6$ alkoxy. In some embodiments, $R^1$ is unsubstituted $C_1$-$C_4$ alkoxy. In some embodiments, $R^1$ is methoxy. In other embodiments, $R^1$ is $C_1$-$C_6$ alkoxy substituted with 1 to 5 halo substituents. In some embodiments, $R^1$ is $C_1$-$C_4$ alkoxy substituted with 1-5 halo substituents. In some embodiments, $R^1$ is trifluoromethoxy.

In some embodiments of Formula (I), $R^1$ is bromo.

In some embodiments of Formula (I), $R^2$ is hydrogen. In some embodiments, $R^3$ is hydrogen. In some embodiments, $R^2$ and $R^3$ are both hydrogen.

In some embodiments of Formula (I), $R^2$ is $C_1$-$C_6$ alkyl. In some embodiments, $R^2$ is $C_1$-$C_4$ alkyl. In some embodiments, $R^2$ is methyl. In other embodiments, $R^2$ is $C_3$-$C_6$ cycloalkyl. In some embodiments, $R^2$ is $C_3$-$C_4$ cycloalkyl. In some embodiments, $R^2$ is cyclopropyl. In other embodiments, $R^2$ is halo. In some embodiments, $R^2$ is chloro. In some embodiments, $R^2$ is fluoro. In other embodiments, $R^2$ is cyano.

In some embodiments of Formula (I), $R^2$ is —NHC(O)$R^c$. In some embodiments, $R^2$ is —NHC(O)$R^c$, and $R^c$ is $C_1$-$C_6$ alkyl. In some embodiments, $R^2$ is —NHC(O)$CH_3$.

In some embodiments of Formula (I), $R^2$ is —$OR^d$. In some embodiments, $R^2$ is —OH. In some embodiments, $R^2$ is —$OR^d$, and $R^d$ is unsubstituted $C_1$-$C_6$ alkyl. In some embodiments, $R^2$ is —$OCH_3$. In some embodiments, $R^2$ is —$OR^d$, and $R^d$ is $C_1$-$C_6$ alkyl substituted with 1 to 5 halo substituents. In some embodiments, $R^2$ is —$OCH_2CF_3$. In some embodiments, $R^2$ is —$OR^d$, and $R^d$ is $C_1$-$C_6$ alkyl substituted with 1 to 5 hydroxy or $C_1$-$C_6$ alkoxy substituents. In some embodiments, $R^2$ is —$OR^d$, and $R^d$ is $C_1$-$C_6$ alkyl substituted with 1 to 5 methoxy substituents. In some embodiments, $R^2$ is —$OCH_2CH_2OCH_3$, —$OCH_2CH_2CH_2OCH_3$, or —$OCH_2CH_2OH$.

In some embodiments of Formula (I), $R^2$ is —OC(O)$R^e$. In some embodiments, $R^2$ is —OC(O)$R^e$, and $R^e$ is $C_1$-$C_6$ alkyl. In some embodiments, $R^2$ is —OCOtBu.

In some embodiments of Formula (I), $R^3$ is $C_1$-$C_6$ alkyl. In some embodiments, $R^3$ is $C_1$-$C_4$ alkyl. In some embodiments, $R^3$ is methyl. In other embodiments, $R^3$ is $C_3$-$C_6$ cycloalkyl. In some embodiments, $R^3$ is $C_3$-$C_4$ cycloalkyl. In some embodiments, $R^3$ is cyclopropyl. In other embodiments, $R^3$ is halo. In some embodiments, $R^3$ is chloro. In some embodiments, $R^3$ is fluoro. In other embodiments, $R^3$ is cyano.

In some embodiments of Formula (I), $R^3$ is —NHC(O)$R^c$. In some embodiments, $R^3$ is —NHC(O)$R^c$, and $R^c$ is $C_1$-$C_6$ alkyl. In some embodiments, $R^3$ is —NHC(O)$CH_3$.

In some embodiments of Formula (I), $R^3$ is —$OR^d$. In some embodiments, $R^3$ is —OH. In some embodiments, $R^3$ is —$OR^d$, and $R^d$ is unsubstituted $C_1$-$C_6$ alkyl. In some embodiments, $R^3$ is —$OCH_3$. In some embodiments, $R^3$ is —$OR^d$, and $R^d$ is $C_1$-$C_6$ alkyl substituted with 1 to 5 halo substituents. In some embodiments, $R^3$ is —$OCH_2CF_3$. In some embodiments, $R^3$ is —$OR^d$, and $R^d$ is $C_1$-$C_6$ alkyl substituted with 1 to 5 hydroxy or $C_1$-$C_6$ alkoxy substituents. In some embodiments, $R^2$ is —$OR^d$, and $R^d$ is $C_1$-$C_6$ alkyl substituted with 1 to 5 methoxy substituents. In some embodiments, $R^3$ is —$OCH_2CH_2OCH_3$, —$OCH_2CH_2CH_2OCH_3$, or —$OCH_2CH_2OH$.

In some embodiments of Formula (I), $R^3$ is —$OC(O)R^e$. In some embodiments, $R^3$ is —$OC(O)R^e$, and $R^e$ is $C_1$-$C_6$ alkyl. In some embodiments, $R^3$ is —OCOtBu.

In some embodiments of Formula (I), $R^1$ is $C_1$-$C_6$ alkyl, and $R^2$ and $R^3$ are both hydrogen. In some embodiments of Formula (I), $R^1$ is $C_1$-$C_6$ alkyl substituted with 1-5 halo substituents, and $R^2$ and $R^3$ are both hydrogen. In other embodiments, $R^1$ is $C_3$-$C_6$ cycloalkyl, and $R^2$ and $R^3$ are both hydrogen. In other embodiments, $R^1$ is bromo, and $R^2$ and $R^3$ are both hydrogen.

In some embodiments of Formula (I), $R^1$ is methyl, and $R^2$ is $C_1$-$C_6$ alkyl, halo, —$NHC(O)R^c$, or —$OR^d$. In other embodiments, $R^1$ is methyl, and $R^3$ is $C_1$-$C_6$ alkyl, halo, cyano, —$OR^d$, or —$OC(O)R^e$.

In some embodiments of Formula (I), $R^1$ is methoxy, and $R^2$ is $C_1$-$C_6$ alkyl or —$OR^d$.

In some embodiments of Formula (I), $R^1$ is bromo, and $R^2$ is $C_1$-$C_6$ alkyl, $C_1$-$C_6$ alkoxy, or halo. In other embodiments, $R^1$ is bromo, and $R^3$ is $C_1$-$C_6$ alkyl, $C_1$-$C_6$ alkoxy, halo, or hydroxyl.

In some embodiments of Formula (I), $R^1$ is $C_1$-$C_6$ alkyl, and $R^2$ is $C_1$-$C_6$ alkyl, halo, or —$OR^d$. In some embodiments, $R^1$ is $C_1$-$C_6$ alkyl, and $R^2$ is methyl, fluoro, chloro, hydroxyl, or methoxy. In some embodiments of Formula (I), $R^1$ is $C_1$-$C_6$ alkyl, and $R^3$ is $C_1$-$C_6$ alkyl, halo, or —$OR^d$. In some embodiments, $R^1$ is $C_1$-$C_6$ alkyl, and $R^3$ is methyl, fluoro, chloro, hydroxyl, or methoxy.

In some embodiments of Formula (I), $R^1$ is $C_1$-$C_6$ alkoxy, and $R^2$ is $C_1$-$C_6$ alkyl or —$OR^d$. In some embodiments, $R^1$ is $C_1$-$C_6$ alkoxy, and $R^2$ is methyl or methoxy.

In some embodiments of Formula (I), $R^1$ is $C_1$-$C_6$ alkyl, $C_3$-$C_6$ cycloalkyl, or bromo, wherein the $C_1$-$C_6$ alkyl or $C_3$-$C_6$ cycloalkyl is unsubstituted or substituted with 1 to 5 halo substituents;

$R^2$ is hydrogen;

$R^3$ is hydrogen, $C_1$-$C_6$ alkyl, $C_3$-$C_6$ cycloalkyl, halo, cyano, —$NR^aR^b$, —$NHC(O)R^c$, —$OR^d$, or —$OC(O)R^e$;

$R^a$, $R^b$, and $R^c$ are each independently hydrogen, unsubstituted $C_1$-$C_6$ alkyl, or unsubstituted $C_3$-$C_6$ cycloalkyl;

$R^d$ is hydrogen, $C_1$-$C_6$ alkyl, or $C_3$-$C_6$ cycloalkyl, wherein the $C_1$-$C_6$ alkyl or $C_3$-$C_6$ cycloalkyl is unsubstituted or substituted with 1 to 5 substituents independently selected from the group consisting of hydroxyl, $C_1$-$C_6$ alkoxy, and halo; and $R^e$ is unsubstituted $C_1$-$C_6$ alkyl or unsubstituted $C_3$-$C_6$ cycloalkyl, or a salt thereof.

In some embodiments of Formula (I), $R^1$ is $C_1$-$C_6$ alkyl, $C_3$-$C_6$ cycloalkyl, or bromo, wherein the $C_1$-$C_6$ alkyl or $C_3$-$C_6$ cycloalkyl is unsubstituted or substituted with 1 to 5 halo substituents;

$R^2$ is hydrogen, $C_1$-$C_6$ alkyl, $C_3$-$C_6$ cycloalkyl, halo, cyano, —$NR^aR^b$, —$NHC(O)R^c$, —$OR^d$, or —$OC(O)R^e$;

$R^3$ is hydrogen;

$R^a$, $R^b$, and $R^c$ are each independently hydrogen, unsubstituted $C_1$-$C_6$ alkyl, or unsubstituted $C_3$-$C_6$ cycloalkyl;

$R^d$ is hydrogen, $C_1$-$C_6$ alkyl, or $C_3$-$C_6$ cycloalkyl, wherein the $C_1$-$C_6$ alkyl or $C_3$-$C_6$ cycloalkyl is unsubstituted or substituted with 1 to 5 substituents independently selected from the group consisting of hydroxyl, $C_1$-$C_6$ alkoxy, and halo; and $R^e$ is unsubstituted $C_1$-$C_6$ alkyl or unsubstituted $C_3$-$C_6$ cycloalkyl, or a salt thereof.

In some embodiments of Formula (I), $R^1$ is $C_1$-$C_6$ alkyl, $C_1$-$C_6$ alkoxy, $C_3$-$C_6$ cycloalkyl, or bromo, wherein the $C_1$-$C_6$ alkyl, $C_1$-$C_6$ alkoxy, or $C_3$-$C_6$ cycloalkyl is unsubstituted or substituted with 1 to 5 halo substituents;

$R^2$ is $C_1$-$C_6$ alkyl, $C_3$-$C_6$ cycloalkyl, halo, cyano, —$NR^aR^b$, —$NHC(O)R^c$, —$OR^d$, or —$OC(O)R^e$;

$R^3$ is hydrogen;

$R^a$, $R^b$, and $R^c$ are each independently hydrogen, unsubstituted $C_1$-$C_6$ alkyl, or unsubstituted $C_3$-$C_6$ cycloalkyl;

$R^d$ is hydrogen, $C_1$-$C_6$ alkyl, or $C_3$-$C_6$ cycloalkyl, wherein the $C_1$-$C_6$ alkyl or $C_3$-$C_6$ cycloalkyl is unsubstituted or substituted with 1 to 5 substituents independently selected from the group consisting of hydroxyl, $C_1$-$C_6$ alkoxy, and halo; and $R^e$ is unsubstituted $C_1$-$C_6$ alkyl or unsubstituted $C_3$-$C_6$ cycloalkyl, or a salt thereof.

Exemplary compounds of Formula (I) are provided in Table 1.

TABLE 1

| Compound No. | Structure | Compound Name |
|---|---|---|
| 21 | 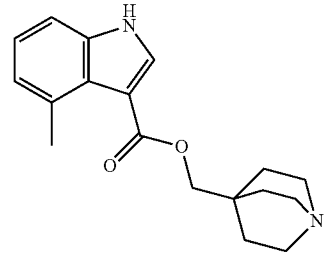 [SMILES: Cc1cccc2[nH]cc(C(=O)OCC34CCN(CC3)CC4)c12] | quinuclidin-4-ylmethyl 4-methyl-1H-indole-3-carboxylate |

TABLE 1-continued

| Compound No. | Structure | Compound Name |
|---|---|---|
| 24 | 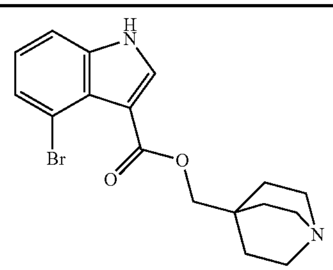 | quinuclidin-4-ylmethyl 4-bromo-1H-indole-3-carboxylate |
| 34 | 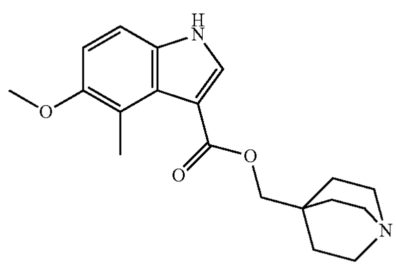 [SMILES: COc1ccc2[nH]cc(C(=O)OCC34CCN(CC3)CC4)c2c1C] | quinuclidin-4-ylmethyl 5-methoxy-4-methyl-1H-indole-3-carboxylate |
| 37 | 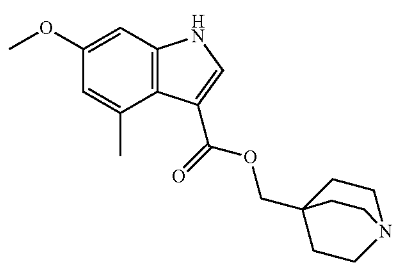 [SMILES: COc1cc(C)c2c(C(=O)OCC34CCN(CC3)CC4)c[nH]c2c1] | quinuclidin-4-ylmethyl 6-methoxy-4-methyl-1H-indole-3-carboxylate |
| 40 | 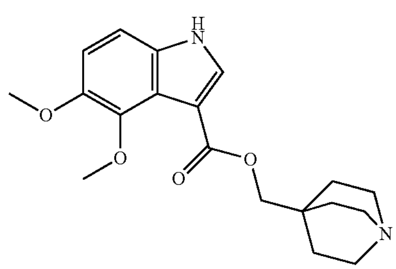 [SMILES: COc1ccc2[nH]cc(C(=O)OCC34CCN(CC3)CC4)c2c1OC] | quinuclidin-4-ylmethyl 4,5-dimethoxy-1H-indole-3-carboxylate |
| 41 | 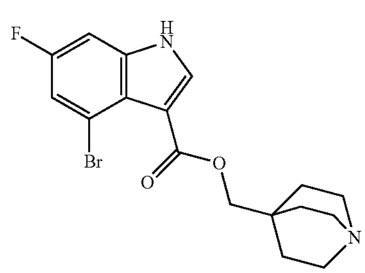 [SMILES: O=C(OCC12CCN(CC1)CC2)c1c[nH]c2cc(F)cc(Br)c12] | quinuclidin-4-ylmethyl 4-bromo-6-fluoro-1H-indole-3-carboxylate |
| 42 | 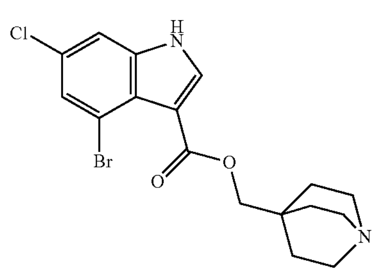 [SMILES: O=C(OCC12CCN(CC1)CC2)c1c[nH]c2cc(Cl)cc(Br)c12] | quinuclidin-4-ylmethyl 4-bromo-6-chloro-1H-indole-3-carboxylate |

TABLE 1-continued

| Compound No. | Structure | Compound Name |
|---|---|---|
| 43 | 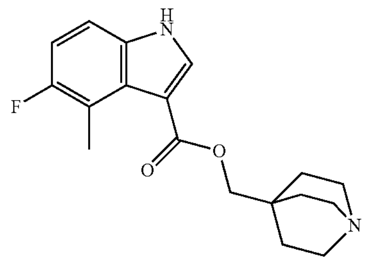 [SMILES: Cc1c(F)ccc2[nH]cc(C(=O)OCC34CCN(CC3)CC4)c12] | quinuclidin-4-ylmethyl 5-fluoro-4-methyl-1H-indole-3-carboxylate |
| 44 | 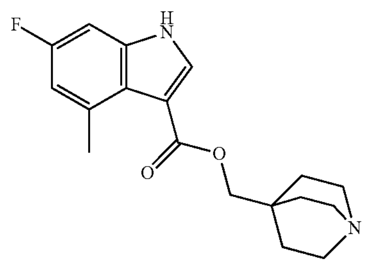 [SMILES: Cc1cc(F)cc2[nH]cc(C(=O)OCC34CCN(CC3)CC4)c12] | quinuclidin-4-ylmethyl 6-fluoro-4-methyl-1H-indole-3-carboxylate |
| 47 | 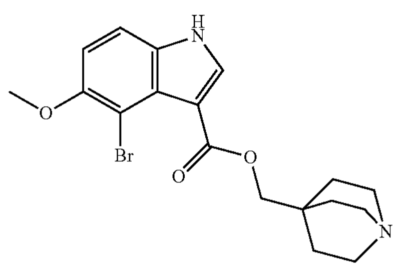 [SMILES: COc1ccc2[nH]cc(C(=O)OCC34CCN(CC3)CC4)c2c1Br] | quinuclidin-4-ylmethyl 4-bromo-5-methoxy-1H-indole-3-carboxylate |
| 48 | 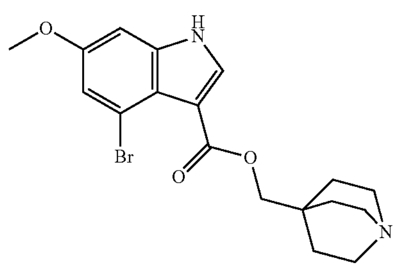 [SMILES: COc1cc(Br)c2c(C(=O)OCC34CCN(CC3)CC4)c[nH]c2c1] | quinuclidin-4-ylmethyl 4-bromo-6-methoxy-1H-indole-3-carboxylate |
| 49 | 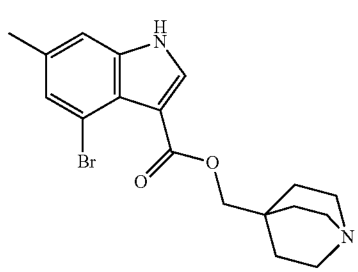 [SMILES: Cc1cc(Br)c2c(C(=O)OCC34CCN(CC3)CC4)c[nH]c2c1] | quinuclidin-4-ylmethyl 4-bromo-6-methyl-1H-indole-3-carboxylate |

TABLE 1-continued

| Compound No. | Structure | Compound Name |
| --- | --- | --- |
| 50 | 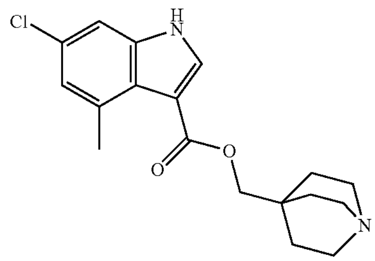 [SMILES: Cc1cc(Cl)cc2[nH]cc(C(=O)OCC34CCN(CC3)CC4)c12] | quinuclidin-4-ylmethyl 6-chloro-4-methyl-1H-indole-3-carboxylate |
| 53 | 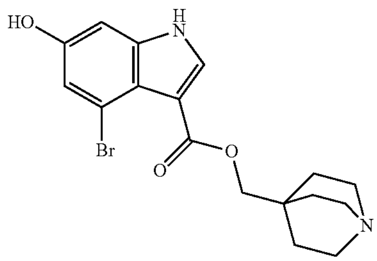 [SMILES: O=C(OCC12CCN(CC1)CC2)c1c[nH]c2cc(O)cc(Br)c12] | quinuclidin-4-ylmethyl 4-bromo-6-hydroxy-1H-indole-3-carboxylate |
| 54 | 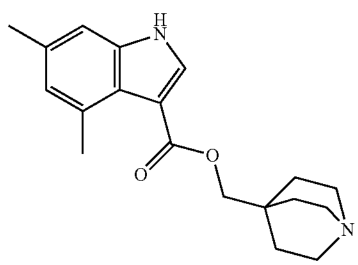 [SMILES: Cc1cc(C)c2c(C(=O)OCC34CCN(CC3)CC4)c[nH]c2c1] | quinuclidin-4-ylmethyl 4,6-dimethyl-1H-indole-3-carboxylate |
| 60 | 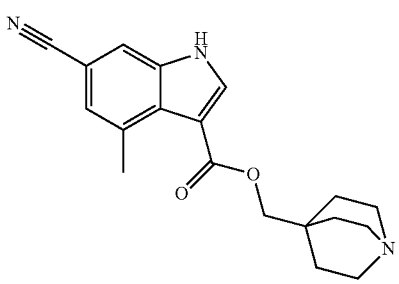 [SMILES: Cc1cc(C#N)cc2[nH]cc(C(=O)OCC34CCN(CC3)CC4)c12] | quinuclidin-4-ylmethyl 6-cyano-4-methyl-1H-indole-3-carboxylate |
| 61 | 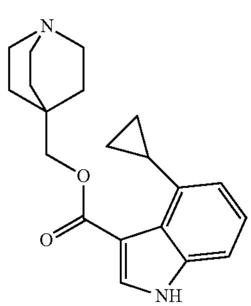 [SMILES: O=C(OCC12CCN(CC1)CC2)c1c[nH]c2cccc(C3CC3)c12] | quinuclidin-4-ylmethyl 4-cyclopropyl-1H-indole-3-carboxylate |

TABLE 1-continued

| Compound No. | Structure | Compound Name |
|---|---|---|
| 67 | 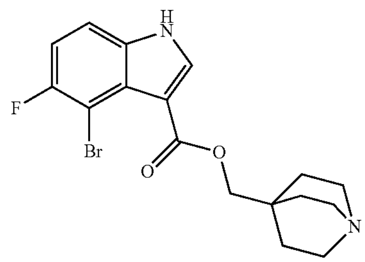 [SMILES: O=C(OCC12CCN(CC1)CC2)c1c[nH]c2ccc(F)c(Br)c12] | quinuclidin-4-ylmethyl 4-bromo-5-fluoro-1H-indole-3-carboxylate |
| 68 | 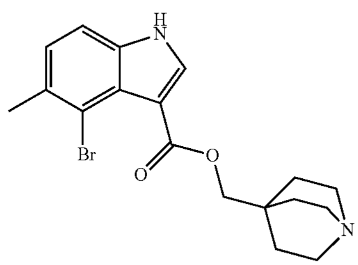 [SMILES: Cc1ccc2[nH]cc(C(=O)OCC34CCN(CC3)CC4)c2c1Br] | quinuclidin-4-ylmethyl 4-bromo-5-methyl-1H-indole-3-carboxylate |
| 70 | 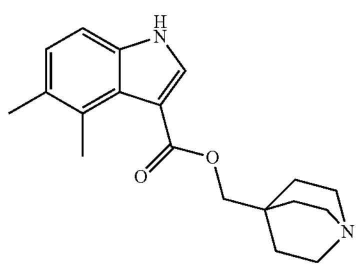 [SMILES: Cc1ccc2[nH]cc(C(=O)OCC34CCN(CC3)CC4)c2c1C] | quinuclidin-4-ylmethyl 4,5-dimethyl-1H-indole-3-carboxylate |
| 75 | 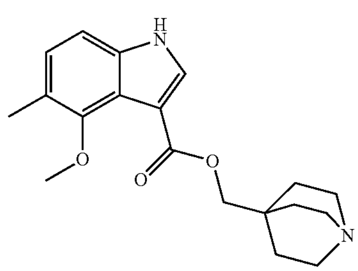 [SMILES: COc1c(C)ccc2[nH]cc(C(=O)OCC34CCN(CC3)CC4)c12] | quinuclidin-4-ylmethyl 4-methoxy-5-methyl-1H-indole-3-carboxylate |
| 80 | 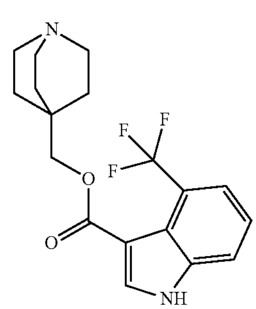 [SMILES: O=C(OCC12CCN(CC1)CC2)c1c[nH]c2cccc(C(F)(F)F)c12] | quinuclidin-4-ylmethyl 4-(trifluoromethyl)-1H-indole-3-carboxylate |

TABLE 1-continued

| Compound No. | Structure | Compound Name |
|---|---|---|
| 83 | 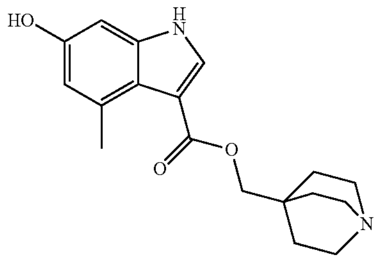 [SMILES: Cc1cc(O)cc2[nH]cc(C(=O)OCC34CCN(CC3)CC4)c12] | quinuclidin-4-ylmethyl 6-hydroxy-4-methyl-1H-indole-3-carboxylate |
| 88 | 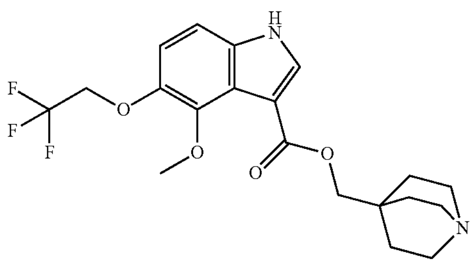 [SMILES: COc1c(OCC(F)(F)F)ccc2[nH]cc(C(=O)OCC34CCN(CC3)CC4)c12] | quinuclidin-4-ylmethyl 4-methoxy-5-(2,2,2-trifluoroethoxy)-1H-indole-3-carboxylate |
| 89 | 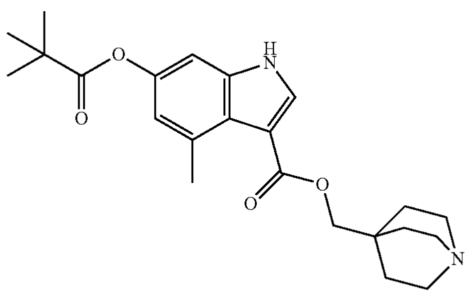 [SMILES: Cc1cc(OC(=O)C(C)(C)C)cc2[nH]cc(C(=O)OCC34CCN(CC3)CC4)c12] | quinuclidin-4-ylmethyl 4-methyl-6-(pivaloyloxy)-1H-indole-3-carboxylate |
| 91 | 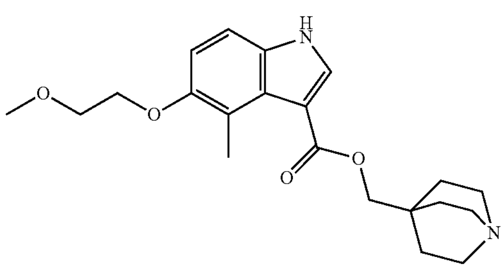 [SMILES: COCCOc1ccc2[nH]cc(C(=O)OCC34CCN(CC3)CC4)c2c1C] | quinuclidin-4-ylmethyl 5-(2-methoxyethoxy)-4-methyl-1H-indole-3-carboxylate |
| 92 | 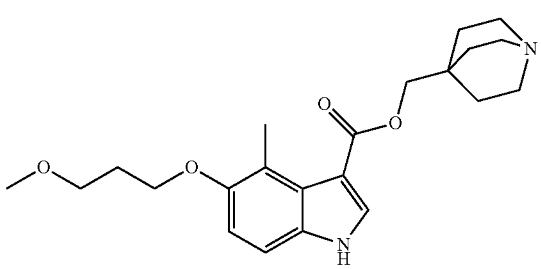 [SMILES: COCCCOc1ccc2[nH]cc(C(=O)OCC34CCN(CC3)CC4)c2c1C] | quinuclidin-4-ylmethyl 5-(3-methoxypropoxy)-4-methyl-1H-indole-3-carboxylate |

TABLE 1-continued

| Compound No. | Structure | Compound Name |
|---|---|---|
| 93 | 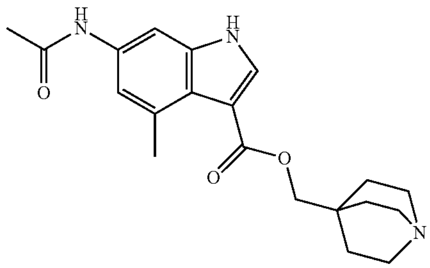 [SMILES: CC(=O)Nc1cc(C)c2c(C(=O)OCC34CCN(CC3)CC4)c[nH]c2c1] | quinuclidin-4-ylmethyl 6-acetamido-4-methyl-1H-indole-3-carboxylate |
| 94 | 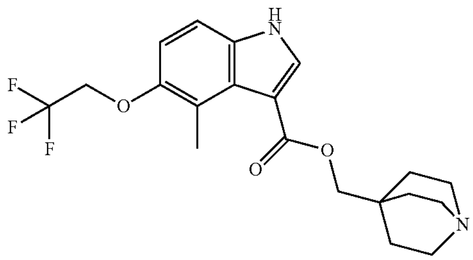 [SMILES: Cc1c(OCC(F)(F)F)ccc2[nH]cc(C(=O)OCC34CCN(CC3)CC4)c12] | quinuclidin-4-ylmethyl 4-methyl-5-(2,2,2-trifluoroethoxy)-1H-indole-3-carboxylate |
| 95 | 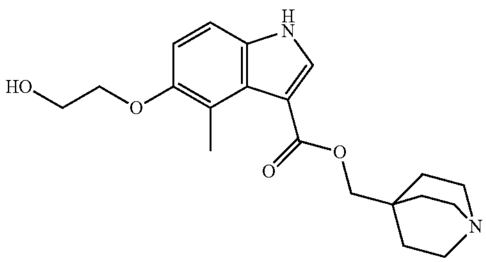 [SMILES: Cc1c(OCCO)ccc2[nH]cc(C(=O)OCC34CCN(CC3)CC4)c12] | quinuclidin-4-ylmethyl 5-(2-hydroxyethoxy)-4-methyl-1H-indole-3-carboxylate |

In another aspect, provided herein are the compounds listed in Table 2 and salts thereof.

TABLE 2

| Compound No. | Structure | Compound Name |
|---|---|---|
| 35 | 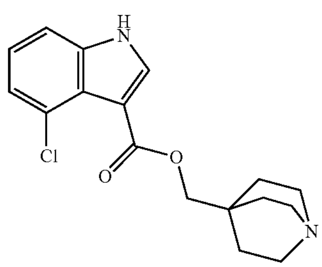 [SMILES: O=C(OCC12CCN(CC1)CC2)c1c[nH]c2cccc(Cl)c12] | quinuclidin-4-ylmethyl 4-chloro-1H-indole-3-carboxylate |
| 38 | 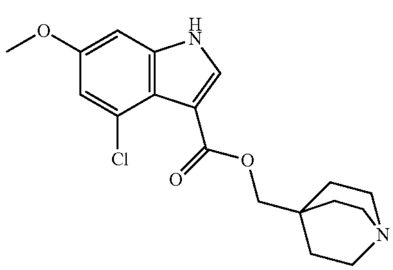 | quinuclidin-4-ylmethyl 4-chloro-6-methoxy-1H-indole-3-carboxylate |

TABLE 2-continued

| Compound No. | Structure | Compound Name |
|---|---|---|
| 46 | 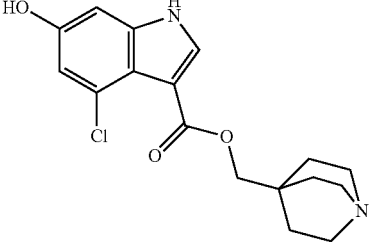 | quinuclidin-4-ylmethyl 4-chloro-6-hydroxy-1H-indole-3-carboxylate |
| 62 | 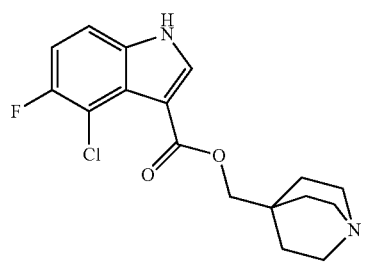 [SMILES: O=C(OCC12CCN(CC1)CC2)c1c[nH]c2ccc(F)c(Cl)c12] | quinuclidin-4-ylmethyl 4-chloro-5-fluoro-1H-indole-3-carboxylate |
| 63 | 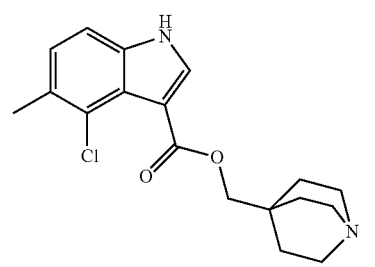 [SMILES: Cc1ccc2[nH]cc(C(=O)OCC34CCN(CC3)CC4)c2c1Cl] | quinuclidin-4-ylmethyl 4-chloro-5-methyl-1H-indole-3-carboxylate |
| 64 | 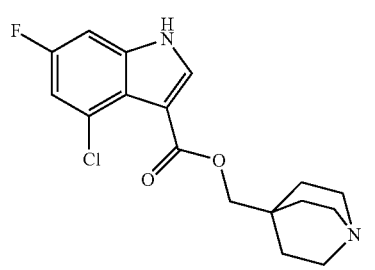 [SMILES: O=C(OCC12CCN(CC1)CC2)c1c[nH]c2cc(F)cc(Cl)c12] | quinuclidin-4-ylmethyl 4-chloro-6-fluoro-1H-indole-3-carboxylate |
| 65 | 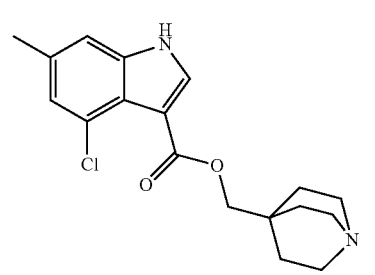 [SMILES: Cc1cc(Cl)c2c(C(=O)OCC34CCN(CC3)CC4)c[nH]c2c1] | quinuclidin-4-ylmethyl 4-chloro-6-methyl-1H-indole-3-carboxylate |
| 71 | 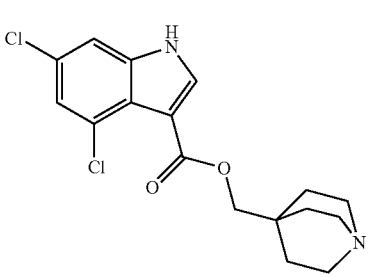 [SMILES: O=C(OCC12CCN(CC1)CC2)c1c[nH]c2cc(Cl)cc(Cl)c12] | quinuclidin-4-ylmethyl 4,6-dichloro-1H-indole-3-carboxylate |

TABLE 2-continued

| Compound No. | Structure | Compound Name |
|---|---|---|
| 74 | 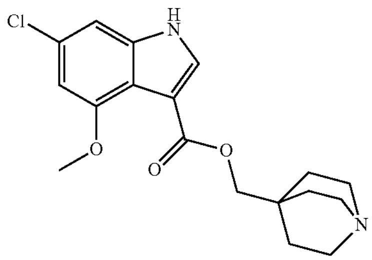 [SMILES: COc1cc(Cl)cc2[nH]cc(C(=O)OCC34CCN(CC3)CC4)c12] | quinuclidin-4-ylmethyl 6-chloro-4-methoxy-1H-indole-3-carboxylate |
| 77 | 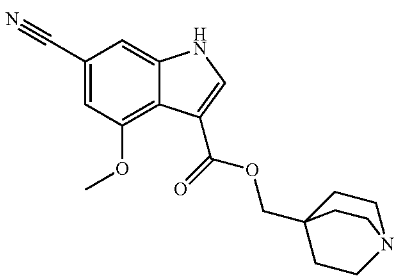 [SMILES: COc1cc(C#N)cc2[nH]cc(C(=O)OCC34CCN(CC3)CC4)c12] | quinuclidin-4-ylmethyl 6-cyano-4-methoxy-1H-indole-3-carboxylate |
| 82 | 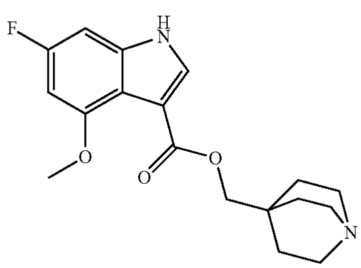 [SMILES: COc1cc(F)cc2[nH]cc(C(=O)OCC34CCN(CC3)CC4)c12] | quinuclidin-4-ylmethyl 6-fluoro-4-methoxy-1H-indole-3-carboxylate |

Additional quinuclidine compounds and salts thereof are provided in Table 3.

TABLE 3

| Compound No. | Structure | Compound Name |
|---|---|---|
| 1 | 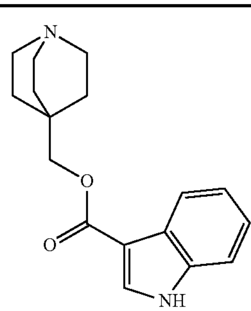 | quinuclidin-4-ylmethyl 1H-indole-3-carboxylate |

TABLE 3-continued

| Compound No. | Structure | Compound Name |
|---|---|---|
| 2 | 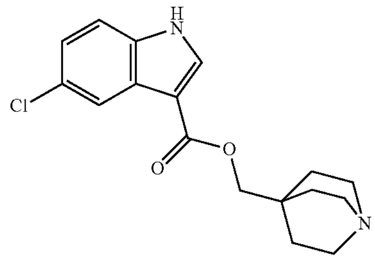 [SMILES: O=C(OCC12CCN(CC1)CC2)c1c[nH]c2ccc(Cl)cc12] | quinuclidin-4-ylmethyl 5-chloro-1H-indole-3-carboxylate |
| 3 | 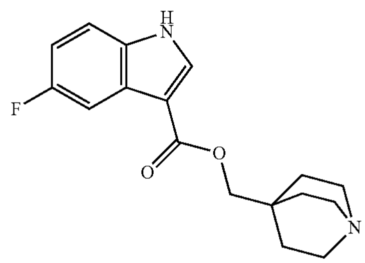 [SMILES: O=C(OCC12CCN(CC1)CC2)c1c[nH]c2ccc(F)cc12] | quinuclidin-4-ylmethyl 5-fluoro-1H-indole-3-carboxylate |
| 4 | 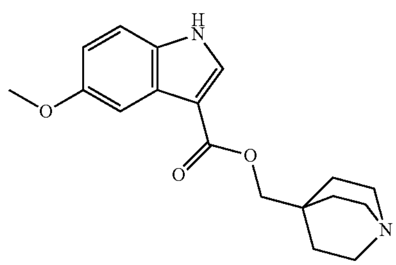 [SMILES: COc1ccc2[nH]cc(C(=O)OCC34CCN(CC3)CC4)c2c1] | quinuclidin-4-ylmethyl 5-methoxy-1H-indole-3-carboxylate |
| 5 | 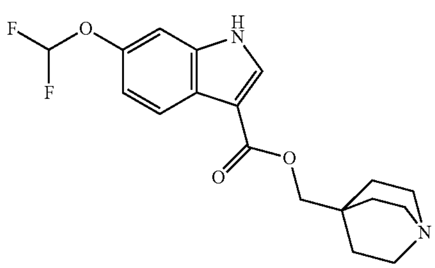 [SMILES: O=C(OCC12CCN(CC1)CC2)c1c[nH]c2cc(OC(F)F)ccc12] | quinuclidin-4-ylmethyl 6-(difluoromethoxy)-1H-indole-3-carboxylate |
| 6 | 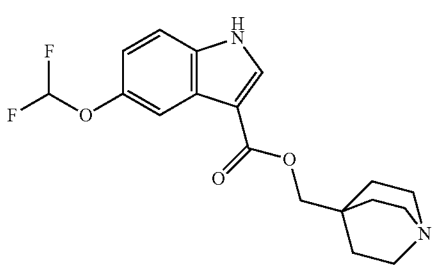 [SMILES: O=C(OCC12CCN(CC1)CC2)c1c[nH]c2ccc(OC(F)F)cc12] | quinuclidin-4-ylmethyl 5-(difluoromethoxy)-1H-indole-3-carboxylate |
| 7 | 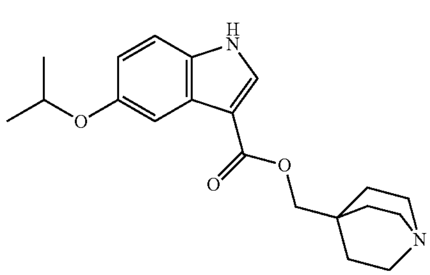 [SMILES: CC(C)Oc1ccc2[nH]cc(C(=O)OCC34CCN(CC3)CC4)c2c1] | quinuclidin-4-ylmethyl 5-isopropoxy-1H-indole-3-carboxylate |

TABLE 3-continued
| Compound No. | Structure | Compound Name |
|---|---|---|
| 8 | 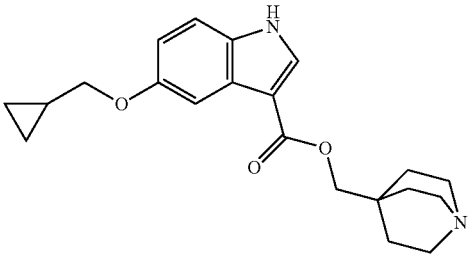 [SMILES: O=C(OCC12CCN(CC1)CC2)c1c[nH]c2ccc(OCC3CC3)cc12] | quinuclidin-4-ylmethyl 5-(cyclopropylmethoxy)-1H-indole-3-carboxylate |
| 9 | 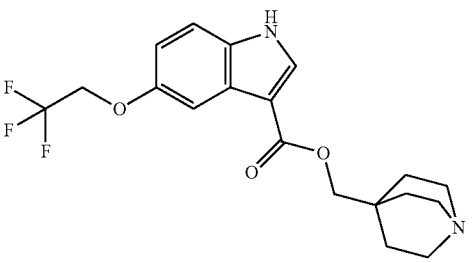 [SMILES: O=C(OCC12CCN(CC1)CC2)c1c[nH]c2ccc(OCC(F)(F)F)cc12] | quinuclidin-4-ylmethyl 5-(2,2,2-trifluoroethoxy)-1H-indole-3-carboxylate |
| 10 | 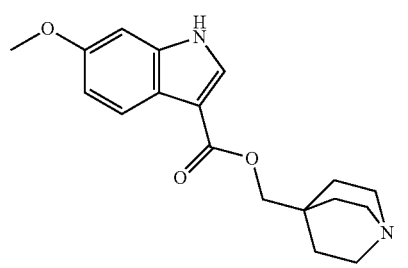 [SMILES: COc1ccc2c(C(=O)OCC34CCN(CC3)CC4)c[nH]c2c1] | quinuclidin-4-ylmethyl 6-methoxy-1H-indole-3-carboxylate |
| 11 | 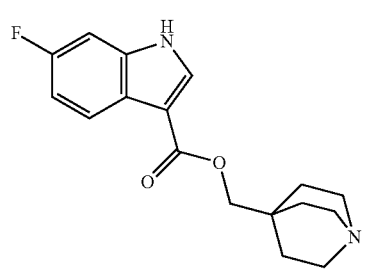 [SMILES: O=C(OCC12CCN(CC1)CC2)c1c[nH]c2cc(F)ccc12] | quinuclidin-4-ylmethyl 6-fluoro-1H-indole-3-carboxylate |
| 12 | 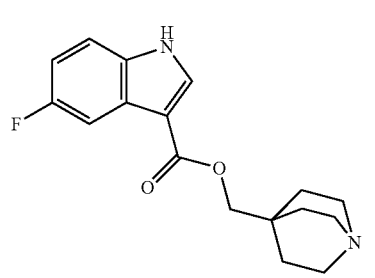 | quinuclidin-4-ylmethyl 5-fluoro-1H-indole-3-carboxylate |

TABLE 3-continued

| Compound No. | Structure | Compound Name |
| --- | --- | --- |
| 13 | 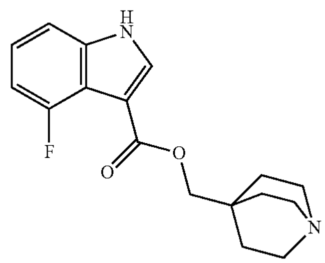 [SMILES: O=C(OCC12CCN(CC1)CC2)c1c[nH]c2cccc(F)c12] | quinuclidin-4-ylmethyl 4-fluoro-1H-indole-3-carboxylate |
| 14 | 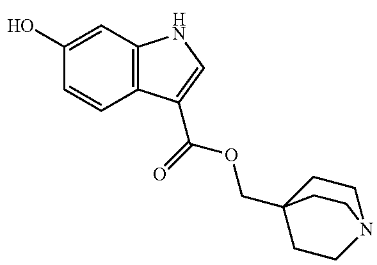 [SMILES: O=C(OCC12CCN(CC1)CC2)c1c[nH]c2cc(O)ccc12] | quinuclidin-4-ylmethyl 6-hydroxy-1H-indole-3-carboxylate |
| 15 | 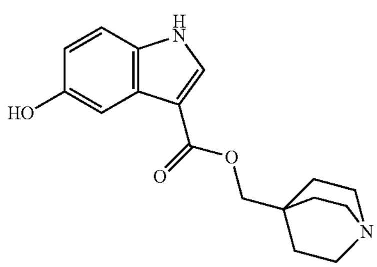 [SMILES: O=C(OCC12CCN(CC1)CC2)c1c[nH]c2ccc(O)cc12] | quinuclidin-4-ylmethyl 5-hydroxy-1H-indole-3-carboxylate |
| 16 | 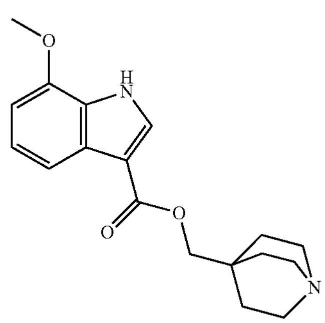 [SMILES: COc1cccc2c(C(=O)OCC34CCN(CC3)CC4)c[nH]c12] | quinuclidin-4-ylmethyl 7-methoxy-1H-indole-3-carboxylate |
| 17 | 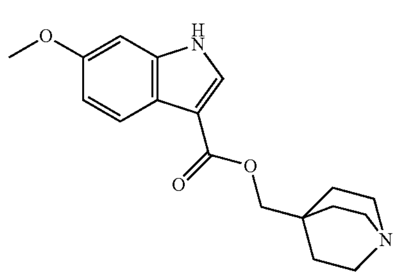 [SMILES: COc1ccc2c(C(=O)OCC34CCN(CC3)CC4)c[nH]c2c1] | quinuclidin-4-ylmethyl 6-methoxy-1H-indole-3-carboxylate |

TABLE 3-continued

| Compound No. | Structure | Compound Name |
|---|---|---|
| 18 | 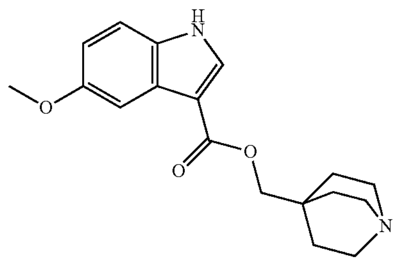 [SMILES: COc1ccc2[nH]cc(C(=O)OCC34CCN(CC3)CC4)c2c1] | quinuclidin-4-ylmethyl 5-methoxy-1H-indole-3-carboxylate |
| 19 | 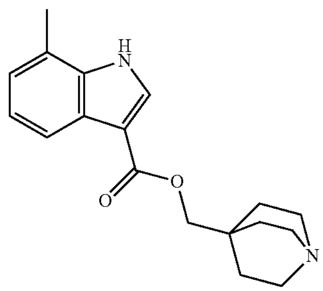 [SMILES: Cc1cccc2c(C(=O)OCC34CCN(CC3)CC4)c[nH]c12] | quinuclidin-4-ylmethyl 7-methyl-1H-indole-3-carboxylate |
| 20 | 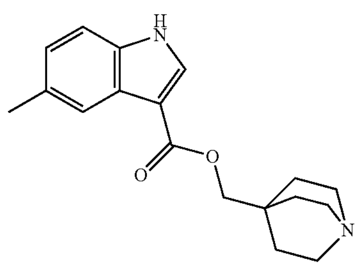 [SMILES: Cc1ccc2[nH]cc(C(=O)OCC34CCN(CC3)CC4)c2c1] | quinuclidin-4-ylmethyl 5-methyl-1H-indole-3-carboxylate |
| 22 | 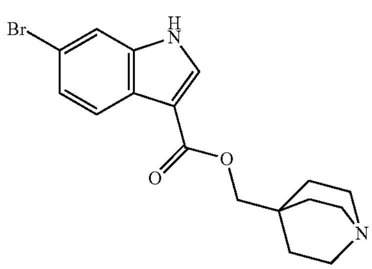 | quinuclidin-4-ylmethyl 6-bromo-1H-indole-3-carboxylate |
| 23 | 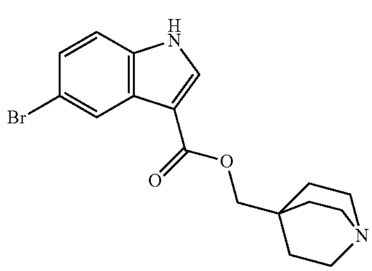 | quinuclidin-4-ylmethyl 5-bromo-1H-indole-3-carboxylate |

TABLE 3-continued

| Compound No. | Structure | Compound Name |
|---|---|---|
| 25 | 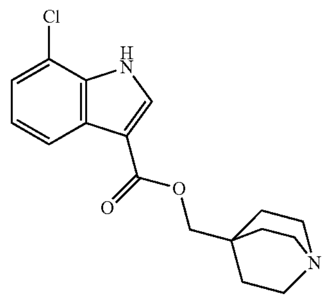 [SMILES: O=C(OCC12CCN(CC1)CC2)c1c[nH]c2c(Cl)cccc12] | quinuclidin-4-ylmethyl 7-chloro-1H-indole-3-carboxylate |
| 26 | 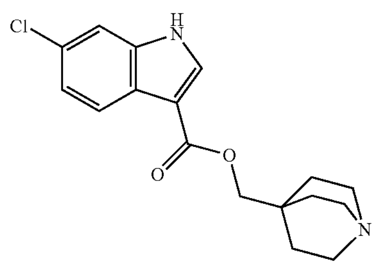 [SMILES: O=C(OCC12CCN(CC1)CC2)c1c[nH]c2cc(Cl)ccc12] | quinuclidin-4-ylmethyl 6-chloro-1H-indole-3-carboxylate |
| 27 | 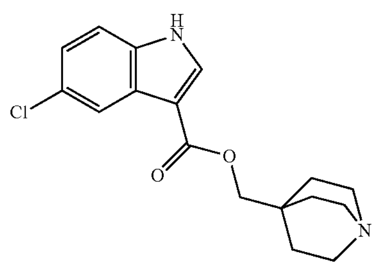 [SMILES: O=C(OCC12CCN(CC1)CC2)c1c[nH]c2ccc(Cl)cc12] | quinuclidin-4-ylmethyl 5-chloro-1H-indole-3-carboxylate |
| 28 | 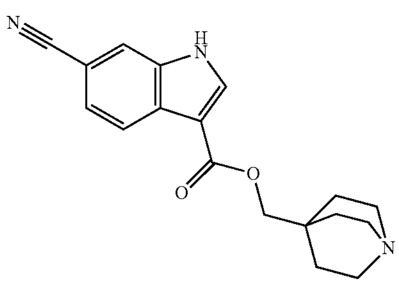 [SMILES: N#Cc1ccc2c(C(=O)OCC34CCN(CC3)CC4)c[nH]c2c1] | quinuclidin-4-ylmethyl 6-cyano-1H-indole-3-carboxylate |
| 29 | 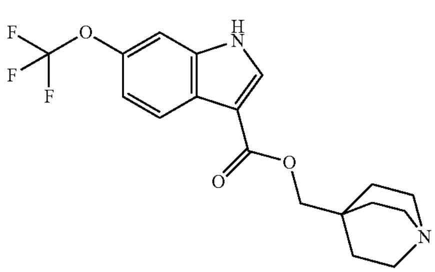 [SMILES: O=C(OCC12CCN(CC1)CC2)c1c[nH]c2cc(OC(F)(F)F)ccc12] | quinuclidin-4-ylmethyl 6-(trifluoromethoxy)-1H-indole-3-carboxylate |

TABLE 3-continued

| Compound No. | Structure | Compound Name |
| --- | --- | --- |
| 30 | 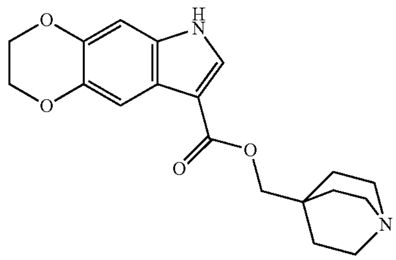 [SMILES: O=C(OCC12CCN(CC1)CC2)c1c[nH]c2cc3c(cc12)OCCO3] | quinuclidin-4-ylmethyl 2,3-dihydro-6H-[1,4]dioxino[2,3-f]indole-8-carboxylate |
| 31 | 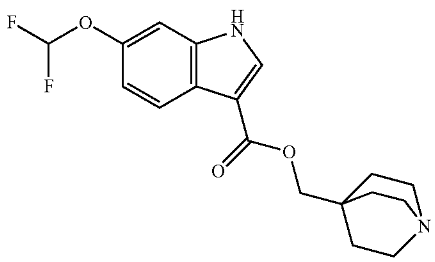 [SMILES: O=C(OCC12CCN(CC1)CC2)c1c[nH]c2cc(OC(F)F)ccc12] | quinuclidin-4-ylmethyl 6-(difluoromethoxy)-1H-indole-3-carboxylate |
| 32 | 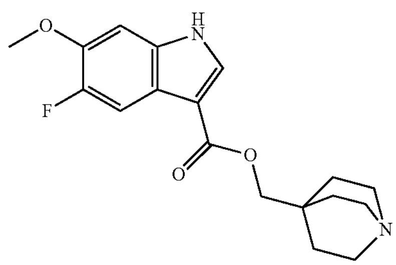 | quinuclidin-4-ylmethyl 5-fluoro-6-methoxy-1H-indole-3-carboxylate |
| 33 | 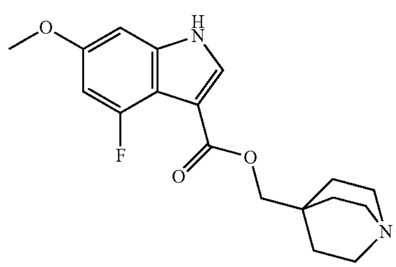 [SMILES: COc1cc(F)c2c(C(=O)OCC34CCN(CC3)CC4)c[nH]c2c1] | quinuclidin-4-ylmethyl 4-fluoro-6-methoxy-1H-indole-3-carboxylate |
| 36 | 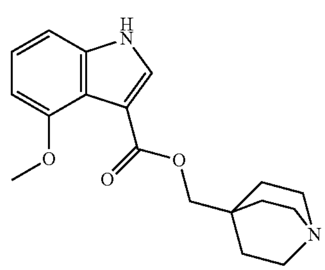 [SMILES: COc1cccc2[nH]cc(C(=O)OCC34CCN(CC3)CC4)c12] | quinuclidin-4-ylmethyl 4-methoxy-1H-indole-3-carboxylate |
| 39 | 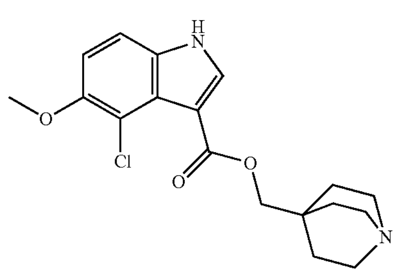 [SMILES: COc1ccc2[nH]cc(C(=O)OCC34CCN(CC3)CC4)c2c1Cl] | quinuclidin-4-ylmethyl 4-chloro-5-methoxy-1H-indole-3-carboxylate |

TABLE 3-continued

| Compound No. | Structure | Compound Name |
|---|---|---|
| 45 | 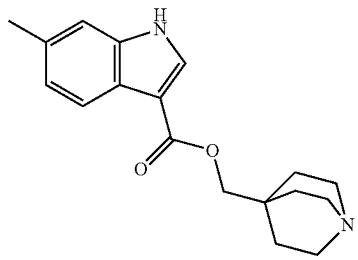 [SMILES: Cc1ccc2c(C(=O)OCC34CCN(CC3)CC4)c[nH]c2c1] | quinuclidin-4-ylmethyl 6-methyl-1H-indole-3-carboxylate |
| 51 | 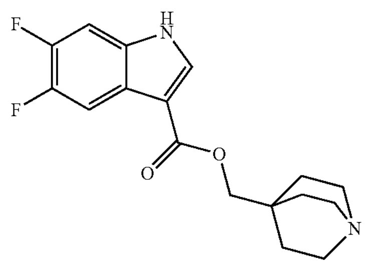 [SMILES: O=C(OCC12CCN(CC1)CC2)c1c[nH]c2cc(F)c(F)cc12] | quinuclidin-4-ylmethyl 5,6-difluoro-1H-indole-3-carboxylate |
| 52 | 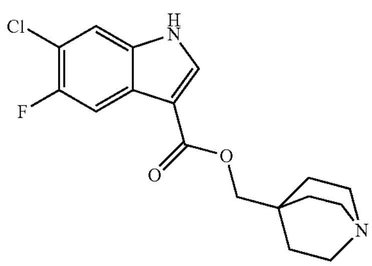 [SMILES: O=C(OCC12CCN(CC1)CC2)c1c[nH]c2cc(Cl)c(F)cc12] | quinuclidin-4-ylmethyl 6-chloro-5-fluoro-1H-indole-3-carboxylate |
| 55 | 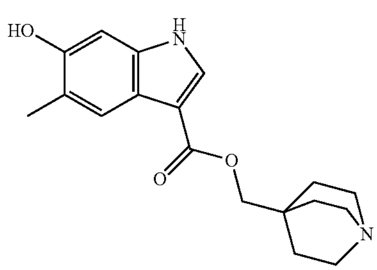 [SMILES: Cc1cc2c(C(=O)OCC34CCN(CC3)CC4)c[nH]c2cc1O] | quinuclidin-4-ylmethyl 6-hydroxy-5-methyl-1H-indole-3-carboxylate |
| 56 | 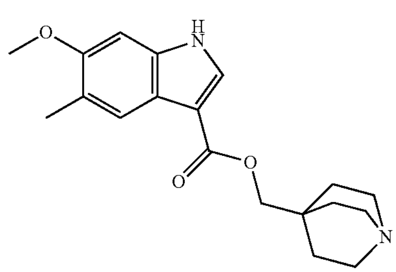 [SMILES: COc1cc2[nH]cc(C(=O)OCC34CCN(CC3)CC4)c2cc1C] | quinuclidin-4-ylmethyl 6-methoxy-5-methyl-1H-indole-3-carboxylate |

TABLE 3-continued

| Compound No. | Structure | Compound Name |
|---|---|---|
| 57 | 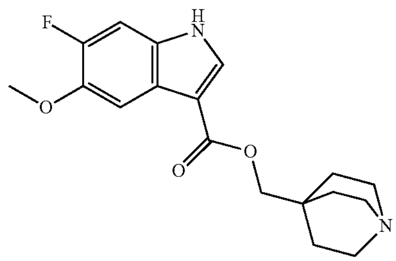 [SMILES: COc1cc2c(C(=O)OCC34CCN(CC3)CC4)c[nH]c2cc1F] | quinuclidin-4-ylmethyl 6-fluoro-5-methoxy-1H-indole-3-carboxylate |
| 58 | 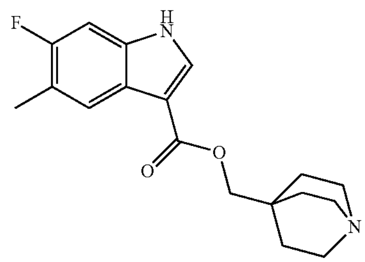 [SMILES: Cc1cc2c(C(=O)OCC34CCN(CC3)CC4)c[nH]c2cc1F] | quinuclidin-4-ylmethyl 6-fluoro-5-methyl-1H-indole-3-carboxylate |
| 59 | 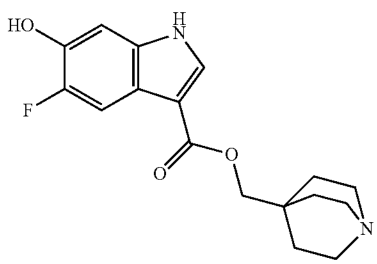 [SMILES: O=C(OCC12CCN(CC1)CC2)c1c[nH]c2cc(O)c(F)cc12] | quinuclidin-4-ylmethyl 5-fluoro-6-hydroxy-1H-indole-3-carboxylate |
| 66 | 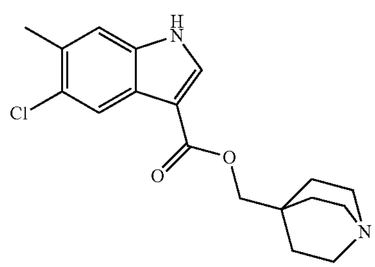 [SMILES: Cc1cc2[nH]cc(C(=O)OCC34CCN(CC3)CC4)c2cc1Cl] | quinuclidin-4-ylmethyl 5-chloro-6-methyl-1H-indole-3-carboxylate |
| 69 | 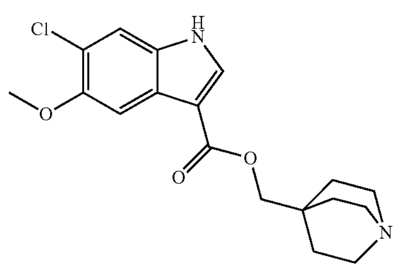 [SMILES: COc1cc2c(C(=O)OCC34CCN(CC3)CC4)c[nH]c2cc1Cl] | quinuclidin-4-ylmethyl 6-chloro-5-methoxy-1H-indole-3-carboxylate |
| 72 | 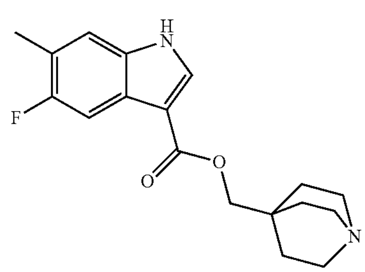 [SMILES: Cc1cc2[nH]cc(C(=O)OCC34CCN(CC3)CC4)c2cc1F] | quinuclidin-4-ylmethyl 5-fluoro-6-methyl-1H-indole-3-carboxylate |

TABLE 3-continued

| Compound No. | Structure | Compound Name |
|---|---|---|
| 73 | 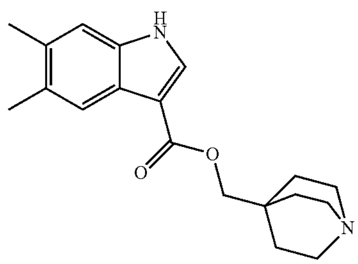 [SMILES: Cc1cc2[nH]cc(C(=O)OCC34CCN(CC3)CC4)c2cc1C] | quinuclidin-4-ylmethyl 5,6-dimethyl-1H-indole-3-carboxylate |
| 76 | 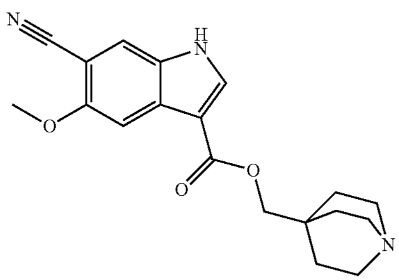 [SMILES: COc1cc2c(C(=O)OCC34CCN(CC3)CC4)c[nH]c2cc1C#N] | quinuclidin-4-ylmethyl 6-cyano-5-methoxy-1H-indole-3-carboxylate |
| 78 | 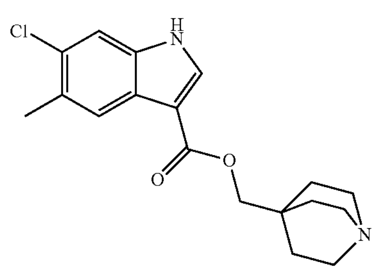 [SMILES: Cc1cc2c(C(=O)OCC34CCN(CC3)CC4)c[nH]c2cc1Cl] | quinuclidin-4-ylmethyl 6-chloro-5-methyl-1H-indole-3-carboxylate |
| 79 | 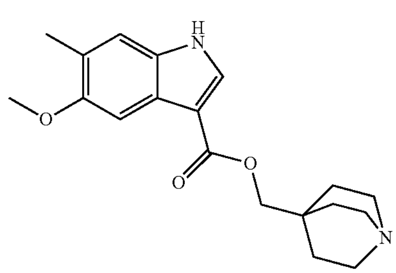 [SMILES: COc1cc2c(C(=O)OCC34CCN(CC3)CC4)c[nH]c2cc1C] | quinuclidin-4-ylmethyl 5-methoxy-6-methyl-1H-indole-3-carboxylate |
| 81 | 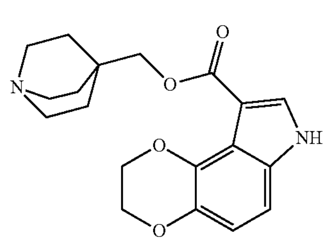 [SMILES: O=C(OCC12CCN(CC1)CC2)c1c[nH]c2ccc3c(c12)OCCO3] | quinuclidin-4-ylmethyl 2,3-dihydro-7H-[1,4]dioxino[2,3-e]indole-9-carboxylate |

TABLE 3-continued

| Compound No. | Structure | Compound Name |
|---|---|---|
| 84 | 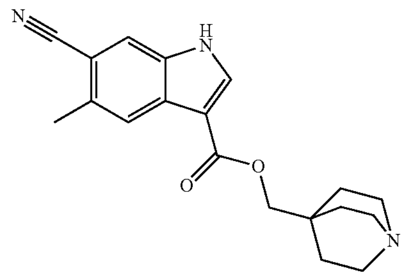 [SMILES: Cc1cc2c(C(=O)OCC34CCN(CC3)CC4)c[nH]c2cc1C#N] | quinuclidin-4-ylmethyl 6-cyano-5-methyl-1H-indole-3-carboxylate |
| 85 | 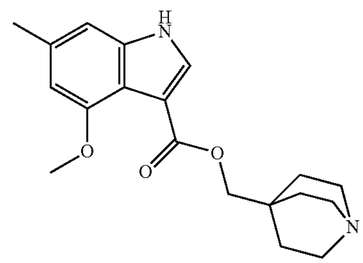 [SMILES: COc1cc(C)cc2[nH]cc(C(=O)OCC34CCN(CC3)CC4)c12] | quinuclidin-4-ylmethyl 4-methoxy-6-methyl-1H-indole-3-carboxylate |
| 86 | 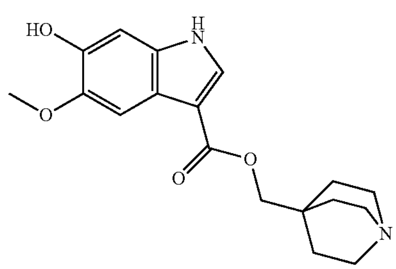 | quinuclidin-4-ylmethyl 6-hydroxy-5-methoxy-1H-indole-3-carboxylate |
| 87 | 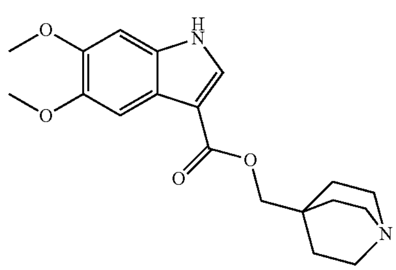 [SMILES: COc1cc2[nH]cc(C(=O)OCC34CCN(CC3)CC4)c2cc1OC] | quinuclidin-4-ylmethyl 5,6-dimethoxy-1H-indole-3-carboxylate |
| 90 | 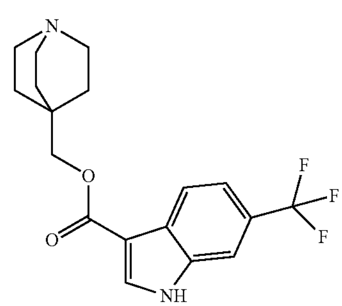 [SMILES: O=C(OCC12CCN(CC1)CC2)c1c[nH]c2cc(C(F)(F)F)ccc12] | quinuclidin-4-ylmethyl 6-(trifluoromethyl)-1H-indole-3-carboxylate |

TABLE 3-continued

| Compound No. | Structure | Compound Name |
|---|---|---|
| 96 | 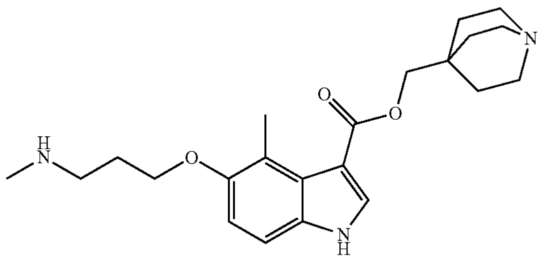 [SMILES: CNCCCOc1ccc2[nH]cc(C(=O)OCC34CCN(CC3)CC4)c2c1C] | quinuclidin-4-ylmethyl 4-methyl-5-(3-(methylamino)propoxy)-1H-indole-3-carboxylate |

Stereochemical, enantiomeric, diastereomeric, conformeric, rotomeric, tautomeric, isotopomeric, solvate, hydrate, polymorphic, crystalline, non-crystalline, salt, and pharmaceutically acceptable salt forms of the compounds above for example, the compounds of Tables 1 and 2, may also be used, provided that they have the α7 NAChR mediation characteristics and/or pharmacokinetic properties as described herein.

Methods of Preparation

The compounds described herein can be readily synthesized by a variety of synthetic methods commonly known in the art. The discussion below is offered to illustrate certain of the diverse methods available for use in assembling the compounds described herein. However, the discussion is not intended to define the scope of the reactions or reaction sequences that are useful in preparing the compounds described herein.

Compounds can generally be synthesized through the coupling of an appropriate indole acid with the borane complex of quinuclidine-4-ylmethanol as shown in Scheme 1 below. The borane complex of the quinuclidine alcohol can be prepared from the nitrile by successive treatment with 6 N HCl and borane-dimethylsulfide. The appropriate indole acid can be transformed into its acid chloride by, for example, reaction of the acid with oxalyl or thionyl chloride. The subsequently formed acid chloride can be coupled with the borane complex of quinuclidin-4-ylmethanol to form the borane complex of the target compound. Alternatively, coupling can be accomplished using common coupling reagents such as N,N'-dicyclohexylcarbodiimide (DCC) or carbonyl diimidazole (CDI). Removal of the borane through acid treatment results in the formation of the salt of the target compound. Alternatively, Raney nickel treatment of the borane complex can be used to generate the free base form of the target compound. In addition, one of skill in the art will recognize that protecting groups may be used to protect certain functional groups (e.g., amino, hydroxyl) from reaction conditions, and that such groups are removed under standard conditions when appropriate.

Scheme 1

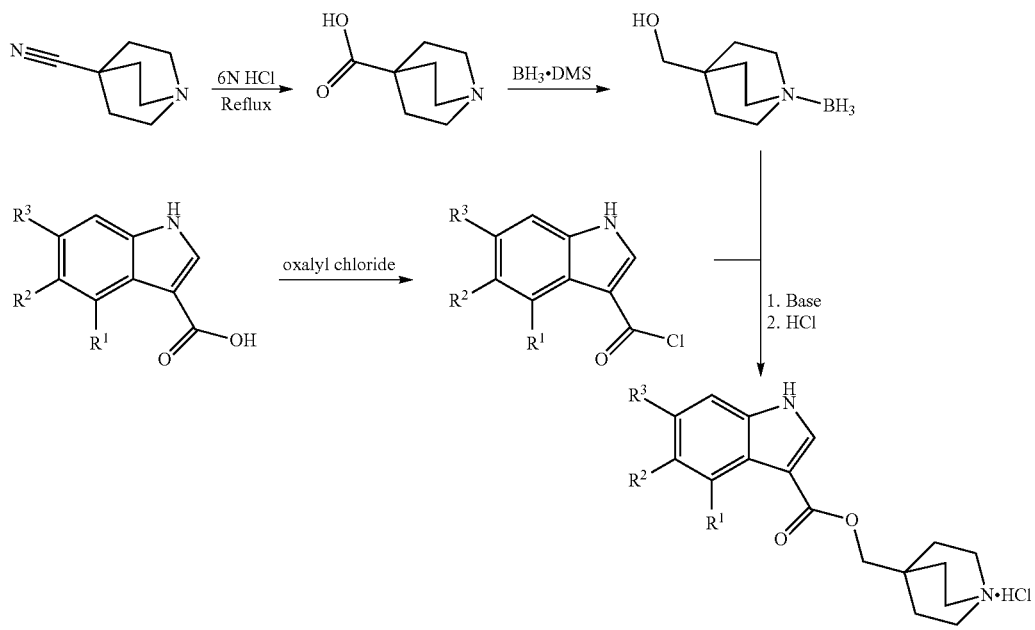

Methods of Use

Development of a drug for use in humans or animals entails optimization of many different variables. Some of these variables include physical properties of a compound allowing, for example, the drug to be dissolved appropriately for oral administration, chemical stability allowing for a drug to be stored appropriately, and metabolic stability allowing for a compound to survive long enough in the body to reach its intended target, among many others. Potency of a compound, or the ability of a compound to elicit a response from its biochemical target, is a primary property that is designed into candidate compounds.

Different biochemical targets require different approaches to the design of potency. For example, development of potency in an enzyme inhibitor, where tight binding to the enzyme active site results in a highly potent molecule, is quite different from development of a full or partial agonist of a ligand-gated ion channel, such as the α7 nicotinic acetylcholine receptor (NAChR). Binding to the α7 NAChR receptor is defined as the ability of a candidate drug to displace compounds such as α-bungarotoxin that are known to bind at the same site as the native agonist ligand acetylcholine. As with α-bungarotoxin, a competitive antagonist of NAChRs, binding of a compound does not directly translate to agonist activity. Likewise, the binding affinity, or degree to which a compound binds to the α7 NAChR, does not correlate to potency of agonist activity. A tight binding compound may act as a potent full or partial agonist, a weak partial agonist, or even an antagonist, actually eliciting the opposite of the desired response by blocking the native ligand activity at the target ion channel. While a compound certainly must bind in order to elicit agonist activity, binding does not correlate with the desired response, even within a structural series. Thus while binding is necessary for agonist activity, the degree of binding does not necessarily predict the degree of agonism potential. Due to this unpredictability, many compounds need to be made in order to determine which possess the appropriate degree of binding and agonism potential. This effort is further complicated when layering in the design and optimization of the other properties needed for discovery of a developable drug candidate (e.g., chemical stability, metabolic stability, solubility, etc.). Likewise, this process of drug development may result in compounds with improved drug properties yet unpredicted loss in agonist potential, despite retaining binding affinity.

The compounds provided herein may exhibit α7 NAChR binding and/or agonism potential. Binding of a compound to α7 NAChR may be measured by any method known in the art including, without limitation, a $[^{125}I]$ α-Bungarotoxin competitive binding assay. Agonism potential of a compound for α7 NAChR may be measured by any method known in the art including, without limitation, electrophysiology screening in *Xenopus laevis* oocytes.

The compounds provided herein may further exhibit desirable pharmacokinetic properties. Desirable pharmacokinetic properties include, without limitation, plasma stability. Plasma stability may be measured by any method known in the art, and may be assessed by measuring, for example, half-life ($T_{1/2}$) or % of the compound remaining after a set period of time (e.g., 2 hours). Compounds with sufficient plasma stability may be more efficacious than drugs with low plasma stability. Furthermore, lower dosages may be required for compounds having a higher plasma stability, which may have beneficial effects such as lower side effects and lower frequency of administration, thereby enhancing the likelihood of an individual's compliance with the dosing regimen and more effective treatment overall.

The compounds and formulations thereof described herein may be capable of modulating (e.g., enhancing) α7-nicotinic acetylcholine receptor (α7 NAChR) activity. In one aspect, is provided a method of reducing α7 NAChR activity, the method comprising contacting an α7-nicotinic acetylcholine receptor with an effective amount of a compound described herein (e.g., a compound of Formula I and/or any compound of Table 1 or Table 2), or a pharmaceutically acceptable salt or solvate thereof. In some variations, the α7-nicotinic acetylcholine receptor is contacted in a cell. In some embodiments, the cell is contacted in vivo. In some embodiments, the cell is contacted in vitro.

α7 NAChR may be contacted in any suitable environment or any suitable sample. For example, the α7 NAChR may be contacted in vitro, within a cell, or within an individual (e.g., a mammal, such as a human). Typically, in vitro solutions are selected such that the components do not substantially interfere with the α7 NAChR (e.g., aqueous solutions). In some embodiments, the in vitro solution includes a biological sample, such as a mammalian sample. Exemplary mammalian samples include plasma or serum samples and tissue samples, such as a brain biopsy. Any appropriate cell or cellular sample may be selected in which to contact the α7 NAChR with the compound. Exemplary cells include human embryonic kidney (HEK293) cells, HeLa cells, Chinese hamster ovary cells, neuroblastoma line M17 cells, and 293 cells.

The compounds provided herein may selectively modulate α7 NAChR. In some embodiments, the compounds selectively modulate α7 NAChR activity over other NAChR receptors (e.g., α4β2 NAChR). In some embodiments, the compounds selectively modulate α7 NAChR activity over hERG activity. In some embodiments, the compounds selectively modulate α7 NAChR activity over 5-HT3 activity.

Compounds and formulations discussed herein may be useful for treatment or prevention of a condition mediated by or characterized by α7 NAChR. Conditions which can be treated or prevented with the compounds and methods provided herein include, but are not limited to schizophrenia, cognitive symptoms of schizophrenia, attention deficit symptoms of schizophrenia, cognitive deficits associated with schizophrenia, Alzheimer's disease, neurodegeneration associated with Alzheimer's disease, pre-senile dementia (mild cognitive impairment), senile dementia, Parkinson's disease, psychosis, cognitive deficits associated with psychosis, attention deficit disorder, attention deficit hyperactivity disorder (ADHD), a mood disorder (e.g., depression, anxiety, and post-traumatic stress disorder), cognitive deficits associated with a mood disorder, an affective disorder, pain, symptoms associated with pain, inflammation, traumatic brain injury, and Huntington's disease.

In some embodiments, the condition to be treated is one or more of schizophrenia, cognitive symptoms of schizophrenia, attention deficit symptoms of schizophrenia, and cognitive Deficits associated with schizophrenia. In some embodiments, the condition to be treated is Alzheimer's disease and/or neurodegeneration associated with Alzheimer's disease. In some embodiments, the condition to be treated is Parkinson's disease.

Formulations

The compounds described herein can be in formulations (including pharmaceutical compositions) by formulation with additives such as excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents), viscosity-increasing agents (e.g., one or more viscosity-increasing agents), and the like, provided that the additional components are pharmaceutically acceptable for the particular condition to be treated. In some embodiments, the formulation may include combinations of two or more of the additional components as described herein (e.g., 2, 3, 4, 5, 6, 7, 8, or more additional components). In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), and "Remington: The Science and Practice of Pharmacy," Lippincott Williams & Wilkins, Philadelphia, 20th edition (2003) and 21st edition (2005), incorporated herein by reference.

The formulations may vary according to the condition to be treated, the amount of compound to be administered, the condition of the individual, and other variables that will readily be apparent to one of ordinary skill in the art in view of the teachings provided herein.

In some embodiments, the pH of the formulations may be from about 3.5 to about 9.5, or from about 4.5 to about 7.5.

Administration and Dosage

The formulations comprising one or more compounds described herein may be administered in conjunction with one or more of the pharmaceutical agents as described herein and as known in the art, including one or more additional pharmaceutical agents to further reduce the occurrence and/or severity of symptoms and/or clinical manifestations thereof, as well as pharmaceutical agents that treat or prevent the underlying conditions, or in conjunction with (e.g., prior to, concurrently with, or after) additional treatment modalities. The formulations as described herein may be administered before, concurrently with, or after the administration of one or more of the pharmaceutical agents described herein. The compounds described herein may also be administered in conjunction with (e.g., prior to, concurrently with, or after) agents to alleviate the symptoms associated with either the condition or the treatment regimen.

In some embodiments, the pharmaceutical agent(s) may be an acetylcholinesterase inhibitor (e.g., donepezil, rivastigmine, or galantamine), an antipsychotic agent (e.g., aripiprazole, ziprasidone, zotepine, risperidone, quetiapine, clozapine, thiothixene, thioridazine, loxapine, haloperidol, fluphenazine, or chlorpromazine), or an NMDA antagonist (e.g., memantine). Combinations of two or more of the foregoing may also be formulated, as can be determined by the skilled artisan in view of the teaching provided herein.

As will be well appreciated by the skilled artisan, for particular conditions, different pharmaceutical agent(s) and/or additional treatment modality(ies) may be indicated.

The formulations and methods described herein may be used alone or in conjunction with (e.g., prior to, concurrently with, or after) other modes of treatments (e.g., adjunctive therapy with additional pharmaceutical agents described herein with reference to pharmaceutical formulations of the claimed compounds or known to the skilled artisan) used to treat or prevent the condition being treated/prevented and/or administration of an additional treatment modality, or combinations of the foregone). For example, in combination with one or more additional pharmaceutical agents as described herein and known to those of skill in the art and/or currently available treatment modalities, including, for example, psychotherapy in the treatment of psychological disorders (e.g., schizophrenia), occupational therapy (e.g., to assist in the prevention or slow the rate of loss of memory, etc.). As used herein, the term "additional treatment modality" refers to treatment/prevention of the conditions described herein without the use of a pharmaceutical agent (e.g., psychotherapy, occupational therapy, etc.). Where combinations of pharmaceutical agent(s) and/or additional treatment modality(ies) are used, they may be, independently, administered prior to, concurrently with, or after administration of one or more of the quinuclidine compound(s) (or formulation(s) thereof) as described herein.

The optimal combination of one or more additional treatment modalities and/or additional pharmaceutical agents in conjunction with administration of the formulations described herein, can be determined by an attending physician or veterinarian based on the individual and taking into consideration the various factors effecting the particular individual, including those described herein.

The formulations described herein will generally be used in an amount effective to achieve the intended result, for example in an amount effective to treat or prevent the particular condition being treated or prevented. The formulations may be administered therapeutically to achieve therapeutic benefit. The term "therapeutic benefit" as used herein refers to eradication or amelioration of the underlying condition being treated and/or eradication or amelioration of one or more of the symptoms associated with the underlying condition such that the individual reports an improvement in feeling or condition, notwithstanding that the individual may still be afflicted with the underlying condition. Therapeutic benefit also includes halting or slowing the progression of the condition, regardless of whether improvement is realized.

The amount of the formulation administered in order to administer an effective amount will depend upon a variety of factors, including, for example, the particular condition being treated, the frequency of administration, the particular formulation being administered, the severity of the condition being treated and the age, weight and general health of the individual, the adverse effects experienced by the individual being treated, etc. Determination of an effective dosage is within the capabilities of those skilled in the art, particularly in view of the teachings provided herein.

Dosages may also be estimated using in vivo animal models.

The compounds provided herein may be administered enterally (e.g., orally or rectally), parenterally (e.g., sublingually, or inhalation (e.g. as mists or sprays)), or topically in dosage unit formulations containing conventional nontoxic pharmaceutically acceptable carriers, adjuvants, and vehicles as desired. For example, suitable modes of administration include oral, subcutaneous, transdermal, transmucosal, iontophoretic, intravenous, intraarterial, intramuscular, intraperitoneal, intranasal (e.g. via nasal mucosa), subdural, rectal, gastrointestinal, and the like, and directly to a specific or affected organ or tissue. For delivery to the central nervous system, spinal and epidural administration, or administration to cerebral ventricles, can be used. Topical administration may also involve the use of transdermal administration such as transdermal patches or iontophoresis devices. The term parenteral as used herein includes subcutaneous injections, intravenous, intramuscular, intrasternal injection, or infusion techniques.

The compounds are mixed with pharmaceutically acceptable carriers, adjuvants, and vehicles appropriate for the desired route of administration. In some embodiments, the route of administration is orally. In other embodiments, formulations are suitable for oral administration. The compounds described for use herein can be administered in solid form, in liquid form, in aerosol form, or in the form of tablets, pills, powder mixtures, capsules, granules, injectables, creams, solutions, suppositories, enemas, colonic irrigations, emulsions, dispersions, food premixes, and in other suitable forms. The compounds can also be administered in liposome formulations. The route of administration may vary according to the condition to be treated. Additional methods of administration are known in the art.

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent, for example, as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols that are solid at room temperature but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such formulations may also comprise adjuvants, such as wetting agents, emulsifying and suspending agents, cyclodextrins, and sweetening, flavoring, and perfuming agents.

The compounds provided herein can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present formulations in liposome form can contain, in addition to a compound provided herein, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq (1976).

The compounds can be administered in prodrug form. Prodrugs are derivatives of the compounds which are relatively inactive, but which convert into the active compound when introduced into the individual in which they are used, by a chemical or biological process in vivo, such as an enzymatic conversion. Suitable prodrug formulations include, but are not limited to, peptide conjugates of the compounds described herein and esters of compounds described herein. Further discussion of suitable prodrugs is provided in H. Bundgaard, Design of Prodrugs, New York: Elsevier, 1985; in R. Silverman, The Organic Chemistry of Drug Design and Drug Action, Boston: Elsevier, 2004; in R. L. Juliano (ed.), Biological Approaches to the Controlled Delivery of Drugs (Annals of the New York Academy of Sciences, v. 507), New York: New York Academy of Sciences, 1987; and in E. B. Roche (ed.), Design of Biopharmaceutical Properties Through Prodrugs and Analogs (Symposium sponsored by Medicinal Chemistry Section, APhA Academy of Pharmaceutical Sciences, November 1976 national meeting, Orlando, Fla.), Washington: The Academy, 1977.

The frequency and duration of administration of the formulation will depend on the condition being treated, the condition of the individual, and the like. The formulation may be administered to the individual one or more times, for example, 2, 3, 4, 5, 10, 15, 20, or more times. The formulation may be administered to the individual, for example, once a day, 2 times a day, 3 times a day, or more than 3 times a day. The formulation may also be administered to the individual, for example, less than once a day, for example, every other day, every third day, every week, or less frequently. The formulation may be administered over a period of days, weeks, or months.

The amount of active ingredient that may be combined with the carrier materials to produce a single dosage form will vary depending upon the host to which the active ingredient is administered and the particular mode of administration. It will be understood, however, that the specific dose level for any particular individual will depend upon a variety of factors including the activity of the specific compound employed, the age, body weight, body area, body mass index (BMI), general health, sex, diet, time of administration, route of administration, rate of excretion, drug combination, and the type, progression, and severity of the particular disease undergoing therapy. The pharmaceutical unit dosage chosen is usually fabricated and administered to provide a defined final concentration of drug in the blood, tissues, organs, or other targeted region of the body. The therapeutically effective amount for a given situation can be readily determined by routine experimentation and is within the skill and judgment of the ordinary clinician.

Examples of dosages which can be used are a therapeutically effective amount within the dosage range of about 0.1 µg/kg to about 300 mg/kg, or within about 1.0 µg/kg to about 40 mg/kg body weight, or within about 1.0 µg/kg to about 20 mg/kg body weight, or within about 1.0 µg/kg to about 10 mg/kg body weight, or within about 10.0 µg/kg to about 10 mg/kg body weight, or within about 100 µg/kg to about 10 mg/kg body weight, or within about 1.0 mg/kg to about 10 mg/kg body weight, or within about 10 mg/kg to about 100 mg/kg body weight, or within about 50 mg/kg to about 150 mg/kg body weight, or within about 100 mg/kg to about 200 mg/kg body weight, or within about 150 mg/kg to about 250 mg/kg body weight, or within about 200 mg/kg to about 300 mg/kg body weight, or within about 250 mg/kg to about 300 mg/kg body weight. Other dosages which can be used are about 0.01 mg/kg body weight, about 0.1 mg/kg body weight, about 1 mg/kg body weight, about 10 mg/kg body weight, about 20 mg/kg body weight, about 30 mg/kg body weight, about 40 mg/kg body weight, about 50 mg/kg body weight, about 75 mg/kg body weight, about 100 mg/kg body weight, about 125 mg/kg body weight, about 150 mg/kg body weight, about 175 mg/kg body weight, about 200 mg/kg body weight, about 225 mg/kg body weight, about 250 mg/kg body weight, about 275 mg/kg body weight, or about 300 mg/kg body weight. Compounds provided herein may be administered in a single daily dose, or the total daily dosage may be administered in divided dosage of two, three or four times daily.

For topical application, the formulation may be administered, for example transdermally at about 1 mg to about 500 mg, about 5 mg to about 100 mg, or about 10 mg to about 50 mg (e.g., over 12, 24, or 48 hours).

For IV administration, the formulation may be administered at a dosage of, for example, from about 0.1 mg per day to about 500 mg per day, from about 0.1 mg per day to about 150 mg per day, from about 1 mg per day to about 50 mg per day, or from about 5 mg per day to about 25 mg per day.

For oral administration, the formulation may be administered at a dosage of, for example, from about 0.5 mg per day to about 2000 mg per day, from about 1 mg per day to about 1500 mg per day, from about 5 mg per day to about 1000 mg per day, from about 10 mg per day to about 500 mg per day, or from about 25 mg per day to about 100 mg per day.

When additional active agents are used in combination with the compounds provided herein, the additional active agents may generally be employed in therapeutic amounts as indicated in the Physicians' Desk Reference (PDR) 53rd Edition (1999), which is incorporated herein by reference, or such therapeutically useful amounts as would be known to one of ordinary skill in the art.

The compounds provided herein and the other therapeutically active agents can be administered at the recommended maximum clinical dosage or at lower doses. Dosage levels of the active compounds in the formulations provided herein may be varied so as to obtain a desired therapeutic response depending on the route of administration, severity of the disease and the response of the individual. When administered in combination with other pharmaceutical agents, the pharmaceutical agents can be formulated as separate formulations that are given at the same time or different times, or the pharmaceutical agents can be given as a single formulation.

Kits

Also provided are articles of manufacture and kits containing materials useful for the treatment or prevention of a condition mediated by the α7 NAChR. The article of manufacture may comprise a container with a label. Suitable containers include, for example, bottles, vials, and test tubes. The containers may be formed from a variety of materials such as glass or plastic. The container may hold a formulation having an active agent which is effective in treating or preventing conditions mediated by α7 NAChR. The active agent in the formulation is one or more of the compounds described herein. The label on the container may indicate that the formulation is used for treating or suppressing conditions mediated by α7 NAChR, and may also indicate directions for either in vivo or in vitro use, such as those described above.

Also provided are kits comprising any one or more of the compounds described herein. In some embodiments, the kit comprises the container described above. In other embodiments, the kit comprises the container described above and a second container comprising a buffer. It may further include other materials desirable from a commercial and user standpoint, including other buffers, diluents, filters, needles, syringes, and package inserts with instructions for performing any methods described herein.

In other aspects, the kits may be used for any of the methods described herein, including, for example, to treat an individual with one or more conditions mediated by or characterized by α7 NAChR, or to suppress one or more conditions mediated by or characterized by α7 NAChR.

In certain embodiments the kits may include a dosage amount of at least one formulation as disclosed herein. Kits may also comprise a means for the delivery of the formulation thereof.

The kits may include other pharmaceutical agents for use in conjunction with the formulation described herein. In some variations, the pharmaceutical agent(s) may be one or more anti-psychotic drugs. These agents may be provided in a separate form, or mixed with the compounds described herein, provided such mixing does not reduce the effectiveness of either the pharmaceutical agent or formulation described herein and is compatible with the route of administration. Similarly, the kits may include additional agents for adjunctive therapy or other agents known to the skilled artisan as effective in the treatment or prevention of the conditions described herein.

The kits may optionally include appropriate instructions for preparation and administration of the formulation, side effects of the formulation, and any other relevant information. The instructions may be in any suitable format, including, but not limited to, printed matter, videotape, computer readable disk, optical disc or directions to internet-based instructions.

In another aspect, kits for treating an individual who suffers from or is susceptible to the conditions described herein are provided, comprising a first container comprising a dosage amount of a composition as disclosed herein, and instructions for use. The container may be any of those known in the art and appropriate for storage and delivery of intravenous formulation. In certain embodiments, the kit further comprises a second container comprising a pharmaceutically acceptable carrier, diluent, adjuvant, etc. for preparation of the formulation to be administered to the individual.

Kits may also be provided that contain sufficient dosages of the compounds described herein (including formulations thereof) to provide effective treatment for an individual for an extended period, such as 1-3 days, 1-5 days, a week, 2 weeks, 3, weeks, 4 weeks, 6 weeks, 8 weeks, 3 months, 4 months, 5 months, 6 months, 7 months, 8 months, 9 months or more.

Kits may also include multiple doses of the formulation and instructions for use and may be packaged in quantities sufficient for storage and use in pharmacies, for example, hospital pharmacies and compounding pharmacies.

The kits may include the composition as described herein packaged in either a unit dosage form or in a multi-use form. The kits may also include multiple units of the unit dose form.

In certain embodiments are provided a formulation described herein in a unit dose form. In other embodiments a formulation may be provided in a multi-dose form (e.g., a blister pack, etc.).

The compositions and methods provided herein are illustrated by the following non-limiting examples.

EXAMPLES

All solvents (reagent grade) were purchased from either Sigma-Aldrich or Fisher Scientific and were used without further purification.

The following abbreviations are used herein:

AcOH: acetic acid
BnCl: benzyl chloride
BOC: tert-butyloxycarbonyl
CDI: carbonyldiimidazole
DCM: dichloromethane
DMAP: 4-dimethylaminopyridine
DMA: dimethylamine
DMF: dimethylformamide
EA: ethyl acetate
Et$_2$O: diethyl ether
EtOAc: ethyl acetate
EtOH: ethanol
MeOH: methanol
NBS: N-bromosuccinamide
NH$_4$Ac: ammonium acetate
NMP: N-methylpyrrolidone
PCC: pyridinium chlorochromate
PE/pet ether: petroleum ether
rt: room temperature
TBAB: tetra-n-butylammonium bromide
tBuOH: tert-butanol
TEA: triethanolamine
TFA: trifluoroacetic acid
TFAA: trifluoroacetic acid anhydride
THF: tetrahydrofuran
TIPS: triisopropylsilyl
TIPSCl: triisopropylsilyl chloride
TLC: thin layer chromatography

Example 1

(Quinuclidin-4-yl)methanol

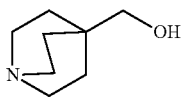

(Quinuclidin-4-yl)carboxylic acid was prepared from 4-cyanoquinuclidine (Oakwood Products) following the procedure of Grob and Renk, *Helv. Chim. Acta*, 37, 1681 (1954). To a stirred suspension of quinuclidine-4-carboxylic acid hydrochloride (100 mg, 0.523 mmol) in 3 mL of anhydrous tetrahydrofuran at 0° C. was added borane methylsulfide complex (42 mg, 0.553 mmol). The mixture was stirred at room temperature for 1 hr and heated to reflux overnight. The reaction was cooled to 0° C. and carefully treated with 1 mL of methanol. The solvent was then removed under reduced pressure to leave the desired alcohol. Yield 36 mg. MS (m/e): 141.

Example 2

Quinuclidin-4-ylmethanol N-borane complex

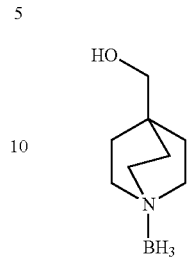

Quinuclidine-4-carbonitrile (4 g, 29.4 mmol) was treated with 30 mL of 6 N aqueous HCl solution and stirred under reflux for 16 hr. The reaction mixture was cooled and evaporated to dryness under reduced pressure. The solid obtained was triturated with 20% ether-hexane to afford the HCl salt of quinuclidine-4-carboxylic acid (5.5 g, quantitative).

To a stirred suspension of quinuclidine-4-carboxylic acid hydrochloride (5.5 g) in 30 mL of dry THF at 0° C. was added borane dimethyl sulfide complex (6.7 g, 3 eq.). The reaction mixture was stirred at room temperature for 1 hr and heated to reflux for 16 hr. It was then quenched with drop-wise addition of methanol (7 mL) at 0° C. The solvent was then removed under reduced pressure, and the crude product obtained was purified by column chromatography (Silica gel, 20% EA:Hexane) to afford the product quinuclidin-4-ylmethanol N-borane complex as a white solid (1.35 g, 30%).

Example 3

5-(difluoromethoxy)-1H-indole-3-carboxylic acid

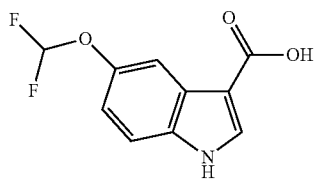 [SMILES: O=C(O)c1c[nH]c2ccc(OC(F)F)cc12]

5-Difluoromethoxyindole (PCT 2007/096395) was formylated at the 3-position using the Vilsmeyer-Haack protocol (phosphorous oxychloride/DMF). The resulting aldehyde was oxidized with sodium chlorite/sodium dihydrogen phosphate in aqueous dioxane. MS (m/e) 227.

Example 4

6-(difluoromethoxy)-1H-indole-3-carboxylic acid

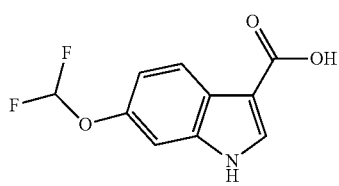 [SMILES: O=C(O)c1c[nH]c2cc(OC(F)F)ccc12]

Prepared as for 5-(difluoromethoxy)-1H-indole-3-carboxylic acid (Example 6) starting with 6-difluoromethoxyindole (WO 97/45408 A1). MS (m/e) 227.

Example 5

5-(2,2,2-trifluoroethoxy)-1H-indole-3-carboxylic acid

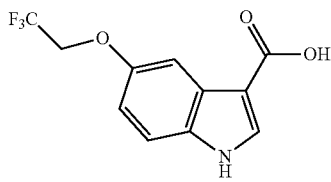 [SMILES: O=C(O)c1c[nH]c2ccc(OCC(F)(F)F)cc12]

5-(2,2,2-trifluoroethoxy)-1H-indole-3-carboxylic acid was prepared following the procedure reported in Synthesis (1980) 727. 3-methyl-4-nitrophenol (Aldrich) was deprotonated with sodium hydride in HMPA, and the resulting phenolate alkylated with 2,2,2-trifluoroethyl tosylate (Aldrich). The resulting trifluoroethyl ether was then converted to the indole using the Batcho-Leimgruber protocol. Formylation and oxidation as described herein gave the title compound as an off-white solid. MS (m/e) 260.

Example 6

5-isopropoxy-1H-indole-3-carboxylic acid

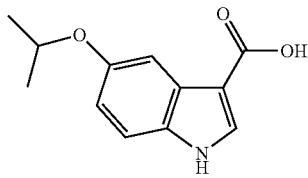 [SMILES: CC(C)Oc1ccc2[nH]cc(C(=O)O)c2c1]

5-isopropoxy-1H-indole-3-carboxylic acid was prepared in a similar manner as described in the examples above. MS (m/e) 219.

Example 7

5-(cyclopropylmethoxy)-1H-indole-3-carboxylic acid

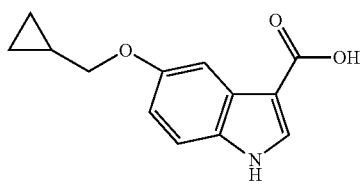 [SMILES: O=C(O)c1c[nH]c2ccc(OCC3CC3)cc12]

5-(cyclopropylmethoxy)-1H-indole-3-carboxylic acid was prepared in a similar manner as described in the examples above. MS (m/e) 231.

Example 8

Table 4 lists indole acids that are commercially available and can be converted into the corresponding target compounds through procedures listed in the section below entitled "Coupling procedures for conversion of indole acids to target compounds."

TABLE 4

| Indole acid | Target Compound No. |
|---|---|
|  | 11 |
|  | 12 |
|  | 13 |
|  | 14 |
|  | 15 |
|  | 16 |
|  | 17 |

TABLE 4-continued

| Indole acid | Target Compound No. |
|---|---|
| 5-methoxy-1H-indole-3-carboxylic acid | 18 |
| 7-methyl-1H-indole-3-carboxylic acid | 19 |
| 5-methyl-1H-indole-3-carboxylic acid | 20 |
| 4-methyl-1H-indole-3-carboxylic acid | 21 |
| 6-bromo-1H-indole-3-carboxylic acid | 22 |
| 5-bromo-1H-indole-3-carboxylic acid | 23 |
| 4-bromo-1H-indole-3-carboxylic acid | 24 |
| 7-chloro-1H-indole-3-carboxylic acid | 25 |
| 6-chloro-1H-indole-3-carboxylic acid | 26 |
| 5-chloro-1H-indole-3-carboxylic acid | 27 |
| 6-cyano-1H-indole-3-carboxylic acid | 28 |

Example 9

4-methoxy-5-methyl-1H-indole-3-carboxylic acid

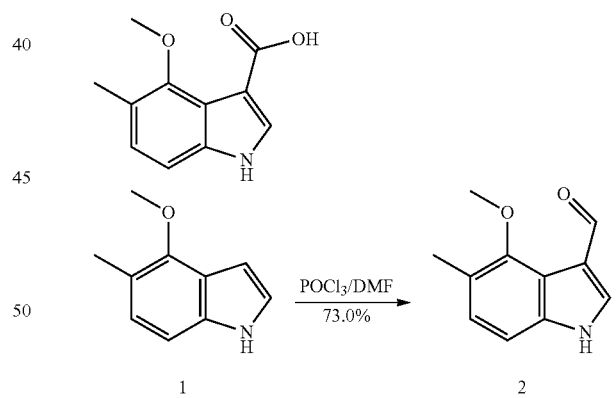

POCl₃ (0.5 mL, 5.22 mmol, 1.2 eq.) was added dropwise to a stirred mixture of DMF (8 mL) and indole 1 (700 mg, 4.35 mmol) at 0° C. The resulting syrup was stirred at 0° C. for 0.5 h then at 40° C. for 1 h, during which an additional 5 mL of DMF was added to keep smooth stirring. The reaction mixture was treated with ice water and brought to pH 11 with sodium hydroxide (2 M) and was refluxed for 30 min. The reaction progress was monitored by TLC (DCM/MeOH=10/1, $R_f$=0.5). On completion, the reaction mixture was cooled and extracted with ethyl acetate. The combined organic extracts were washed with brine, dried over $Na_2SO_4$ and concentrated to give the desired product (600 mg, 3.17 mmol, 73.0%) as a yellow solid.

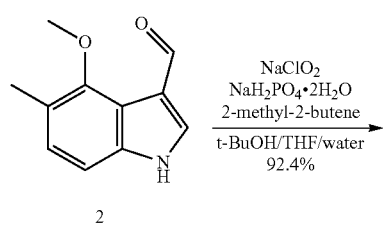

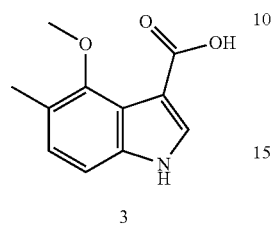

A solution of NaClO$_2$ (1.43 g, 15.85 mmol, 5 eq.) and NaH$_2$PO$_4$·2H$_2$O (5.71 g, 47.55 mmol, 15 eq.) in H$_2$O (6 mL) was added to a solution of aldehyde 2 (600 mg, 3.17 mmol) in t-BuOH (6 mL), THF (6 mL) and 2-methyl-2-butene (5.5 mL) at 0° C. The reaction mixture was stirred at 25° C. for 16 h and layers were separated. The aqueous layer was extracted with ethyl acetate. The combined organic extracts were washed with brine, dried over Na$_2$SO$_4$ and concentrated. The residue was washed with EA/PE (1/10) to give the desired product (520 mg, 2.93 mmol, 92.4%) as a yellow solid.

Example 10

6-cyano-4-methoxy-1H-indole-3-carboxylic acid

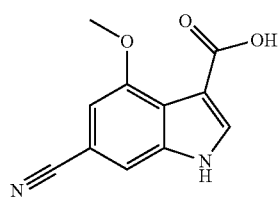 [SMILES: COc1cc(C#N)cc2[nH]cc(C(=O)O)c12]

6-cyano-4-methoxy-1H-indole-3-carboxylic acid was prepared using a procedure similar to Example 9.

Example 11

4-fluoro-6-methoxy-1H-indole-3-carboxylic acid

4-fluoro-6-methoxy-1H-indole-3-carboxylic acid was prepared using a procedure similar to Example 9.

Example 12

6-chloro-5-methyl-1H-indole-3-carboxylic acid

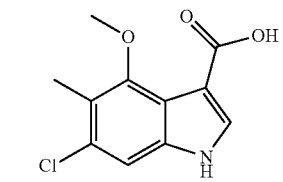

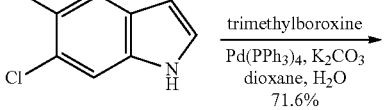

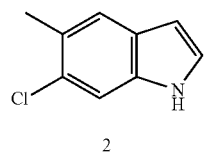

A mixture of compound 1 (1 g, 5.06 mmol), trimethylboroxine (1.25 g, 10 mmol), K$_2$CO$_3$ (1.4 g, 10 mmol) and Pd(PPh$_3$)$_4$ (0.58 g, 0.5 mmol) in H$_2$O (5 mL) and 1,4-dioxane (30 mL) was stirred and heated to 100° C. for 12 h under nitrogen atmosphere. The reaction mixture was cooled and extracted with DCM. The combined organic layers were dried over Na$_2$SO$_4$, filtered and concentrated. The residue was purified by silica gel chromatography (PE/EA=5/1) to give the desired product (0.60 g, 3.62 mmol, 71.6%) as a light yellow solid.

The resulting indole was converted to the corresponding indole acid using a procedure similar to Example 9.

Example 13

6-cyano-5-methoxy-1H-indole-3-carboxylic acid

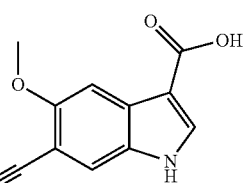

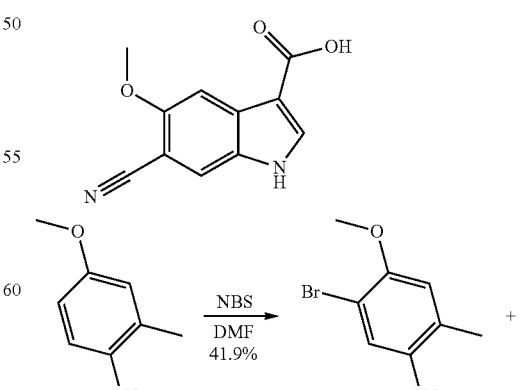

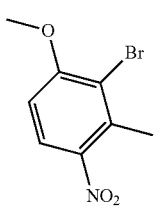

2a

To a solution of nitrobenzene 1 (22.0 g, 131 mmol) in DMF (80 mL) was added NBS (82.0 g, 458 mmol). The reaction mixture was heated to 140° C. for 1.5 h, cooled to rt and quenched with sat. Na₂S₂O₃ and extracted with EA. The combined organic layers were dried over Na₂SO₄, filtered and concentrated. The residue was purified by silica gel chromatography (PE/EA=3/1) to give a mixture of regioisomers (13.5 g, 41.9%) as a yellow solid. The isomers that cannot be separated were used directly for next step.

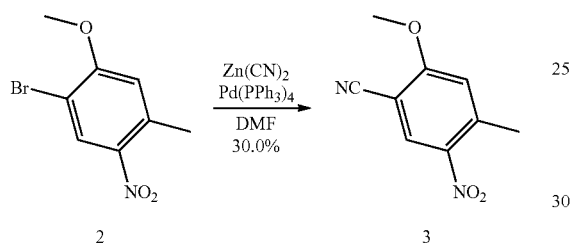

A mixture of compound 2 (12 g, 48.8 mmol), Pd(PPh₃)₄ (0.58 g, 0.50 mmol), zinc cyanide (0.59 g, 50 mmol) and DMF (30 mL) was stirred at 80° C. for 16 h under nitrogen atmosphere. The reaction mixture was cooled, diluted with ether and washed with water. The organic layer was separated, dried over magnesium sulfate, filtered and concentrated. The residue was purified by silica gel chromatography (PE/EA=10/1) to give the desired product (2.8 g, 14.6 mmol, 30.0%) as a yellow solid.

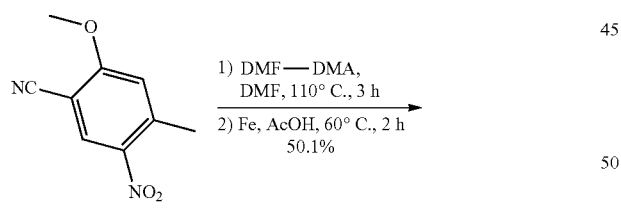

To a mixture of compound 3 (2.8 g, 14.6 mmol) in DMF (20 mL) was added DMF-DMA (9 mL). The reaction mixture turned dark red and was stirred at 110° C. for 3 h and concentrated. The residue was taken up in a mixture of EtOH/acetic acid (80 mL/80 mL) and heated to 80° C. Iron powder (3.3 g, 59.4 mmol) was added in portions. The reaction mixture was refluxed for 2 h, cooled to rt and extracted with EA. The combined organic layers were washed with brine, dried over Na₂SO₄, filtered and concentrated. The residue was purified by silica gel chromatography (PE/EA=2/1) to give the desired product (1.26 g, 7.32 mmol, 50.1%) as a yellow solid.

The resulting indole was converted to the corresponding indole acid using a procedure similar to Example 9.

Example 14

4-bromo-6-fluoro-1H-indole-3-carboxylic acid

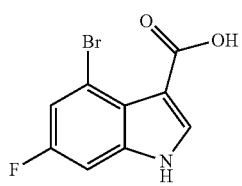 [SMILES: O=C(O)c1c[nH]c2cc(F)cc(Br)c12]

4-bromo-6-fluoro-1H-indole-3-carboxylic acid was prepared using a procedure similar to Example 9.

Example 15

4-bromo-6-chloro-1H-indole-3-carboxylic acid

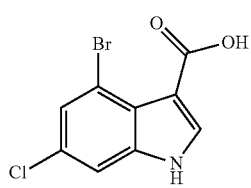 [SMILES: O=C(O)c1c[nH]c2cc(Cl)cc(Br)c12]

4-bromo-6-chloro-1H-indole-3-carboxylic acid was prepared using a procedure similar to Example 9.

Example 16

5-fluoro-4-methyl-1H-indole-3-carboxylic acid

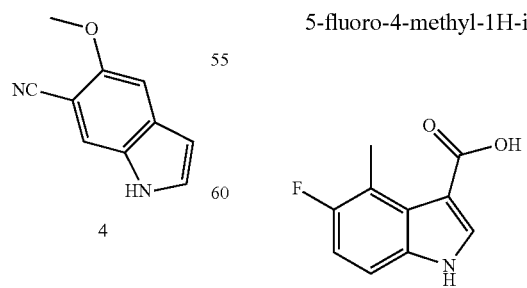

5-fluoro-4-methyl-1H-indole-3-carboxylic acid was prepared using a procedure similar to Example 9.

Example 17

6-fluoro-4-methyl-1H-indole-3-carboxylic acid

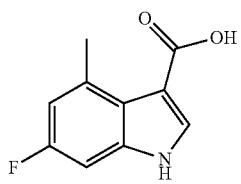

6-fluoro-4-methyl-1H-indole-3-carboxylic acid was prepared using a procedure similar to Example 9.

Example 18

4-bromo-5-methyl-1H-indole-3-carboxylic acid

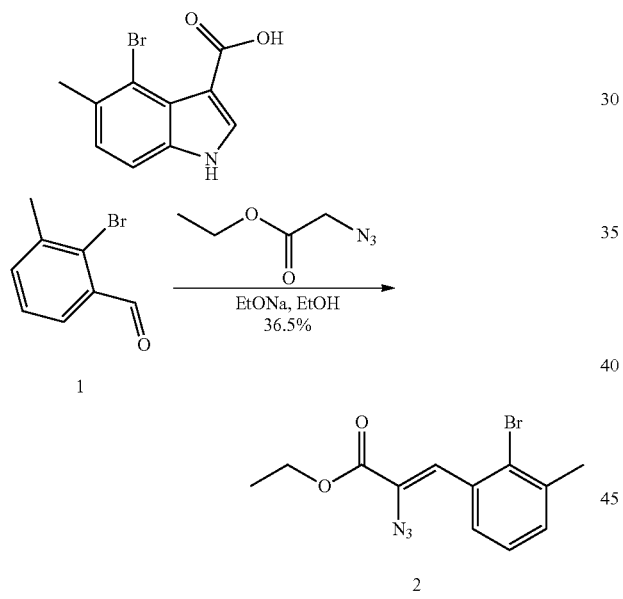

Finely sliced sodium (2.76 g, 120 mmol, 4 eq.) was stirred in ethanol (50 mL) until the sodium was completely consumed. To the mixture of freshly prepared sodium ethoxide was added a mixture of compound 1 (5.94 g, 30.0 mmol) and ethyl azidoacetate (15.5 g, 120 mmol, 4 eq.) in ethanol (50 mL) dropwise over 1.5 h. The inner temperature was kept at −10° C. (Caution: The reaction proceeds vigorously without careful cooling.) After addition, the mixture was stirred at −10° C. for an additional 1.5 h, poured into ice-water, and extracted with petroleum ether (3×200 mL). The combined extracts were washed with brine, dried over $Na_2SO_4$, and concentrated to give the crude product (3.38 g, 11.0 mmol, 36.5%) as a yellow solid. TLC shows a less polar spot than the starting material (TLC, petroleum ether, $R_f$=0.8). The crude product was used directly for the next step without further purification.

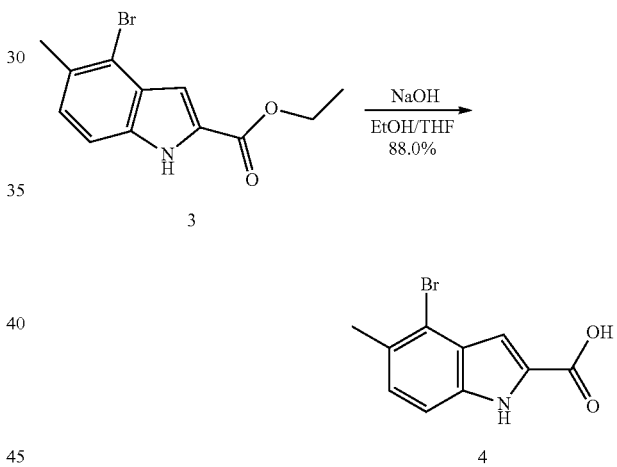

To the refluxing xylene (30 mL) was added azido ester 2 (3.38 g, 11.0 mmol) in xylene (20 mL) dropwise under nitrogen. The solution was refluxed at 140° C. for 1 h and concentrated. The residue was washed with petroleum ether/EtOAc (10/1) to give the desired product (1.88 g, 6.68 mmol, 60.7%) as a yellow solid.

A mixture of carboxylate 3 (2.02 g, 7.20 mmol) in EtOH/THF (10 mL/10 mL) was treated with a solution of aqueous sodium hydroxide (2 M, 25 mL). The reaction mixture was heated at reflux for 30 min. The mixture was acidified with 1M HCl to pH 7, and the suspension was extracted with EtOAc. The combined extracts were washed with water, dried over $Na_2SO_4$, and concentrated to give the desired product (1.60 g, 6.34 mmol, 88.0%) as a white solid.

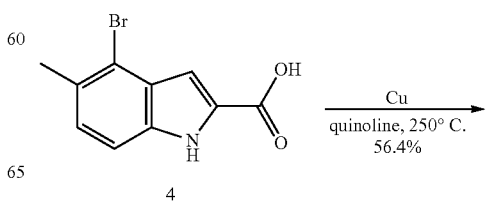

Example 20

6-chloro-5-methoxy-1H-indole-3-carboxylic acid

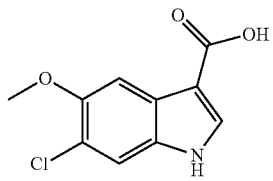

6-chloro-5-methoxy-1H-indole-3-carboxylic acid was prepared using a similar procedure to Example 18.

Example 21

4-bromo-5-fluoro-1H-indole-3-carboxylic acid

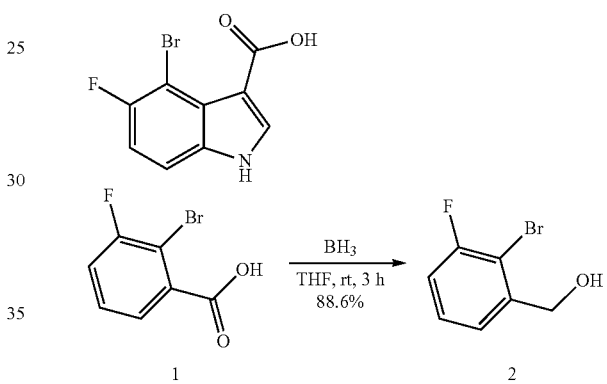

To a solution of compound 1 (10 g, 45.7 mmol) in THF (50 mL) was added BH$_3$ (183 mL, 1.0 M in THF) dropwise at 0° C. over 1 h. The mixture was stirred at rt for an additional 3 h, poured into ice-water, and extracted with EA (3×100 mL). The combined extracts were washed with brine, dried over Na$_2$SO$_4$, and concentrated to give the crude product (8.30 g, 40.5 mmol, 88.6%) as a white solid. The crude product was used directly for the next step without further purification.

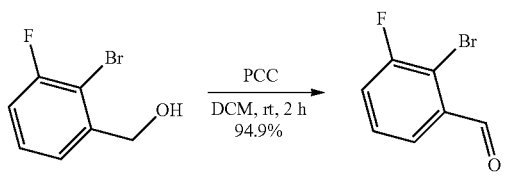

A mixture of 2 (8.30 g, 40.5 mmol), PCC (10.4 g, 48.6 mmol) and DCM (200 mL) was stirred at rt for 2 h. The reaction mixture was concentrated, and the residue was purified by silica gel chromatography (eluting with DCM) to give the desired product (7.80 g, 38.4 mmol, 94.8%) as a white solid.

The resulting aldehyde was converted into the target indole acid using a similar procedure to Example 18.

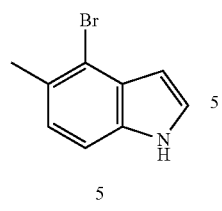

A mixture of carboxylic acid 4 (1.58 g, 6.24 mmol), copper powder (280 mg, 4.37 mmol, 0.7 eq.) and quinoline (10 mL) was refluxed at 250° C. for 2 h under N$_2$. The mixture was then cooled and poured into ice-water. The solution was brought to pH 4 with concentrated HCl and extracted with EtOAc. The combined extracts were washed with HCl (2 M), saturated NaHCO$_3$ and brine, dried over Na$_2$SO$_4$ and concentrated. The residue was purified by silica gel chromatography (petroleum ether/EtOAc=5/1) to give the desired product (736 mg, 3.52 mmol, 56.4%) as a gray solid. To avoid side reactions at high temperature, the reaction was carried out under inert atmosphere.

The resulting indole was converted to the corresponding indole acid using a similar procedure to Example 9.

Example 19

4,5-dimethyl-1H-indole-3-carboxylic acid

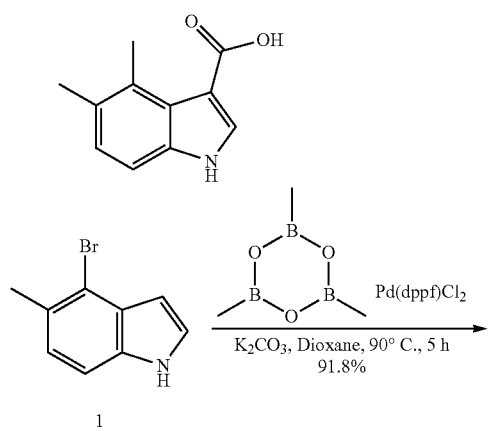

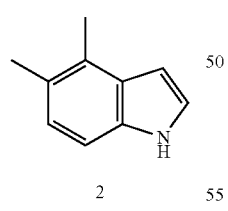

A mixture of bromide 1 (1.0 g, 4.78 mmol), methyl boronic acid (860 mg, 14.3 mmol), Pd(dppf)$_2$Cl$_2$ (194 mg, 0.239 mmol), and K$_2$CO$_3$ (1.32 g, 9.56 mmol) in dioxane (20 mL) was degassed and stirred at 90° C. for 5 h under nitrogen. The reaction mixture was concentrated, and the residue was purified by silica gel chromatography (EtOAc/petroleum ether=1/4) to give the desired product (636 mg, 4.39 mmol, 91.8%) as a white solid.

The resulting indole was converted to the corresponding indole acid using a similar procedure to Example 9.

Example 22

6-cyano-4-methyl-1H-indole-3-carboxylic acid

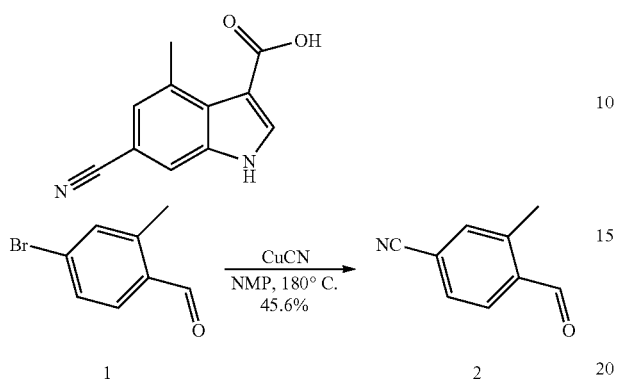

A mixture of compound 1 (10.0 g, 50.0 mmol), CuCN (9.0 g, 100 mmol) and NMP (60 mL) was heated at 180° C. for 6 h. The mixture was cooled to room temperature, diluted with EA, then washed with $H_2O$, brine, dried and concentrated. The residue was purified by silica gel chromatography (petroleum ether/EtOAc=10/1) to give the desired product (3.30 g, 22.8 mmol, 45.6%) as a yellow solid.

The resulting aldehyde was converted into the target indole acid using a similar procedure to Example 18.

Example 23

4,6-dimethyl-1H-indole-3-carboxylic acid

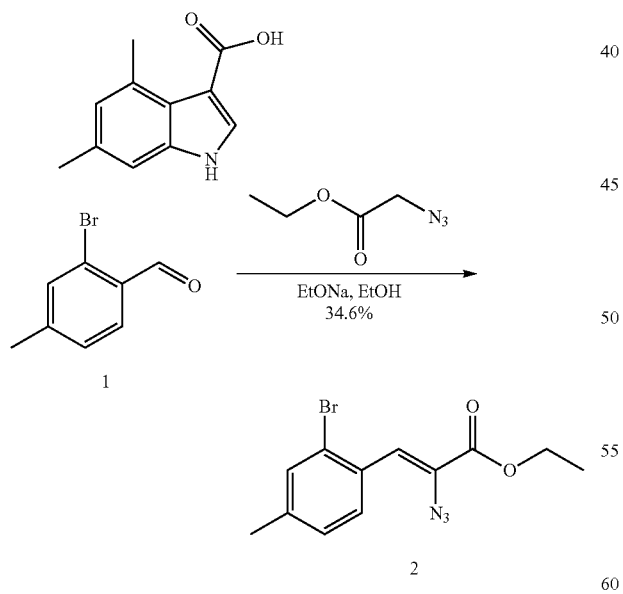

Finely sliced sodium (2.90 g, 125 mmol, 5 eq.) was stirred in ethanol (50 mL) until the sodium was completely consumed. To the mixture of freshly prepared sodium ethoxide was added a mixture of compound 1 (5.00 g, 25.1 mmol) and ethyl azidoacetate (16.2 g, 125 mmol, 5 eq.) in ethanol (50 mL) dropwise over 1.5 h. The inner temperature was kept at −10° C. (Caution: The reaction proceeds vigorously without careful cooling.) After addition, the mixture was stirred at −10° C. for an additional 1.5 h, poured into ice-water, and extracted with petroleum ether (3×200 mL). The combined extracts were washed with brine, dried over $Na_2SO_4$, and concentrated to give the crude product (2.70 g, 8.70 mmol, 34.6%) as a yellow solid. TLC showed a less polar spot than the starting material (TLC, petroleum ether, $R_f$=0.8). The crude product was used directly for the next step without further purification.

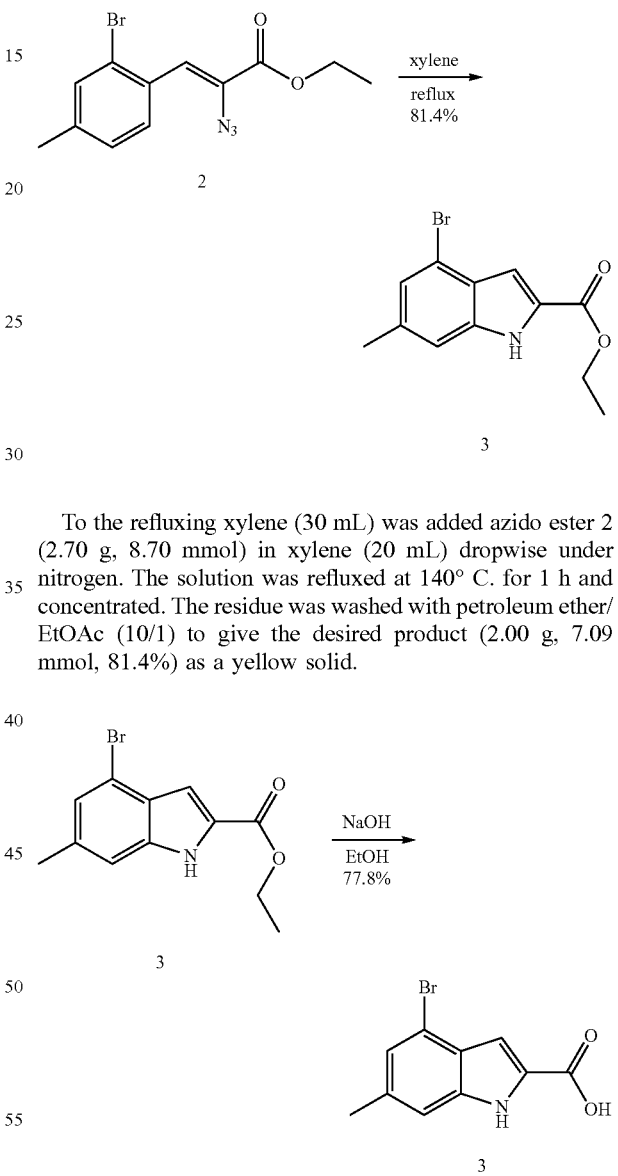

To the refluxing xylene (30 mL) was added azido ester 2 (2.70 g, 8.70 mmol) in xylene (20 mL) dropwise under nitrogen. The solution was refluxed at 140° C. for 1 h and concentrated. The residue was washed with petroleum ether/EtOAc (10/1) to give the desired product (2.00 g, 7.09 mmol, 81.4%) as a yellow solid.

A mixture of carboxylate 3 (2.00 g, 7.09 mmol) in EtOH (10 mL) was treated with a solution of aqueous sodium hydroxide (2 M, 25 mL). The reaction mixture was heated at reflux for 30 min. The mixture was acidified with 1 M HCl to pH 7, and the suspension was extracted with EtOAc. The combined extracts were washed with water, dried over $Na_2SO_4$, and concentrated to give the desired product (1.40 g, 5.51 mmol, 77.8%) as a white solid.

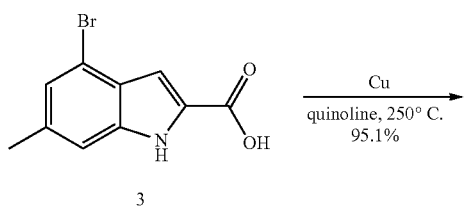

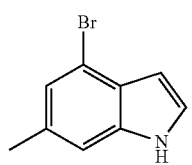

A mixture of carboxylic acid 4 (1.40 g, 5.51 mmol) and copper powder (529 mg, 8.26 mmol, 1.5 eq.) in quinoline (10 mL) was refluxed at 250° C. for 4 h under N₂. The mixture was then cooled and poured into ice-water. The solution was brought to pH 4 with concentrated HCl and extracted with EtOAc. The combined extracts were washed with HCl (2 M), saturated NaHCO₃ and brine, dried over Na₂SO₄ and concentrated. To avoid side reactions at high temperature, the reaction was carried out under inert atmosphere. The residue was purified by silica gel chromatography (petroleum ether/EtOAc=5/1) to give the desired product (1.10 g, 5.24 mmol, 95.1%) as a brown solid.

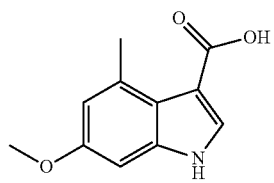

A mixture of indole 5 (690 mg, 3.28 mmol), methylboronic acid (495 mg, 3.94 mmol, 1.2 eq.), Pd(dppf)Cl₂ (180 mg, 0.656 mmol, 0.2 eq.) and Cs₂CO₃ (3.20 g, 9.84 mmol, 3.0 eq.) in dioxane (21 mL) and water (3 mL) was stirred at 110° C. overnight under N₂. The mixture was diluted with water and extracted with EtOAc. The combined extracts were washed with brine, dried over Na₂SO₄ and concentrated. The residue was purified by silica gel chromatography (petroleum ether/EtOAc=5/1) to give the desired product (170 mg, 1.17 mmol, 40.9%) as a white solid.

The resulting indole was converted into the corresponding indole acid using a similar procedure to Example 9.

Example 24

6-methoxy-4-methyl-1H-indole-3-carboxylic acid

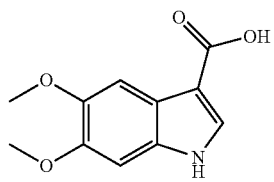 [SMILES: COc1cc2[nH]cc(C(=O)O)c2cc1OC]

6-methoxy-4-methyl-1H-indole-3-carboxylic acid was prepared using a similar procedure to Example 9.

Example 25

5,6-dimethoxy-1H-indole-3-carboxylic acid

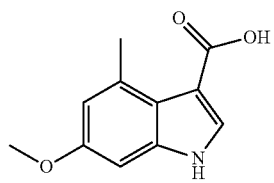

5,6-dimethoxy-1H-indole-3-carboxylic acid was prepared using a similar procedure to Example 9.

The resulting indole acid was protected with a BOC protecting group as follows prior to being carried through the quinuclidine coupling step:

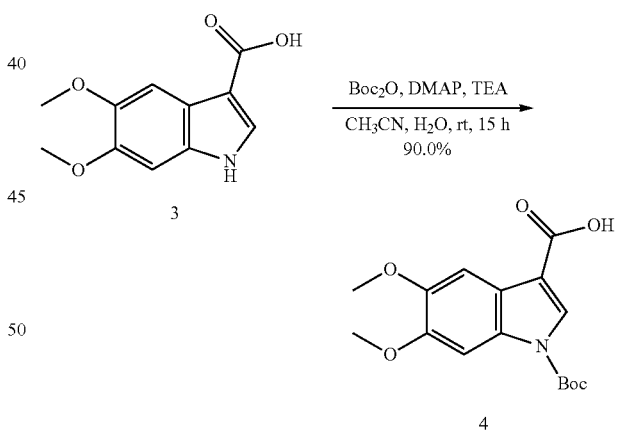

To a solution of compound 3 (442 mg, 2.0 mmol) in CH₃CN (30 mL) and H₂O (5 mL), was added TEA (600 mg, 6.0 mmol, 3 eq.), DMAP (12 mg, 0.1 mmol, 0.05 eq.) and Boc₂O (1.3 g, 6 mmol, 3 eq.). The reaction mixture was stirred at 25° C. for 16 h, and the layers were separated. The aqueous layer was extracted with EtOAc. The combined organic extracts were washed with brine, dried over Na₂SO₄ and concentrated. The residue was purified by silica gel chromatography (1% to 3% MeOH in DCM) to give the desired product (578 mg, 1.80 mmol, 90.0%) as a yellow solid.

Example 26

4-methoxy-6-methyl-1H-indole-3-carboxylic acid

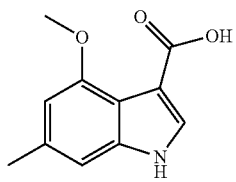

4-methoxy-6-methyl-1H-indole-3-carboxylic acid was prepared using a similar procedure to Example 9.

The resulting indole acid was protected with a BOC protecting group as follows prior to being carried through the quinuclidine coupling step:

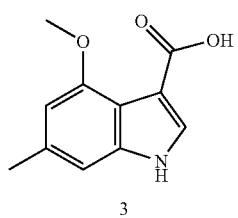

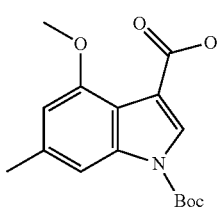

To a solution of compound 3 (410 mg, 2 mmol) in CH₃CN (30 mL) and H₂O (5 mL) was added TEA (600 mg, 6 mmol, 3 eq.), DMAP (12 mg, 0.1 mmol, 0.05 eq.) and Boc₂O (1.3 g, 6 mmol, 3 eq.). The reaction mixture was stirred at 25° C. for 16 h, and the layers were separated. The aqueous layer was extracted with EtOAc. The combined organic extracts were washed with brine, dried over Na₂SO₄ and concentrated. The residue was purified by silica gel chromatography (1% to 3% MeOH in DCM) to give the desired product (488 mg, 1.6 mmol, 80.0%) as a yellow solid.

Example 27

4-chloro-6-methyl-1H-indole-3-carboxylic acid

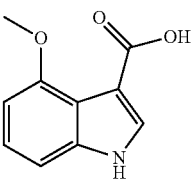

4-chloro-6-methoxy-1H-indole-3-carboxylic acid was prepared using a similar procedure to Example 18.

Example 28

4-methoxy-1H-indole-3-carboxylic acid

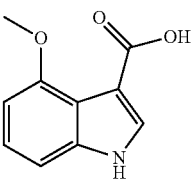

4-methoxy-1H-indole-3-carboxylic acid was prepared using a similar procedure to Example 9.

Example 29

6-(benzyloxy)-1-(tert-butoxycarbonyl)-5-methoxy-1H-indole-3-carboxylic acid

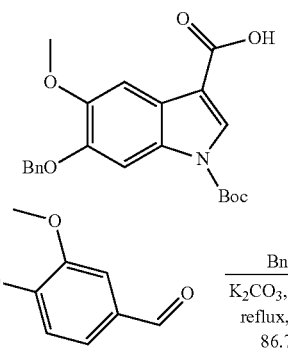

To a mixture of compound 1 (15 g, 100 mmol) in EtOH (100 mL) was added BnCl (12.6 g, 100 mmol) and K₂CO₃ (27.6 g, 200 mmol). The mixture was heated to 80° C. for 15 h and concentrated. The residue was partitioned between water and EtOAc. The organic layer was separated, dried over Na₂SO₄, filtered and concentrated. The residue was purified by silica gel chromatography (petroleum ether/EtOAc=10/1) to give the desired product (21 g, 86.7 mmol, 86.7%) as a white solid.

-continued

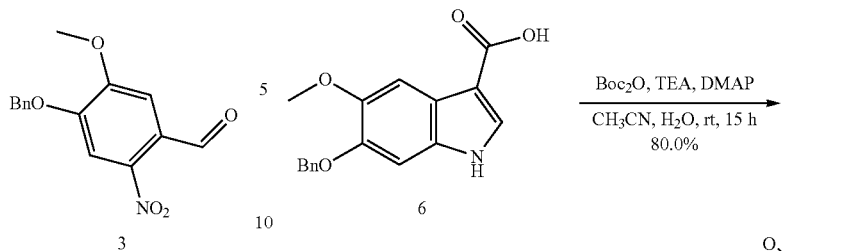

Compound 2 (21 g, 86.7 mmol) was added to HNO₃ (30 mL) at 0° C. and stirred for 1 h. The reaction mixture was poured into the ice water and extracted with EtOAc. The combined extracts were washed with water, dried over MgSO₄, filtered and concentrated. The residue was purified by silica gel chromatography (petroleum ether/EtOAc=10/1) to give the desired product (18.7 g, 65.1 mmol, 75.0%) as a yellow solid.

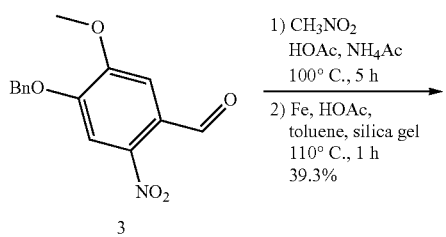

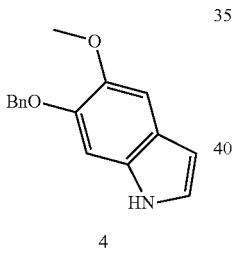

To a mixture of compound 3 (8.60 g, 30 mmol) in acetic acid (80 mL) was added CH₃NO₂ (10 mL) and NH₄Ac (3.66 g, 60 mmol, 2 eq.). The reaction mixture was stirred at 100° C. for 5 h. The reaction mixture was concentrated, and the residue was taken up in a mixture of toluene (80 mL) and acetic acid (10 mL). To the reaction mixture was added iron powder (3.3 g, 60 mmol, 2 eq.) and silica gel (10 g). The reaction mixture was refluxed for 1 h, cooled to rt and filtered. The filtrate was concentrated, and the residue was partitioned between water and EtOAc. The organic layer was separated, dried over Na₂SO4, filtered and concentrated. The residue was purified by silica gel chromatography (petroleum ether/EtOAc=3/1) to give the desired product (3.0 g, 11.8 mmol, 39.3%) as a yellow solid The resulting indole was converted into the corresponding indole acid using a similar procedure to Example 9, which was then BOC protected as follows prior to coupling with the quinuclidine fragment.

To a solution of compound 6 (594 mg, 2.0 mmol) in CH₃CN (30 mL) and H₂O (5 mL) was added TEA (600 mg, 6.0 mmol, 3 eq.), DMAP (12 mg, 0.1 mmol, 0.05 eq.) and Boc₂O (1.3 g, 6 mmol, 3 eq.). The reaction mixture was stirred at 25° C. for 16 h, and the layers were separated. The aqueous layer was extracted with EtOAc. The combined organic extracts were washed with brine, dried over Na₂SO₄ and concentrated. The residue was purified by silica gel chromatography (1% to 3% MeOH in DCM) to give the desired product (635 mg, 1.60 mmol, 80.0%) as a yellow solid.

Example 30

6-cyano-5-methyl-1H-indole-3-carboxylic acid

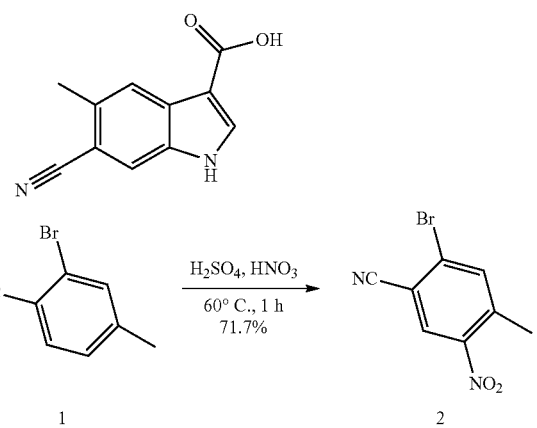

To a solution of compound 1 (19.6 g, 100 mmol) in H₂SO₄ (80 mL) was added HNO₃ (80 mL) at 0° C. The mixture was heated to 60° C. for 1 h, cooled to rt and poured into ice water and extracted with EtOAc. The combined extracts were dried over Na₂SO₄, filtered and concentrated. The residue was purified by silica gel chromatography (petroleum ether/EtOAc=3/1) to give the desired product (17.3 g, 71.7 mmol, 71.7%) as a yellow solid.

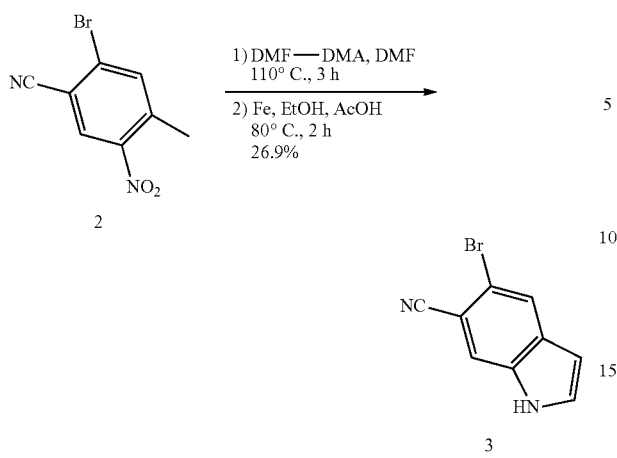

2

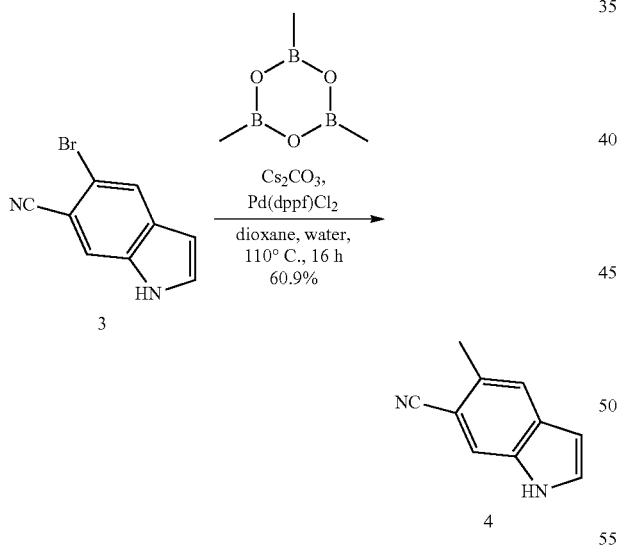

To a solution of compound 2 (3.5 g, 14.6 mmol) in DMF (20 mL) was added DMF-DMA (9 mL). The reaction mixture turned dark red and was heated at 110° C. for 3 h. The reaction mixture was concentrated and the residue was taken up in a mixture of EtOH/acetic acid (80 mL/80 mL). The reaction mixture was heated at 80° C. and iron powder (3.3 g, 59.4 mmol) was added in portions. The reaction mixture was refluxed for 2 h and filtered. The filtrate was concentrated and the residue was partitioned between EtOAc and water. The organic layer was separated, washed with brine, dried over $Na_2SO_4$, filtered and concentrated. The residue was purified by silica gel chromatography (petroleum ether/EtOAc=2/1) to give the desired product (0.87 g, 3.93 mmol, 26.9%) as a yellow solid.

A mixture of compound 3 (3.20 g, 14.6 mmol), trimethylboroxin (1.83 g, 15.0 mmol), Pd(dppf)Cl$_2$ (534 mg, 0.73 mmol), and Cs$_2$CO$_3$ (9.50 g, 30.0 mmol) in dioxane (100 mL) and H$_2$O (5 mL) was heated at 110° C. for 16 h. The reaction mixture was cooled and concentrated. The residue was partitioned between EtOAc and water. The organic layer was separated, washed with brine, dried over Na$_2$SO$_4$, filtered and concentrated. The residue was purified by silica gel chromatography (petroleum ether/EtOAc=2/1) to give the desired product (1.39 g, 8.90 mmol, 60.9%) as a yellow solid.

The resulting indole was converted to the corresponding indole acid using a procedure similar to Example 9.

Example 31

6-fluoro-5-methyl-1H-indole-3-carboxylic acid

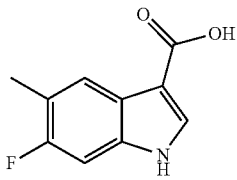

6-fluoro-5-methyl-1H-indole-3-carboxylic acid was prepared using a similar procedure to Example 9.

Example 32

6-fluoro-5-methoxy-1H-indole-3-carboxylic acid

6-fluoro-5-methoxy-1H-indole-3-carboxylic acid was prepared using a similar procedure to Example 18.

Example 33

6-methoxy-5-methyl-1H-indole-3-carboxylic acid

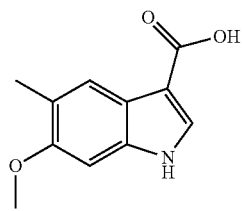

6-methoxy-5-methyl-1H-indole-3-carboxylic acid was prepared using a similar procedure to Example 18.

Example 34

6-chloro-4-methyl-1H-indole-3-carboxylic acid

6-chloro-4-methyl-1H-indole-3-carboxylic acid was prepared using a similar procedure to Example 18.

Example 35

4-bromo-6-methoxy-1H-indole-3-carboxylic acid

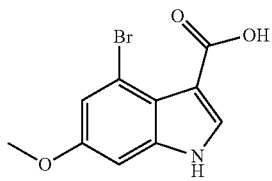

4-bromo-6-methoxy-1H-indole-3-carboxylic acid was prepared using a similar procedure to Example 18.

Example 36

4-bromo-5-methoxy-1H-indole-3-carboxylic acid

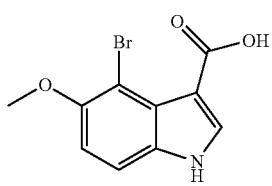

4-bromo-5-methoxy-1H-indole-3-carboxylic acid was prepared using a similar procedure to Example 18.

Example 37

5-methoxy-4-methyl-1H-indole-3-carboxylic acid

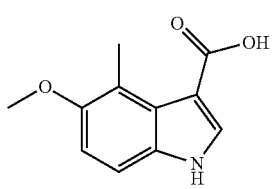

5-methoxy-4-methyl-1H-indole-3-carboxylic acid was prepared using a similar procedure to Example 9.

Example 38

4-chloro-1H-indole-3-carboxylic acid

4-chloro-1H-indole-3-carboxylic acid was prepared using a similar procedure to Example 9.

Example 39

4,5-dimethoxy-1H-indole-3-carboxylic acid

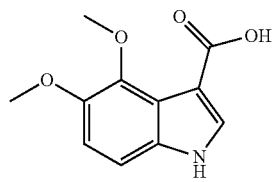 [SMILES: COc1ccc2[nH]cc(C(=O)O)c2c1OC]

4,5-dimethoxy-1H-indole-3-carboxylic acid was prepared using a similar procedure to Example 18.

Example 40

4-chloro-5-methoxy-1H-indole-3-carboxylic acid

4-chloro-5-methoxy-1H-indole-3-carboxylic acid was prepared using a similar procedure to Example 18.

Example 41

4-bromo-6-methyl-1H-indole-3-carboxylic acid

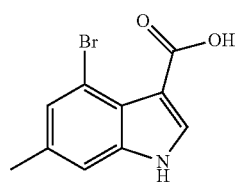

4-bromo-6-methyl-1H-indole-3-carboxylic acid was prepared using a similar procedure to Example 18.

Example 42

2,3-dihydro-7H-[1,4]dioxino[2,3-e]indole-9-carboxylic acid

-continued

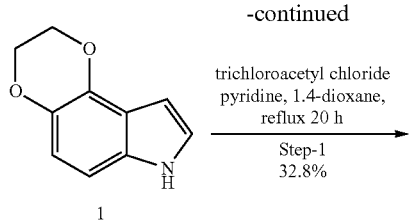

trichloroacetyl chloride
pyridine, 1.4-dioxane,
reflux 20 h
──────────────→
Step-1
32.8%

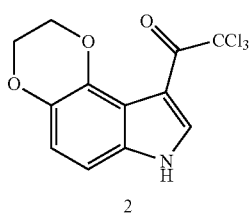

To a stirred solution of pyridine (0.28 mL, 3.5 mmol) in dry 1,4-dioxane (20.0 mL) was added trichloroacetyl chloride (0.39 mL, 3.5 mmol). The reaction mixture was stirred for 15 min. A solution of compound 1 (0.500 g, 2.85 mmol) in 1,4-dioxane (10.0 mL) was added to the above mixture and heated at reflux for 20 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The $R_f$ values of the starting material and product were 0.3 and 0.2, respectively. The reaction mixture was concentrated, quenched with cold-water and extracted with ethyl acetate. The organic layer was dried over $Na_2SO_4$ and filtered, and the filtrate was concentrated to afford crude compound 2. The crude product was purified by column chromatography using 100-200 silica gel eluted on 20% EtOAc/pet ether to afford compound 2 as a yellow solid. TLC system: 30% EtOAc in Petroleum ether. Yield 0.300 g (32.8%).

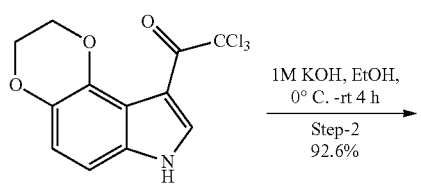

1M KOH, EtOH,
0° C. -rt 4 h
──────────────→
Step-2
92.6%

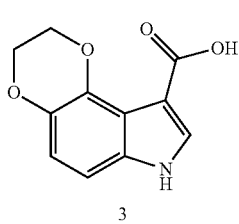

To an ice-cold stirred solution of compound 2 (0.300 g, 0.935 mmol) in EtOH (5.70 mL) was added 1M aqueous KOH (4.60 mL). The reaction mixture was stirred at rt for 4 h. The reaction progress was monitored by acidifying an aliquot of the reaction mixture with 2 N aqueous HCl solution and extraction with EtOAc. The organic layer was spotted over an analytical silica gel TLC plate and visualized using 254 nm UV light. The reaction progressed to completion with the formation of one polar spot and one non polar spot. The $R_f$ values of the starting material and product were 0.4 and 0.2, respectively. The reaction mixture was diluted with water and extracted with diethyl ether to remove impurities. The aqueous layer was cooled to 0° C., and the reaction mixture was acidified with 2 N aqueous HCl to pH~2 and extracted with EtOAc. The organic layer was dried over anhydrous $Na_2SO_4$, filtered and concentrated under reduced pressure to afford crude compound (bath temperature 30° C.). The crude compound was triturated with n-pentane to afford compound 3 as a brown solid. TLC system: 40% EtOAc in petroleum ether. Yield 0.190 g (92.6%).

Example 43

4-(trifluoromethyl)-1H-indole-3-carboxylic acid

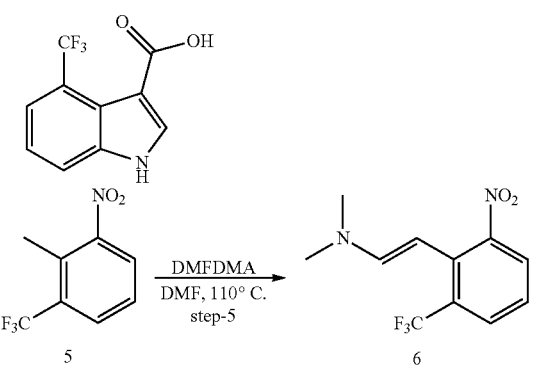

To a stirred suspension of compound 5 (5.000 g, 24.43 mmol) in DMF (30.0 mL), DMF-DMA (18.0 mL) was added at rt. The reaction mixture was then refluxed for 16 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The $R_f$ values of the starting material and product were 0.6 and 0.4, respectively. The reaction mixture was diluted with cold water and extracted with EtOAc. The organic layer was dried over anhydrous $Na_2SO_4$, filtered and concentrated under reduced pressure to afford crude compound 6 as a dark brown liquid. The crude compound was directly used for the next step. TLC system: 10% EtOAc in petroleum ether. Yield 6.300 g (crude).

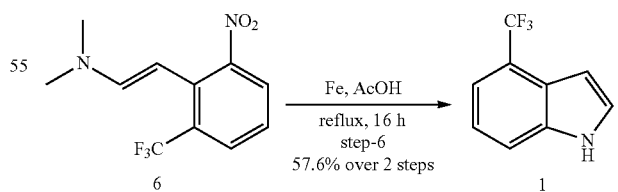

To a stirred suspension of compound 6 (6.300 g, 24.21 mmol) in AcOH (150.0 mL) was added Fe powder (4.30 g, 76.9 mmol). The reaction mixture was refluxed for 16 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a non-polar spot. The $R_f$ values of the starting material and product were 0.4 and 0.6, respectively. The reaction mixture was diluted with cold water and extracted with EtOAc. The organic layer was washed with sat. aq. $K_2CO_3$, followed by water and brine solution, dried over anhydrous $Na_2SO_4$, filtered and concentrated under reduced pressure to afford crude compound 1. The crude compound was purified by flash column using 230-400 mesh silica gel and eluted with 10-15% EtOAc-hexane to afford compound 1 as a light blue liquid. TLC system: 10% EtOAc in petroleum ether. Yield: 2.60 g (57.6% over 2 steps).

Compound 1 was converted into the corresponding target indole acid using a procedure similar to Example 42.

Example 44

5-fluoro-6-methyl-1H-indole-3-carboxylic acid

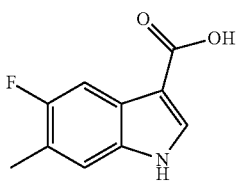

5-fluoro-6-methyl-1H-indole-3-carboxylic acid was prepared using a similar procedure to Example 42.

Example 45

5,6-dimethyl-1H-indole-3-carboxylic acid

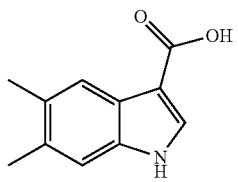

5,6-dimethyl-1H-indole-3-carboxylic acid was prepared using a similar procedure to Example 42.

Example 46

4,6-dichloro-1H-indole-3-carboxylic acid

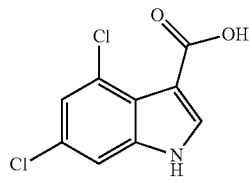 [SMILES: O=C(O)c1c[nH]c2cc(Cl)cc(Cl)c12]

4,6-dichloro-1H-indole-3-carboxylic acid was prepared using a similar procedure to Example 42.

Example 47

4-cyclopropyl-1H-indole-3-carboxylic acid

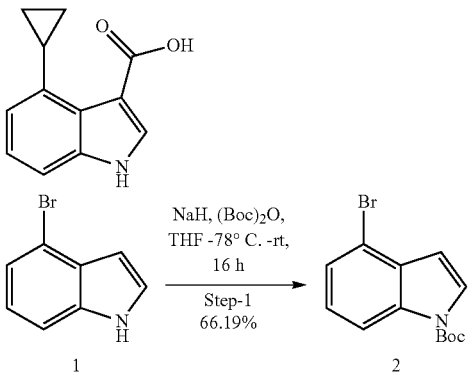

To a suspension of 60% NaH (0.449 g, 11.2 mmol) in dry THF (20.0 mL) was added a solution of compound 1 (2.000 g, 10.20 mmol) in THF (20.0 mL) at −78° C. The reaction mixture was stirred for 1 h. A solution of ditertiary butyl dicarbonate (2.58 mL, 11.2 mmol) in THF (20.0 mL) was added to the above solution drop-wise at −78° C. and stirred at rt for 16 h The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a non-polar spot. The $R_f$ values of the starting material and product were 0.3 and 0.5, respectively. The reaction mixture was poured into ice water (75.0 mL) and extracted with EtOAc (2×100.0 mL). The organic layer was dried over anhydrous $Na_2SO_4$, filtered and concentrated under reduced pressure to afford crude compound 2. The crude compound was purified by flash column using 230-400 mesh silica gel and eluted with 8% EtOAc in petroleum ether to afford compound 2 as a brown liquid. TLC system: 5% EtOAc in petroleum ether. Yield 2.000 g (66.19%).

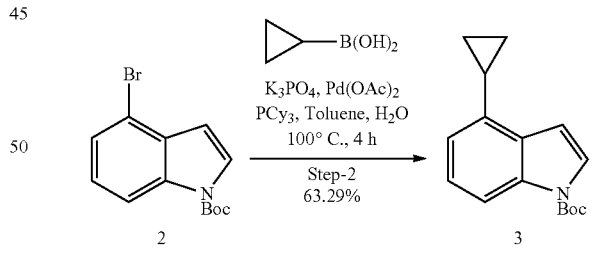

In a degassed suspension of compound 2 (2.000 g, 6.753 mmol), cyclopropylboronic acid (0.754 g, 8.78 mmol), $K_3PO_4$ (5.017 g, 23.64 mmol) and tricyclohexyl phosphine (0.189 g, 0.675 mmol) in toluene (60.0 mL) and water (2.0 mL) was added palladium (II) acetate (0.076 g, 0.34 mmol). The reaction mixture was heated at 100° C. for 4 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The $R_f$ values of the starting material and product were 0.3 and 0.2, respectively. The reaction mixture was allowed to cool to rt and filtered through a pad of celite, and the filtrate was concentrated under reduced pressure to afford crude compound. The crude compound was purified by flash column using 230-400 mesh silica gel and eluted with 10% EtOAc in petroleum ether to afford compound 2 as a brown liquid. TLC system: 5% EtOAc in petroleum ether. Yield 1.100 g (63.29%).

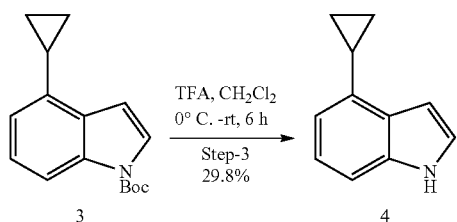 [SMILES: CC(C)(C)OC(=O)n1ccc2c(C3CC3)cccc21 ; c1cc(C2CC2)c2cc[nH]c2c1]

To an ice cold stirred solution of compound 3 (1.100 g, 4.275 mmol) in CH$_2$Cl$_2$ (20.0 mL) was added TFA (2.0 mL). The reaction was stirred at rt for 6 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The R$_f$ values of the starting material and product were 0.5 and 0.2, respectively. The reaction mixture was poured into saturated aqueous NaHCO$_3$ (50.0 mL) and extracted with EtOAc (2×75.0 mL). The organic layer was dried over anhydrous Na$_2$SO$_4$, filtered and concentrated under reduced pressure to afford crude compound 4. The crude compound was purified by flash column using 230-400 mesh silica gel and eluted with 12% EtOAc in petroleum ether to afford compound 4 as a brown liquid. TLC system: 10% EtOAc in petroleum ether. Yield 0.200 g (29.8%).

Compound 4 was converted into the target indole acid using a similar procedure to Example 42.

Example 48

5-fluoro-6-hydroxy-1H-indole-3-carboxylic acid

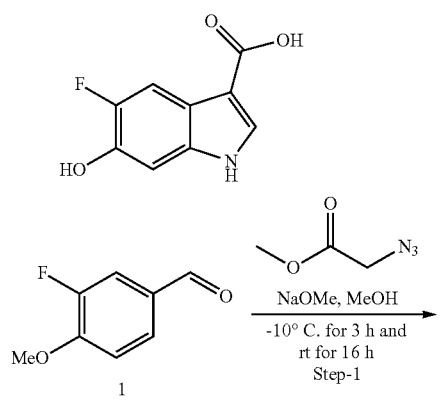

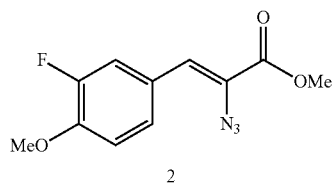

To a stirred solution of compound 1 (25.000 g, 162.19 mmol) and methyl-2-azidoacetate (63.17 mL, 648.8 mmol) in dry MeOH (350.0 mL) at −10° C., was added a solution of NaOMe (35.046 g, 648.76 mmol) in MeOH (400.0 mL). The reaction mixture was stirred at the same temperature for 3 h and then rt for 16 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a non-polar spot. The R$_f$ values of the starting material and product were 0.3 and 0.4, respectively. The reaction mixture was poured into saturated aqueous NH$_4$Cl solution (150.0 mL) and extracted with Et$_2$O (2×500.0 mL). The organic layer was dried over anhydrous Na$_2$SO$_4$, filtered and concentrated under reduced pressure to afford crude compound 2 as a brown liquid. The crude compound was directly used in the next step without purification. TLC system: 30% EtOAc in petroleum ether. Yield 25.000 g (crude).

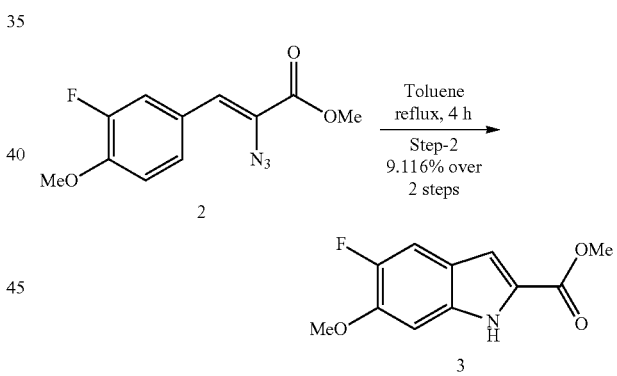

A solution of compound 2 (25.000 g, 99.518 mmol) in toluene (500.0 mL) was heated at reflux temperature for 4 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The R$_f$ values of the starting material and product were 0.4 and 0.2, respectively. The reaction mixture was concentrated under reduced pressure to afford crude compound 3. The crude compound was purified by flash column using 230-400 mesh silica gel and eluted with 15% EtOAc in petroleum ether to afford compound 3 as a pale yellow solid. TLC system: 30% EtOAc acetate in pet ether. Yield 3.300 g (9.116%, over 2 steps).

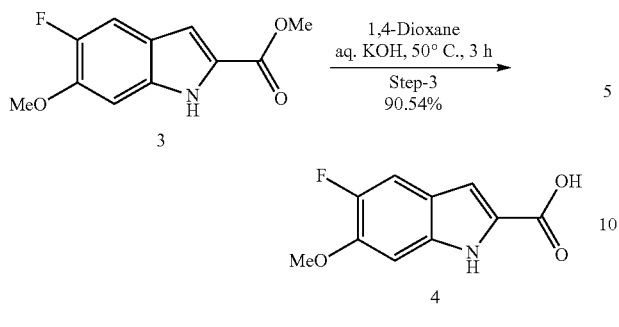

To a stirred solution of compound 3 (3.300 g, 14.78 mmol) in 1,4-dioxane (50.0 mL) was added KOH (3.318 g, 59.13 mmol) in water (5 mL). The reaction mixture was heated at 50° C. for 3 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The $R_f$ values of the starting material and product were 0.5 and 0.2, respectively. The reaction mixture was allowed to cool to rt, acidified with aqueous 2N HCl (50.0 mL) and extracted with EtOAc (2×150.0 mL). The organic layer was dried over $Na_2SO_4$, filtered and concentrated under reduced pressure to afford crude compound 4. The crude compound was triturated with n-pentane to afford compound 4 as a brown solid. TLC system: 50% EtOAc in pet ether. Yield 2.800 g (90.54%).

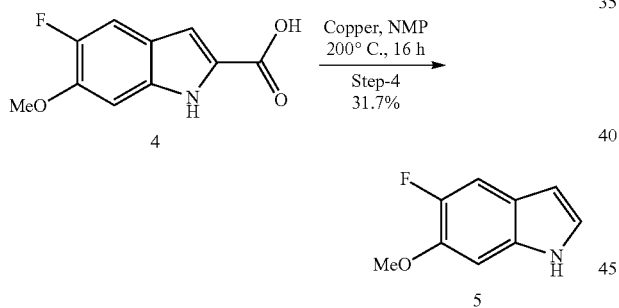

To a stirred solution of compound 4 (2.800 g, 13.39 mmol) in NMP (40.0 mL) was added copper powder (4.253 g, 66.93 mmol). The reaction mixture was heated at 200° C. for 16 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a non-polar spot. The $R_f$ values of the starting material and product were 0.1 and 0.3, respectively. The reaction mixture was cooled to rt, poured into ice cold water (150.0 mL) and extracted with EtOAc (2×250.0 mL). The organic layer was dried over anhydrous $Na_2SO_4$, filtered and concentrated under reduced pressure to afford crude compound 5. The crude compound was purified by flash column using 230-400 mesh silica gel and eluted with 20% EtOAc in pet ether to afford compound 5 as a brown liquid. TLC system: 30% EtOAc in pet ether. Yield 0.700 g (31.7%).

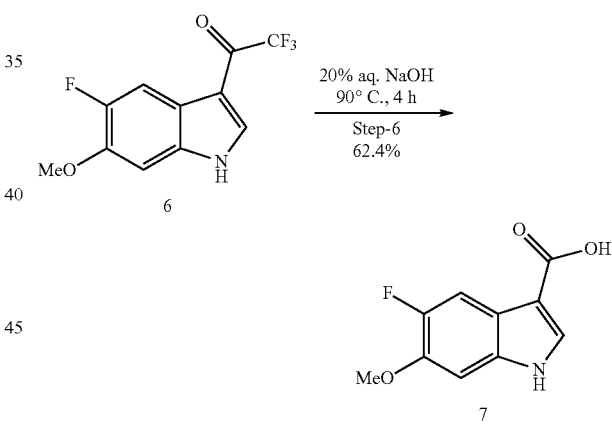

To an ice cold stirred solution of compound 5 (0.070 g, 4.2 mmol) in dry THF (15.0 mL) was added trifluoroacetic anhydride (0.90 mL, 6.4 mmol). The reaction mixture was stirred at rt for 16 h. The $R_f$ values of the starting material and product were 0.8 and 0.4, respectively. The reaction mixture was diluted with ice cold water (50.0 mL) and extracted with EtOAc (2×75.0 mL). The organic layer was dried over anhydrous $Na_2SO_4$, filtered and concentrated under reduced pressure to afford crude compound 6. The crude compound was purified by triturating with n-pentane to afford compound 6 as a brown solid. TLC system: 50% EtOAc acetate in pet ether. Yield 0.700 g (63.2%).

A mixture of compound 6 (0.700 g, 2.68 mmol) in 20% aqueous NaOH (14.0 mL) was heated at 90° C. for 4 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The $R_f$ values of the starting material and product were 0.5 and 0.2, respectively. The reaction mixture was cooled to 0° C., acidified with 2 N aqueous HCl (30.0 mL) and extracted with EtOAc (2×75.0 mL). The combined organic layers were washed, dried over anhydrous $Na_2SO_4$, filtered and concentrated under reduced pressure to afford crude compound 7. The crude compound was purified by triturating with n-pentane to afford compound 7 as a green solid. TLC system: 50% EtOAc in pet ether. Yield 0.350 g (62.4%).

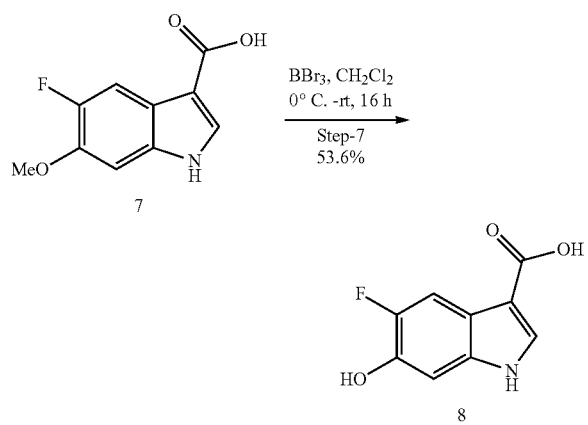

To an ice cold stirred solution of compound 7 (0.400 g, 1.91 mmol) in dry CH$_2$Cl$_2$ (15.0 mL) was added boron tribromide (0.54 mL, 5.7 mmol) drop-wise. The reaction mixture was stirred at rt for 6 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The R$_f$ values of the starting material and product were 0.3 and 0.2, respectively. The reaction mixture was poured into saturated aqueous NaHCO$_3$ solution (50.0 mL) and extracted with EtOAc (2×75.0 mL). The organic layer was dried over anhydrous Na$_2$SO$_4$, filtered and concentrated under reduced pressure to afford crude compound 8. The crude compound was purified by flash column using 230-400 mesh silica gel and eluted with 5% MeOH in CH$_2$Cl$_2$ to afford compound 8 as a brown solid. TLC system: 50% EtOAc in pet ether. Yield 0.200 g (53.6%).

Example 49

5,6-difluoro-M-indole-3-carboxylic acid

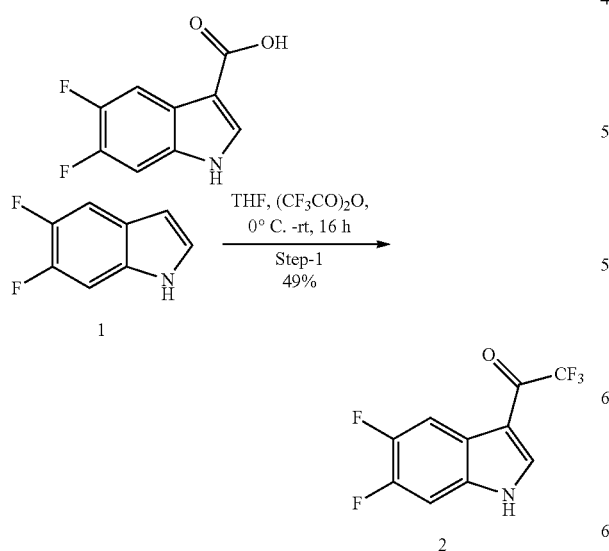

To an ice cold stirred solution of compound 1 (0.100 g, 0.653 mmol) in dry THF (10.0 mL) was added trifluoroacetic anhydride (0.14 mL, 0.98 mmol). The reaction mixture was allowed to warm to rt and stirred for 16 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The R$_f$ values of the starting material and product were 0.6 and 0.2, respectively. The reaction mixture was quenched with ice cold water (25.0 mL) and extracted with EtOAc (2×50.0 mL). The organic layer was dried over Na$_2$SO$_4$, filtered and concentrated under reduced pressure to afford crude compound 2. The crude compound was triturated with n-pentane to afford compound 2 as a brown solid. TLC system: 20% EtOAc acetate in pet ether. Yield 0.080 g (49%).

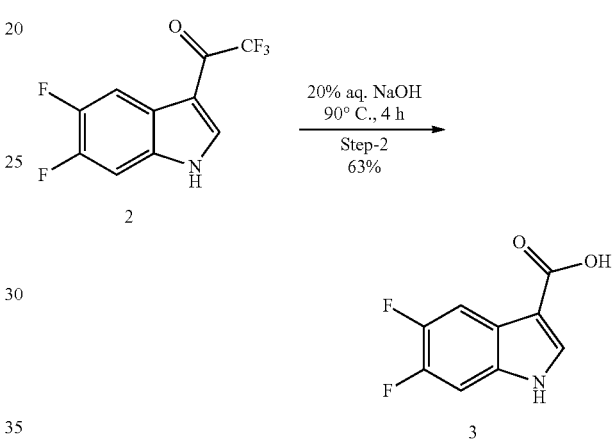

A mixture of compound 2 (0.08 g, 0.32 mmol) in 20% aqueous NaOH (1.6 mL) was heated at 90° C. for 4 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The R$_f$ values of the starting material and product were 0.8 and 0.2, respectively. The reaction mixture was cooled to 0° C., acidified with 2 N aqueous HCl (25.0 mL) solution and extracted with EtOAc (2×50.0 mL). The organic layer was dried over Na$_2$SO$_4$, filtered and concentrated under reduced pressure to afford crude compound 3. The crude compound was triturated with n-pentane to afford compound 3 as a green solid. TLC system: 60% EtOAc in pet ether. Yield 0.040 g (63%).

Example 50

6-methyl-1H-indole-3-carboxylic acid

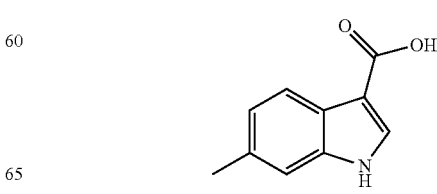

6-methyl-1H-indole-3-carboxylic acid is commercially available and can be used directly in the coupling reactions described below.

Example 51

6-chloro-5-fluoro-1H-indole-3-carboxylic acid

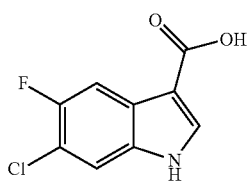 [SMILES: O=C(O)c1c[nH]c2cc(Cl)c(F)cc12]

6-chloro-5-fluoro-1H-indole-3-carboxylic acid was prepared using a similar procedure to Example 49.

Example 52

5-fluoro-6-methoxy-1H-indole-3-carboxylic acid

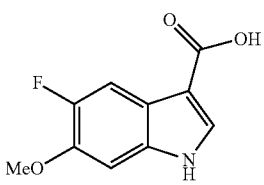 [SMILES: COc1cc2[nH]cc(C(=O)O)c2cc1F]

5-fluoro-6-methoxy-1H-indole-3-carboxylic acid was prepared using a similar procedure to Example 48.

Example 53

4-fluoro-6-methoxy-1H-indole-3-carboxylic acid

4-fluoro-6-methoxy-1H-indole-3-carboxylic acid was prepared using a similar procedure to Example 48, where the installation of the acid functionality was achieved using trifluoroacetic anhydride as follows:

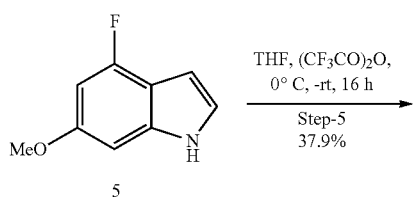

To a stirred solution of compound 5 (0.250 g, 1.51 mmol) in dry THF (10.0 mL) was added trifluoroacetic anhydride (0.32 mL, 2.3 mmol) at 0° C. The reaction mixture was allowed to warm to rt and was stirred for 16 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The $R_f$ values of the starting material and product were 0.4 and 0.2, respectively. The reaction mixture was quenched with ice cold water (25.0 mL) and extracted with EtOAc (2×50.0 mL). The organic layer was washed with brine, dried over $Na_2SO_4$, filtered and concentrated under reduced pressure to afford crude compound 6. Trituration of crude compound with n-pentane afforded compound 6 as a brown solid. TLC system: 40% EtOAc acetate in pet ether. Yield 0.150 g (37.9%).

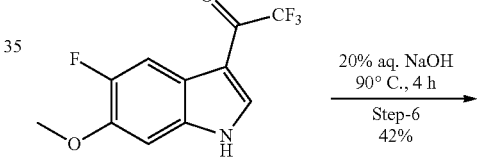

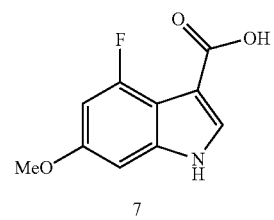

A solution of compound 6 (0.150 g, 0.574 mmol) in 20% aqueous NaOH (3.0 mL) was heated at 90° C. for 4 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The $R_f$ values of the starting material and product were 0.5 and 0.3, respectively. The reaction mixture was cooled to 0° C., acidified with 2 N aqueous HCl (15.0 mL) solution and extracted with EtOAc (2×25.0 mL). The organic layer was dried over $Na_2SO_4$, filtered and concentrated under reduced pressure to afford crude compound 7. Trituration of crude compound with n-pentane afforded compound 7 as a green solid. TLC system: 50% EtOAc in pet ether. Yield 0.050 g (42%).

Example 54

2,3-dihydro-6H-[1,4]dioxino[2,3-f]indole-8-carboxylic acid

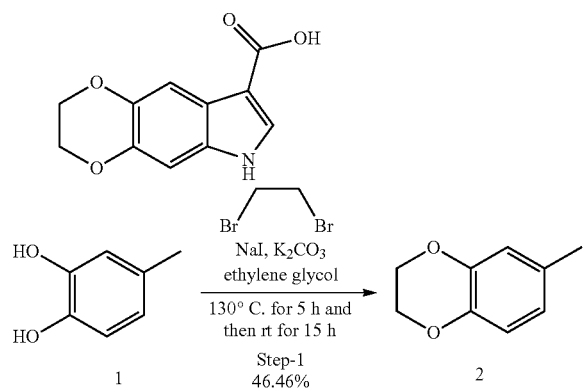

To solution of 4-methylcatechol 1 (5.000 g, 40.28 mmol) in ethylene glycol (80.0 mL) were added 1,2-dibromethane (15.13 g, 80.56 mmol), K$_2$CO$_3$ (11.13 g, 80.55 mmol) and NaI (0.03 g, 0.2 mmol) at rt. The reaction mixture was stirred at 130° C. for 5 h and then at rt for 15 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a non-polar spot. The R$_f$ values of the starting material and product were 0.2 and 0.5, respectively. The reaction mixture was filtered through a pad of celite and the filtrate was diluted with brine solution (120.0 mL) and extracted with a mixture of solvents (CH$_2$Cl$_2$/hexane/EtOAc; 1:3:1). The organic layer was dried over anhydrous Na$_2$SO$_4$ and concentrated to obtain the crude product. The crude product was purified by column chromatography using 100-200 mesh silica gel and eluted on 12% EtOAc in pet ether to afford compound 2 as a colorless liquid. TLC system: 20% EtOAc in pet ether. Yield 2.810 g (46.46%).

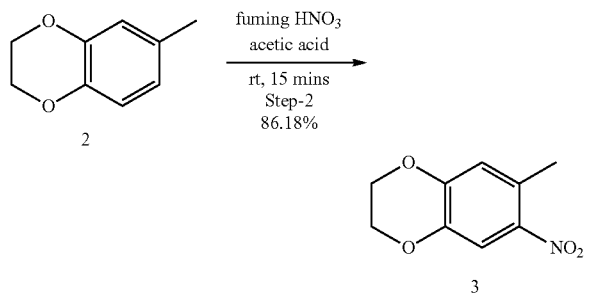

To a solution of compound 2 (2.500 g, 16.65 mmol) in acetic acid (17.0 mL) was added a solution of fuming nitric acid (1.30 mL) in acetic acid (7.0 mL) drop-wise at room temperature. The reaction mixture was stirred at rt for 15 minutes. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The R$_f$ values of the starting material and product were 0.5 and 0.3, respectively. The reaction mixture was poured into ice water, and the precipitated solid was filtered and dried under vacuum to obtain the desired product as an off-white solid. TLC system: 20% EtOAc in pet ether. Yield 2.800 g (86.18%).

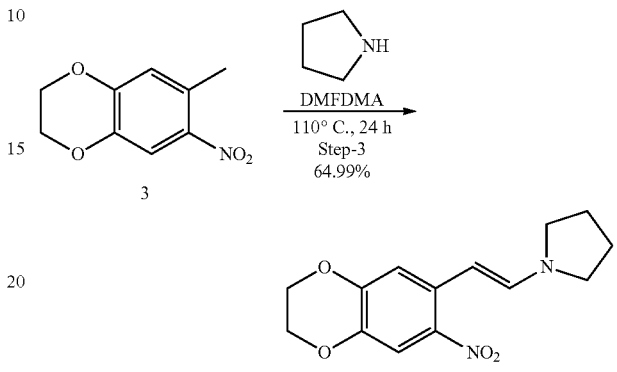

A solution of compound 3 (10.000 g, 51.237 mmol), N,N-dimethylformamide dimethylacetal (13.61 mL, 102.5 mmol) and pyrrolidine (8.42 mL, 102 mmol) was heated to 110° C. for 24 h under N$_2$ atmosphere. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The R$_f$ values of the starting material and product were 0.5 and 0.3, respectively. The reaction mixture was cooled to room temperature and diluted with methanol. The product crystallized as a bright red solid. The solid was filtered and dried to obtain pure compound 4 as a bright red solid. TLC system: 30% EtOAc in pet ether. Yield: 9.200 g (64.99%).

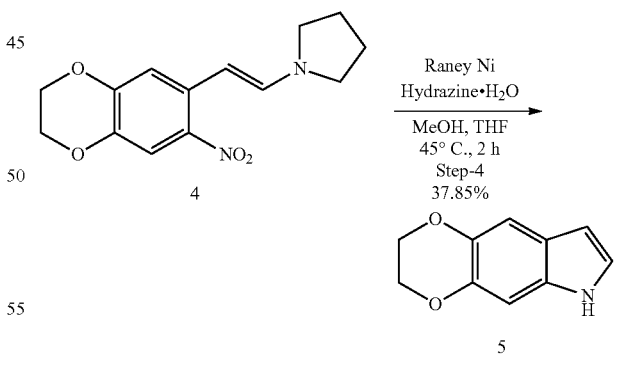

To a solution of compound 4 (5.000 g, 18.09 mmol) in methanol and THF (100 mL, 1:1) was added Raney Ni (0.450 g) and hydrazine hydrate (3×1.17 mL, 72.4 mmol) every half an hour at rt under N$_2$ atmosphere. The reaction mixture was then stirred at 45° C. for 2 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The $R_f$ values of the starting material and product were 0.3 and 0.15, respectively. The reaction mixture was cooled to room temperature and filtered through a pad of celite and washed with $CH_2Cl_2$. The filtrate was concentrated under reduced pressure to obtain a residue, which was taken up in toluene (2×30.0 mL) and azeotroped to obtain the crude compound 5. The crude compound was then purified by column chromatography using 100-200 mesh silica gel and eluted on 40% ethyl acetate in pet ether to afford compound 5 as an off-white solid. TLC system: 30% ethyl acetate in pet ether. Yield 1.200 g (37.85%).

Compound 5 was converted into the corresponding indole acid using a similar procedure to Example 48.

Example 55

6-(difluoromethoxy)-1H-indole-3-carboxylic acid

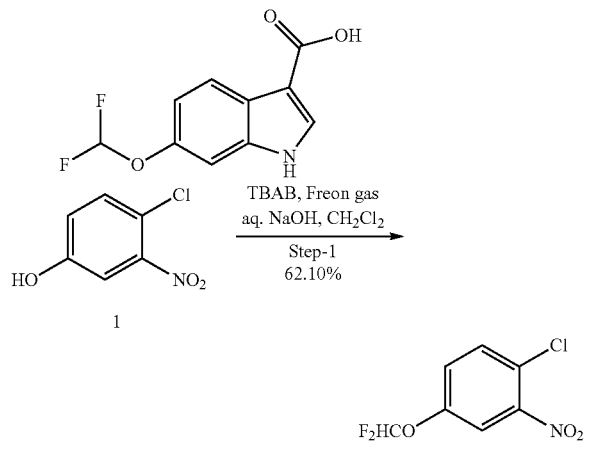

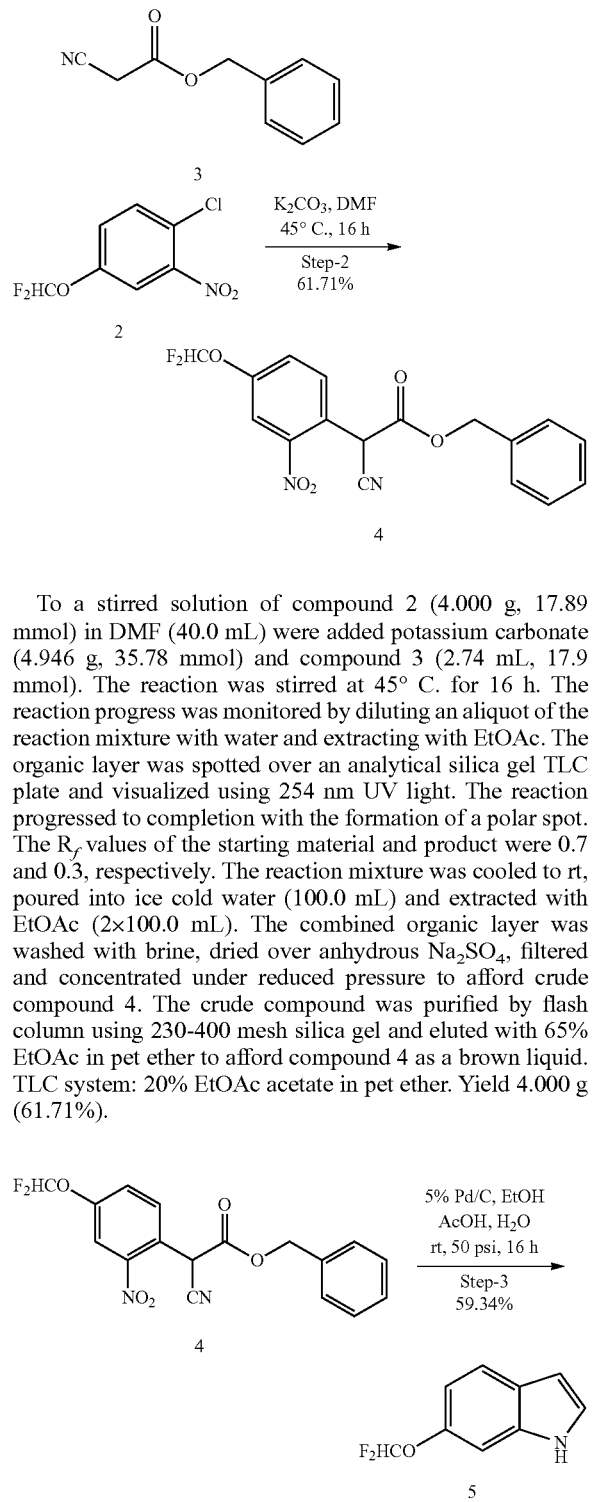

A stream of Freon gas was passed into a stirred solution of compound 1 (5.000 g, 28.81 mmol) and TBAB (14.86 g, 46.10 mmol) in $CH_2Cl_2$ (50.0 mL). To the reaction was added a solution of NaOH (4.610 g, 115.2 mmol) in $H_2O$ (15.0 mL) over a period of 30 min. Freon gas was passed through the reaction mixture for a further 3 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a non-polar spot. The $R_f$ values of the starting material and product were 0.1 and 0.3, respectively. The reaction mixture was poured into water (50.0 mL) and extracted with $CH_2Cl_2$ (2×100.0 mL). The organic layer was washed with brine, dried over $Na_2SO_4$, filtered and concentrated under reduced pressure to afford crude compound 2. The crude compound was purified by flash column using 230-400 mesh silica gel and eluted with 20% EtOAc in pet ether to afford compound 2 as a brown liquid. TLC system: 10% EtOAc in pet ether. Yield: 4.000 g (62.10%).

To a stirred solution of compound 2 (4.000 g, 17.89 mmol) in DMF (40.0 mL) were added potassium carbonate (4.946 g, 35.78 mmol) and compound 3 (2.74 mL, 17.9 mmol). The reaction was stirred at 45° C. for 16 h. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a polar spot. The $R_f$ values of the starting material and product were 0.7 and 0.3, respectively. The reaction mixture was cooled to rt, poured into ice cold water (100.0 mL) and extracted with EtOAc (2×100.0 mL). The combined organic layer was washed with brine, dried over anhydrous $Na_2SO_4$, filtered and concentrated under reduced pressure to afford crude compound 4. The crude compound was purified by flash column using 230-400 mesh silica gel and eluted with 65% EtOAc in pet ether to afford compound 4 as a brown liquid. TLC system: 20% EtOAc acetate in pet ether. Yield 4.000 g (61.71%).

A suspension of 5% Pd/C (1.200 g), compound 4 (4.000 g, 11.04 mmol) in a mixture of EtOH (60.0 mL), acetic acid (6.0 mL) and $H_2O$ (6.0 mL) was hydrogenated in a 500.0 mL glass parr hydrogenator at 50 psi for 16 h at rt. The reaction progress was monitored by diluting an aliquot of the reaction mixture with water and extracting with EtOAc. The organic layer was spotted over an analytical silica gel TLC plate and visualized using 254 nm UV light. The reaction progressed to completion with the formation of a non-polar spot. The $R_f$ values of the starting material and product were 0.2 and 0.5, respectively. The reaction mixture was filtered through a pad of celite, and the filtrate was concentrated under reduced pressure to afford crude compound 5. The crude compound was purified by flash column using 230-400 mesh silica gel and eluted with 80% EtOAc in pet ether as the eluent to afford compound 5 as a brown liquid. TLC system: 20% EtOAc in pet ether. Yield: 1.200 g (59.34%).

Compound 5 was converted into the corresponding indole acid using a similar procedure to Example 53.

Example 56

6-(trifluoromethoxy)-1H-indole-3-carboxylic acid

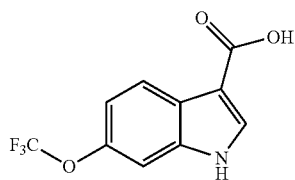 [SMILES: O=C(O)c1c[nH]c2cc(OC(F)(F)F)ccc12]

6-(trifluoromethoxy)-1H-indole-3-carboxylic acid was prepared using a similar procedure to Example 55.

Example 57

4-chloro-5-fluoro-1H-indole-3-carboxylic acid

The residue was purified by $SiO_2$ column chromatography (PE) to provide the title compound (2.1 g, 72.6%) as a colorless oil.

2,2,6,6-Tetramethylpiperidine (1.06 g, 7.5 mmol), N,N', N'',N''-pentamethyldiethylene triamine (3.46 g, 20 mmol) and compound 1 (1.45 g, 5.0 mmol) were added consecutively to a solution of n-BuLi (2.5 M in hexanes, 8 mL, 20 mmol) in THF (20 mL) and hexanes (6 mL) at −78° C. After stirring for 4 h at −78° C., the mixture was treated with 1,1,2-trichloro-1,2,2-trifluoroethane (1.18 g, 6.0 mmol) before it was warmed to 25° C. Water was added to the mixture. The organic phase was washed with brine, dried with sodium sulfate, filtered, and concentrated in vacuo. The residue was purified by $SiO_2$ column chromatography (PE) to provide title compound (1.2 g, 73.8%) as a colorless liquid.

A solution of tetrabutylammonium fluoride hydrate (1.9 g, 7.38 mmol) and compound 2 (1.2 g, 3.69 mmol) in THF (30 mL) was stirred for 30 min at room temperature. The mixture was diluted with diethyl ether (30 mL), washed with brine (30 mL), dried with sodium sulfate, filtered, and concentrated in vacuo. Purification by column chromatography (PE/EA=50:1) provided compound 3 (0.5 g, 80.1%) as a brown oil.

$POCl_3$ (2.2 g, 14.5 mmol) was added dropwise to a solution of compound 3 (1.69 g, 10 mmol) in DMF (15 mL) at 0° C. The resulting mixture was stirred at 0° C. for 0.5 h, and additional DMF (5 mL) was added. The reaction mixture was stirred at 40° C. for 1 h. After it was cooled to rt, ice water (3 mL) was added and aqueous sodium hydroxide (4 M) was added to adjust pH to 11. The mixture was heated

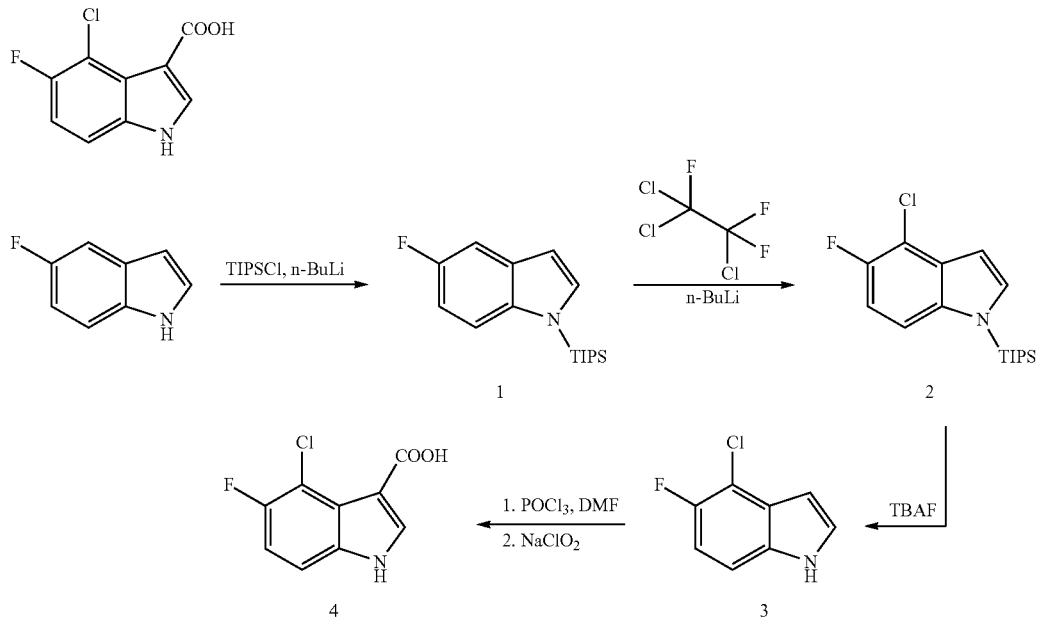

n-BuLi (2.5 M in hexanes, 4 mL, 10 mmol) was added to a solution of 5-fluoro-1H-indole (1.35 g, 10 mmol) in THF (15 mL) at −78° C. After stirring at this temperature for 10 minutes, TIPSCl (1.92 g, 10 mmol) were added to the mixture. The mixture was warmed to rt and stirred for 30 min before partitioned between water and diethyl ether (2×30 mL). The combined organic layers were washed with brine, dried with sodium sulfate, filtered, and concentrated.

to reflux for 0.5 h. After it was cooled to rt, the mixture was extracted with ethyl acetate (2×50 mL). The combined organic layers were washed with brine, dried with sodium sulfate, filtered, and concentrated in vacuo. The residue was purified by column chromatography (PE/EA=10:1) to provide the aldehyde (1.35 g, 69%) as a yellow solid.

A solution of $NaClO_2$ (963 mg, 10.65 mmol) and $NaH_2PO_4 \cdot 2H_2O$ (4.15 g, 26.63 mmol) in water (10 mL) was added to a solution of the above aldehyde (700 mg, 3.55 mmol) and 2-methyl-2-butene (1.99 g, 28.4 mmol) in tBuOH (10 mL) and THF (10 mL) at 0° C. The mixture was stirred at room temperature for 1 day before it was extracted with ethyl acetate (2×30 mL). The combined organic layers were washed with NaHSO$_3$. The organic extract was washed with 1 M NaOH solution (3×10 mL), and the aqueous layers were combined and acidified with concentrated HCl to pH=4-5. The resulting mixture was extracted with ethyl acetate (2×50 mL). The combined organic layers were washed with brine (2×50 mL), dried with sodium sulfate, filtered, and concentrated in vacuo to afford 4-chloro-5-fluoro-1H-indole-3-carboxylic acid (600 mg, 79.3%) as a yellow solid.

Example 58

4-chloro-5-methyl-1H-indole-3-carboxylic acid

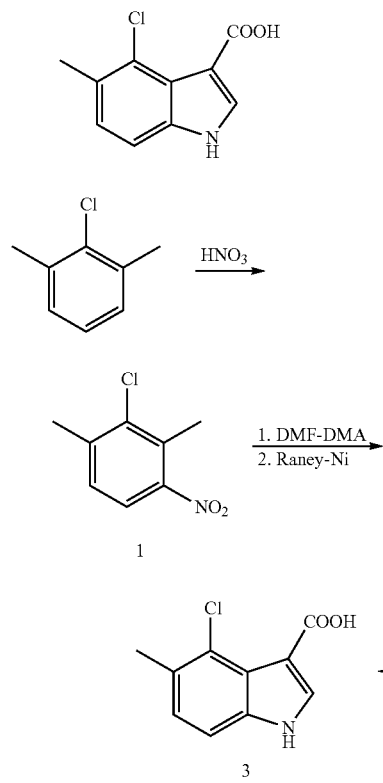

Conc. nitric acid (1.8 g, 20 mmol) was added dropwise to a solution of 2-chloro-1,3-dimethylbenzene (2.8 g, 20 mmol) in conc. H$_2$SO$_4$ (10 mL) at 0° C. The mixture was stirred for 2 h at room temperature. After the reaction completed, the mixture was poured into ice water (100 mL) and extracted with ethyl acetate (2×50 mL). The combined organic phase was washed with brine (50 mL) and concentrated to dryness in vacuo. The residue was purified by column chromatography (PE: EA=50:1) to give compound 1 (2.1 g, 56.8%) as a yellow oil.

Compound 1 (1.85 g, 10 mmol) was added to a solution of DMF-DMA (3.57 g, 30 mmol) in DMF (20 mL). The mixture was heated to 120° C. and stirred overnight. Then the mixture was poured to water (100 mL) and extracted with ethyl acetate (2×50 mL). The combined organic phase was washed with brine (100 mL) and concentrated in vacuo. The resulting red oil was used in the next step without further purification.

The red oil from above was dissolved in ethanol (50 mL), and Raney-nickel (0.5 g) was added. The mixture was hydrogenated at 1 atm at rt overnight. After the reaction completed, the Raney-nickel was filtered off and the filtrate was concentrated to dryness in vacuo. The residue was purified by column chromatography (PE: EA=50:1) to give compound 2 (0.8 g, 46.5% over two steps) as a brown solid.

The resulting indole was converted into 4-chloro-5-methyl-1H-indole-3-carboxylic acid using a similar procedure to Example 57.

Example 59

4-chloro-6-fluoro-1H-indole-3-carboxylic acid

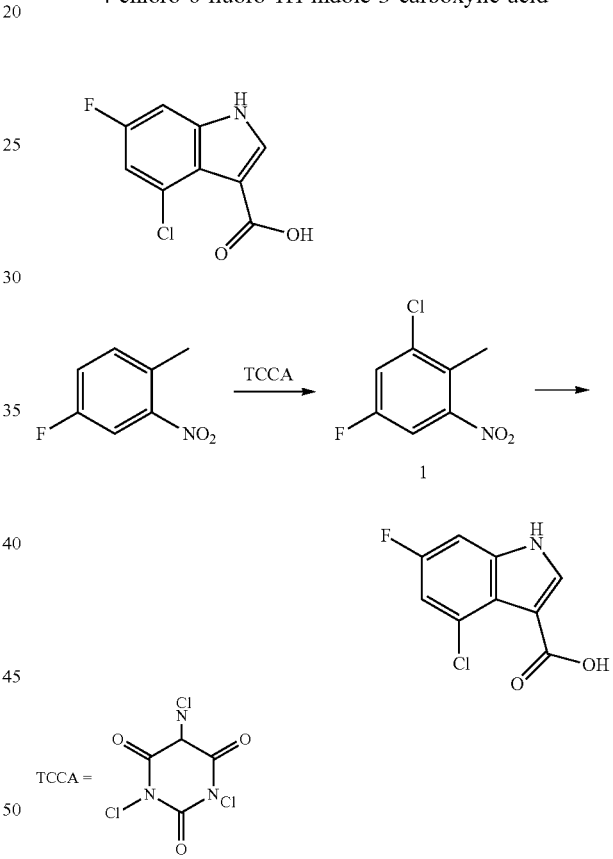

TCCA (16.7 g, 72 mmol) was added to a solution of 4-fluoro-1-methyl-2-nitrobenzene (12.4 g, 80 mmol) in CH$_3$CO$_2$H/H$_2$SO$_4$ (80 mL/80 mL). The mixture was heated to 70° C. and stirred overnight. After cooling to room temperature, the reaction mixture was poured into ice water (1000 mL) and extracted with DCM (2×200 mL). The combined organic phase was washed with brine and concentrated in vacuo. The residue was purified by column chromatography (PE: EA=50:1) to give compound 1 (5.0 g, 33.1%) as a yellow oil.

The resulting chlorinated compound was converted into 4-chloro-6-fluoro-1H-indole-3-carboxylic acid using a similar procedure to Example 58.

Example 60

4-chloro-6-methyl-1H-indole-3-carboxylic acid and 5-chloro-6-methyl-1H-indole-3-carboxylic acid

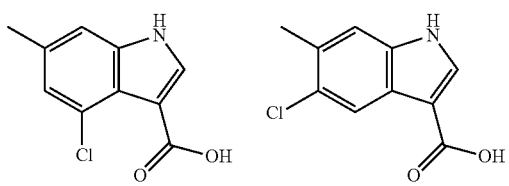

4-chloro-6-methyl-1H-indole-3-carboxylic acid and 5-chloro-6-methyl-1H-indole-3-carboxylic acid were synthesized using a similar procedure to Example 58. The compounds were separated using flash chromatography after the POCl₃ reaction.

Example 61

6-chloro-4-methoxy-1H-indole-3-carboxylic acid

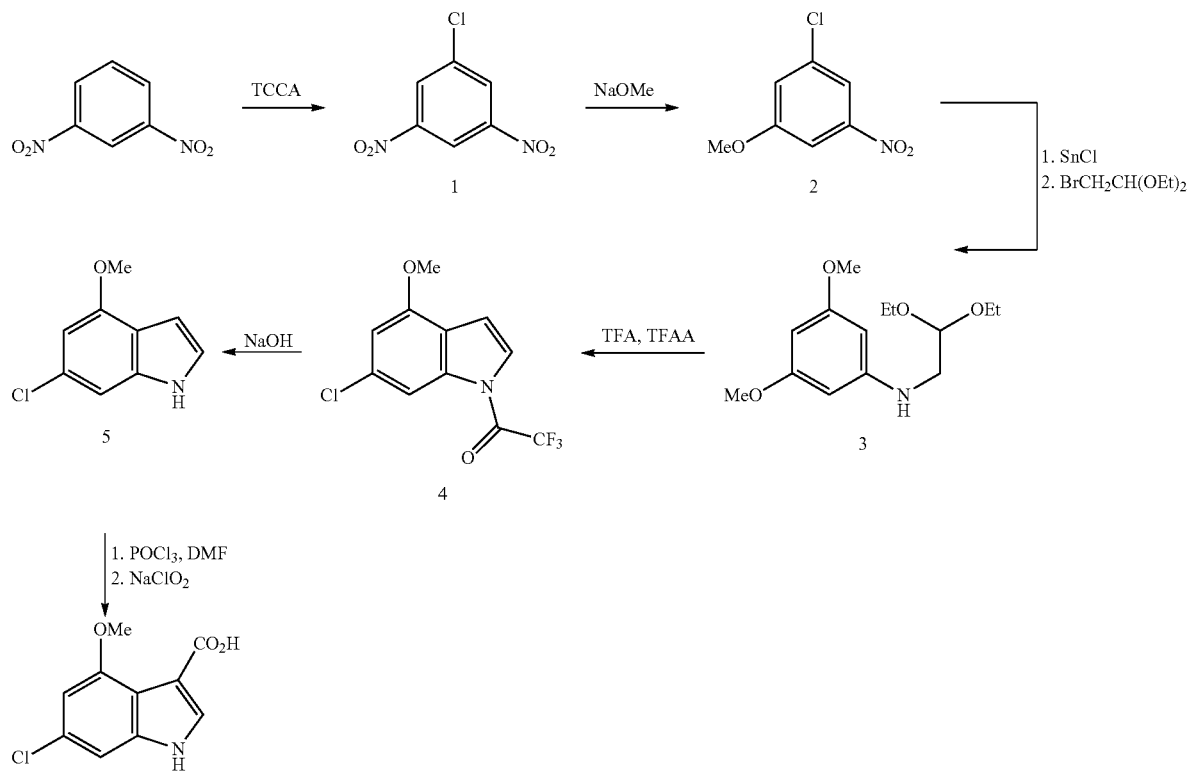

TCCA (14 g, 60 mmol) was added to a solution of 1,3-dinitrobenzene (30 g, 179 mmol) in conc. H₂SO₄ (200 mL). The mixture was heated to 130° C. and stirred for 4 h. Then the mixture was poured to ice water (1000 mL) and extracted with ethyl acetate (2×300 mL). The combined organic phase was washed with brine and concentrated in vacuo to dryness. The residue was purified by column chromatography (PE: EA=20:1) to give compound 1 (26 g, 72%) as a yellow solid.

NaOMe (11.23 g, 25% in MeOH, 52 mmol) was added to a solution of compound 1 (10.5 g, 52 mmol) in MeOH (100 mL). The mixture was refluxed overnight before concentrated in vacuo to dryness. The residue was purified by column chromatography (PE: EA=10:1) to give compound 2 (7.6 g, 78.3%) as a yellow solid.

SnCl₂.2H₂O (50.5 g, 224 mmol) was added to a solution of compound 2 (8.4 g, 44.8 mmol) in ethanol (300 mL). The mixture was refluxed for 2 h before 2 M sodium carbonate solution (1000 mL) was added. The resulting slurry was filtered, and the filtrate was extracted with ethyl acetate (3×300 mL). The combined organic layers were washed with brine and concentrated in vacuo to dryness to give crude aniline which was used to next step without further purification.

2-bromo-1,1-diethoxyethane (10 g, 50.1 mmol) and K₂CO₃ (7.4 g, 53.6 mmol) was added to the solution of the above crude aniline in DMF (100 mL). The mixture was heated to 100° C. and stirred overnight. Then the mixture was poured to ice water (500 mL) and extracted with ethyl acetate (3×100 mL). The combined organic layers were washed with brine and concentrated in vacuo to dryness. The residue was purified by column chromatography (PE: EA=10:1) to give compound 3 (5.3 g, 48.2%) as a brown oil.

Compound 3 (5.0 g, 18.3 mmol) was added to a mixture of TFA (30 mL) and TFAA (30 mL), and the mixture was heated to reflux overnight. After the reaction completed, the mixture was concentrated in vacuo to dryness. The residue was purified by column chromatography (EA:PE=1:10) to give compound 4 (1.2 g, 23.8%) as a brown oil.

Compound 4 (2.77 g, 10 mmol) was added to a 5% solution of KOH in MeOH (100 mL). The mixture was stirred at room temperature for 0.5 h before it was concentrated in vacuo. The residue was purified by column chromatography (EA:PE=1:15) to give compound 5 (780 mg, 43.1%) as a redish solid.

POCl$_3$ (0.99 g, 6.5 mmol) was added dropwise to a solution of DMF (10 mL) and compound 5 (780 mg, 4.3 mmol) at 0° C. The resulting mixture was stirred at 0° C. for 0.5 h and additional DMF (10 mL) was added. The reaction mixture was stirred at 40° C. for 1 h. After it was cooled to rt, ice water (5 mL) was added and 4 M aqueous sodium hydroxide was added to adjust the pH to 11. The mixture was heated to reflux for 0.5 h. After it was cooled to rt, the mixture was extracted with ethyl acetate (2×50 mL). The combined organic layers were washed with brine, dried with sodium sulfate, filtered, and concentrated in vacuo. The residue was purified by column chromatography (PE/EA=10:1) to provide 4-chloro-6-methoxy-1H-indole-3-carbaldehyde (690 mg, 76.0%) as a yellow solid.

A solution of NaClO$_2$ (881 mg, 9.74 mmol) and NaH$_2$PO$_4$.2H$_2$O (3.86 g, 24.8 mmol) was added to a solution of 4-chloro-6-methyl-1H-indole-3-carbaldehyde (690 mg, 3.3 mmol) in tBuOH (15 mL), THF (15 mL) and 2-methyl-2-butene (1.85 g, 26.4 mmol) at 0° C. The mixture was stirred at room temperature overnight. The mixture was extracted with ethyl acetate (2×30 mL). The combined organic layers were washed with NaHSO$_3$. The organic extracts treated with aqueous NaOH (3×10 mL), and the aqueous phase were combined and acidified with conc. HCl to pH=4-5. The resulting mixture was extracted with ethyl acetate (2×50 mL). The combined organic layers were washed with brine (2×50 mL), dried under vacuum to afford 6-chloro-4-methoxy-1H-indole-3-carboxylic acid (370 mg, 49.8%) as a yellow solid.

Example 62

5-methoxy-6-methyl-1H-indole-3-carboxylic acid

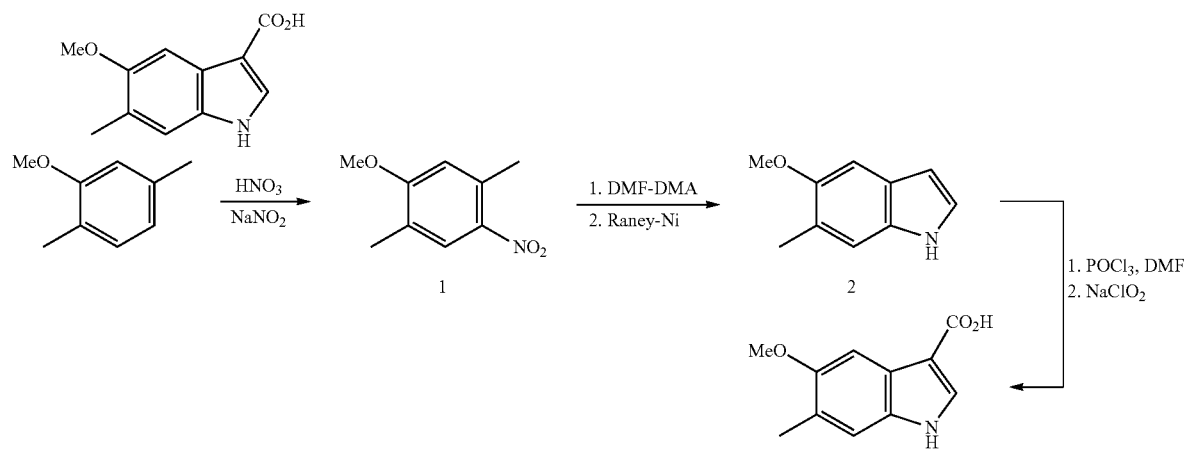

To an ice-cold concentrated nitric acid (200 mL) was added slowly under stirring over a period of 20 minutes 2-methoxy-1,4-dimethylbenzene (25 g, 184 mmol). To this cold reaction mixture, sodium nitrite (38 g, 552 mmol) was added slowly in lots over a period of 1 h while maintaining the temperature below 2° C. The reaction mixture was stirred at between 0-5° C. for 5 h. The reaction mass was poured into ice-cold water (1000 mL), and the precipitated solid was filtered, washed with cold water (100 mL) and dried. The crude solid was crystallized from ethanol and water (7:1) to yield compound 1 (15 g, 45%).

The resulting nitro compound was converted into 5-methoxy-6-methyl-1H-indole-3-carboxylic acid using a similar procedure to Example 58.

Coupling Procedures for Conversion of Indole Acids to Target Compounds

Example 63

Coupling Protocol C1

Step 1: Indole acid was taken in a 10 mL round-bottom flask under nitrogen atmosphere. Thionyl chloride (10 mL/mmol) was added to it. The reaction mixture was refluxed for 3 hr. Formation of the acid chloride was monitored by quenching an aliquot with methanol and comparing the formation of the methyl ester with respect to the indole acid. Thionyl chloride was evaporated under reduced pressure and the residue was used directly for step 2.

Step 2: The acid chloride obtained from step 1 was taken in dichloromethane (10 mL/mmol), and Quinuclidin-4-yl-methanol N-borane complex (1 eq.) and triethyl amine (1.5 eq.) was added to it. The reaction was stirred at 25° C. for 16 hr. It was then diluted with dichloromethane, and washed successively with ammonium chloride, sodium bicarbonate and brine. The crude material obtained was purified by column chromatography (silica gel, 1% to 3% acetone in DCM) to get pure compound which was taken forward for step 3.

Step 3: The product of step 2 (20 mg to 40 mg) was dissolved in a mixture of acetone (3 mL) and ethanol (1.5 mL). Ethanolic HCl (0.5 mL) was added drop-wise into it and stirred for 1 hr. Absence of starting material was monitored by TLC. The solvent was evaporated and the crude obtained was triturated with ether to get pure compound.

Example 64

Coupling Protocol C2

Step 1: Toluene (10 mL/mmol) and thionyl chloride (10 eq.) was added to indole acid and refluxed for 16 hr. Formation of the acid chloride was monitored by quenching an aliquot with methanol and comparing the formation of the methyl ester with respect to the indole acid. The un-dissolved solid was filtered, the filtrate was evaporated under reduced pressure and the residue was used directly for step 2.

Step 2: The acid chloride obtained from step 1 was taken in dichloromethane (10 mL/mmol), and Quinuclidin-4-yl-methanol N-borane complex (1 eq.) and triethyl amine (1.5 eq.) was added to it. The reaction was stirred at 25° C. for 16 hr. It was then diluted with dichloromethane and washed successively with ammonium chloride, sodium bicarbonate and brine. The crude material obtained was purified by column chromatography (silica gel, 1% to 3% acetone in DCM) to get pure compound which was taken forward for step 3.

Step 3: The product from step 2 (20 mg to 40 mg) was dissolved in a mixture of acetone (3 mL) and ethanol (1.5 mL). Ethanolic HCl (0.5 mL) was added drop-wise into it and stirred for 1 hr. Absence of starting material was monitored by TLC. The solvent was evaporated and the crude obtained was triturated with ether to get pure compound.

Example 65

Coupling Protocol C3

Step 1: Indole acid was taken in a 10 mL round-bottom flask under nitrogen atmosphere. Dichloromethane (10 mL/mmol) was added to it. The reaction mixture was cooled. Oxalyl chloride (freshly distilled, 1.5 eq.) and 1 drop of DMF was added to it. Reaction mixture was stirred at 25° C. for 2 hr. Formation of acid chloride was monitored by quenching an aliquot with methanol and comparing the formation of the methyl ester with respect to the indole acid. The solvent was evaporated under reduced pressure and the residue was used directly for step 2.

Step 2: The acid chloride obtained from step 1 was taken in dichloromethane (10 mL/mmol), and Quinuclidin-4-yl-methanol N-borane complex (1 eq.) and triethyl amine (1.5 eq.) was added to it. The reaction was stirred at 25° C. for 16 hr. It was then diluted with dichloromethane, washed successively with ammonium chloride, sodium bicarbonate and brine. The crude material obtained was purified by column chromatography (silica gel, 1% to 3% acetone in DCM) to get pure compound which was taken forward for step 3.

Step 3: The product from step 2 (20 mg to 40 mg) was dissolved in a mixture of acetone (3 mL) and ethanol (1.5 mL). Ethanolic HCl (0.5 mL) was added drop-wise into it and stirred for 1 hr. Absence of starting material was monitored by TLC. The solvent was evaporated and the crude obtained was triturated with ether to get pure compound.

Example 66

Compound prepared by coupling protocols C1, C2, or C3 are listed in Table 5.

TABLE 5

| Indole acid | Target Compound No. | Coupling Protocol | Salt Form | MS [M + H] |
|---|---|---|---|---|
| 6-fluoro-1H-indole-3-carboxylic acid | 11 | C1 | HCl | 303 |
| 5-fluoro-1H-indole-3-carboxylic acid | 12 | C1 | HCl | 303 |
| 4-fluoro-1H-indole-3-carboxylic acid | 13 | C1 | HCl | 303 |
| 6-hydroxy-1H-indole-3-carboxylic acid | 14 | C2 | HCl | 301 |
| 5-hydroxy-1H-indole-3-carboxylic acid | 15 | C2 | HCl | 301 |
| 7-methoxy-1H-indole-3-carboxylic acid | 16 | C3 | HCl | 315 |
| 6-methoxy-1H-indole-3-carboxylic acid | 17 | C3 | HCl | 315 |
| 5-methoxy-1H-indole-3-carboxylic acid | 18 | C3 | HCl | 315 |

TABLE 5-continued

| Indole acid | Target Compound No. | Coupling Protocol | Salt Form | MS [M + H] |
|---|---|---|---|---|
| 7-methyl-1H-indole-3-carboxylic acid | 19 | C3 | HCl | 299 |
| 5-methyl-1H-indole-3-carboxylic acid | 20 | C3 | HCl | 299 |
| 4-methyl-1H-indole-3-carboxylic acid | 21 | C3 | HCl | 299 |
| 6-bromo-1H-indole-3-carboxylic acid | 22 | C3 | HCl | 363 |
| 5-bromo-1H-indole-3-carboxylic acid | 23 | C3 | HCl | 363 |
| 4-bromo-1H-indole-3-carboxylic acid | 24 | C3 | HCl | 363 |
| 7-chloro-1H-indole-3-carboxylic acid | 25 | C3 | HCl | 319 |
| 6-chloro-1H-indole-3-carboxylic acid | 26 | C3 | HCl | 319 |
| 5-chloro-1H-indole-3-carboxylic acid | 27 | C3 | HCl | 319 |
| 6-cyano-1H-indole-3-carboxylic acid | 28 | C3 | HCl | 310 |

Example 67

(Quinuclidin-4-yl)methyl 1H-indole-3-carboxylate (Compound 1)

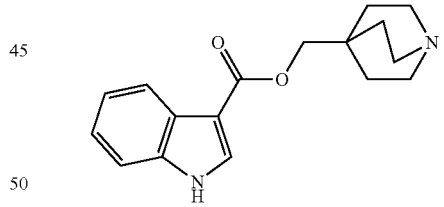

To a solution of 1H-indole-3-carbonyl chloride (45 mg, 0.25 mmol) in 3 mL of methylene chloride at 0° C. was added (quinuclidin-4-yl)methanol (36 mg, 0.25 mmol) in 2 mL of methylene chloride. The mixture was stirred at room temperature overnight. The solvent was evaporated and water (10 mL) was added. The water layer was basified to pH 12 using 10% aqueous potassium hydroxide and extracted three times with 25 mL each of ethyl acetate. The combined organic layers were dried over sodium sulfate and concentrated to yield 8 mg of desired product. $^1$HNMR: 12.02 (bs, 1H); 8.13 (d, 1H); 7.9 (m, 1H); 7.42 (m, 1H); 7.18 (m, 2H); 4.3 (bs, 2H); 3.03 (m, 6H); 1.75 (m, 6H). MS (m/e): 285.

Example 68

Quinuclidin-4-ylmethyl 5-chloro-1H-indole-3-carboxylate (Compound 2)

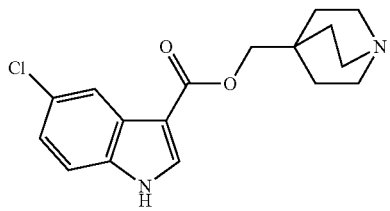 [SMILES: O=C(OCC12CCN(CC1)CC2)c1c[nH]c2ccc(Cl)cc12]

Quinuclidin-4-ylmethyl 5-chloro-1H-indole-3-carboxylate was prepared using a similar procedure to Example 67, substituting 5-chloro-1H-indole-3-carbonyl chloride as the electrophile.

Example 69

Quinuclidin-4-ylmethyl 5-methoxy-1H-indole-3-carboxylate (Compound 4)

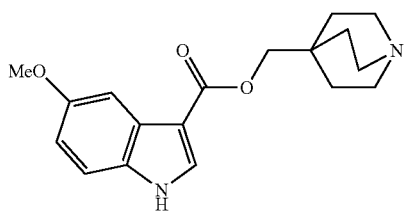 [SMILES: COc1ccc2[nH]cc(C(=O)OCC34CCN(CC3)CC4)c2c1]

Quinuclidin-4-ylmethyl 5-methoxy-1H-indole-3-carboxylate was prepared starting from 5-methoxyindole-3-carboxylic acid (synthesized as described in J. Med. Chem. 49, 1125 (2006)) using a similar procedure to Example 67. MS (m/e): 314.

Example 70

Quinuclidin-4-ylmethyl 6-methoxy-1H-indole-3-carboxylate (Compound 10)

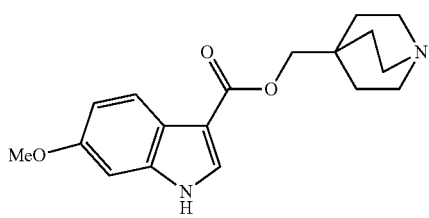 [SMILES: COc1ccc2c(C(=O)OCC34CCN(CC3)CC4)c[nH]c2c1]

Quinuclidin-4-ylmethyl 6-methoxy-1H-indole-3-carboxylate was prepared starting from 6-methoxyindole-3-carboxylic acid (synthesized as described in J. Med. Chem. 51, 1849 (2008)) using a similar procedure to Example 67. MS (m/e): 314.

Example 71

Quinuclidin-4-ylmethyl 5-(difluoromethoxy)-1H-indole-3-carboxylate (Compound 6)

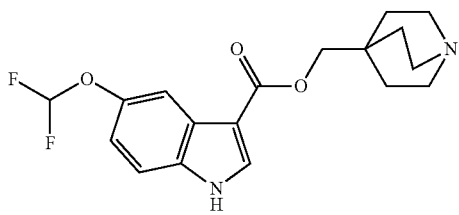 [SMILES: O=C(OCC12CCN(CC1)CC2)c1c[nH]c2ccc(OC(F)F)cc12]

Quinuclidin-4-ylmethyl 5-(difluoromethoxy)-1H-indole-3-carboxylate was synthesized using a similar procedure to Example 67. MS: (m/e) 350.

Example 72

Quinuclidin-4-ylmethyl 6-(difluoromethoxy)-1H-indole-3-carboxylate (Compound 5)

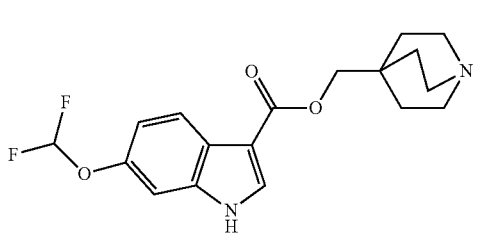 [SMILES: O=C(OCC12CCN(CC1)CC2)c1c[nH]c2cc(OC(F)F)ccc12]

Quinuclidin-4-ylmethyl 6-(difluoromethoxy)-1H-indole-3-carboxylate was synthesized using a similar procedure to Example 67. MS: (m/e) 350.

Example 73

Quinuclidin-4-ylmethyl 5-((trifluoromethoxy)methyl)-1H-indole-3-carboxylate (Compound 9)

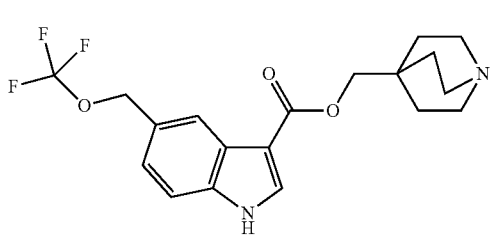 [SMILES: O=C(OCC12CCN(CC1)CC2)c1c[nH]c2ccc(COC(F)(F)F)cc12]

Quinuclidin-4-ylmethyl 5-((trifluoromethoxy)methyl)-1H-indole-3-carboxylate was synthesized using a similar procedure to Example 67. MS: (m/e) 382.

Example 74

Quinuclidin-4-ylmethyl 5-isopropoxy-1H-indole-3-carboxylate (Compound 7)

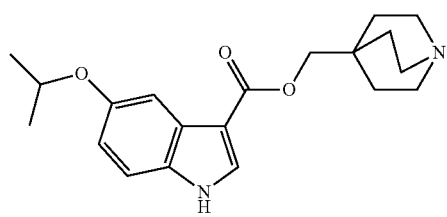 [SMILES: CC(C)Oc1ccc2[nH]cc(C(=O)OCC34CCN(CC3)CC4)c2c1]

Quinuclidin-4-ylmethyl 5-isopropoxy-1H-indole-3-carboxylate was synthesized using a similar procedure to Example 67. MS: (m/e) 342.

Example 75

Quinuclidin-4-ylmethyl 5-(cyclopropylmethoxy)-1H-indole-3-carboxylate (Compound 8)

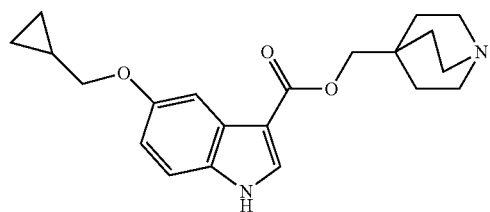 [SMILES: O=C(OCC12CCN(CC1)CC2)c1c[nH]c2ccc(OCC3CC3)cc12]

Quinuclidin-4-ylmethyl 5-(cyclopropylmethoxy)-1H-indole-3-carboxylate was synthesized using a similar procedure to Example 67 MS: (m/e) 354.

Example 76

Quinuclidin-4-ylmethyl 4-methoxy-5-methyl-1H-indole-3-carboxylate hydrochloride (Compound 75)

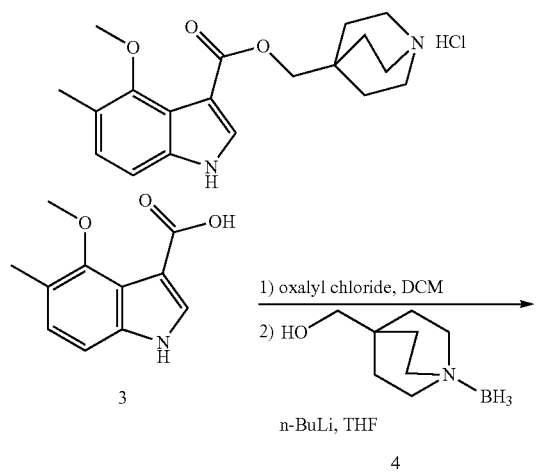

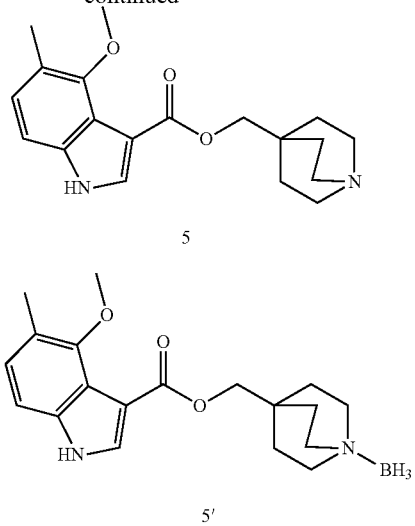

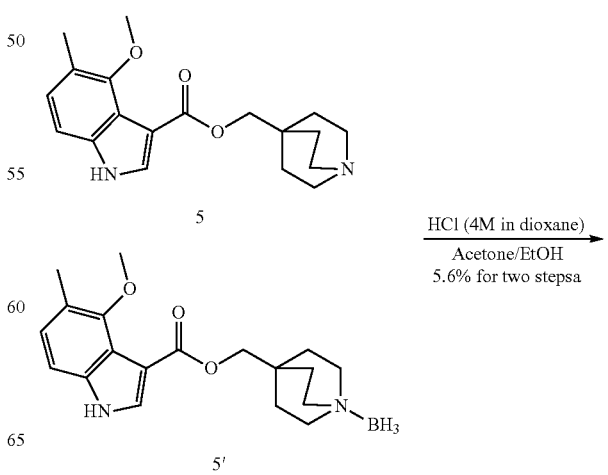

To an ice-cooled mixture of compound 3 (200 mg, 0.976 mmol) in DCM (5 mL) were added oxalyl chloride (0.2 mL, 1.46 mmol, 1.5 eq.) and DMF (0.1 mL). The reaction mixture was stirred at rt for 30 min until the gas generation ceased. Formation of the acid chloride was monitored by quenching an aliquot with methanol and analyzing by TLC to check the formation of methyl ester with respect to acid. At the end of the reaction, the solvent was evaporated under reduced pressure and the residue was used directly for the next step.

To a solution of alcohol 4 (454 mg, 2.93 mmol, 3 eq.) in dry THF (5 mL) was added n-butyllithium (1.2 mL, 2.93 mmol, 3 eq.). The suspension was stirred at 0° C. for 0.5 h. Acid chloride obtained from the previous step was taken up in dichloromethane (3 mL) and was added dropwise at 0° C. The reaction was stirred at 25° C. for 30 min. The reaction progress was monitored by TLC. On completion, the reaction was quenched and brought to pH 7 with ammonium chloride. The mixture was extracted with ethyl acetate, washed with brine, dried over $Na_2SO_4$ and concentrated. The crude product was purified by silica gel chromatography (1% to 3% acetone in DCM) to give a mixture of compound 5 and compound 5' (90 mg) as a white solid.

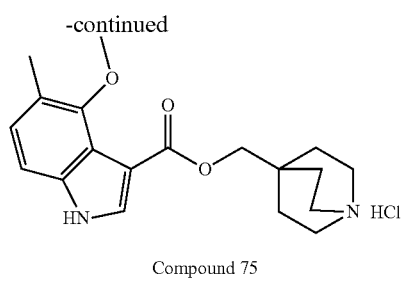

Compound 75

A suspension of compound 5 and compound 5' (90 mg, 0.274 mmol) in acetone (8 mL) and ethanol (4 mL) was treated with HCl (4M in dioxane, 3 mL) at 0° C. The reaction mixture became clear and was stirred at rt for 30 min. The reaction progress was monitored by TLC. The reaction mixture was then concentrated to dryness, purified by prep-HPLC, treated with conc. HCl and lyophilized to give the desired product (18 mg, 0.055 mmol, 5.6% for two steps) as a white solid. m/z=329 $[C_{19}H_{24}N_2O_3+H]^+$.

Example 77

Quinuclidin-4-ylmethyl 6-cyano-4-methoxy-1H-indole-3-carboxylate hydrochloride (Compound 77)

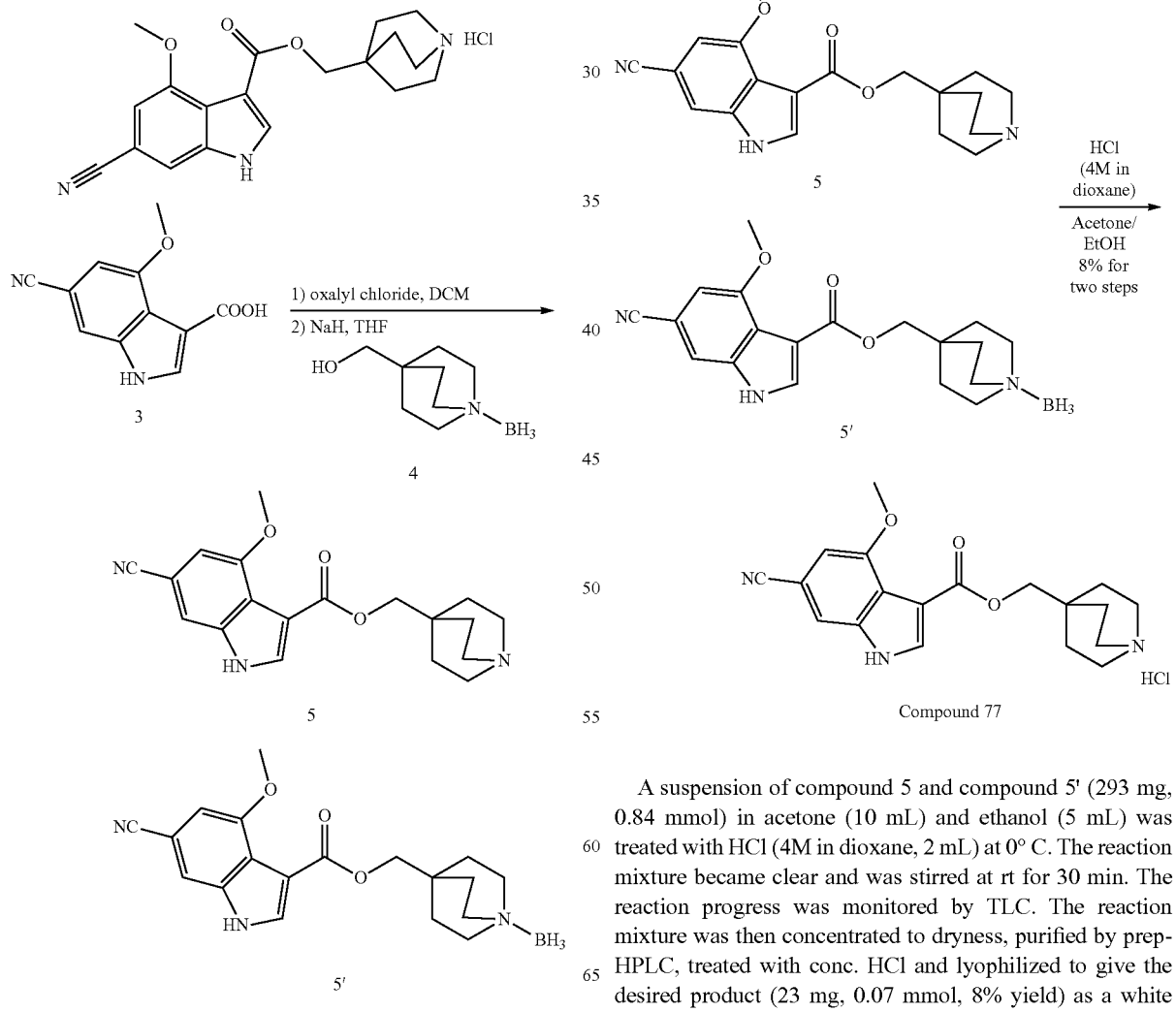

To an ice-cooled mixture of compound 3 (350 mg, 1.6 mmol) in DCM (10 mL) were added oxalyl chloride (0.6 mL, 6.8 mmol, 1.5 eq.) and DMF (0.1 mL). The reaction mixture was stirred at rt for 2 h until the gas generation ceased. Formation of the acid chloride was monitored by quenching an aliquot with methanol and analyzing by TLC to check the formation of methyl ester with respect to acid. At the end of the reaction, solvent was evaporated under reduced pressure and the residue was used directly for the next step.

To a solution of alcohol 4 (250 mg, 1.6 mmol, 1 eq.) in dry THF (10 mL) was added NaH (100 mg, 2.43 mmol, 1.5 eq., 60%) dropwise at 0° C. The reaction mixture was stirred at rt for 30 min. To this reaction mixture was added slowly the acyl chloride at 0° C. and stirred at rt for 30 min. The reaction progress was monitored by TLC. The reaction mixture was washed successively with ammonium chloride, sodium bicarbonate and brine. The crude product was purified by silica gel chromatography (1% to 3% acetone in DCM) to give a mixture of compound 5 (293 mg) as a white solid.

A suspension of compound 5 and compound 5' (293 mg, 0.84 mmol) in acetone (10 mL) and ethanol (5 mL) was treated with HCl (4M in dioxane, 2 mL) at 0° C. The reaction mixture became clear and was stirred at rt for 30 min. The reaction progress was monitored by TLC. The reaction mixture was then concentrated to dryness, purified by prep-HPLC, treated with conc. HCl and lyophilized to give the desired product (23 mg, 0.07 mmol, 8% yield) as a white solid. m/z=340 $[C_{19}H_{21}N_3O_3+H]^+$.

Example 78

Quinuclidin-4-ylmethyl 4-fluoro-6-methoxy-1H-indole-3-carboxylate hydrochloride (Compound 82)

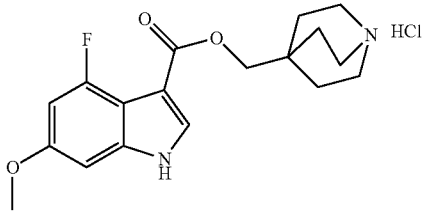 [SMILES: COc1cc(F)c2c(C(=O)OCC34CCN(CC3)CC4)c[nH]c2c1 ; Cl]

Quinuclidin-4-ylmethyl 4-fluoro-6-methoxy-1H-indole-3-carboxylate hydrochloride was prepared using a similar procedure to Example 76. m/z=333[$C_{18}H_{21}FN_2O_3$+H]$^+$.

Example 79

Quinuclidin-4-ylmethyl 6-chloro-5-methyl-1H-indole-3-carboxylate hydrochloride (Compound 78)

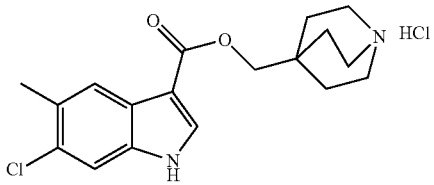 [SMILES: Cc1cc2c(C(=O)OCC34CCN(CC3)CC4)c[nH]c2cc1Cl ; Cl]

Quinuclidin-4-ylmethyl 6-chloro-5-methyl-1H-indole-3-carboxylate hydrochloride was prepared using a similar procedure to Example 76. m/z=333 [$C_{18}H_{21}ClN_2O_2$+H]$^+$.

Example 80

Quinuclidin-4-ylmethyl 6-cyano-5-methoxy-1H-indole-3-carboxylate hydrochloride (Compound 76)

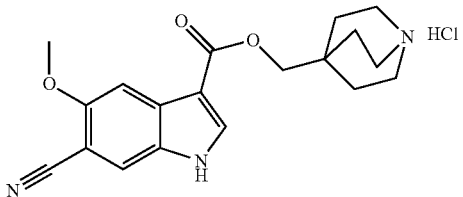 [SMILES: COc1cc2c(C(=O)OCC34CCN(CC3)CC4)c[nH]c2cc1C#N ; Cl]

Quinuclidin-4-ylmethyl 6-cyano-5-methoxy-1H-indole-3-carboxylate hydrochloride was prepared using a similar procedure to Example 77. m/z=340 [$C_{19}H_{21}N_3O_3$+H]$^+$.

Example 81

Quinuclidin-4-ylmethyl 4-bromo-6-fluoro-1H-indole-3-carboxylate hydrochloride (Compound 41)

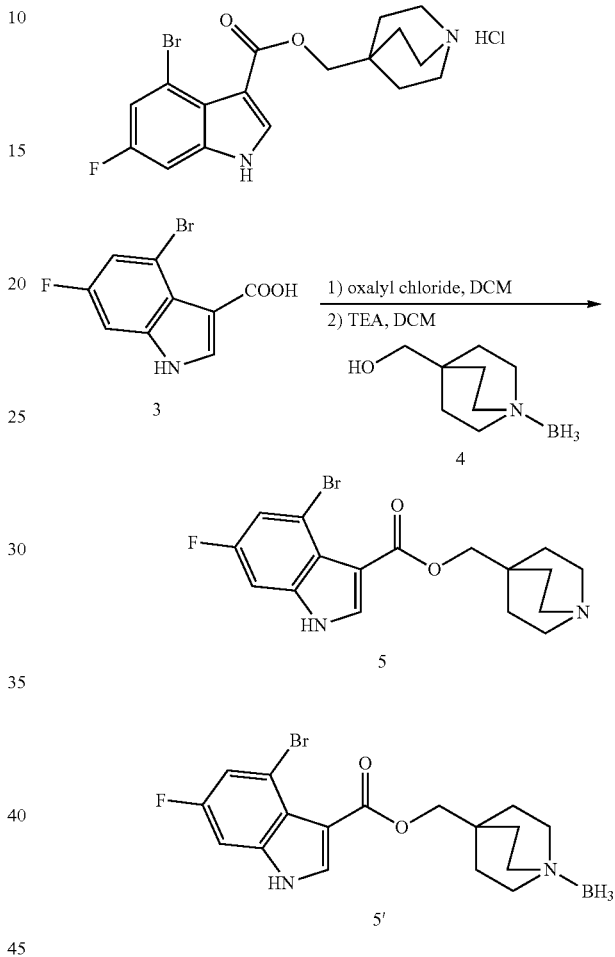

To an ice-cooled mixture of compound 3 (210 mg, 0.81 mmol) in DCM (10 mL) were added oxalyl chloride (0.15 mL, 1.21 mmol, 1.5 eq.) and DMF (0.1 mL). The reaction mixture was stirred at rt for 30 min until the gas generation ceased. Formation of the acid chloride was monitored by quenching an aliquot with methanol and analyzing by TLC to check the formation of methyl ester with respect to acid. At the end of the reaction, solvent was evaporated under reduced pressure and the residue was used directly for the next step.

Acid chloride obtained from the previous step was taken up in DCM (10 mL) and a solution of alcohol 4 (112 mg, 0.73 mmol, 0.9 eq.) and triethyl amine (156 mg, 1.55 mmol, 1.5 eq.) in DCM (10 mL) was added dropwise at 0° C. The reaction was stirred at rt for 30 min. The reaction mixture was washed successively with ammonium chloride, sodium bicarbonate and brine. The crude product was purified by silica gel chromatography (1% to 3% acetone in DCM) to give a mixture of compound 5 and compound 5' (130 mg) as a white solid.

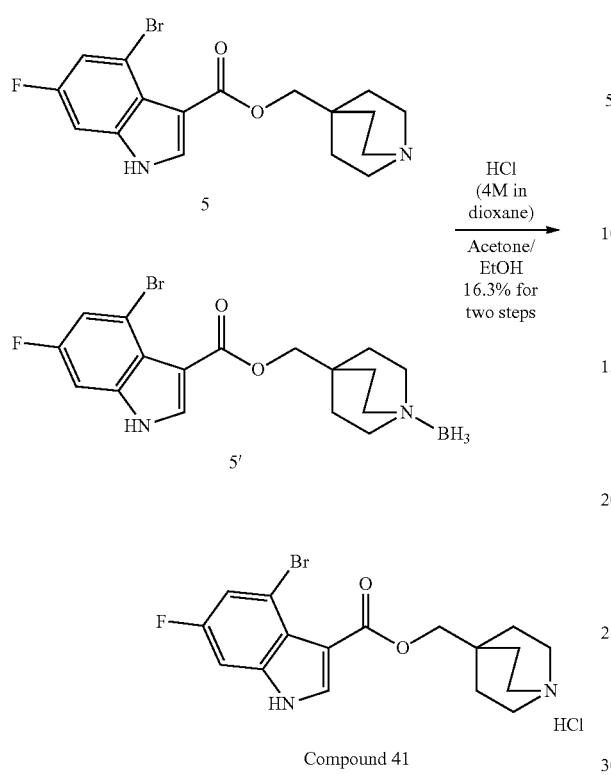

2A suspension of compound 5 and compound 5' (130 mg, 0.341 mmol) in acetone (8 mL) and ethanol (4 mL) was treated with HCl (4M in dioxane, 3 mL) at 0° C. The reaction mixture became clear and was stirred at rt for 30 min. The reaction progress was monitored by TLC. The reaction mixture was then concentrated to dryness and washed with DCM (to remove the byproduct). The residue was dried to give the desired product (55 mg, 0.132 mmol, 16.3% for two steps) as a white solid. m/z=381 $[C_{17}H_{18}BrFN_2O_2+H]^+$.

Example 82

Quinuclidin-4-ylmethyl 4-bromo-6-chloro-1H-indole-3-carboxylate hydrochloride (Compound 42)

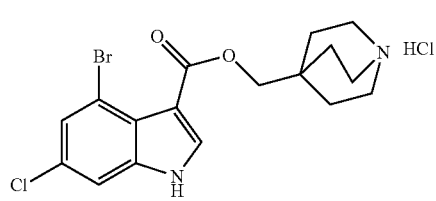 [SMILES: O=C(OCC12CCN(CC1)CC2)c1c[nH]c2cc(Cl)cc(Br)c12 ; Cl]

Quinuclidin-4-ylmethyl 4-bromo-6-chloro-1H-indole-3-carboxylate hydrochloride was prepared using a similar procedure to Example 81. m/z=399 $[C_{17}H_{18}BrClN_2O_2+H]^+$.

Example 83

Quinuclidin-4-ylmethyl 5-fluoro-4-methyl-1H-indole-3-carboxylate hydrochloride (Compound 43)

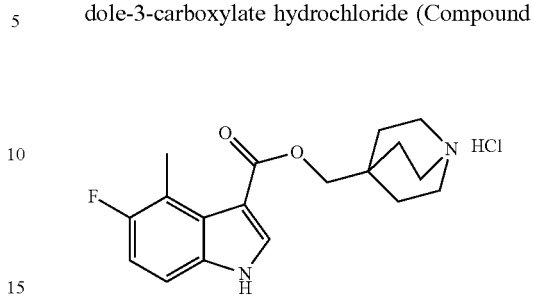

Quinuclidin-4-ylmethyl 5-fluoro-4-methyl-1H-indole-3-carboxylate hydrochloride was prepared using a similar procedure to Example 81. m/z=317 $[C_{18}H_{21}FN_2O_2+H]^+$.

Example 84

Quinuclidin-4-ylmethyl 6-fluoro-4-methyl-1H-indole-3-carboxylate hydrochloride (Compound 44)

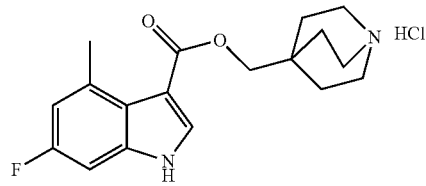 [SMILES: Cc1cc(F)cc2[nH]cc(C(=O)OCC34CCN(CC3)CC4)c12 ; Cl]

Quinuclidin-4-ylmethyl 6-fluoro-4-methyl-1H-indole-3-carboxylate hydrochloride was prepared using a similar procedure to Example 81. m/z=317 $[C_{18}H_{21}FN_2O_2+H]^+$.

Example 85 quinuclidin-4-ylmethyl 4-bromo-5-methyl-1H-indole-3-carboxylate hydrochloride (Compound 68)

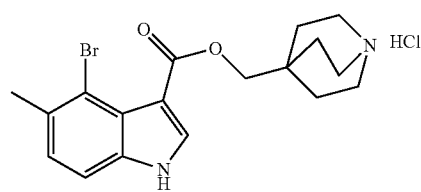 [SMILES: Cc1ccc2[nH]cc(C(=O)OCC34CCN(CC3)CC4)c2c1Br ; Cl]

Quinuclidin-4-ylmethyl 4-bromo-5-methyl-1H-indole-3-carboxylate hydrochloride was prepared using a similar procedure to Example 81. m/z=377 $[C_{18}H_{21}BrN_2O_2+H]^+$.

Example 86

Quinuclidin-4-ylmethyl 4,5-dimethyl-1H-indole-3-carboxylate hydrochloride (Compound 70)

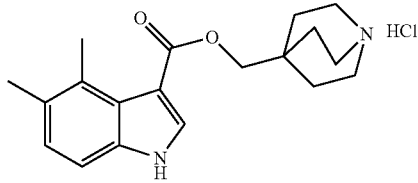 [SMILES: Cc1ccc2[nH]cc(C(=O)OCC34CCN(CC3)CC4)c2c1C ; Cl]

Quinuclidin-4-ylmethyl 4,5-dimethyl-1H-indole-3-carboxylate hydrochloride was prepared using a similar procedure to Example 81. m/z=313 [$C_{19}H_{24}N_2O_2$+H]$^+$.

Example 87 quinuclidin-4-ylmethyl 6-chloro-5-methoxy-1H-indole-3-carboxylate hydrochloride (Compound 69)

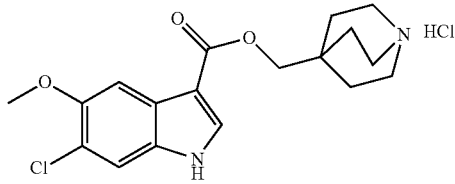 [SMILES: COc1cc2c(C(=O)OCC34CCN(CC3)CC4)c[nH]c2cc1Cl ; Cl]

Quinuclidin-4-ylmethyl 6-chloro-5-methoxy-1H-indole-3-carboxylate hydrochloride was prepared using a similar procedure to Example 81. m/z=349 [$C_{18}H_{21}ClN_2O_3$+H]$^+$.

Example 88

Quinuclidin-4-ylmethyl 4-bromo-5-fluoro-1H-indole-3-carboxylate hydrochloride (Compound 67)

Quinuclidin-4-ylmethyl 4-bromo-5-fluoro-1H-indole-3-carboxylate hydrochloride was prepared using a similar procedure to Example 81. m/z=381 [$C_{17}H_{18}BrFN_2O_2$+H]$^+$.

Example 89

Quinuclidin-4-ylmethyl 6-cyano-4-methyl-1H-indole-3-carboxylate hydrochloride (Compound 60)

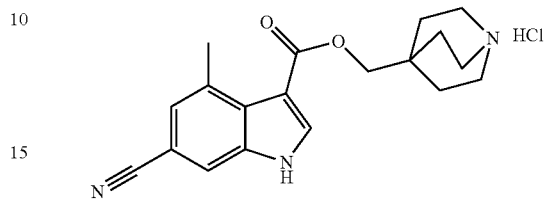

Quinuclidin-4-ylmethyl 6-cyano-4-methyl-1H-indole-3-carboxylate hydrochloride was prepared using a similar procedure to Example 81. m/z=324 [$C_{19}H_{21}N_3O_2$+H]$^+$.

Example 90

Quinuclidin-4-ylmethyl 4,6-dimethyl-1H-indole-3-carboxylate hydrochloride (Compound 54)

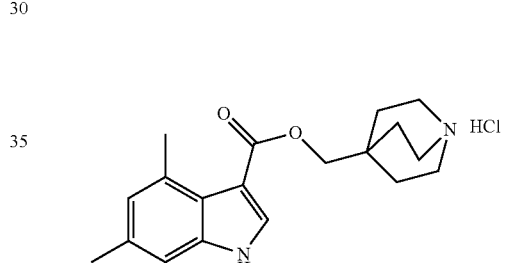

Quinuclidin-4-ylmethyl 4,6-dimethyl-1H-indole-3-carboxylate hydrochloride was prepared using a similar procedure to Example 81. m/z=313 [$C_{19}H_{24}N_2O_2$+H]$^+$.

Example 91

Quinuclidin-4-ylmethyl 6-methoxy-4-methyl-1H-indole-3-carboxylate hydrochloride (Compound 37)

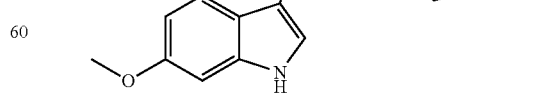

Quinuclidin-4-ylmethyl 6-methoxy-4-methyl-1H-indole-3-carboxylate hydrochloride was prepared using a similar procedure to Example 81. m/z=329 [$C_{19}H_{24}N_2O_3$+H]$^+$

Example 92

Quinuclidin-4-ylmethyl 5,6-dimethoxy-1H-indole-3-carboxylate hydrochloride (Compound 87)

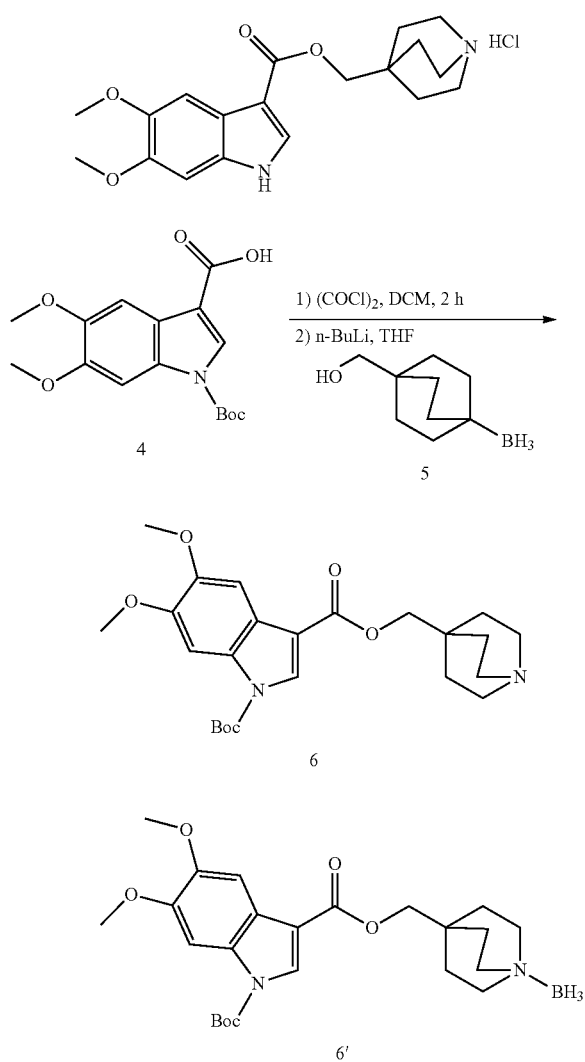

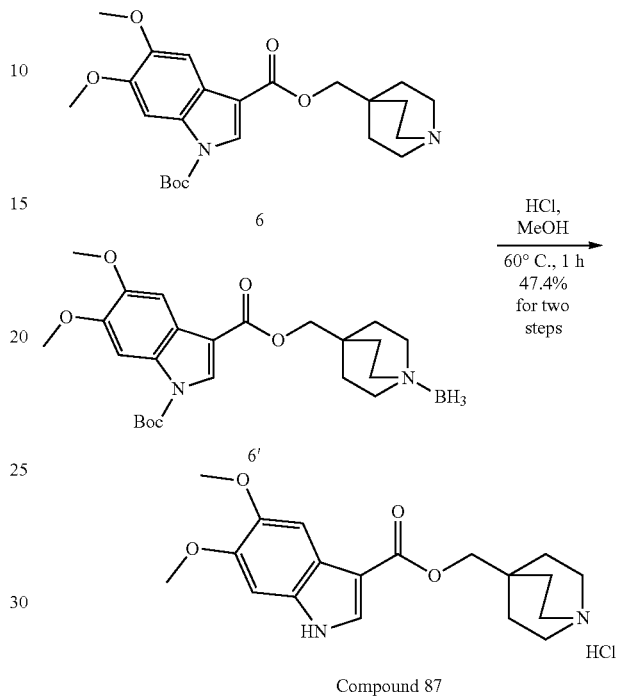

To an ice-cooled mixture of compound 4 (514 mg, 1.6 mmol) in DCM (10 mL) were added oxalyl chloride (0.6 mL, 6.8 mmol, 1.5 eq.) and DMF (0.1 mL). The reaction mixture was stirred at rt for 2 h until the gas generation ceased. Formation of the acid chloride was monitored by quenching an aliquot with methanol and analyzing by TLC to check the formation of methyl ester with respect to acid. The reaction mixture was concentrated, and the residue was used directly for next step.

To a solution of alcohol 5 (250 mg, 1.6 mmol, 1 eq.) in dry THF (10 mL) was added n-BuLi (1 mL, 2.43 mmol, 2.5 M, 1.5 eq.) dropwise at 0° C. The reaction was stirred at 25° C. for 30 min. To this reaction mixture was added slowly the acyl chloride in THF (2 mL) at 0° C. and stirred at rt for 30 min. The reaction mixture was washed successively with ammonium chloride, sodium bicarbonate and brine. The crude product was purified by silica gel chromatography (1% to 3% acetone in DCM) to give a mixture of compound 6 and compound 6' (293 mg) as a white solid.

A suspension of compound 6 (430 mg, 0.94 mmol) in MeOH (15 mL) was treated with HCl (4M in dioxane, 2 mL) at 0° C. The reaction mixture was stirred at 60° C. for 1 h and concentrated. The residue was purified by prep-HPLC. The collected eluents are treated again with excess diluted HCl and lyophilized to give the desired product (249 mg, 0.65 mmol, 47.4% for two steps) as a white solid. m/z=345 $[C_{19}H_{25}ClN_2O_3+H]^+$.

Example 93

Quinuclidin-4-ylmethyl 4-methoxy-6-methyl-1H-indole-3-carboxylate hydrochloride (Compound 85)

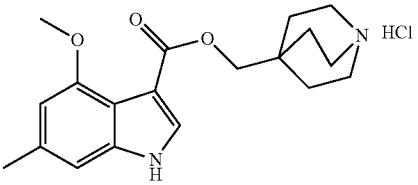 [SMILES: COc1cc(C)cc2[nH]cc(C(=O)OCC34CCN(CC3)CC4)c12 ; Cl]

Quinuclidin-4-ylmethyl 4-methoxy-6-methyl-1H-indole-3-carboxylate hydrochloride was prepared using a similar procedure to Example 92. m/z=329 $[C_{19}H_{25}ClN_2O_3+H]^+$.

Example 94

Quinuclidin-4-ylmethyl 4-chloro-6-methoxy-1H-indole-3-carboxylate hydrochloride (Compound 38)

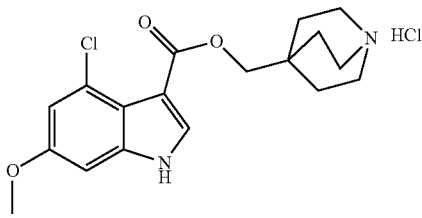

Quinuclidin-4-ylmethyl 4-chloro-6-methoxy-1H-indole-3-carboxylate hydrochloride was prepared using a similar procedure to Example 81. m/z=349 $[C_{18}H_{21}ClN_2O_3+H]^+$.

Example 95

Quinuclidin-4-ylmethyl 4-chloro-6-hydroxy-1H-indole-3-carboxylate hydrochloride (Compound 46)

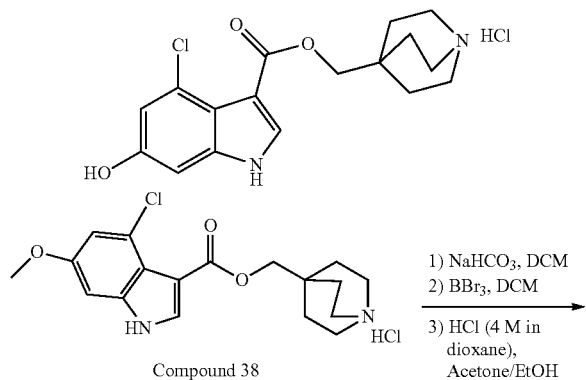

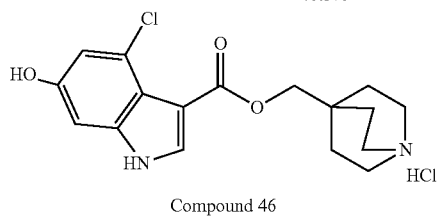

Compound 46

A suspension of compound 38 (90 mg, 0.234 mmol) in DCM (10 mL) was treated with sat. NaHCO₃ at 0° C. to pH 8.0. The reaction mixture was stirred at rt for 30 min. The organic phase was separated, washed with brine, dried over Na₂SO₄ and concentrated. The residue was used directly for the next step.

Free base obtained from the previous step was taken up in DCM (20 mL), and BBr₃ (0.5 mL) was added dropwise at 0° C. The reaction was stirred at 25° C. for 30 min, poured into ice-water, and extracted with DCM. The combined extracts were washed with sat. NaHCO₃, brine, dried over Na₂SO₄, and concentrated. The residue was used directly for the next step.

The demethylated intermediate obtained from the previous step was taken up in acetone (4 mL) and ethanol (2 mL) and was treated with HCl (4M in dioxane, 1.0 mL) at 0° C. The reaction mixture became clear and was stirred at rt for 30 min. The reaction mixture was then concentrated to dryness, and the residue was purified by prep-HPLC. The collected eluents were treated again with excess diluted HCl and lyophilized to give the desired product (35.0 mg, 0.0942 mmol, 40.3%) as a white solid. m/z=335.0 $[C_{18}H_{21}BrN_2O_2]^+$.

Example 96

Quinuclidin-4-ylmethyl 4-methoxy-1H-indole-3-carboxylate hydrochloride (Compound 36)

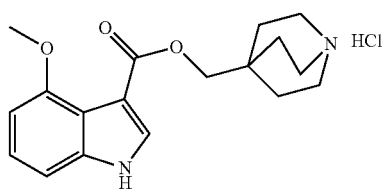 [SMILES: COc1cccc2[nH]cc(C(=O)OCC34CCN(CC3)CC4)c12 ; Cl]

Quinuclidin-4-ylmethyl 4-methoxy-1H-indole-3-carboxylate hydrochloride was prepared using a similar procedure to Example 81. m/z=315 $[C_{18}H_{22}N_2O_3+H]^+$.

Example 97

Quinuclidin-4-ylmethyl 6-hydroxy-5-methoxy-1H-indole-3-carboxylate hydrochloride (Compound 86)

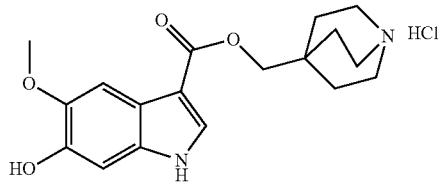 [SMILES: COc1cc2c(C(=O)OCC34CCN(CC3)CC4)c[nH]c2cc1O ; Cl]

Quinuclidin-4-ylmethyl 6-hydroxy-5-methoxy-1H-indole-3-carboxylate hydrochloride was prepared using a similar procedure to Example 92. The resulting product was debenzylated using the following procedure:

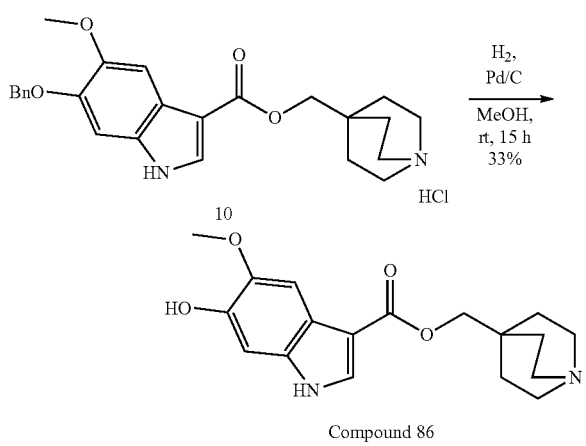

Compound 86

A mixture of compound 10 (150 mg, 0.36 mmol) and Pd/C (10 wt %, 10 mg) in MeOH (10 mL) was hydrogenated (balloon) at rt for 15 h. The reaction mixture was filtered, and the filtrate was concentrated. The residue was purified by prep-HPLC to give the desired product (39 mg, 0.12 mmol, 33.3%) as a red solid. m/z=331 $[C_{18}H_{22}N_2O_4+H]^+$.

Example 98

Quinuclidin-4-ylmethyl 6-cyano-5-methyl-1H-indole-3-carboxylate hydrochloride (Compound 84)

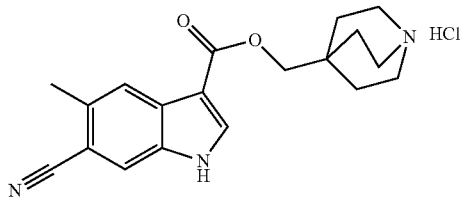 [SMILES: Cc1cc2c(C(=O)OCC34CCN(CC3)CC4)c[nH]c2cc1C#N ; Cl]

Quinuclidin-4-ylmethyl 6-cyano-5-methyl-1H-indole-3-carboxylate hydrochloride was prepared using a similar procedure to Example 76. m/z=324.2 $[C_{19}H_{21}N_3O_3+H]^+$.

Example 99

Quinuclidin-4-ylmethyl 6-fluoro-5-methyl-1H-indole-3-carboxylate hydrochloride (Compound 58)

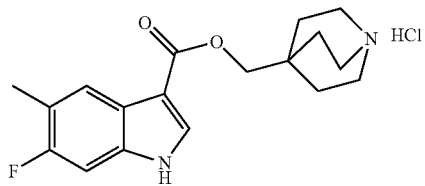 [SMILES: Cc1cc2c(C(=O)OCC34CCN(CC3)CC4)c[nH]c2cc1F ; Cl]

Quinuclidin-4-ylmethyl 6-fluoro-5-methyl-1H-indole-3-carboxylate hydrochloride was prepared using a similar procedure to Example 81. m/z=317 $[C_{18}H_{21}FN_2O_2+H]^+$.

Example 100

Quinuclidin-4-ylmethyl 6-fluoro-5-methoxy-1H-indole-3-carboxylate hydrochloride (Compound 57)

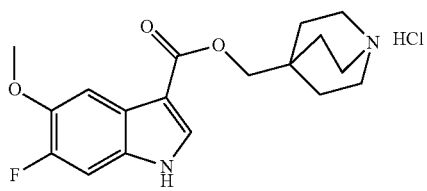 [SMILES: COc1cc2c(C(=O)OCC34CCN(CC3)CC4)c[nH]c2cc1F ; Cl]

Quinuclidin-4-ylmethyl 6-fluoro-5-methoxy-1H-indole-3-carboxylate hydrochloride was prepared using a similar procedure to Example 81. m/z=333 $[C_{18}H_{21}FN_2O_3+H]^+$.

Example 101

Quinuclidin-4-ylmethyl 6-methoxy-5-methyl-1H-indole-3-carboxylate hydrochloride (Compound 56)

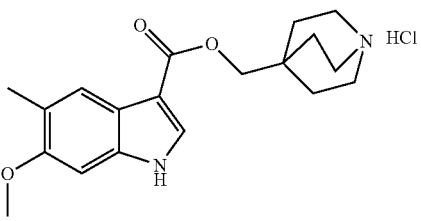 [SMILES: COc1cc2[nH]cc(C(=O)OCC34CCN(CC3)CC4)c2cc1C ; Cl]

Quinuclidin-4-ylmethyl 6-methoxy-5-methyl-1H-indole-3-carboxylate hydrochloride was prepared using a similar procedure to Example 81. m/z=329 $[C_{19}H_{24}N_2O_3+H]^+$.

Example 102

Quinuclidin-4-ylmethyl 6-hydroxy-5-methyl-1H-indole-3-carboxylate hydrochloride (Compound 55)

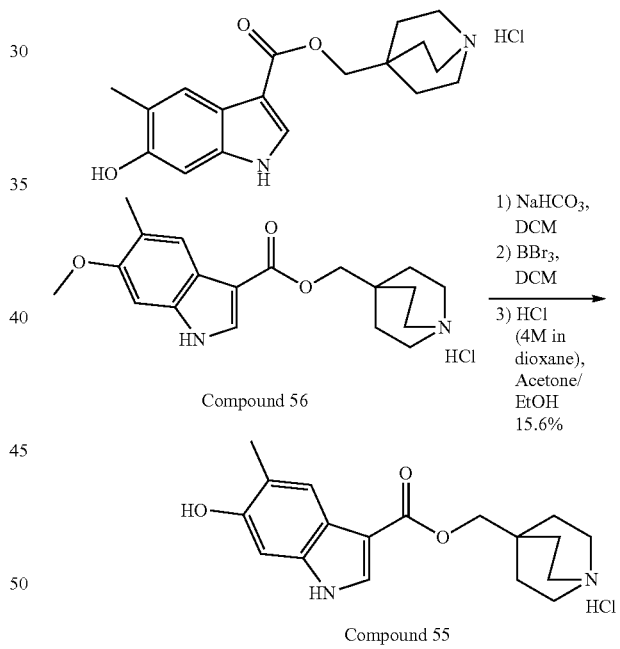

A suspension of compound 56 (120 mg, 0.33 mmol) in DCM (10 mL) was treated with sat.NaHCO$_3$ at 0° C. to pH 8.0. The reaction mixture was stirred at rt for 30 min. The organic phase was separated, washed with brine, dried over Na$_2$SO$_4$ and concentrated. The residue was used directly for the next step.

Free base obtained from the previous step was taken up in DCM (20 mL), and BBr$_3$ (0.5 mL) was added dropwise at 0° C. The reaction was stirred at 25° C. for 30 min, poured into ice-water, and extracted with DCM. The combined extracts were washed with sat. NaHCO$_3$, brine, dried over Na$_2$SO$_4$, and concentrated. The residue was used directly for the next step.

The demethylated intermediate obtained from the previous step was taken up in acetone (4 mL) and ethanol (2 mL) and was treated with HCl (4M in dioxane, 1.0 mL) at 0° C. The reaction mixture became clear and was stirred at rt for 30 min. The reaction mixture was then concentrated to dryness and the residue was purified by prep-HPLC. The collected eluents are treated again with excess diluted HCl and lyophilized to give the desired product (18 mg, 0.051 mmol, 15.6%) as a white solid. m/z=315 $[C_{18}H_{22}N_2O_3+H]^+$.

Example 103

Quinuclidin-4-ylmethyl 6-chloro-4-methyl-1H-indole-3-carboxylate hydrochloride (Compound 50)

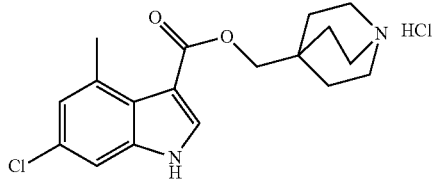 [SMILES: Cc1cc(Cl)cc2[nH]cc(C(=O)OCC34CCN(CC3)CC4)c12 ; Cl]

Quinuclidin-4-ylmethyl 6-chloro-4-methyl-1H-indole-3-carboxylate hydrochloride was prepared using a similar procedure to Example 81. m/z=332.9 $[C_{18}H_{21}ClN_2O_2+H]^+$.

Example 104

Quinuclidin-4-ylmethyl 4-bromo-6-methoxy-1H-indole-3-carboxylate hydrochloride (Compound 48)

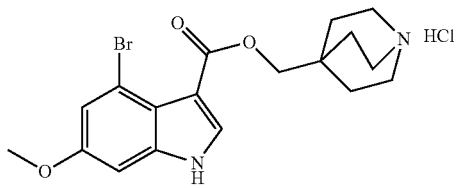

Quinuclidin-4-ylmethyl 4-bromo-6-methoxy-1H-indole-3-carboxylate hydrochloride was prepared using a similar procedure to Example 81. m/z=393, 395 $[C_{18}H_{21}BrN_2O_2+H]^+$.

Example 105

Quinuclidin-4-ylmethyl 4-bromo-6-hydroxy-1H-indole-3-carboxylate hydrochloride (Compound 53)

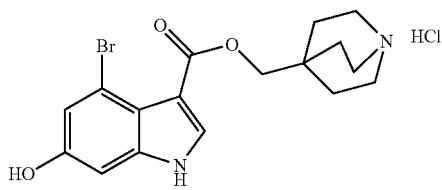

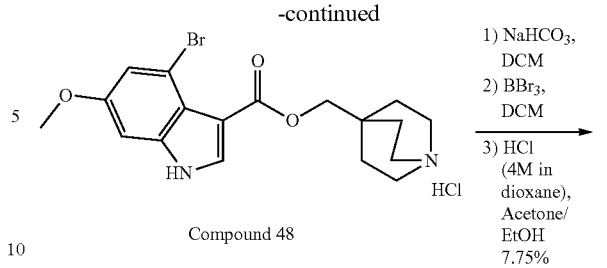

A suspension of compound 48 (200 mg, 0.465 mmol) in DCM (10 mL) was treated with sat.NaHCO$_3$ at 0° C. to pH 8.0. The reaction mixture was stirred at rt for 30 min. The organic phase was separated, washed with brine, dried over Na$_2$SO$_4$ and concentrated. The residue was used directly for the next step.

Free base obtained from the previous step was taken up in DCM (20 mL) and BBr$_3$ (0.5 mL) was added dropwise at 0° C. The reaction was stirred at 25° C. for 30 min, poured into ice-water, and extracted with DCM. The combined extracts were washed with sat. NaHCO$_3$, brine, dried over Na$_2$SO$_4$, and concentrated. The residue was used directly for the next step.

The demethylated intermediate obtained from the previous step was taken up in acetone (4 mL) and ethanol (2 mL) and was treated with HCl (4M in dioxane, 1.0 mL) at 0° C. The reaction mixture became clear and was stirred at rt for 30 min. The reaction mixture was then concentrated to dryness, and the residue was purified by prep-HPLC. The collected eluents were treated again with excess diluted HCl and lyophilized to give the desired product (15 mg, 0.0360 mmol, 7.75%) as a white solid. m/z=379, 381 $[C_{17}H_{19}BrN_2O_3+H]^+$.

Example 106

Quinuclidin-4-ylmethyl 4-bromo-5-methoxy-1H-indole-3-carboxylate hydrochloride (Compound 47)

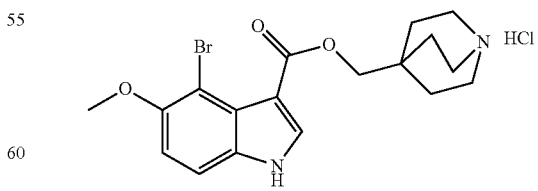

Quinuclidin-4-ylmethyl 4-bromo-5-methoxy-1H-indole-3-carboxylate hydrochloride was prepared using a similar procedure to Example 81. m/z=392.7, 294.9 $[C_{18}H_{21}BrN_2O_3+H]^+$.

Example 107

Quinuclidin-4-ylmethyl 5-methoxy-4-methyl-1H-indole-3-carboxylate hydrochloride (Compound 34)

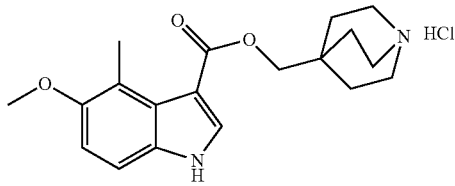 [SMILES: COc1ccc2[nH]cc(C(=O)OCC34CCN(CC3)CC4)c2c1C ; Cl]

Quinuclidin-4-ylmethyl 5-methoxy-4-methyl-1H-indole-3-carboxylate hydrochloride was prepared using a similar procedure to Example 81. m/z=329 $[C_{19}H_{24}N_2O_3+H]^+$.

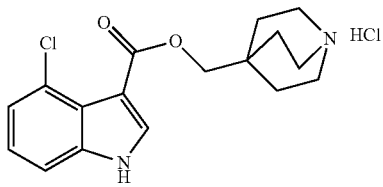 [SMILES: O=C(OCC12CCN(CC1)CC2)c1c[nH]c2cccc(Cl)c12 ; Cl]

Quinuclidin-4-ylmethyl 4-chloro-1H-indole-3-carboxylate hydrochloride was prepared using a similar procedure to Example 81. m/z=319 $[C_{17}H_{19}ClN_2O_2+H]^+$.

Example 109

Quinuclidin-4-ylmethyl 4,5-dimethoxy-1H-indole-3-carboxylate hydrochloride (Compound 40)

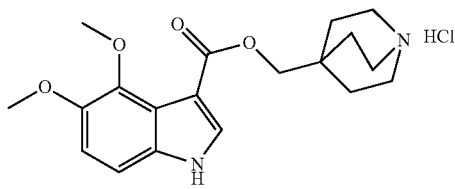 [SMILES: COc1ccc2[nH]cc(C(=O)OCC34CCN(CC3)CC4)c2c1OC ; Cl]

Quinuclidin-4-ylmethyl 4,5-dimethoxy-1H-indole-3-carboxylate hydrochloride was prepared using a similar procedure to Example 81. m/z=345 $[C_{19}H_{24}N_2O_4+H]^+$.

Example 110

Quinuclidin-4-ylmethyl 4-chloro-5-methoxy-1H-indole-3-carboxylate hydrochloride (Compound 39)

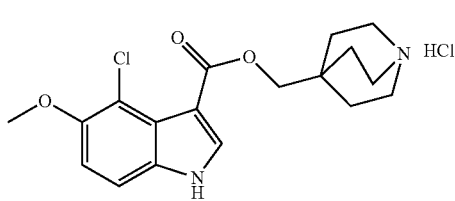 [SMILES: COc1ccc2[nH]cc(C(=O)OCC34CCN(CC3)CC4)c2c1Cl ; Cl]

Quinuclidin-4-ylmethyl 4-chloro-5-methoxy-1H-indole-3-carboxylate hydrochloride was prepared using a similar procedure to Example 81. m/z=349 $[C_{18}H_{21}ClN_2O_3+H]^+$.

Example 111

Quinuclidin-4-ylmethyl 4-bromo-6-methyl-1H-indole-3-carboxylate hydrochloride (Compound 49)

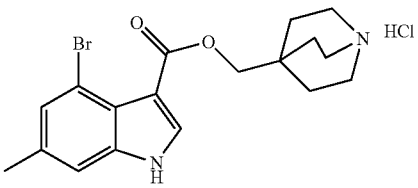 [SMILES: Cc1cc(Br)c2c(C(=O)OCC34CCN(CC3)CC4)c[nH]c2c1 ; Cl]

Quinuclidin-4-ylmethyl 4-bromo-6-methyl-1H-indole-3-carboxylate hydrochloride was prepared using a similar procedure to Example 81. m/z=376.9 $[C_{18}H_{21}BrN_2O_2]^+$.

Example 112

Quinuclidin-4-ylmethyl 2,3-dihydro-7H-[1,4]dioxino[2,3-e]indole-9-carboxylate hydrochloride (Compound 81)

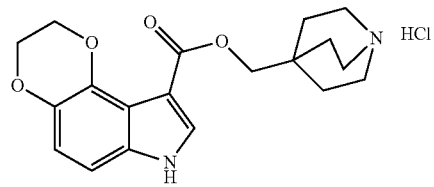

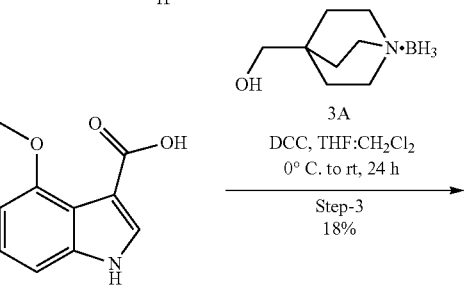

3

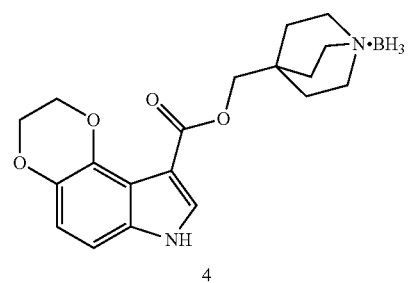

4

To a stirred solution of compound 3 (70 mg, 0.32 mmol) in dry CH$_2$Cl$_2$: THF (3.0+3.0 mL) was added DCC (198 mg, 0.960 mmol) and compound 3A (48 mg, 0.31 mmol) at 0° C. The reaction mixture was allowed warm to rt and was stirred for 24 h. The reaction progress was monitored by quenching an aliquot of the reaction mixture with water, spotting over an analytical silica gel TLC plate and visualizing under 254 nm UV light. The reaction progressed to completion with the formation of two non-polar spots. The $R_f$ values of the starting material and product were 0.2 and 0.3, respectively. The reaction mixture was quenched with ice cold water and extracted with EtOAc. The organic layer was washed with water and brine, dried over anhydrous $Na_2SO_4$, filtered and concentrated under reduced pressure to afford crude compound 4. The crude product was purified by mass trigger purification to afford compound 4 as a yellow solid. TLC system: 50% EtOAc in pet ether. Yield 20 mg (18%).

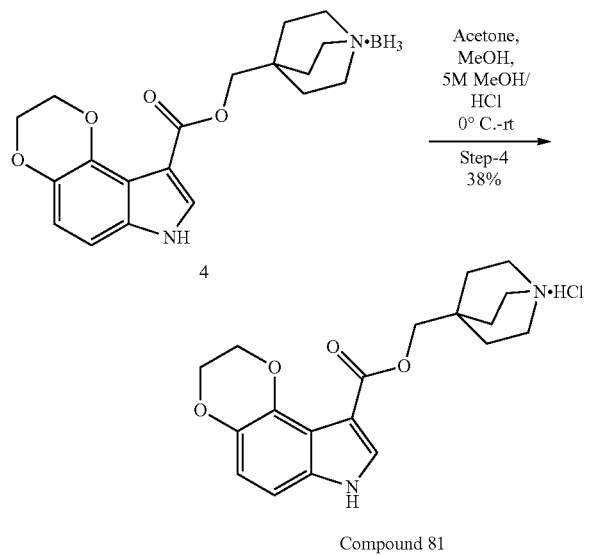

Compound 81

To a stirred suspension of compound 4 (10 mg, 0.028 mmol) in acetone (0.50 mL) and MeOH (0.20 mL) was added 5M HCl in MeOH (0.20 mL) at 0° C. The reaction was allowed to warm to rt and was stirred for 3 h. The reaction progress was monitored by spotting an aliquot of the reaction mass directly over an analytical silica gel TLC plate and visualizing under 254 nm UV light. The reaction progressed to completion with the formation of one polar spot. The $R_f$ values of the starting material and product were 0.5 and 0.1, respectively. The reaction mixture was concentrated under reduced pressure to afford crude compound. The crude compound was purified by triturating with acetone to afford compound 81 as a brown solid. TLC system: 10% $MeOH/CH_2Cl_2$. Yield: 4 mg (38%); m/z=342.84 [(M–HCl)+H]$^+$.

Example 113

Quinuclidin-4-ylmethyl 4-(trifluoromethyl)-1H-indole-3-carboxylate hydrochloride (Compound 80)

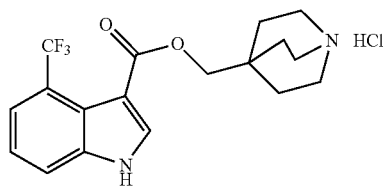 [SMILES: O=C(OCC12CCN(CC1)CC2)c1c[nH]c2cccc(C(F)(F)F)c12 ; Cl]

Quinuclidin-4-ylmethyl 4-(trifluoromethyl)-1H-indole-3-carboxylate hydrochloride was prepared using a similar procedure to Example 106. m/z=352.84 [(M–HCl)+H]$^+$.

Example 114

Quinuclidin-4-ylmethyl 5-fluoro-6-methyl-1H-indole-3-carboxylate hydrochloride (Compound 72)

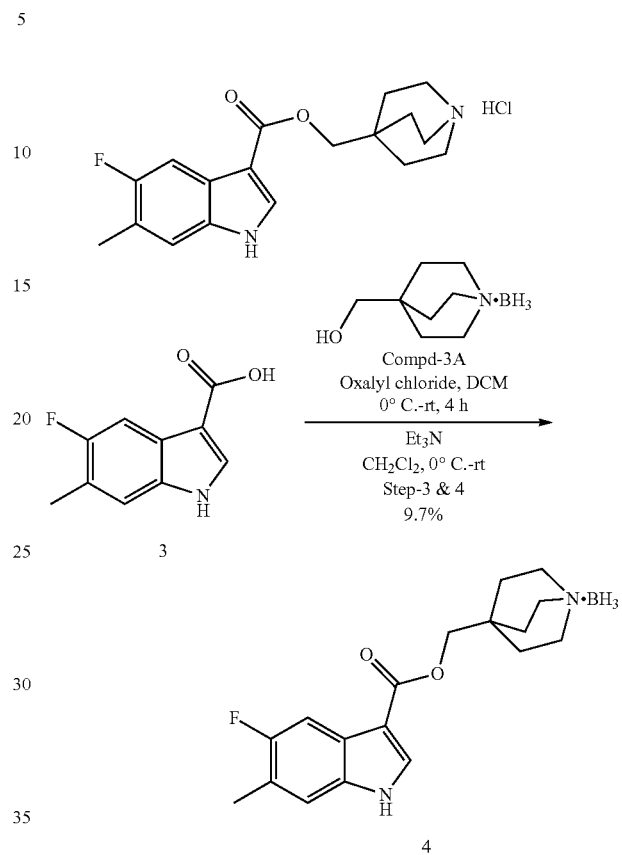

To a stirred solution of compound 3 (300 mg, 1.553 mmol) in dry $CH_2Cl_2$ (10 mL) was added oxalyl chloride (0.213 mL, 2.484 mmol) at 0° C. followed by one drop of anhydrous DMF. The reaction mixture was stirred at rt for 4 h. The reaction progress was monitored by quenching an aliquot of the reaction mixture with MeOH, spotting over an analytical silica gel TLC plate and visualizing under 254 nm UV light. The reaction progressed to completion with the formation of a non-polar spot (methyl ester). The solvent was evaporated to dryness under inert atmosphere to obtain the acid chloride (crude).

The above acid chloride was dissolved in dry $CH_2Cl_2$ (10 mL) at 0° C., and a solution of compound 3A (240 mg, 1.553 mmol) in dry $CH_2Cl_2$ (10 mL) followed by $Et_3N$ (0.301 mL, 2.329 mmol) was added. The reaction mixture was stirred at rt for 16 h. The reaction progress was monitored by quenching an aliquot of the reaction mixture with saturated aqueous $NaHCO_3$ solution and extracting with EtOAc. The organic layer was spotted over an analytical silica gel TLC plate and visualized using 254 nm UV light. The reaction progressed to completion with the formation of a non-polar spot. The $R_f$ values of the starting material and product were 0.2 and 0.5, respectively. The reaction mixture was diluted with saturated aqueous $NaHCO_3$ solution and extracted with EtOAc. The organic layer was washed with water and brine, dried over anhydrous $Na_2SO_4$, filtered and concentrated under reduced pressure to afford crude compound 4. The crude compound was purified by mass-based HPLC to afford compound 4 as an off-white solid. TLC system: 50% EtOAc in pet ether. Yield: 50 mg (9.7%).

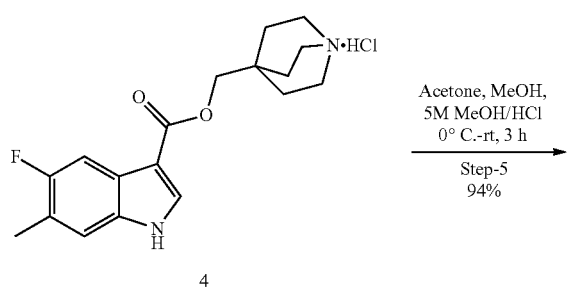

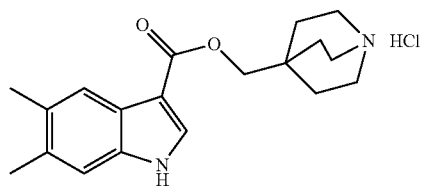 [SMILES: Cc1cc2[nH]cc(C(=O)OCC34CCN(CC3)CC4)c2cc1C ; Cl]

Compound 72

To a stirred suspension of compound 4 (45 mg, 0.1362 mmol) in acetone (1.0 mL) and MeOH (0.5 mL) was added 5M HCl in MeOH (0.5 mL) at 0° C. The reaction mixture was allowed to warm to rt and was stirred for 3 h. The reaction progress was monitored by spotting an aliquot of the reaction mass directly over an analytical silica gel TLC plate and visualizing under 254 nm UV light. The reaction progressed to completion with the formation of one polar spot. The $R_f$ values of the starting material and product were 0.5 and 0.0, respectively. The reaction mixture was concentrated under reduced pressure to afford crude compound. The crude compound was purified by triturating with acetone to afford an off-white solid. TLC system: 50% EtOAc in pet ether. Yield 45 mg (94%); m/z=317.20 [(M−HCl)+H]$^+$.

Example 115

Quinuclidin-4-ylmethyl 5,6-dimethyl-1H-indole-3-carboxylate hydrochloride (Compound 73)

Quinuclidin-4-ylmethyl 5,6-dimethyl-1H-indole-3-carboxylate hydrochloride was prepared using a similar procedure to Example 114. m/z=313.18 [(M−HCl)+H]$^+$.

Example 116 quinuclidin-4-ylmethyl 4,6-dichloro-1H-indole-3-carboxylate hydrochloride (Compound 71)

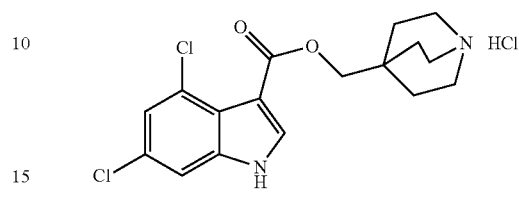

Quinuclidin-4-ylmethyl 4,6-dichloro-1H-indole-3-carboxylate hydrochloride was prepared using a similar procedure to Example 114. m/z=351.12 [(M−HCl)+H]$^+$.

Example 117

Quinuclidin-4-ylmethyl 4-cyclopropyl-1H-indole-3-carboxylate (Compound 61)

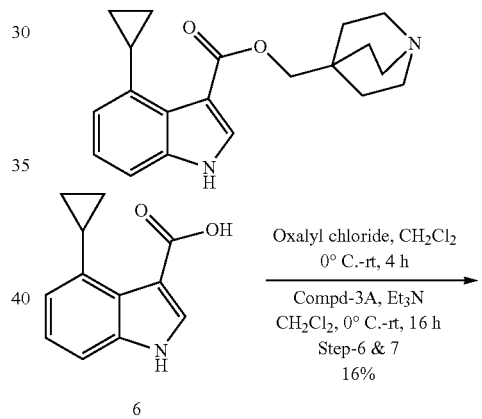

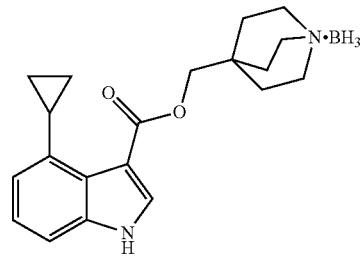

To a stirred solution of compound 6 (0.210 g, 1.04 mmol) in dry CH$_2$Cl$_2$ (10.0 mL) was added oxalyl chloride (0.14 mL, 1.7 mmol) at 0° C. followed by one drop of anhydrous DMF. The reaction was stirred at rt for 4 h. The reaction progress was monitored by quenching an aliquot of the reaction mixture with MeOH, spotting over an analytical silica gel TLC plate and visualizing under 254 nm UV light. The reaction progressed to completion with the formation of a non-polar spot (methyl ester). The solvent was evaporated to dryness under inert atmosphere to obtain the acid chloride (0.210 g, crude). The above acid chloride was dissolved in dry $CH_2Cl_2$ (10.0 mL) at 0° C., and a solution of compound 3A (0.162 g, 1.04 mmol) in dry $CH_2Cl_2$ (10.0 mL) followed by $Et_3N$ (0.23 mL, 1.7 mmol) was added. The reaction was then stirred at rt for 16 h. The reaction progress was monitored by quenching an aliquot of the reaction mixture with saturated aqueous $NaHCO_3$ solution and extracted with EtOAc. The organic layer was spotted over an analytical silica gel TLC plate and visualized using 254 nm UV light. The reaction progressed to completion with the formation of a nonpolar spot. The $R_f$ values of the starting material and product were 0.2 and 0.3, respectively. The reaction mixture was diluted with saturated aqueous $NaHCO_3$ solution (25.0 mL) and extracted with EtOAc (2×50.0 mL). The organic layer was dried over anhydrous $Na_2SO_4$, filtered and concentrated under reduced pressure to afford crude compound 7. The crude compound was purified by flash column using 230-400 mesh silica gel and eluted with 38% EtOAc in Pet-ether to afford compound 7 as an off-white solid. TLC system: 30% EtOAc in pet ether. Yield 0.056 g (16%).

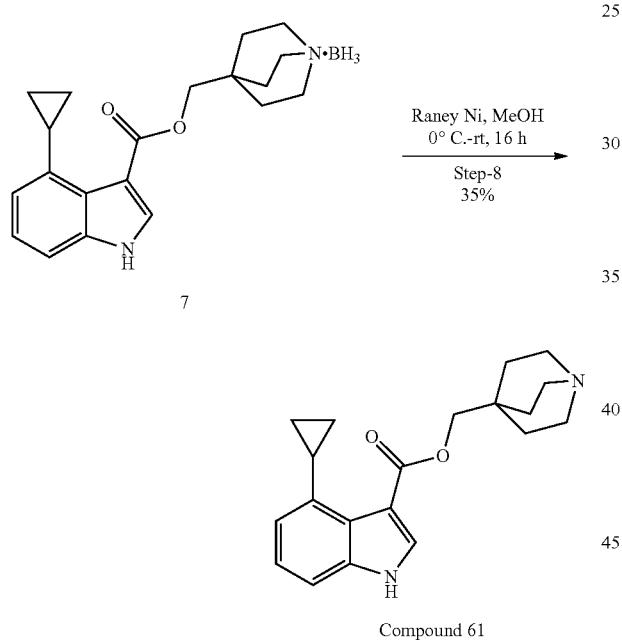

To an ice cold stirred solution of compound 7 (0.120 g, 0.355 mmol) in MeOH (10.0 mL) was added Raney nickel (0.104 g, 1.77 mmol). The reaction was stirred at rt for 16 h. The reaction progress was monitored by directly spotting the reaction mass over an analytical silica gel TLC plate and visualizing under 254 nm UV light. The reaction progressed to completion with the formation of a polar spot. The $R_f$ values of the starting material and product were 0.8 and 0.2, respectively. The reaction mixture was filtered through a pad of celite, and the filtrate was concentrated under reduced pressure to afford crude compound. The crude compound was purified by preparative TLC to afford compound 61 as an off-white solid. TLC system: 20% MeOH in $CH_2Cl_2$. Yield 0.040 g (35%); m/z=325.21 $[M+H]^+$.

Example 118

Quinuclidin-4-ylmethyl 5-fluoro-6-hydroxy-1H-indole-3-carboxylate hydrochloride (Compound 59)

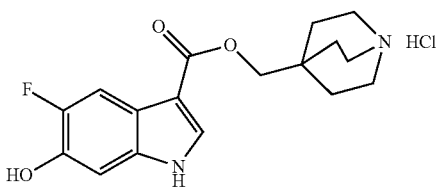 [SMILES: O=C(OCC12CCN(CC1)CC2)c1c[nH]c2cc(O)c(F)cc12 ; Cl]

Quinuclidin-4-ylmethyl 5-fluoro-6-hydroxy-1H-indole-3-carboxylate hydrochloride was prepared using a similar procedure to Example 114. m/z=316.70 $[(M-H)-HCl]^-$.

Example 119

Quinuclidin-4-ylmethyl 5,6-difluoro-1H-indole-3-carboxylate hydrochloride (Compound 51)

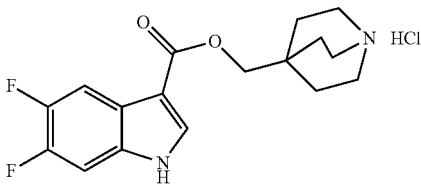 [SMILES: O=C(OCC12CCN(CC1)CC2)c1c[nH]c2cc(F)c(F)cc12 ; Cl]

Quinuclidin-4-ylmethyl 5,6-difluoro-1H-indole-3-carboxylate hydrochloride was prepared using a similar procedure to Example 114. m/z=321.05 $[(M-HCl)+H]^+$.

Example 120

Quinuclidin-4-ylmethyl 6-methyl-1H-indole-3-carboxylate hydrochloride (Compound 45)

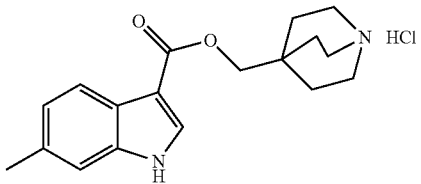 [SMILES: Cc1ccc2c(C(=O)OCC34CCN(CC3)CC4)c[nH]c2c1 ; Cl]

Quinuclidin-4-ylmethyl 6-methyl-1H-indole-3-carboxylate hydrochloride was prepared using a similar procedure to Example 114. m/z=299.10 $[(M-HCl)+H]^+$.

Example 121

Quinuclidin-4-ylmethyl 6-chloro-5-fluoro-1H-indole-3-carboxylate hydrochloride (Compound 52)

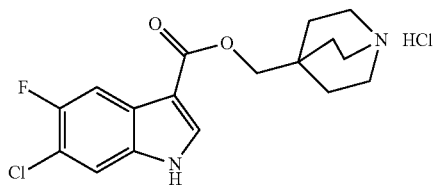 [SMILES: O=C(OCC12CCN(CC1)CC2)c1c[nH]c2cc(Cl)c(F)cc12 ; Cl]

Quinuclidin-4-ylmethyl 6-chloro-5-fluoro-1H-indole-3-carboxylate hydrochloride was prepared using a similar procedure to Example 114. m/z=337.06 [(M−HCl)+H]⁺.

Example 122

Quinuclidin-4-ylmethyl 5-fluoro-6-methoxy-1H-indole-3-carboxylate hydrochloride (Compound 32)

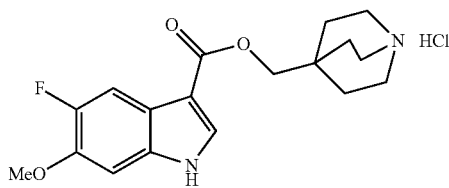 [SMILES: COc1cc2[nH]cc(C(=O)OCC34CCN(CC3)CC4)c2cc1F ; Cl]

Quinuclidin-4-ylmethyl 5-fluoro-6-methoxy-1H-indole-3-carboxylate hydrochloride was prepared using a similar procedure to Example 114. m/z=333.12 [(M−HCl)+H]⁺.

Example 123

Quinuclidin-4-ylmethyl 4-fluoro-6-methoxy-1H-indole-3-carboxylate hydrochloride (Compound 33)

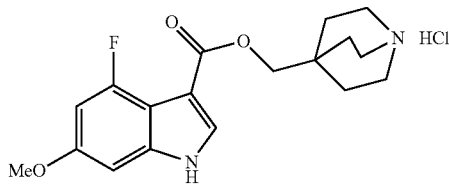 [SMILES: COc1cc(F)c2c(C(=O)OCC34CCN(CC3)CC4)c[nH]c2c1 ; Cl]

Quinuclidin-4-ylmethyl 4-fluoro-6-methoxy-1H-indole-3-carboxylate hydrochloride was prepared using a similar procedure to Example 114. m/z=333.12 [(M−HCl)+H]⁺.

Example 124

Quinuclidin-4-ylmethyl 2,3-dihydro-6H-[1,4]dioxino[2,3-f]indole-8-carboxylate hydrochloride (Compound 30)

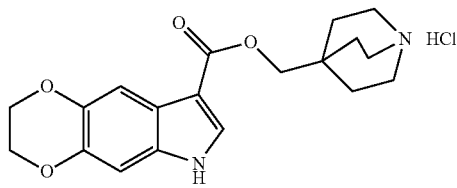 [SMILES: O=C(OCC12CCN(CC1)CC2)c1c[nH]c2cc3c(cc12)OCCO3 ; Cl]

Quinuclidin-4-ylmethyl 2,3-dihydro-6H-[1,4]dioxino[2,3-f]indole-8-carboxylate hydrochloride was prepared using a similar procedure to Example 114. m/z=343.13 [(M−HCl)+H]⁺.

Example 125

Quinuclidin-4-ylmethyl 6-(difluoromethoxy)-1H-indole-3-carboxylate hydrochloride (Compound 31)

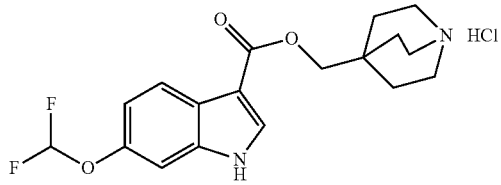 [SMILES: O=C(OCC12CCN(CC1)CC2)c1c[nH]c2cc(OC(F)F)ccc12 ; Cl]

Quinuclidin-4-ylmethyl 6-(difluoromethoxy)-1H-indole-3-carboxylate hydrochloride was prepared using a similar procedure to Example 114. m/z=351.2 [(M−HCl)+H]⁺.

Example 126

Quinuclidin-4-ylmethyl 6-(trifluoromethoxy)-1H-indole-3-carboxylate hydrochloride (Compound 29)

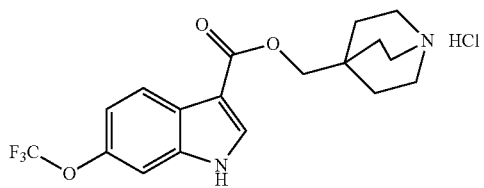 [SMILES: O=C(OCC12CCN(CC1)CC2)c1c[nH]c2cc(OC(F)(F)F)ccc12 ; Cl]

Quinuclidin-4-ylmethyl 6-(trifluoromethoxy)-1H-indole-3-carboxylate hydrochloride was prepared using a similar procedure to Example 114. m/z=369.05 [(M−HCl)+H]⁺.

Example 127 quinuclidin-4-ylmethyl 4-chloro-5-fluoro-1H-indole-3-carboxylate hydrochloride (Compound 62)

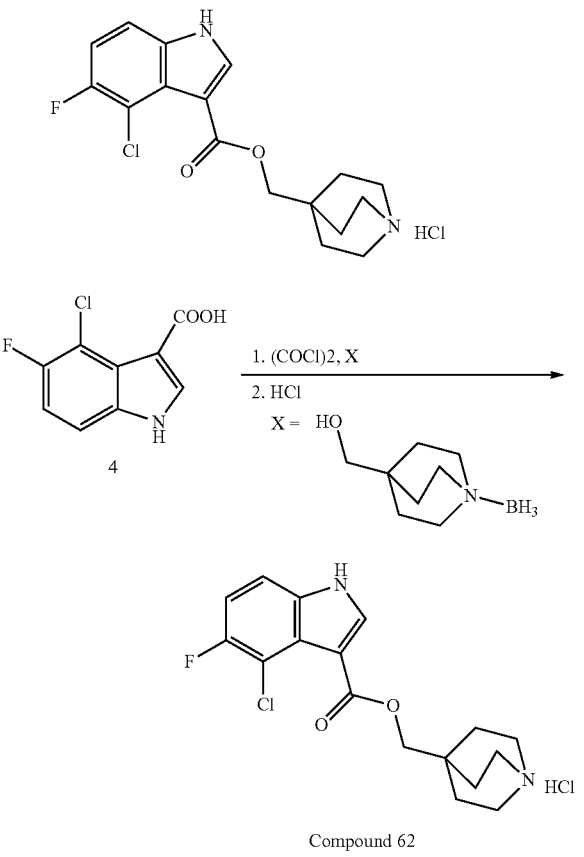

To an ice-cooled mixture of compound 4 (213 mg, 1 mmol) in DCM (10 mL) were added oxalyl chloride (252 mg, 2 mmol) and DMF (one drop). The reaction mixture was stirred at rt for 30 min and then concentrated. To the residue was added DCM (3 mL), and a cloudy mixture was formed (crude acid chloride). To another flask charged with quinuclidin-4-ylmethanol borane complex (140 mg, 0.9 mmol) was added DCM (5 mL) and TEA (151 mg, 1.5 mmol). The mixture was cooled to 0° C., and previously prepared crude acid chloride solution was added over 10 min. The reaction mixture was stirred at room temperature for 0.5 h and then quenched with saturated aqueous ammonium chloride solution (10 mL). The two phases were separated, and the organic phase was washed with saturated aqueous $NaHCO_3$ (10 mL) and brine (10 mL). The combined organic layers were washed, dried, concentrated, and purified by column chromatography (DCM:PE:Acetone=50:20:1) to provide $BH_3$—Compound 62 (150 mg, 39.6%) as a yellow solid.

A suspension of $BH_3$—Compound 62 (150 mg, 0.43 mmol) in acetone (1.0 mL) and ethanol (1.0 mL) was treated with HCl (5.0 M in ethyl acetate, 5 mL) at 0° C. After 50 min, the reaction mixture was concentrated. The residue was dissolved in MeOH (2 mL) and partitioned between ethyl acetate and water. The combined aqueous layers were concentrated under reduced pressure to a volume of 1 mL. The mixture was cooled to rt, and the resulting precipitate was collected by filtration. The solid was dried under vacuum to afford compound 62 (80 mg, 50%) as a white solid. m/z=337.22 $[M+H]^+$.

Example 128 quinuclidin-4-ylmethyl 4-chloro-5-methyl-1H-indole-3-carboxylate (Compound 63)

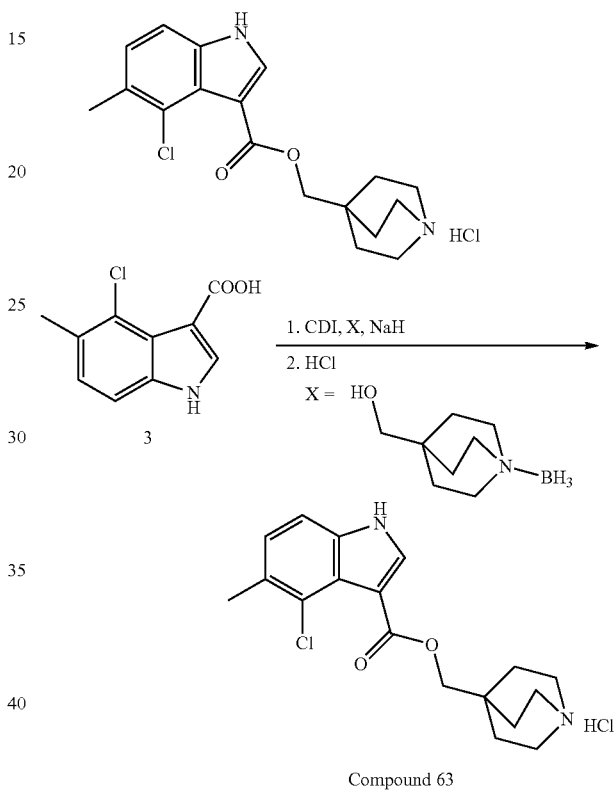

CDI (464 mg, 2.87 mmol) was added to a solution of compound 3 (400 mg, 1.91 mmol) in DMF (10 mL). The mixture was stirred at rt for 0.5 h before quinuclidin-4-ylmethanol borane complex (266 mg, 1.72 mmol) was added. The mixture was cooled to 0° C., and NaH (60%, 206 mg, 5.16 mmol) was added portion-wise. The reaction mixture was stirred at room temperature for 0.5 h and then quenched with saturated ammonium chloride solution (10 mL). The aqueous phase was extracted with ethyl acetate (2×50 mL). The organic phase was combined and washed over brine and concentrated in vacuo. DCM (5 mL) was added to the residue and stirred for 10 min. The resulting solid was collected by filtration to give $BH_3$—Compound 63 (380 mg, 57.4%) as a white solid.

A suspension of $BH_3$—Compound 63 (300 mg, 0.87 mmol) in acetone (3 mL) and ethanol (3 mL) was treated with HCl (5.0 M in ethyl acetate 3 mL) at 0° C. After 50 min, the reaction mixture was concentrated in vacuo. DCM (5 mL) was added to the residue and stirred for 10 min. The resulting solid was collected by filtration to give compound 63 (161 mg, 55.9%) as a white solid. m/z=333.25 $[M+H]^+$.

Example 129 quinuclidin-4-ylmethyl 4-chloro-6-fluoro-1H-indole-3-carboxylate hydrochloride (Compound 64)

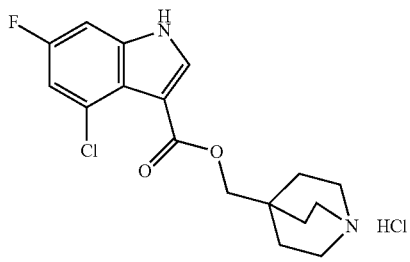 [SMILES: O=C(OCC12CCN(CC1)CC2)c1c[nH]c2cc(F)cc(Cl)c12 ; Cl]

Quinuclidin-4-ylmethyl 4-chloro-6-fluoro-1H-indole-3-carboxylate hydrochloride was prepared using a similar procedure to Example 128. m/z=337.22 [M+H]$^+$.

Example 130 quinuclidin-4-ylmethyl 4-chloro-6-methyl-1H-indole-3-carboxylate hydrochloride (Compound 65)

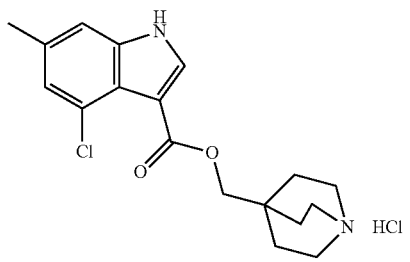 [SMILES: Cc1cc(Cl)c2c(C(=O)OCC34CCN(CC3)CC4)c[nH]c2c1 ; Cl]

Quinuclidin-4-ylmethyl 4-chloro-6-methyl-1H-indole-3-carboxylate hydrochloride was prepared using a similar procedure to Example 128. m/z=333.25 [M+H]$^+$.

Example 131 quinuclidin-4-ylmethyl 5-chloro-6-methyl-1H-indole-3-carboxylate hydrochloride (Compound 66)

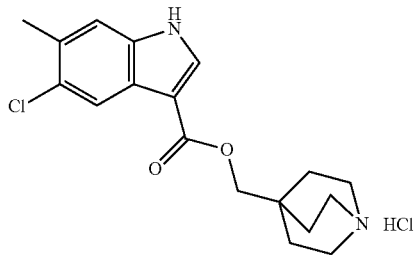 [SMILES: Cc1cc2[nH]cc(C(=O)OCC34CCN(CC3)CC4)c2cc1Cl ; Cl]

Quinuclidin-4-ylmethyl 5-chloro-6-methyl-1H-indole-3-carboxylate hydrochloride was prepared using a similar procedure to Example 128. m/z=333.12 [M+H]$^+$.

Example 132 quinuclidin-4-ylmethyl 6-chloro-4-methoxy-1H-indole-3-carboxylate hydrochloride (Compound 74)

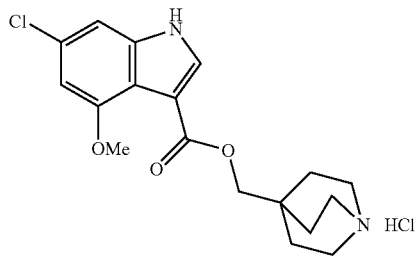 [SMILES: COc1cc(Cl)cc2[nH]cc(C(=O)OCC34CCN(CC3)CC4)c12 ; Cl]

Quinuclidin-4-ylmethyl 6-chloro-4-methoxy-1H-indole-3-carboxylate hydrochloride was prepared using a similar procedure to Example 128. m/z=349.19 [M+H]$^+$.

Example 133 quinuclidin-4-ylmethyl 5-methoxy-6-methyl-1H-indole-3-carboxylate hydrochloride (Compound 79)

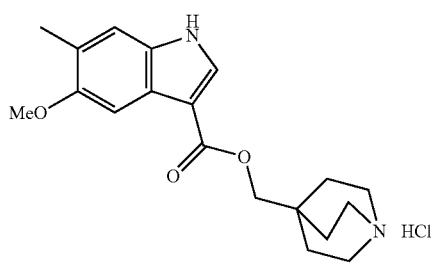 [SMILES: COc1cc2c(C(=O)OCC34CCN(CC3)CC4)c[nH]c2cc1C ; Cl]

Quinuclidin-4-ylmethyl 5-methoxy-6-methyl-1H-indole-3-carboxylate hydrochloride was prepared in a similar manner to other compounds described herein. m/z=329.84 [M+H]$^+$.

Example 134 quinuclidin-4-ylmethyl 6-hydroxy-4-methyl-1H-indole-3-carboxylate (Compound 83)

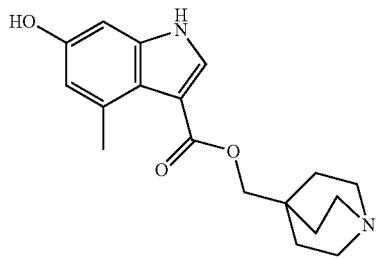 [SMILES: Cc1cc(O)cc2[nH]cc(C(=O)OCC34CCN(CC3)CC4)c12]

Quinuclidin-4-ylmethyl 6-hydroxy-4-methyl-1H-indole-3-carboxylate was prepared in a similar manner to other compounds described herein. m/z=315.20 [M+H]$^+$.

Example 135 quinuclidin-4-ylmethyl 4-methoxy-5-(2,2,2-trifluoroethoxy)-1H-indole-3-carboxylate (Compound 88)

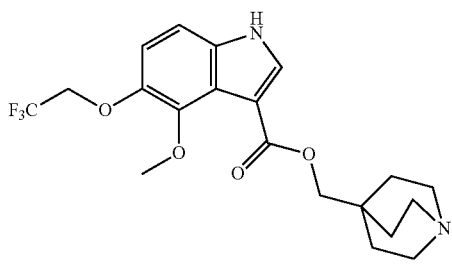 [SMILES: COc1c(OCC(F)(F)F)ccc2[nH]cc(C(=O)OCC34CCN(CC3)CC4)c12]

Quinuclidin-4-ylmethyl 4-methoxy-5-(2,2,2-trifluoroethoxy)-1H-indole-3-carboxylate was prepared in a similar manner to other compounds described herein. m/z=413.35 [M+H]$^+$.

Example 136 quinuclidin-4-ylmethyl 4-methyl-6-(pivaloyloxy)-1H-indole-3-carboxylate (Compound 89)

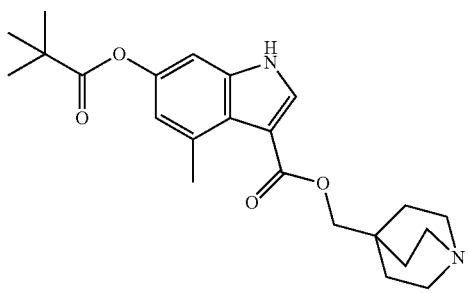 [SMILES: Cc1cc(OC(=O)C(C)(C)C)cc2[nH]cc(C(=O)OCC34CCN(CC3)CC4)c12]

Quinuclidin-4-ylmethyl 4-methyl-6-(pivaloyloxy)-1H-indole-3-carboxylate was prepared in a similar manner to other compounds described herein. m/z=399.33 [M+H]$^+$.

Example 137 quinuclidin-4-ylmethyl 6-(trifluoromethyl)-1H-indole-3-carboxylate (Compound 90)

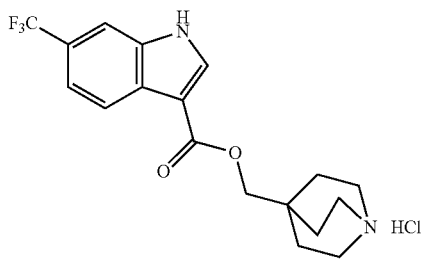 [SMILES: O=C(OCC12CCN(CC1)CC2)c1c[nH]c2cc(C(F)(F)F)ccc12 ; Cl]

Quinuclidin-4-ylmethyl 6-(trifluoromethyl)-1H-indole-3-carboxylate was prepared in a similar manner to other compounds described herein. m/z=353.16 [M+H]$^+$.

Example 138 quinuclidin-4-ylmethyl 5-(2-methoxyethoxy)-4-methyl-1H-indole-3-carboxylate (Compound 91)

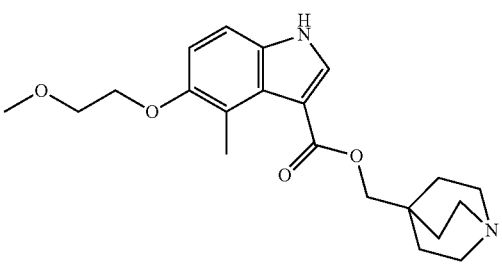 [SMILES: COCCOc1ccc2[nH]cc(C(=O)OCC34CCN(CC3)CC4)c2c1C]

Quinuclidin-4-ylmethyl 5-(2-methoxyethoxy)-4-methyl-1H-indole-3-carboxylate was prepared in a similar manner to other compounds described herein. m/z=373.30 [M+H]$^+$.

Example 139 quinuclidin-4-ylmethyl 5-(3-methoxypropoxy)-4-methyl-1H-indole-3-carboxylate (Compound 92)

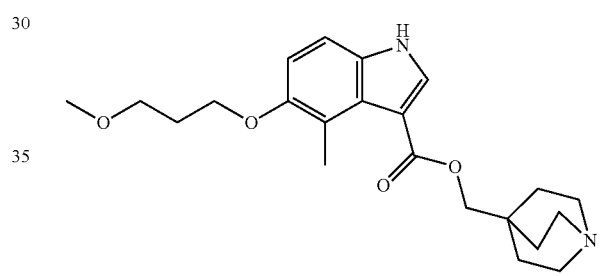

Quinuclidin-4-ylmethyl 5-(3-methoxypropoxy)-4-methyl-1H-indole-3-carboxylate was prepared in a similar manner to other compounds described herein. m/z=385.21 [M−H]

Example 140 quinuclidin-4-ylmethyl 6-acetamido-4-methyl-1H-indole-3-carboxylate (Compound 93)

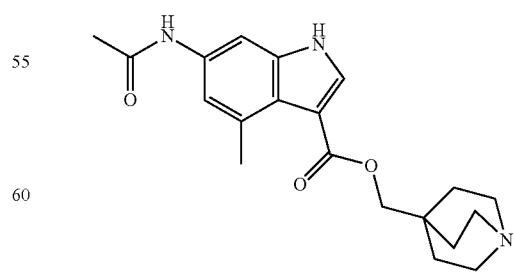

Quinuclidin-4-ylmethyl 6-acetamido-4-methyl-1H-indole-3-carboxylate was prepared in a similar manner to other compounds described herein. m/z=356.23 [M+H]$^+$.

Example 141 quinuclidin-4-ylmethyl 4-methyl-5-(2,2,2-trifluoroethoxy)-1H-indole-3-carboxylate (Compound 94)

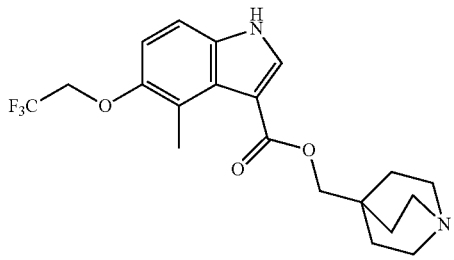 [SMILES: Cc1c(OCC(F)(F)F)ccc2[nH]cc(C(=O)OCC34CCN(CC3)CC4)c12]

Quinuclidin-4-ylmethyl 4-methyl-5-(2,2,2-trifluoroethoxy)-1H-indole-3-carboxylate was prepared in a similar manner to other compounds described herein. m/z=395.11 [M−H]⁻.

Example 142 quinuclidin-4-ylmethyl 5-(2-hydroxyethoxy)-4-methyl-1H-indole-3-carboxylate, 2,2,2-trifluoroacetate salt (Compound 95)

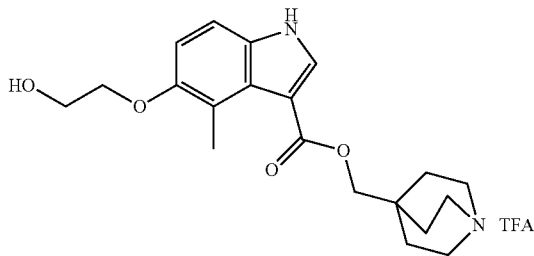 [SMILES: Cc1c(OCCO)ccc2[nH]cc(C(=O)OCC34CCN(CC3)CC4)c12 ; "TFA"]

Quinuclidin-4-ylmethyl 5-(2-hydroxyethoxy)-4-methyl-1H-indole-3-carboxylate, 2,2,2-trifluoroacetate salt was prepared in a similar manner to other compounds described herein. m/z=359.32 [M+H]⁺.

Example 143 quinuclidin-4-ylmethyl 4-methyl-5-(3-(methylamino)propoxy)-1H-indole-3-carboxylate dihydrochloride (Compound 96)

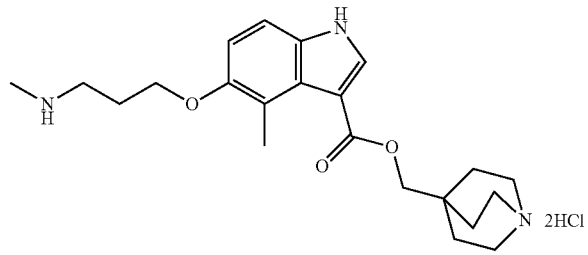 [SMILES: CNCCCOc1ccc2[nH]cc(C(=O)OCC34CCN(CC3)CC4)c2c1C ; "2HCl"]

Quinuclidin-4-ylmethyl 4-methyl-5-(3-(methylamino)propoxy)-1H-indole-3-carboxylate dihydrochloride was prepared in a similar manner to other compounds described herein. m/z=386.35 [M+H]⁺.

Example B1

Rat Brain Nicotinic Receptor Radioligand Binding Assay

Protocol 1: The assay was conducted following the literature reference Meyer E. M., et al., Analysis of 3-(4-Hydroxy, 2-Methoxybenzylidene) Anabaseine Selectivity and Activity at Human and Rat Alpha-7 Nicotinic Receptors, *J. Pharmacol. Exp. Ther.*, 287: 918-925, 1998. The assay was conducted using the following materials: receptor source: rat brain, radioligand: [$^{125}$I] α-Bungarotoxin (2200 $C_i$/mmol) with a final concentration of 1 nM, non-specific determinant: Methyllycaconitine (MLA) [1 μM], reference compound: Methyllycaconitine (MLA), and positive control: Methyllycaconitine (MLA). Results for compounds tested are presented in Table 4.

Incubation Conditions: Reactions were carried out in 20 mM HEPES (pH 7.4) containing 120 mM NaCl, 5 mM KCl, 2.5 mM $CaCl_2$ and 1.2 mM $MgSO_4$ at 37° C. for 90 minutes. The reaction was terminated by rapid vacuum filtration onto glass fiber filters. Radioactivity trapped onto the filters was determined by liquid scintillation counting and compared to control values in order to ascertain any interactions of test compound with the nicotinic, ganglionic binding site. $IC_{50}$ was calculated, fitting to a sigmoidal dose-response (variable slope) equation.

Protocol 2: Studies were carried out using rat brain P2 membrane. All membrane was obtained from male Sprague-Dawley (SD) rats and collected on phosphate buffer. Protein concentration was determined using the bicinchoninic acid (BCA) protein assay reagent. In an α-Bungarotoxin binding assay, membrane was diluted with assay buffer (50 mM potassium phosphate, 1 mM pH 8.0 EDTA, 0.1 mM PMSF, 0.1% BSA). Test compounds were prepared in 100% DMSO solution. The starting concentration of the test compound was 3 μM, 8 points in 3 fold dilution. Assays were performed in a total volume of 200 μL containing [$^3$H] α-Bungarotoxin (final concentration 0.4 nM), membrane suspension (80 μL containing 150 μg of membrane protein) and 20 μL of test compound. Non-specific binding (NSB) was determined with 1 μM α-Bungarotoxin. After 3 hours incubation (37° C.), the assay solution was transferred to a GF/B plate (Millipore). The assay was terminated by adding 100 μL ice-cold PBS dilution and then rapidly filtering over glass fiber filters presoaked in 0.5% polyethylenimine. The filters were washed 4 times with 200 μL/well of ice-cold PBS. They were then were transferred to the reading plate, and 250 μL of microscine 40 was added. The radioactivity trapped by the filters was determined by liquid scintillation counting MicroBeta. $IC_{50}$ was calculated using GraphPad Prism V5.0 software, fitting to a sigmoidal dose-response (variable slope) equation. Results for the compounds tested are presented in Table 6.

TABLE 6

Nicotinic Receptor Radioligand Binding Assay Data

| Compound No. | $IC_{50}$ (μM) | $K_i$ (μM) | Protocol No. |
|---|---|---|---|
| 1 | 0.0318 | 0.0276 | 1 |
| 2 | 0.328 | 0.287 | 1 |
| 10 | 0.321 | 0.279 | 1 |
| 11 | 0.261 | 0.228 | 1 |
| 12 | 0.08655 | 0.07505 | 1 |
| 13 | 0.0141 | 0.0122 | 1 |

TABLE 6-continued

Nicotinic Receptor Radioligand Binding Assay Data

| Compound No. | IC$_{50}$ (μM) | K$_i$ (μM) | Protocol No. |
|---|---|---|---|
| 14 | 0.06195 | 0.0537 | 1 |
| 15 | 0.153 | 0.132 | 1 |
| 16 | 1.4 | 1.21 | 1 |
| 17 | 0.376 | 0.329 | 1 |
| 18 | 0.0326 | 0.0283 | 1 |
| 19 | 0.764 | 0.665 | 1 |
| 20 | 0.0681 | 0.0601 | 1 |
| 21 | 0.0588 | 0.0509 | 1 |
| 22 | 0.607 | 0.532 | 1 |
| 23 | 0.424 | 0.374 | 1 |
| 24 | 0.0581 | 0.0504 | 1 |
| 25 | 1.65 | 1.45 | 1 |
| 26 | 0.451 | 0.398 | 1 |
| 27 | 0.282 | 0.247 | 1 |
| 28 | 0.92 | 0.7955 | 1 |
| 29 | 3.71 | 3.24 | 1 |
| 30 | 0.0925 | 0.0811 | 1 |
| 31 | 0.788 | 0.689 | 1 |
| 32 | 0.306 | 0.267 | 1 |
| 33 | 0.0496 | 0.0432 | 1 |
| 34 | 0.0236 | 0.0204 | 1 |
| 35 | 0.0266 | 0.02295 | 1 |
| 36 | 0.0489 | 0.0423 | 1 |
| 37 | 1.11 | 0.957 | 1 |
| 38 | 0.396 | 0.341 | 1 |
| 39 | 0.0239 | 0.0206 | 1 |
| 40 | 0.0696 | 0.06 | 1 |
| 41 | 0.76 | 0.655 | 1 |
| 42 | 1.1 | 0.944 | 1 |
| 43 | 0.207 | 0.177 | 1 |
| 44 | 0.48 | 0.412 | 1 |
| 45 | 0.0736 | 0.0631 | 1 |
| 46 | 0.0334 | 0.0286 | 1 |
| 47 | 0.0333 | 0.0285 | 1 |
| 48 | 0.42 | 0.36 | 1 |
| 49 | 0.25 | 0.214 | 1 |
| 50 | 1.29 | 1.1 | 1 |
| 51 | 0.662 | 0.568 | 1 |
| 52 | 0.938 | 0.805 | 1 |
| 53 | 0.0536 | 0.046 | 1 |
| 54 | 0.4 | 0.343 | 1 |
| 55 | 0.0523 | 0.0448 | 1 |
| 56 | 0.644 | 0.552 | 1 |
| 57 | 0.257 | 0.221 | 1 |
| 58 | 1.81 | 1.55 | 1 |
| 59 | 0.0701 | 0.0602 | 1 |
| 60 | 0.474 | 0.407 | 1 |
| 61 | 1.89 | 1.62 | 1 |
| 62 | 0.113 | 0.0976 | 1 |
| 63 | 0.117 | 0.101 | 1 |
| 64 | 0.337 | 0.291 | 1 |
| 65 | 0.0636 | 0.0546 | 1 |
| 66 | 1.19 | 1.01 | 1 |
| 67 | 0.201 | 0.173 | 1 |
| 68 | 0.266 | 0.229 | 1 |
| 69 | 0.394 | 0.34 | 1 |
| 70 | 0.315 | 0.272 | 1 |
| 71 | 0.457 | 0.394 | 1 |
| 72 | 0.145 | 0.125 | 1 |
| 73 | 0.168 | 0.145 | 1 |
| 74 | 0.181 | 0.154 | 1 |
| 75 | 0.0525 | 0.045 | 1 |
| 76 | 0.643 | 0.552 | 1 |
| 77 | 0.423 | 0.363 | 1 |
| 78 | 1.13 | 0.97 | 1 |
| 79 | 0.159 | 0.137 | 1 |
| 80 | 0.203 | 0.176 | 1 |
| 82 | 0.412 | 0.357 | 1 |
| 83 | 0.0318 | 0.0279 | 1 |
| 84 | 3.336 | 7.183 | 2 |
| 85 | 0.1797 | 0.3569 | 2 |
| 87 | 1.558 | 2.707 | 2 |
| 88 | 0.2111 | 0.3559 | 2 |
| 89 | 1.071 | 2.133 | 2 |
| 90 | >3 | >3 | 2 |
| 91 | 0.2206 | 0.8591 | 2 |
| 92 | 0.0761 | 0.1334 | 2 |
| 93 | 1.312 | 2.872 | 2 |
| 94 | 0.1622 | 0.2298 | 2 |
| 95 | 0.2133 | 0.4142 | 2 |

Example B2

Electrophysiology Screen at 1 μM in *Xenopus Laevis* Oocytes

Human α7 NAChR mRNA Preparation:

Human α7 NAChR plasmid was prepared by GeneWiz from accession NM_000746.5. Human α7 NAChR mRNA was prepared by TriLink at a concentration near 1 μg/μL. The human α7 NAChR mRNA was diluted in sterile water to a working concentration near 10 ng/μL.

*Xenopus laevis* Oocyte Injection and Maintenance:

Oocytes were obtained from *Xenopus laevis* frogs and treated with collagenase by Ecocyte Bioscience. Oocytes were injected with the working concentration of α7 NAChR mRNA at a volume of 50 nL for a total of approximately 0.5 ng of α7 NAChR mRNA. Oocytes were maintained in Barth's solution at a temperature of 16° C. The Barth's solution was replaced daily.

Electrophysiology Measurement:

Two-electrode voltage clamp recordings were made 3-14 days following mRNA injections at a holding voltage of −70 mV. The NAChR recordings were performed in $Ca^{++}$-free Ringer solution (115 mM NaCl, 2 mM KCl, 1.8 mM $BaCl_2$, 5 mM HEPES; pH~7.4) to limit $Ca^{++}$-activated chloride currents.

In all oocyte recordings, drug and wash solutions were applied using a custom-designed microcapillary "linear array" which allows rapid application of agonists. Currents were recorded on a PC-based computer (PClamp, Molecular Devices, Sunnyvale, Calif.). Responses were reported as $(I/I_{max})$, where I is the amount of current given by a selected concentration of drug and $I_{max}$ is the amount of maximal current produced by a 3 mM solution of ACh.

Stocks of test compounds were prepared in DMSO. Test solutions in Ringer were prepared immediately before application of test compound (final DMSO concentration of 0.1%). The final concentration of test compound in the test solution was 1 μM. The test solution was perfused onto the oocyte until a peak current was recorded. There was approximately two minutes of wash time with only the Ringer solution between each application of agonist. Measurement of the test solution was repeated between 2 and 6 times with a two minute wash time between each application of test solution. An average of the currents for each test compound was used to define the response for the test compound. Results for compounds tested are shown in Table 7.

TABLE 7

Electrophysiology Screen at 1 μM in *Xenopus Laevis* Oocytes Data

| Compound No. | $I/I_{max}$ |
| --- | --- |
| 21 | 0.308 |
| 62 | 0.171 |
| 63 | 0.118 |
| 65 | 0.212 |
| 72 | 0.347 |
| 73 | 0.367 |
| 74 | 0.157 |
| 79 | 0.259 |
| 80 | 0.032 |
| 88 | 0.185 |
| 91 | 0.205 |
| 92 | 0.266 |

Example B3

Electrophysiology in *Xenopus Laevis* Oocytes

Human α7 NAChR mRNA Preparation:

Human α7 NAChR plasmid is prepared by GeneWiz from accession NM_000746.5. Human α7 NAChR mRNA is prepared by TriLink at a concentration near 1 μg/μL. The human α7 NAChR mRNA is diluted in sterile water to a working concentration near 10 ng/μL.

*Xenopus laevis* Oocyte Injection and Maintenance:

Oocytes are obtained from *Xenopus laevis* frogs and treated with collagenase by Ecocyte Bioscience. Oocytes are injected with the working concentration of α7 NAChR mRNA at a volume of 50 nL for a total of approximately 0.5 ng of α7 NAChR mRNA. Oocytes are maintained in Barth's solution at a temperature of 16° C. The Barth's solution is replaced daily.

Electrophysiology Measurement:

Two-electrode voltage clamp recordings are made 3-14 days following mRNA injections at a holding voltage of −70 mV. The NAChR recordings are performed in $Ca^{++}$-free Ringer solution (115 mM NaCl, 2 mM KCl, 1.8 mM $BaCl_2$, 5 mM HEPES; pH~7.4) to limit $Ca^{++}$-activated chloride currents.

In all oocyte recordings, drug and wash solutions are applied using a custom-designed microcapillary "linear array" which allows rapid application of agonists. Currents are recorded on a PC-based computer (PClamp, Molecular Devices, Sunnyvale, Calif.). Responses are reported as ($I/I_{max}$), where I is the amount of current given by a selected concentration of drug and $I_{max}$ is the amount of maximal current.

Stocks of agonist are prepared of test drug in DMSO. Test solutions of agonist in Ringer are prepared immediately before application of the test drug (final DMSO concentration of 0.1%). The lowest concentration of agonist is perfused onto the oocyte until a peak current is recorded. There is approximately two minutes of wash time with only the Ringer solution between each application of agonist. The next lowest concentration of agonist is then tested, followed by another two minute wash time. This continues until all concentrations of the agonist have been tested. An average of the currents for each concentration from at least three different oocytes defines the response for the drug. The data is entered into Graphpad Prism and an $EC_{50}$ and $E_{max}$ are calculated.

Example B4

Metabolic Stability Assays

Protocol 1: Studies were carried out in human and rat liver microsomes ("HLM" and "RLM," respectively). Human and rat liver microsomes were purchased from BD Gentest. DMSO stocks were prepared for the test compounds. Aliquots of the DMSO solutions were diluted to 0.5 mM by acetonitrile, then further diluted by liver microsomes/buffer to 1.5 μM. 30 μL of 1.5 μM solutions were mixed with 15 μL of 6 mM NADPH, which had been pre-warmed to 37° C., at a final test compound concentration of 1 μM. The plates were kept in a 37° C. water bath for the duration of the experiment. At each time point (0, 5, 15, 30, 45 minutes), 135 μL of acetonitrile was added into corresponding wells. After the final time point was sampled, the plates were shaken at a vibrator (IKA, MTS 2/4) for 10 min (600 rpm/min) and then centrifuged at 5594 g for 15 min (Thermo Multifugex3R). Aliquots of the supernatant were removed, diluted 1:1 into distilled water, and analyzed by LC-MS/MS. The peak area response ratio to internal standard (PARR) of the compounds at 5, 15, 30, 45 minutes was compared to the PARR at time 0 to determine the percent of test compound remaining at each time point. Half-lives were calculated using Excel software, fitting to a single-phase exponential decay equation.

Protocol 2: Studies were carried out in human and rat liver microsomes. Buffer solutions were prepared as follows: Buffer A: 1.0 L of 0.1 M monobasic Potassium Phosphate buffer containing 1.0 mM EDTA; Buffer B: 1.0 L of 0.1 M Dibasic Potassium Phosphate buffer containing 1.0 mM EDTA; Buffer C: 0.1 M Potassium Phosphate buffer, 1.0 mM EDTA, pH 7.4 by titrating 700 mL of buffer B with buffer A while monitoring with a pH meter.

Reference compound (Ketanserin) and test compound spiking solutions were prepared as follows: 500 μM spiking solution: add 10 μL of 10 mM DMSO stock solution into 190 μL ACN; 1.5 μM spiking solution in microsomes (0.75 mg/mL): add 1.5 μL of 500 μM spiking solution and 18.75 μL of 20 mg/mL liver microsomes into 479.75 μL of Buffer C.

NADPH stock solution (6 mM) was prepared by dissolving NADPH into buffer C.

Assay procedure: 30 μL of 1.5 μM spiking solution containing 0.75 mg/mL microsomes solution was dispensed to the wells designated for 45 mM, 30 mM, 15 mM, 5 mM, and 0 mM. The plate was pre-incubated at 37° C. for 10 minutes. 15 μL of NADPH stock solution (6 mM) was added to the wells designated as Time 45, and the timer was started. At 30 mM, 15 mM, and 5 mM, 15 μL NADPH stock solution (6 mM) was added to the wells, respectively. At the end of incubation (0 mM), 135 μL of ACN containing IS was added to all the wells. Then 15 μL of NADPH stock solution (6 mM) was added to the wells designated as Time 0. After quenching, the reaction mixtures were centrifuged at 3220 g for 10 mM. Following centrifugation, 50 μL of the supernatant was transferred from each well into a 96-well sample plate containing 50 μL of ultra-pure water (Millipore) for LC/MS analysis. The peak area response (PARR) ratio to internal standard of the compounds at 5, 15, 30, and 45 minutes was compared to the PARR at time 0 to determine the percent of test compound remaining at each time point. Half-lives were calculated using Excel software, fitting to a single-phase exponential decay equation. Results for compounds tested are presented in Table 8.

TABLE 8

Metabolic Stability Assay Data

| Compound No. | HLM (mL/min/kg) | RLM (mL/min/kg) | Protocol No. |
|---|---|---|---|
| 1 | <13.608 | 105.84 | 2 |
| 2 | <13.608 | 127.44 | 2 |
| 10 | <13.608 | 36.72 | 2 |
| 11 | <13.608 | 97.6892 | 2 |
| 12 | <13.608 | 208.73 | 2 |
| 13 | <13.608 | 94.3866 | 2 |
| 14 | <13.608 | 25.92 | 2 |
| 15 | <13.608 | 25.92 | 2 |
| 16 | <13.608 | 82.6672 | 2 |
| 17 | <13.608 | 38.1652 | 2 |
| 18 | <13.608 | 47.8757 | 2 |
| 19 | <13.608 | 280.991 | 2 |
| 20 | <13.608 | 276.124 | 2 |
| 21 | <13.608 | 379.107 | 2 |
| 22 | <13.608 | 49.5027 | 2 |
| 23 | <13.608 | 81.6815 | 2 |
| 24 | <13.608 | 175.569 | 2 |
| 25 | <13.608 | 219.053 | 2 |
| 26 | <13.608 | 75.0501 | 2 |
| 27 | <13.608 | 106.429 | 2 |
| 28 | <13.608 | 28.4342 | 2 |
| 29 | <13.608 | 25.92 | 2 |
| 30 | <13.608 | 55.98 | 2 |
| 31 | <13.608 | 25.92 | 2 |
| 32 | <13.608 | 85.5 | 2 |
| 33 | <13.608 | 47.7 | 2 |
| 34 | <13.608 | 125.64 | 2 |
| 35 | <13.608 | 183.6 | 2 |
| 36 | <13.608 | 52.02 | 2 |
| 37 | 20.18 | 33.07 | 1 |
| 38 | 8.15 | 76.79 | 1 |
| 39 | 9.18 | 262.35 | 1 |
| 40 | 7.67 | 49.42 | 1 |
| 41 | 7.55 | 86.59 | 1 |
| 42 | 12.43 | 55.27 | 1 |
| 43 | 5.57 | 469.04 | 1 |
| 44 | 3.5 | 531.35 | 1 |
| 45 | 2.97628 | 170.981 | 1 |
| 46 | 7.38479 | 32.4827 | 1 |
| 47 | 13.5926 | 541.358 | 1 |
| 48 | 7.53934 | 69.1781 | 1 |
| 49 | 5.96284 | 254.566 | 1 |
| 50 | 2.98045 | 187.575 | 1 |
| 51 | 1.00357 | 716.882 | 1 |
| 52 | 4.00269 | 345.506 | 1 |
| 53 | 8.30367 | 29.9085 | 1 |
| 54 | 5.29444 | 175.357 | 1 |
| 55 | 10.3473 | 45.1417 | 1 |
| 56 | 4.86753 | 1196.24 | 1 |
| 57 | 0 | 153.227 | 1 |
| 59 | 0 | 24.713 | 1 |
| 60 | 15.0953 | 78.5875 | 1 |
| 61 | 10.81 | 434.65 | 1 |
| 62 | 7.06135 | 498.991 | 1 |
| 63 | 0.462296 | 1465.43 | 1 |
| 64 | 2.7474 | 77.4932 | 1 |
| 65 | 2.25274 | 286.666 | 1 |
| 66 | 0 | 934.845 | 1 |
| 67 | 6.65 | 594.86 | 1 |
| 68 | 3.48 | 1271.39 | 1 |
| 69 | 8.8 | 238.87 | 1 |
| 70 | 0 | 1349.06 | 1 |
| 71 | 6.76839 | 121.175 | 1 |
| 72 | 3.03233 | 339.452 | 1 |
| 73 | 2.82461 | 766.779 | 1 |
| 74 | 9.6502 | 342.736 | 1 |
| 75 | 5.74872 | 474.267 | 1 |
| 76 | 20.5897 | 41.0701 | 1 |
| 77 | 10.4452 | 87.668 | 1 |
| 78 | 0 | 679.777 | 1 |
| 79 | 10.72 | 576.18 | 1 |
| 80 | 5.54 | 1443.16 | 1 |
| 81 | 5.94 | 75.96 | 1 |
| 82 | 8 | 433.66 | 1 |
| 83 | 2.7 | 14.09 | 1 |
| 84 | 10.24 | 116.21 | 1 |
| 85 | 8.18 | 59.67 | 1 |
| 86 | 7.35 | 17.38 | 1 |
| 87 | 0.5 | 257.71 | 1 |
| 88 | 3.31 | 25.96 | 1 |
| 89 | 347.66 | 1154.15 | 1 |
| 90 | 5.21 | 72.22 | 1 |
| 91 | 6.14 | 235.4 | 1 |
| 92 | 10.37 | 149.88 | 1 |
| 93 | 12.96 | 12.66 | 1 |
| 94 | 2.62 | 26.52 | 1 |
| 95 | 2.86 | 17.75 | 1 |

Example B5

Rat Plasma Stability Assay

Protocol 1: Studies are carried out in plasma. Plasma is prepared under approval of IRB and IACUC on sodium heparin. The pH of plasma is monitored and used within the range of pH 7.4 to pH 8.0. DMSO stocks are prepared for the test compounds. Aliquots of the DMSO solutions are diluted to 0.05 mM by 0.05 mM sodium phosphate buffer with 0.5% BSA. Then 10 μL of 0.05 mM solutions are dosed into 90 μL of plasma in duplicates (n=2), which are pre-warmed to 37° C., at a final test compound concentration of 5 μM. The plates are kept in a 37° C. water bath for the duration of the experiment. At each time point (0, 5, 15, 30, 45, 60, and 120 minutes), 400 μL of acetonitrile is added into corresponding wells. After the final time point is sampled, the plates are shaken at a vibrator (IKA, MTS 2/4) for 10 mM (600 rpm/min) and then centrifuged at 5594 g for 15 mM (Thermo Multifuge×3R). Aliquots of the supernatant are removed, diluted 1:1 into distilled water, and analyzed by LC-MS/MS. The peak area response ratio to internal standard (PARR) of the compounds at 5, 15, 30, 45, 60, and 120 minutes is compared to the PARR at time 0 to determine the percent of test compound remaining at each time point. Half-lives are calculated using Excel software, fitting to a single-phase exponential decay equation.

Protocol 2: Studies are carried out in Sprague-Dawley rat plasma. All plasma is obtained from Bioreclamation and collected on sodium heparin. Plasma is adjusted to pH 7.4 prior to initiating the experiments. A DMSO stock is first prepared for the test compound. An aliquot of the DMSO solution is dosed into 1 mL of plasma, which is pre-warmed to 37° C., at a final test compound concentration of 1 μM. The vials are kept in a benchtop Thermomixer® for the duration of the experiment. Aliquots (100 μL) are taken at each time point (0, 15, 30, 60, and 120 minutes) and added to 96-well plates which are pre-filled with 300 μL of acetonitrile. Samples are stored at 4° C. until the end of the experiment. After the final time point is sampled, the plate is mixed and then centrifuged at 3,000 rpm for 10 minutes. Aliquots of the supernatant are removed, diluted 1:1 into distilled water, and analyzed by LC-MS/MS. The peak area response ratio to internal standard (PARR) of the compound at 15, 30, 60 and 120 minutes is compared to the PARR at time 0 to determine the percent of test compound remaining at each time point. Half-lives are calculated using GraphPad software, fitting to a single-phase exponential decay equation.

Example B6

Human Plasma Stability

Protocol 1: Studies were carried out in human plasma. All plasma was obtained from Bioreclamation and collected on sodium heparin. Plasma was adjusted to pH 7.4. A DMSO stock was first prepared for the test compound. An aliquot of the DMSO solution was dosed into 1 mL of plasma, which had been pre-warmed to 37° C., at a final test compound concentration of 1 µM. The vials were kept in a benchtop Thermomixer® for the duration of the experiment. Aliquots (100 µL) were taken at each time point (0, 15, 30, 60, and 120 minutes) and added to 96-well plates which had been pre-filled with 300 µL of acetonitrile. Samples were stored at 4° C. until the end of the experiment. After the final time point was sampled, the plate was mixed and then centrifuged at 3,000 rpm for 10 minutes. Aliquots of the supernatant were removed, diluted 1:1 into distilled water, and analyzed by LC-MS/MS. The peak area response ratio to internal standard (PARR) of the compound at 15, 30, 60 and 120 minutes was compared to the PARR at time 0 to determine the percent of test compound remaining at each time point. Half-lives were calculated using GraphPad software, fitting to a single-phase exponential decay equation. Results for compounds tested are provided in Table 7.

Protocol 2: Studies were carried out in plasma. Plasma was prepared under approval of IRB and IACUC on sodium heparin. The pH of plasma was monitored and used within the range of pH 7.4 to pH 8.0. DMSO stocks were prepared for the test compounds. Aliquots of the DMSO solutions were diluted to 0.05 mM by 0.05 mM Sodium phosphate buffer with 0.5% BSA. Then 10 µL of 0.05 mM solutions were dosed into 90 µL of plasma in duplicates (n=2), which had been pre-warmed to 37° C., at a final test compound concentration of 5 µM. The plates were kept in a 37° C. water bath for the duration of the experiment. At each time point (0, 5, 15, 30, 45, 60, and 120 minutes), 400 µL of acetonitrile was added into corresponding wells. After the final time point was sampled, the plates were shaken at the vibrator (IKA, MTS 2/4) for 10 min (600 rpm/min) and then centrifuged at 5594 g for 15 min (Thermo Multifuge×3R). Aliquots of the supernatant were removed, diluted 1:1 into distilled water, and analyzed by LC-MS/MS. The peak area response ratio to internal standard (PARR) of the compounds at 5, 15, 30, 45, 60, and 120 minutes was compared to the PARR at time 0 to determine the percent of test compound remaining at each time point. Half-lives were calculated using Excel software, fitting to a single-phase exponential decay equation. Results for compounds tested are provided in Table 9.

TABLE 9

Human Plasma Stability Data

| Compound No. | $T_{1/2}$ (min) | % Remaining @ 2 h | Protocol No. |
| --- | --- | --- | --- |
| 1 | 38.5 | 11 | 1 |
| 10 | >120 | | 1 |
| 12 | 73.8 | 31 | 1 |
| 13 | 15 | BQL* | 1 |
| 14 | 65.6 | 26 | 1 |
| 18 | 29.2 | 5.8 | 1 |
| 20 | 41.2 | 14 | 1 |
| 21 | >120 | 83 | 1 |
| 22 | >120 | 58 | 1 |
| 23 | 52.9 | 21 | 1 |

TABLE 9-continued

Human Plasma Stability Data

| Compound No. | $T_{1/2}$ (min) | % Remaining @ 2 h | Protocol No. |
| --- | --- | --- | --- |
| 24 | >120 | 89 | 1 |
| 26 | >120 | 65 | 1 |
| 28 | >120 | 79 | 1 |
| 30 | 34.7 | 10 | 1 |
| 32 | >120 | | 1 |
| 33 | 17.6 | | 1 |
| 34 | >120 | 55 | 1 |
| 35 | >120 | 56 | 1 |
| 36 | 28 | 2.5 | 1 |
| 37 | ∞ | 108.49 | 2 |
| 38 | ∞ | 96.52 | 2 |
| 39 | 42.69 | 14.05 | 2 |
| 40 | ∞ | 106.8 | 2 |
| 41 | ∞ | 120.27 | 2 |
| 42 | 172.39 | 72.21 | 2 |
| 43 | ∞ | 112.99 | 2 |
| 44 | ∞ | 95.72 | 2 |
| 45 | 115.74 | 47.32 | 2 |
| 46 | 855.11 | 91.9 | 2 |
| 47 | 260.68 | 72.43 | 2 |
| 48 | 58930.8 | 101.03 | 2 |
| 49 | 825.03 | 93.39 | 2 |
| 50 | ∞ | 100.92 | 2 |
| 51 | 353.268 | 79.3649 | 2 |
| 52 | 532.955 | 85.8425 | 2 |
| 53 | 1866.33 | 95.5 | 2 |
| 54 | 671.98 | 89.87 | 2 |
| 55 | 92.45 | 40.33 | 2 |
| 56 | 343.2 | 77.82 | 2 |
| 57 | 328.18 | 76.33 | 2 |
| 59 | 136.06 | 53.78 | 2 |
| 60 | 1375.45 | 89.46 | 2 |
| 61 | 837.51 | 93.59 | 2 |
| 62 | 354.38 | 74.02 | 2 |
| 63 | 423.02 | 74.47 | 2 |
| 64 | 725.77 | 76.61 | 2 |
| 65 | 333.85 | 72.66 | 2 |
| 66 | 315.52 | 71.77 | 2 |
| 67 | 5813.86 | 98.92 | 2 |
| 68 | ∞ | 103.13 | 2 |
| 69 | 415.94 | 78.66 | 2 |
| 70 | 249.42 | 71.56 | 2 |
| 71 | 282.83 | 72.03 | 2 |
| 72 | 227.76 | 70.78 | 2 |
| 73 | 94.39 | 41.93 | 2 |
| 74 | 176.48 | 61.85 | 2 |
| 75 | ∞ | 120.98 | 2 |
| 76 | 292.75 | 72.92 | 2 |
| 77 | 232.11 | 71.03 | 2 |
| 78 | 286.06 | 77.57 | 2 |
| 79 | 162.88 | 56.12 | 2 |
| 80 | 653.74 | 81.31 | 2 |
| 81 | 270.2 | 70.89 | 2 |
| 82 | 124.43 | 48.22 | 2 |
| 83 | 388.6 | 71.57 | 2 |
| 84 | 209.34 | 59.79 | 2 |
| 85 | 69.34 | 27.28 | 2 |
| 86 | 57.25 | 22.88 | 2 |
| 87 | 144.63 | 55.42 | 2 |
| 88 | ∞ | 110.47 | 2 |
| 89 | 309.85 | 77.23 | 2 |
| 90 | 183.28 | 63.18 | 2 |
| 91 | 499.33 | 81.12 | 2 |
| 92 | 187.71 | 64.72 | 2 |
| 93 | 641.16 | 81.38 | 2 |
| 94 | 344.12 | 76.38 | 2 |
| 95 | 396.55 | 73.17 | 2 |
| 96 | 6.83 | BQL* | 2 |

*BQL: below quantification limit

Example B7

Cytochrome P450 Inhibition

Protocol 1: Studies were carried out in human liver microsomes. Human liver microsomes were purchased from BD Gentest. DMSO stocks were prepared for the test compounds. Aliquots of the DMSO solutions were diluted 1:3 by acetonitrile:ACN mixture (v/v: 40:60) to "400×" intermediate solutions, then further diluted by liver microsomes/buffer to "2×" intermediate solutions. "2×" intermediate solutions were mixed with "2×" NADPH/substrate solutions, which had been pre-warmed to 37° C. (final test compound concentrations were 10 µM, 3.3 µM, 1.1 µM, 0.37 µM, 0.122 µM, 0.041 µM, 0.0136 µM, and 0 µM). The plates were kept in a 37° C. water bath for the duration of the experiment. At the end of incubation (5 minutes for 3A4; 45 minutes for 2C19; 10 minutes for 1A2, 2C9, 2D6), 120 µL of acetonitrile was added into corresponding wells. After the final time point was sampled, the plates were shaken at a vibrator (IKA, MTS 2/4) for 10 mM (600 rpm/min) and then centrifuged at 5594 g for 15 mM (Thermo Multifugex3R). Aliquots of the supernatant were removed, diluted 1:1 into distilled water, and analyzed by LC-MS/MS. The peak area response ratio to internal standard (PARR) of the compounds at 10 µM, 3.3 µM, 1.1 µM, 0.37 µM, 0.122 µM, 0.041 µM, and 0.0136 µM was compared to the PARR at 0 µM to determine the percent of metabolite generation from substrate at each test compound concentration. $IC_{50}$ values were calculated using XLfit or Graphpad software, fitting to a sigmoidal dose-response (variable slope) equation.

Protocol 2: Stock solution for NCEs (test articles) and standard inhibitors were prepared at a concentration of 20 mM in DMSO. Stock solutions were diluted with DMSO to get substocks which were further diluted 10-fold in 80:20 MeCN:water to obtain intermediate substocks. Working stocks were prepared by diluting the intermediate substocks 50-fold in buffer. The final concentrations of the various solutions are listed in Table 10 below.

TABLE 10

| Stock conc. (mM) | Volume added from stock* (µl) | Volume of DMSO added (µl) | Substock (mM) | Intermed. stock* (µM) | Working Stock** (µM) | Reaction (µM) |
|---|---|---|---|---|---|---|
| 20.00 | 40 | 0 | 20.00 | 2000.00 | 40.00 | 20.00 |
| 20.00 | 50 | 50 | 10.00 | 1000.00 | 20.00 | 10.00 |
| 10.00 | 50 | 50 | 5.00 | 500.00 | 10.00 | 5.00 |
| 10.00 | 15 | 35 | 3.00 | 300.00 | 6.00 | 3.00 |
| 3.00 | 15 | 30 | 1.00 | 100.00 | 2.00 | 1.00 |
| 1.00 | 15 | 35 | 0.30 | 30.00 | 0.60 | 0.30 |
| 0.30 | 25 | 50 | 0.10 | 10.00 | 0.20 | 0.10 |

*Intermediate substock:
Inhibitor 180 µL 80:20 (ACN:Water) + 20 µL of each substock
**Working stock:
Inhibitor 98 µL Buffer + 2 µL of each intermediate stock Substrate cocktail (4 CYPs) was prepared according to Table 11 below. The substrates below were then added to 9.9 mL of 33 mM $MgCl_2$ solution with 100 mg NADPH to make substrate cocktail.

TABLE 11

| Substrate | Solvent | Stock Conc. (mM) | Stock added (µL) | Final Reaction Concentration (µM) | CYP |
|---|---|---|---|---|---|
| Midazolam | 100% Methanol | 10 | 20 | 2 | 3A4 |
| Tacrine | 50:50 Methanol:Water | 10 | 20 | 2 | 1A2 |
| Diclofenac | Water | 20 | 40 | 8 | 2C9 |
| Dextromethorphan | 50:50 Methanol:Water | 10 | 20 | 2 | 2D6 |

Assay procedure: A solvent control (blank) was run by adding 100 µL of buffer containing 0.82% CAN, and 0.1% DMSO was added (instead of compound). For measurement of the 4 CYPs, 80 µL of HLM Mix-1 was added to the working stocks and mixed well. The plates were incubated at 37° C. for 5 min. The reaction was initiated by adding 20 µL of substrate cocktail. The plate was placed in a 37° C. water bath for 10 min. The reaction was terminated by adding 200 µL of ice-cold acetonitrile and mixed at 850 rpm for 10 min in a Thermomixer. The plates were centrifuged at 3500 rpm for 20 min at 15° C., and the supernatant was loaded for LC-MS/MS quantitation. The final reaction concentrations are listed in Table 12 below:

TABLE 12

| CYP Source | Pooled human liver microsomes |
|---|---|
| Microsomal protein Concentration | 0.1 mg/mL for 4 CYPs and 0.2 mg/mL for 2C19 |
| Buffer | 100 mM Phosphate Buffer pH 7.40 (±0.02) |
| Cofactor | NADPH (1.2 mM) |
| $MgCl_2, 6H_2O$ | 3.3 mM |
| Incubation period | 10 min @37° C. for 4 CYPs and 20 min @37° C. for 2C19 |
| Standard Inhibitor | Miconazole (20, 10, 5, 3, 1, 0.3 and 0.1 µM), n = 2 |
| NCE (test article) | 7 concentrations (20, 10, 5, 3, 1, 0.3 and 0.1 µM), n = 2 |
| Substrates Cocktail for 4 CYPs (1A2, 2C9, 2D6, 3A4) | |
| Tacrine | 2 µM |
| Diclofenac | 8 µM |
| Dextromethorphan | 2 µM |
| Midazolam | 2 µM |
| Organic Solvent Content(4 CYPs) | |
| ACN | 0.72% (v/v) |
| MeOH | 0.04% (v/v) |
| DMSO | 0.1% (v/v) |
| Chemicals | Source |
| NADPH | Sigma |
| $MgCl_2, 6H_2O$ | Sigma |

Results for compounds tested are presented in Table 13.

TABLE 13

Cytochrome P450 Inhibition Assay Data

| Compound No. | 3A4 IC$_{50}$ (Midazolam) (μM) | 3A4 IC$_{50}$ (Testosterone) (μM) | 2D6 IC$_{50}$ (μM) | 1A2 IC$_{50}$ (μM) | 2C9 IC$_{50}$ (μM) | 2C19 IC$_{50}$ (μM) | Protocol No. |
|---|---|---|---|---|---|---|---|
| 1 | >10 | | >10 | >10 | >10 | >10 | 2 |
| 2 | >10 | | >10 | >10 | >10 | >10 | 2 |
| 10 | >10 | | >10 | >10 | >10 | >10 | 2 |
| 11 | >10 | | >10 | >10 | >10 | >10 | 2 |
| 12 | >10 | | >10 | >10 | >10 | >10 | 2 |
| 13 | >10 | | >10 | >10 | >10 | >10 | 2 |
| 14 | >10 | | >10 | >10 | >10 | >10 | 2 |
| 15 | >10 | | >10 | >10 | >10 | >10 | 2 |
| 16 | >10 | | >10 | >10 | >10 | >10 | 2 |
| 17 | >10 | | >10 | >10 | >10 | >10 | 2 |
| 18 | >10 | | >10 | >10 | >10 | >10 | 2 |
| 19 | >10 | | >10 | >10 | >10 | >10 | 2 |
| 20 | >10 | | >10 | >10 | >10 | >10 | 2 |
| 21 | >10 | | >10 | >10 | >10 | >10 | 2 |
| 22 | >10 | | >10 | >10 | >10 | >10 | 2 |
| 23 | >10 | | >10 | >10 | >10 | >10 | 2 |
| 24 | >10 | | >10 | >10 | >10 | >10 | 2 |
| 25 | >10 | | >10 | >10 | >10 | >10 | 2 |
| 26 | >10 | | >10 | >10 | >10 | >10 | 2 |
| 27 | >10 | | >10 | >10 | >10 | >10 | 2 |
| 28 | >10 | | >10 | >10 | >10 | >10 | 2 |
| 29 | >10 | | >10 | >10 | >10 | >10 | 2 |
| 30 | >10 | | >10 | >10 | >10 | >10 | 2 |
| 31 | >10 | | >10 | >10 | >10 | >10 | 2 |
| 32 | >10 | | >10 | >10 | >10 | >10 | 2 |
| 33 | >10 | | >10 | >10 | >10 | >10 | 2 |
| 34 | >10 | | >10 | >10 | >10 | >10 | 2 |
| 35 | >10 | | >10 | >10 | >10 | >10 | 2 |
| 36 | >10 | | >10 | >10 | >10 | >10 | 2 |
| 37 | >10 | >10 | >10 | >10 | >10 | >10 | 1 |
| 38 | >10 | >10 | >10 | >10 | >10 | >10 | 1 |
| 39 | >10 | >10 | >10 | >10 | >10 | >10 | 1 |
| 40 | >10 | >10 | >10 | >10 | >10 | >10 | 1 |
| 41 | >10 | >10 | >10 | >10 | >10 | >10 | 1 |
| 42 | >10 | >10 | >10 | >10 | >10 | >10 | 1 |
| 43 | >10 | >10 | >10 | >10 | >10 | >10 | 1 |
| 44 | >10 | >10 | >10 | >10 | >10 | >10 | 1 |
| 45 | >10 | >10 | >10 | >10 | >10 | >10 | 1 |
| 46 | >10 | >10 | >10 | >10 | >10 | >10 | 1 |
| 47 | >10 | >10 | >10 | >10 | >10 | >10 | 1 |
| 48 | >10 | >10 | >10 | >10 | >10 | >10 | 1 |
| 49 | >10 | >10 | >10 | >10 | >10 | >10 | 1 |
| 50 | >10 | >10 | >10 | >10 | >10 | >10 | 1 |
| 51 | >10 | >10 | >10 | >10 | >10 | >10 | 1 |
| 52 | >10 | >10 | >10 | >10 | >10 | >10 | 1 |
| 53 | >10 | >10 | >10 | >10 | >10 | >10 | 1 |
| 54 | >10 | >10 | >10 | >10 | >10 | >10 | 1 |
| 55 | >10 | >10 | >10 | >10 | >10 | >10 | 1 |
| 56 | >10 | >10 | >10 | >10 | >10 | >10 | 1 |
| 57 | >10 | >10 | >10 | >10 | >10 | >10 | 1 |
| 59 | >10 | >10 | >10 | >10 | >10 | 20.85 | 1 |
| 60 | >10 | >10 | >10 | >10 | >10 | >10 | 1 |
| 83 | >10 | >10 | >10 | >10 | >10 | >10 | 1 |

Example B8

Time-Dependent Cytochrome P450 Inhibition Assays

The potential for time-dependent inhibition (TDI) of CYP2C9, CYP2D6, and CYP3A in HLM (0.25 mg protein/mL) by a test article is evaluated by the IC$_{50}$ shift approach (30-minute pre-incubation of the test article with HLM in the presence and absence of NADPH) and LC-MS/MS.

The stock solution of the test article is prepared in dimethyl sulfoxide (DMSO) and diluted using methanol. CYP probe substrates, metabolites, and positive inhibitors are purchased from Sigma-Aldrich (St. Louis, Mo., USA) and TRC (Toronto Research Chemicals, Toronto, Ontario, Canada). β-Nicotinamide adenine dinucleotide phosphate (NADPH, a co-factor for CYP-mediated reactions) is obtained from Calbiochem (San Diego, Calif., USA). All other chemicals and reagents are of analytical grade. HLM (mixed gender, pooled from 11 donors) are prepared by Absorption Systems (Exton, Pa., USA) and stored at −80° C. until use.

CYP TDI is evaluated by a 30-minute pre-incubation of the test article with HLM in the presence and absence of NADPH followed by the CYP enzyme activity assay. The CYP reaction is performed in an incubation volume of 200 μL. Briefly, the test article, at eight concentrations (0-100 μM), is pre-incubated at 37° C. for 30 minutes with HLM (0.25 mg protein/mL) in phosphate buffer (100 mM, pH 7.4) containing $MgCl_2$ (5 mM) in the presence and absence of NADPH (1 mM). CYP reaction is initiated by adding a CYP probe substrate (at approximately $K_m$, Table 14) with (when NADPH was not added in the preincubation step) or without (when NADPH was added in the pre-incubation step) the addition of NADPH (1 mM).

TABLE 14

CYP Probe Substrates and Metabolites

| CYP | Probe Substrate (concentration) | Metabolite |
|---|---|---|
| CYP2C9 | Diclofenac (6 µM) | 4'-OH diclofenac |
| CYP2D6 | Bufuralol (7 µM) | 1'-OH bufuralol |
| CYP3A | Testosterone (75 µM) | 6b-OH testosterone |
|  | Midazolam (1.4 µM) | 1'-OH midazolam |

The reaction mixture is incubated at 37° C. for 10-30 minutes depending on the individual CYP isoform. The reaction is terminated with ice-cold acetonitrile (ACN) containing an internal standard (IS, deuterium-labeled CYP probe metabolite). Negative (vehicle) controls are conducted using the incubation medium without the test article. Positive controls (CYP3A) are performed in parallel using a known time-dependent inhibitor (troleandomycin). After the removal of protein by centrifugation at 1,640 g (3,000 rpm) for 10 minutes at 4° C., the supernatants are transferred to HPLC sample vials. The formation of CYP probe metabolite is determined by LC-MS/MS.

Example B9

Cyto chrome P450 Induction in Hepatocytes

Stock solutions of the test compounds are prepared in dimethyl sulfoxide (DMSO). CYP-specific probe substrates, metabolites, positive inducers, and Williams' Medium E (WME) are purchased from Sigma-Aldrich (St. Louis, Mo., USA). Dulbecco's phosphate buffered saline (DPBS, pH 7.4) is purchased from Invitrogen (Carlsbad, Calif., USA). The CellTiter 96® AQueous ONE Solution Cell Proliferation Assay is obtained from Promega (Madison, Wis., USA). All other chemicals and reagents are of analytical grade.

Freshly plated hepatocytes are recovered by incubating with induction medium in a 95% air/5% $CO_2$ incubator at 37° C. for 24 hours prior to the induction experiments. Hepatocytes are then treated with induction medium spiked with the test compound at one concentration (30 µM). Positive controls are treated in parallel with induction medium spiked with omeprazole (OME) at 50 µM for CYP1A2, phenobarbital (PB) at 1,000 µM for CYP2B6, or rifampicin (RIF) at 50 µM for CYP3A. Vehicle controls are treated in parallel with induction medium. The hepatocyte incubation is conducted in a 95% air/5% $CO_2$ incubator at 37° C. for three days with daily replacement of the incubation mixture containing the test compound, positive controls, and vehicle. All experiments are conducted in triplicate (n=3). CYP enzyme activity is determined by measuring the formation of the CYP-specific probe substrate metabolite. Briefly, the wells are washed with DPBS and incubated with 200 µL of WME containing the CYP probe substrate at 37° C. for 1 hour in a 95% air/5% $CO_2$ incubator. After the incubation, 150 µL of the CYP incubation mixture from each well is transferred into a 96-well plate containing 150 µL of ice-cold acetonitrile (ACN) per well. The solutions are mixed and centrifuged at 1,640 g (3,000 rpm) for 10 minutes. The supernatants are transferred to HPLC sample vials and the concentrations of the CYP-specific probe metabolite are analyzed by LC-MS/MS.

The viability of the cells is measured by analyzing the cellular conversion of a tetrazolium salt (MTS) into a formazan produced by dehydrogenases, which are active only in viable cells. The absorbance of formazan, which is proportional to the number of viable cells, is measured spectrophotometrically using the CellTiter 96® AQueous ONE Solution Cell Proliferation Assay. The results of cell viability are also used for the normalization of CYP enzyme activity or mRNA to viable cell numbers. Briefly, the wells are rinsed with DPBS, and then 200 µL of hepatocyte induction medium and 40 µL of the CellTiter 96® Aqueous ONE Solution Cell Proliferation Assay reagent are added to each well, and the cells are incubated for 1 hour at 37° C. in a 95% air/5% $CO_2$ incubator. The absorbance of formazan in each well is measured at 492 nm using a FLUOStar OPTIMA Microplate Reader (BMG Lab Technologies, Durham, N.C., USA).

Example B10

Caco-2 Permeability Assay

Caco-2 cells were obtained from American Tissue Culture Collection (Rockville, Md.). The cells were maintained in Modified Eagle's medium (MEM), containing 10% heat-inactivated fetal bovine serum (FCS) and 1% non-essential amino acids, in $CO_2$ at 37° C. Cells were seeded on polycarbonate filter inserts (Millipore, CAT#PSHT 010 R5).

The cells were cultivated for 21-28 days prior to the transport experiments. The transepithelial electric resistance (TEER) and Lucifer Yellow permeability were checked routinely before and after the assay. Compounds were dissolved at 10 mM in 100% dimethyl sulfoxide (DMSO) and diluted for studies in Hank's Balanced Salt Solution (HBSS, Invitrogen, Cat#14025-092) with 25 mM HEPES, pH 7.4. Compounds were tested at 10 µM, and in both the apical-to-basolateral (A-B) and basolateral-to-apical (B-A) directions, at 37° C. for 90 min. At the end of incubation, donor samples were diluted 10-fold by assay buffer, then 60 µL of receiver and diluted-donor samples were mixed with 60 µL of acetonitrile, and analyzed by LC-MS/MS. The concentrations of the compounds were quantified by standard curve.

TABLE 15

Caco-2 Permeability Assay Data

| Compound No. | Efflux Ratio | A-B, Papp (x>$10^{-6}$ cm/s) | B-A, Papp (x>$10^{-6}$ cm/s) |
|---|---|---|---|
| 88 | 7.86 | 3.25 | 25.53 |

Example B11

P-gp Inhibition Potential

Cell monolayers are grown to confluence on collagen-coated, microporous, polycarbonate membranes in 12-well Costar Transwell® plates. The permeability assay buffer is Hank's Balanced Salt Solution (HBSS) containing 10 mM HEPES and 15 mM glucose at a pH of 7.4. The dosing solution concentration is 10 µM digoxin in the assay buffer+/−10 µM test compound or 1 µM valspodar. Cells are first pre-incubated for 30 minutes with HBSS containing +/−10 µM test compound or 1 µM valspodar. Cell monolayers are dosed on the apical side (A-to-B) or basolateral side (B-to-A) and incubated at 37° C. with 5% $CO_2$ in a humidified incubator. Samples are taken from the donor and receiver chambers at 120 minutes. Each determination is performed in duplicate. The co-dosed lucifer yellow flux is also measured for each monolayer to ensure no damage is inflicted to the cell monolayers during the flux period. All samples are assayed by LCMS/MS using electrospray ionization. The apparent permeability, $P_{app}$, and percent recovery are calculated as follows:

$$P_{app}=(dCr/dt) \times V_r/(A \times CN) \quad (1)$$

$$\text{Percent Recovery}=100 \times ((V_r \times C_{r\,final})+(V_d \times C_{d\,final}))/(V_d \times CN) \quad (2)$$

where, dCr/dt is the slope of the cumulative concentration in the receiver compartment versus time in µM $s^{-1}$; $V_r$ is the volume of the receiver compartment in $cm^3$; $V_d$ is the volume of the donor compartment in $cm^3$; A is the area of the insert (1.13 $cm^2$ for 12-well Transwell®); CN is the nominal concentration of the dosing solution in µM; $C_{r\,final}$ is the cumulative receiver concentration in µM at the end of the incubation period; and $C_{d\,final}$ is the concentration of the donor in µM at the end of the incubation period.

Example B12

BCRP Substrate and Inhibition Assessment

Caco-2 cells (clone C2BBe1) are obtained from American Type Culture Collection (Manassas, Va.). Cell monolayers are grown to confluence on collagen-coated, microporous, polycarbonate membranes in 12-well Costar Transwell® plates. The permeability assay buffer is Hanks Balanced Salt Solution (HBSS) containing 10 mM HEPES and 15 mM glucose at a pH of 7.4. The buffer in the receiver chamber also contains 1% bovine serum albumin. The dosing solution concentration is 5 µM for the test article in the assay buffer+/−10 µM Ko143. Cells are first preincubated for 30 minutes with HBSS+/−10 µM Ko143. Cell monolayers are dosed on the apical side (A-to-B) or basolateral side (B-to-A) and incubated at 37° C. with 5% $CO_2$ in a humidified incubator. Samples are taken from the donor and receiver chambers at 120 minutes. Each determination is performed in duplicate. The co-dosed lucifer yellow flux is also measured for each monolayer to ensure that no damage is inflicted to the cell monolayers during the flux period. All samples are assayed by LC-MS/MS using electrospray ionization.

The apparent permeability, $P_{app}$, and percent recovery are calculated as follows:

$$Papp=(dCr/dt) \times V_r/(A \times CA)$$

$$\text{Percent Recovery}=100 \times ((V_r \times C_{r\,final})+(V_d \times C_{d\,final}))/(V_d \times CN)$$

where, dCr/dt is the slope of the cumulative concentration in the receiver compartment versus time in µM $s^{-1}$; $V_r$ is the volume of the receiver compartment in $cm^3$; $V_d$ is the volume of the donor compartment in $cm^3$; A is the area of the insert (1.13 $cm^2$ for 12-well Transwell®); CA is the average of the nominal dosing concentration and the measured 120 minute donor concentration in µM; CN is the nominal concentration of the dosing solution in µM; $C_{r\,final}$ is the cumulative receiver concentration in µM at the end of the incubation period; and $C_{d\,final}$ is the concentration of the donor in µM at the end of the incubation period.

Example B13

Human and Rat Plasma Protein Binding

Studies were carried out in human plasma and Sprague-Dawley rat plasma, obtained from Bioreclamation and collected on sodium heparin. A Pierce Rapid Equilibrium Dialysis Device (RED) was used for all experiments. Stock solutions of the test and control compounds were first prepared in DMSO. Aliquots of the DMSO solutions were dosed into 1.5 mL of plasma at a dosing concentration of 5 µM for the test compound and 10 µM for the co-dosed control compound warfarin. Plasma (300 µL) containing the test and control compounds was loaded into two wells of the 96-well dialysis plate. Blank PBS (500 µL) was added to each corresponding receiver chamber. The device was then placed into an enclosed heated rocker that was pre-warmed to 37° C., and allowed to incubate for four hours. After 4 hours of incubation, both sides were sampled.

Aliquots (50 µL for donor, 200 µL for receiver) were removed from the chambers and placed into a 96-well plate. Plasma (50 µL) was added to the wells containing the receiver samples, and 200 µL of PBS was added to the wells containing the donor samples. Two volumes of acetonitrile were added to each well, and the plate was mixed and then centrifuged at 3,000 rpm for 10 minutes. Aliquots of the supernatant were removed, diluted 1:1 into distilled water and analyzed by LC-MS/MS. Protein binding values were calculated as follows: % Bound=[(PARR in Donor−PARR in Receiver)/(PARR in Donor)]×100%, where PARR=peak area response ratio of compound to internal standard, including applicable dilution factors.

Example B14

Monkey and Dog Plasma Stability

Studies are carried out using cynomolgus monkey plasma and beagle dog plasma. All plasma is obtained from Bioreclamation and collected on sodium heparin. Plasma is adjusted to pH 7.4 prior to initiating the experiments. A DMSO stock is first prepared for the test compound. An aliquot of the DMSO solution is dosed into 1 mL of plasma, which has been pre-warmed to 37° C., at a final test compound concentration of 1 µM. The vials are kept in a benchtop Thermomixer® for the duration of the experiment. Aliquots (100 µL) are taken at each time point (0, 15, 30, 60, and 120 minutes) and added to 96-well plates which had been pre-filled with 300 µL of acetonitrile. Samples are stored at 4° C. until the end of the experiment. After the final time point is sampled, the plate is mixed and then centrifuged at 3,000 rpm for 10 minutes. Aliquots of the supernatant are removed, diluted 1:1 into distilled water and analyzed by LC-MS/MS. The peak area response ratio to internal standard (PARR) of the compound at 15, 30, 60 and 120 minutes is compared to the PARR at time 0 to determine the percent of test compound remaining at each time point. Half-lives are calculated using GraphPad software, fitting to a single-phase exponential decay equation.

Example B15

Monkey and Dog Plasma Protein Binding

Studies are carried out in cynomologus monkey plasma and beagle dog plasma, obtained from Bioreclamation and collected on sodium heparin. A Pierce Rapid Equilibrium Dialysis Device (RED) is used for all experiments. Stock solutions of the test and control compounds are first prepared in DMSO. Aliquots of the DMSO solutions are dosed into 1.5 mL of plasma at a dosing concentration of 5 μM for the test compound and 10 μM for the co-dosed control compound warfarin. Plasma (300 μL) containing the test and control compounds is loaded into two wells of the 96-well dialysis plate. Blank PBS (500 μL) is added to each corresponding receiver chamber. The device is then placed into an enclosed heated rocker that is pre-warmed to 37° C. and allowed to incubate for four hours. After 4 hours of incubation, both sides are sampled.

Aliquots (50 μL for donor, 200 μL for receiver) are removed from the chambers and placed into a 96-well plate. Plasma (50 μL) is added to the wells containing the receiver samples, and 200 μL of PBS is added to the wells containing the donor samples. Two volumes of acetonitrile are added to each well, and the plate is mixed and then centrifuged at 3,000 rpm for 10 minutes. Aliquots of the supernatant are removed, diluted 1:1 into distilled water, and analyzed by LC-MS/MS.

Protein binding values are calculated as follows: % Bound=[(PARR in Donor−PARR in Receiver)/(PARR in Donor)]×100%, where PARR=peak area response ratio of compound to internal standard, including applicable dilution factors.

Example B16

Binding to Rat Brain Homogenate

Studies are carried out in Sprague-Dawley rat brain, obtained from Bioreclamation. A Pierce Rapid Equilibrium Dialysis Device (RED) is used for all experiments. Brains are homogenized with two volumes of PBS prior to initiating the experiment. Stock solutions of the test and control compounds are first prepared in DMSO. Aliquots of the DMSO solutions are dosed into 1.5 mL of brain homogenate at a dosing concentration of 5 μM for the test compound and 5 μM for the co-dosed control compound fluoxetine. Brain homogenate (300 μL) containing the test and control compound is loaded into two wells of the 96-well dialysis plate. Blank PBS (500 μL) is added to each corresponding receiver chamber. The device is then placed into an enclosed heated rocker that is pre-warmed to 37° C., and allowed to incubate for four hours. After 4 hours of incubation, both sides are sampled. Aliquots (50 μL for donor, 200 μL for receiver) are removed from the chambers and placed into a 96-well plate. Brain homogenate (50 μL) is added to the wells containing the receiver samples, and 200 μL of PBS is added to the wells containing the donor samples. Two volumes of acetonitrile are added to each well, and the plate is mixed and then centrifuged at 3,000 rpm for 10 minutes. Aliquots of the supernatant are removed, diluted 1:1 into distilled water, and analyzed by LC-MS/MS.

Fraction unbound values are calculated as follows: D/(PARR in Donor/PARR in Receiver-1+D) where D=Dilution factor of homogenized brains (1/3) and PARR=peak area response ratio of compound to internal standard, including applicable dilution factors.

Example B17 hERG Inhibition Assay hERG study was conducted with an automated patch clamp machine, Qpatch-48HT (Sophion Biosciences, Denmark). Cultured CHO cells stably expressing hERG channels (provided by Sophion Biosciences, Denmark) were harvested from culture flasks of 70-90% cell confluence rate and prepared as cell suspension with a cell density of $3-8\times10^6$ cells/mL in serum-free media (CHO-S-SFM II, cat#12052 Invitrogen; 25 mM HEPES). Cells in such condition were placed into a Qpatch cell stir chamber and used within 4 hours.

For each run, cells were first spun down by the built-in Qpatch centrifuge and re-suspended in an extracellular solution (in mM, 2 $CaCl_2$, 1 $MgCl_2$, 4 KCl, 145 NaCl, 10 Glucose, 10 HEPES, pH 7.4, osmolarity ~305 mOsm). Qplate-48 that holds one cell in each of its 48 channels for the later voltage-clamped assay were primed with the extracellular solution and intracellular solution (in mM, 5.4 $CaCl_2$, 1.75 $MgCl_2$, 120 KCl, 10 HEPES, 5 EGTA, 4 NaATP, pH 7.25, Osmolarity ~280-295 mOsm). Cells were dispatched by Qpatch robotic dispensing guns into each Qplate channel and went through the process of giga-ohm sealing and whole cell configuration. Whole-cell recordings were performed in voltage-clamp mode at a holding potential of −80 mV. The hERG current was activated by depolarizing at +20 mV for 5 sec, after which the current was taken back to −50 mV for 5 sec to remove the inactivation and observe the deactivating tail current. The maximum amount of tail current size was used to determine the hERG current amplitude. The above voltage protocol was applied to the cells every 15 sec throughout the whole procedure. External solution containing 0.1% DMSO (vehicle) was applied to the cells to establish the baseline. Compound solution was added, and the cells were kept in the test solution until the compound's effect reached a steady state or for a maximum of 4 min. For dose response assays (0.1, 0.3, 1, 3, 10 and 30 μM), the compound was applied to the cells accumulatively from low to high concentrations. Washout with extracellular solution was performed after compound testing. Positive control cisapride 0.1 μM was used on each cell after compound testing to ensure the normal response and the good quality of the cell. hERG current sizes of each cell at each compound concentration were compared to that at the vehicle stage, and the % of inhibition at each dose was thus calculated. hERG $IC_{50}$ curve was plotted with Graphpad Prism.

TABLE 16 hERG Inhibition Assay Data

| Compound Number | $IC_{50}$ (μM) |
|---|---|
| 46 | >30 |
| 65 | 2.43 |

Example B18

P50 Auditory Gating Assay

Male DBA/2 mice (18-25 g) are obtained from Harlan SD (Indianapolis, Ind.) and group housed until recorded. Food (Purina Rodent Chow) and water are available ad libitum, and lighting is cycled at 12-hour intervals (lights on at 6:00 am) in shoe box housing in ventilated racks.

The mice are anesthetized with chloral hydrate (400 mg/kg, IP) and pyrazole (400 mg/kg, IP) to retard the metabolism of the chloral hydrate. Anesthesia is supplemented periodically to maintain a surgical plane of anesthesia (2.0 mg/kg, IP, each of chloral hydrate and pyrazole as needed; at ~20 minute intervals).

The animal is placed in a mouse adapter (Neuroprobe, Cabin John, Md.) for a Kopf stereotaxic instrument (Kopf Instruments, Tujunga, Calif.). Hollow ear bars, attached to miniature earphones which are connected to a sound amplifier (RadioShack), are placed adjacent to the externalization of the aural canal. Because the auditory evoked potentials are more consistent at a stable temperature of 36° C., body temperature is maintained at this level with a heating pad. The scalp is incised and a burr hole is opened over the CA3 region of hippocampus (−1.8 mm anterior-posterior to bregma, +2.70 mm medial-lateral to midline (Franklin and Paxinos 1997)). A Teflon-coated, stainless steel wire microelectrode is inserted into the CA3 pyramidal cell layer of the hippocampus (1.65-1.70 mm below the dorsal brain surface). Final electrode location is identified by the presence of complex action potentials typical of hippocampal pyramidal neurons (Miller et al. 1995). A reference electrode is placed on dura, anterior to bregma, contralateral to the recording electrode. The electrical activity is amplified 1000 times with bandpass 1 to 500 Hz (Miller et al. 1995) and led to an analog to digital converter (RC Electronics, Bakersfield, Calif.) for averaging by computer. Tones, 3000 Hz, 10-msec duration, 72 dB SPL generated as a sine wave are presented in pairs with a 500-msec intrapair interval and 10 sec between pairs. Although DBA/2 mice suffer hearing loss as they age, these tones are within the audible range for the mice (Willott et al. 1982). Responses to 16 pairs of tones are averaged at 5-min intervals. Each average is filtered digitally with bandpass between 10 and 250 Hz. The maximum negativity between 20 and 60 msec after the first stimulus is selected as the N40 wave and measured relative to the preceding positivity, a P20 wave. This composite wave has been found to be less variable than either component individually (Hashimoto et al 2005). The ratio of the amplitudes of response to the second (test) stimulus and the first (conditioning) stimulus provide a measure of sensory inhibition; the ratio of the test to the conditioning amplitude (TC ratio) is 0.5 or less for most rodent strains and normal humans (Stevens et al. 1996). Six records are obtained before any drug injection to establish baseline sensory processing performance. Each mouse is drug naive at the time of experimentation. Following drug administration, 5 minute records are obtained for 90 minutes.

Example B19

Novel Object Recognition (NOR)

The purpose of an NOR study is to further evaluate a test article (for oral efficacy over a range of different pretreatment times) for cognition-related behavioral effects in an experimental animal model. The behavioral procedure utilized, the Spontaneous Novel Object Recognition Test (NOR) (Ennaceur and Delacour 1988) for rats is commonly used for the preclinical evaluation of novel drugs that have potential pro-cognitive effects. NOR is a rodent model of (non-spatial) recognition memory, which is assumed to consist of two components, a recollective (episodic) component and a familiarity component (Squire et al., 2004). While debated, there is considerable evidence that the hippocampus is involved in object recognition memory in both rodents (Myhrer, 1988; Rampon et al., 2000; Broadbent et al., 2004) and humans (Reed and Squire, 1997; Squire, 1992) and further, object recognition memory has also been observed to be negatively affected in non-demented, aged individuals as well as in patients with AD (Flicker et al., 1987, Purdy et al., 2002 and Schiavetto et al., 2002). In the rodent NOR task, subjects initially explore two identical objects, and later (after a predetermined delay) they explore a novel object and an identical copy of the old object. Recognition memory is demonstrated when animals explore the novel object more than the old (familiar) object.

NOR Study Protocol/Experimental Design:

Male albino Wistar rats (Harlan Sprague-Dawley, Inc. Indianapolis, Ind., USA) approximately 3 months old are double housed in polycarbonate cages with Bed-O-Cob® bedding in a temperature-controlled room (25° C.) with a 12 hr light/dark cycle. Test subjects are handled beginning the day after arrival and allowed free access to food (Teklad Rodent Diet 8604 pellets, Harlan, Madison, Wis.) and water throughout the study. All procedures employed during this study are reviewed and approved by an appropriate Committee on Animal Use for Research (CAURE).

Drug Administration—

Test article is dissolved in a vehicle composed of 10% hydroxypropyl-beta-cyclodextrin (HPbetaCD) in sterile normal (0.9%) saline. Test article and vehicle are administered in a volume of 2.0 mL/kg by oral gavage. Pretreatment times before A/A sessions in the novel object recognition task are as follows: vehicle—4 and 24 hours, test article—1.0, 2.0, 4.0, 6.0, 18.0, and 24.0 hours.

Spontaneous Novel Object Recognition Test (NOR) Procedure—

The novel object recognition memory procedure is conducted as described previously (Callahan et al., 2013) and adapted from the original work of Ennaceur and Delacour (1988). Briefly, test subjects are transported in their home cages from the colony room to the laboratory and acclimated to laboratory conditions (i.e., tail marking, daily handling and weighing) for at least 3 days prior to the start of behavioral experimentation. During experimentation, animals are acclimated for at least 30 min prior to the beginning of each experimental phase and remained in the holding room for approximately 15 min at the end of testing before being returned to the colony room.

Habituation—

Animals are acclimated, weighed and individually placed in the training/testing environment (an opaque plastic chamber, 78.74 cm×39.37 cm×31.75 cm with bedding on the floor) for 10 minutes of chamber exploration.

Training Trial—

24 hr after the habituation session, animals are acclimated, weighed and injected with the test compound (drug or vehicle) and after an appropriate pretreatment interval then placed in the chamber with their nose facing the center of a long wall and allowed to explore two identical objects for 10 min. The animal's behavior is observed and video recorded via a camera located 69 cm above the chamber and a DVD recorder.

Test Trial— after a retention delay interval of 48 hr (a delay interval that produced complete forgetting), the animals are returned to the lab, acclimated and then tested for object novelty (i.e., recognition memory). Two objects, one object similar to training (familiar) and a new (novel) object are placed in the chamber and the animal is allowed to explore the objects during a 5 min trial. The experimental objects to be discriminated are a plastic multi-colored Duplo-Lego block configured tower (12 cm in height, 6 cm in width) paired with a ceramic conical-shaped green Christmas tree salt/pepper shaker (12 cm in height, 5 cm in diameter); all objects exist in duplicate. The objects are placed 19.3 cm from the sides of the two short walls and 19.3 cm from the sides of the long walls of the chamber; the distance between the two objects is approximately 40 cm. The role of familiar and novel object as well as chamber position of object are randomly assigned across subjects and treatments and objects are cleaned between sessions with a dilute 50% EtOH solution to eliminate olfactory cues. Object exploration occurs when the animal directed its nose to the object at a distance of 2 cm and/or touches it with its nose; rearing up against the object to investigate the object is also considered exploration, whereas physically climbing on the object, using the object to support itself while rearing to investigate the chamber arena or digging at the base of the object is not considered appropriate object exploratory behavior.

Exploration Times of the Novel and Familiar Objects— discrimination (d2) ratios=(novel−familiar)/(novel+familiar), and recognition indexes=(novel)/(novel+familiar) are analyzed statistically (for the A/B retention sessions). For data inclusion, the test subjects have to explore each individual object for a minimum of 4 sec and at least 12 sec with both objects combined. Animals are tested only once in this behavioral task and the experiments are conducted under blind testing conditions.

Statistical Analyses—

All data are collated and entered into Microsoft Excel spreadsheets. The data are subsequently imported into SigmaPlot 11.0 for statistical analyses. For the object exploration time analysis, a two-way repeated measures Analysis of variance (ANOVA) is used with a Student Newman Keuls post hoc test. For the discrimination (d2) ratio and recognition index (RI) comparisons, a one-way ANOVA is used with a Student Newman Keuls post hoc test.

EXEMPLARY EMBODIMENTS

Exemplary aspects and embodiments of the compositions and methods provided herein are listed below. The listed aspects and embodiments are intended to be non-limiting, and other aspects and embodiments are contemplated as described herein.

Embodiment 1

A compound having the formula (I):

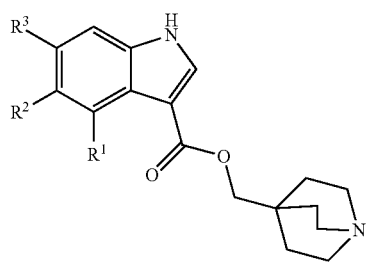

wherein $R^1$ is $C_1$-$C_6$ alkyl, $C_1$-$C_6$ alkoxy, $C_3$-$C_6$ cycloalkyl, or bromo, wherein the $C_1$-$C_6$ alkyl, $C_1$-$C_6$ alkoxy, or $C_3$-$C_6$ cycloalkyl is unsubstituted or substituted with 1 to 5 halo substituents;

$R^2$ and $R^3$ are each independently hydrogen, $C_1$-$C_6$ alkyl, $C_3$-$C_6$ cycloalkyl, halo, cyano, —$NR^aR^b$, —$NHC(O)R^c$, —$OR^d$, or —$OC(O)R^e$;

$R^a$, $R^b$, and $R^c$ are each independently hydrogen, unsubstituted $C_1$-$C_6$ alkyl, or unsubstituted $C_3$-$C_6$ cycloalkyl;

$R^d$ is hydrogen, $C_1$-$C_6$ alkyl, or $C_3$-$C_6$ cycloalkyl, wherein the $C_1$-$C_6$ alkyl or $C_3$-$C_6$ cycloalkyl is unsubstituted or substituted with 1 to 5 substituents independently selected from the group consisting of hydroxyl, $C_1$-$C_6$ alkoxy, and halo; and $R^e$ is unsubstituted $C_1$-$C_6$ alkyl or unsubstituted $C_3$-$C_6$ cycloalkyl;

provided that 1) at least one of $R^2$ and $R^3$ is hydrogen, and 2) when $R^1$ is $C_1$-$C_6$ alkoxy, $R^2$ is other than hydrogen, or a salt thereof.

Embodiment 2

The compound of embodiment 1, or a salt thereof, wherein $R^1$ is $C_1$-$C_6$ alkyl or $C_3$-$C_6$ cycloalkyl, wherein the $C_1$-$C_6$ alkyl or $C_3$-$C_6$ cycloalkyl is unsubstituted or substituted with 1 to 5 halo substituents.

Embodiment 3

The compound of embodiment 1, or a salt thereof, wherein $R^1$ is unsubstituted $C_1$-$C_6$ alkyl.

Embodiment 4

The compound of embodiment 1, or a salt thereof, wherein $R^1$ is —$CH_3$.

Embodiment 5

The compound of embodiment 1, or a salt thereof, wherein $R^1$ is $C_1$-$C_6$ alkoxy, which is unsubstituted or substituted with 1 to 5 halo substituents.

Embodiment 6

The compound of embodiment 1, or a salt thereof, wherein $R^1$ is —$OCH_3$.

Embodiment 7

The compound of embodiment 1, or a salt thereof, wherein $R^1$ is bromo.

Embodiment 8

The compound of any of embodiments 1-4 and 7, or a salt thereof, wherein $R^2$ is hydrogen.

Embodiment 9

The compound of any one of embodiments 1-7, or a salt thereof, wherein $R^2$ is $C_1$-$C_6$ alkyl or $C_3$-$C_6$ cycloalkyl.

Embodiment 10

The compound of any one of embodiments 1-7, or a salt thereof, wherein $R^2$ is —$CH_3$.

Embodiment 11

The compound of any one of embodiments 1-7, or a salt thereof, wherein $R^2$ is halo.

Embodiment 12

The compound of any one of embodiments 1-7, or a salt thereof, wherein $R^2$ is fluoro or chloro.

Embodiment 13

The compound of any one of embodiments 1-7, or a salt thereof, wherein $R^2$ is cyano.

Embodiment 14

The compound of any one of embodiments 1-7, or a salt thereof, wherein $R^2$ is $-OR^d$, and $R^d$ is hydrogen or unsubstituted $C_1$-$C_6$ alkyl.

Embodiment 15

The compound of embodiment 14, or a salt thereof, wherein $R^d$ is $-CH_3$.

Embodiment 16

The compound of any one of embodiments 1-7, or a salt thereof, wherein $R^2$ is $-OR^d$, and $R^d$ is $C_1$-$C_6$ alkyl substituted with $C_1$-$C_6$ alkoxy.

Embodiment 17

The compound of any one of embodiments 1-16, or a salt thereof, wherein $R^3$ is hydrogen.

Embodiment 18

The compound of any one of embodiments 1-8, or a salt thereof, wherein $R^3$ is $C_1$-$C_6$ alkyl or $C_3$-$C_6$ cycloalkyl.

Embodiment 19

The compound of any one of embodiments 1-8, or a salt thereof, wherein $R^3$ is $-CH_3$.

Embodiment 20

The compound of any one of embodiments 1-8, or a salt thereof, wherein $R^3$ is halo.

Embodiment 21

The compound of any one of embodiments 1-8, or a salt thereof, wherein $R^3$ is fluoro or chloro.

Embodiment 22

The compound of any one of embodiments 1-8, or a salt thereof, wherein $R^3$ is cyano.

Embodiment 23

The compound of any one of embodiments 1-8, or a salt thereof, wherein $R^3$ is $-OR^d$, and $R^d$ is hydrogen or unsubstituted $C_1$-$C_6$ alkyl.

Embodiment 24

The compound of embodiment 23, or a salt thereof, wherein $R^d$ is $-CH_3$.

Embodiment 25

The compound of embodiment 1, wherein
$R^1$ is $C_1$-$C_4$ alkyl, $C_1$-$C_4$ alkoxy, $C_3$-$C_4$ cycloalkyl, or bromo, wherein the $C_1$-$C_4$ alkyl is unsubstituted or substituted with 1 to 5 fluoro substituents;
$R^2$ and $R^3$ are each independently hydrogen, $C_1$-$C_6$ alkyl, fluoro, chloro, cyano, $-NHC(O)R^c$, $-OR^d$, or $-OC(O)R^e$;
$R^c$ is hydrogen or unsubstituted $C_1$-$C_6$ alkyl;
$R^d$ is hydrogen or $C_1$-$C_6$ alkyl, wherein the $C_1$-$C_6$ alkyl is unsubstituted or substituted with 1 to 5 substituents independently selected from the group consisting of hydroxyl, $C_1$-$C_6$ alkoxy, and halo; and
$R^e$ is unsubstituted $C_1$-$C_6$ alkyl;
provided that 1) at least one of $R^2$ and $R^3$ is hydrogen, and 2) when $R^1$ is $C_1$-$C_4$ alkoxy, $R^2$ is other than hydrogen, or a salt thereof.

Embodiment 26

The compound of embodiment 1, or a salt thereof, wherein the compound is selected from the group consisting of:

| Compound No. | Structure |
|---|---|
| 21 | 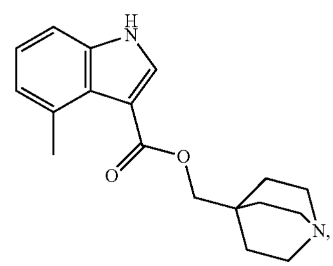 [SMILES: Cc1cccc2[nH]cc(C(=O)OCC34CCN(CC3)CC4)c12] |
| 24 | 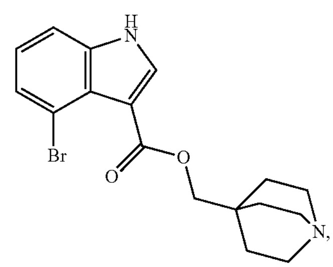 |
| 34 | 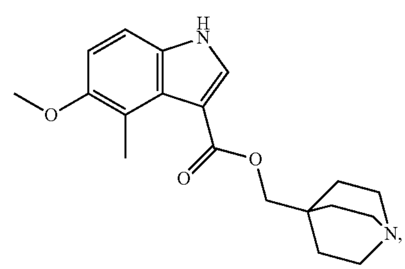 [SMILES: COc1ccc2[nH]cc(C(=O)OCC34CCN(CC3)CC4)c2c1C] |
| 37 | 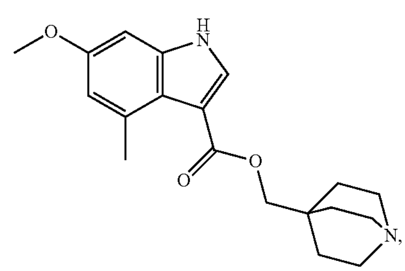 [SMILES: COc1cc(C)c2c(C(=O)OCC34CCN(CC3)CC4)c[nH]c2c1] |

| Compound No. | Structure |
|---|---|
| 40 | 4,5-dimethoxy-1H-indole-3-carboxylic acid quinuclidin-4-ylmethyl ester |
| 41 | 4-bromo-6-fluoro-1H-indole-3-carboxylic acid quinuclidin-4-ylmethyl ester |
| 42 | 4-bromo-6-chloro-1H-indole-3-carboxylic acid quinuclidin-4-ylmethyl ester |
| 43 | 5-fluoro-4-methyl-1H-indole-3-carboxylic acid quinuclidin-4-ylmethyl ester |
| 44 | 6-fluoro-4-methyl-1H-indole-3-carboxylic acid quinuclidin-4-ylmethyl ester |

| Compound No. | Structure |
|---|---|
| 47 | 4-bromo-5-methoxy-1H-indole-3-carboxylic acid quinuclidin-4-ylmethyl ester |
| 48 | 4-bromo-6-methoxy-1H-indole-3-carboxylic acid quinuclidin-4-ylmethyl ester |
| 49 | 4-bromo-6-methyl-1H-indole-3-carboxylic acid quinuclidin-4-ylmethyl ester |
| 50 | 6-chloro-4-methyl-1H-indole-3-carboxylic acid quinuclidin-4-ylmethyl ester |
| 53 | 4-bromo-6-hydroxy-1H-indole-3-carboxylic acid quinuclidin-4-ylmethyl ester |

| Compound No. | Structure |
|---|---|
| 54 | 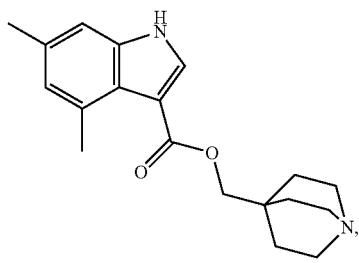 [SMILES: Cc1cc(C)c2c(C(=O)OCC34CCN(CC3)CC4)c[nH]c2c1] |
| 60 | 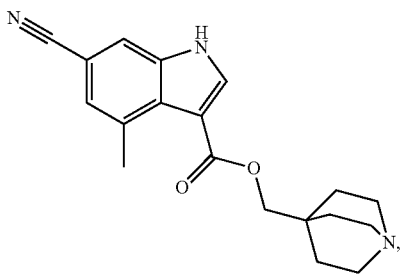 [SMILES: Cc1cc(C#N)cc2[nH]cc(C(=O)OCC34CCN(CC3)CC4)c12] |
| 61 | 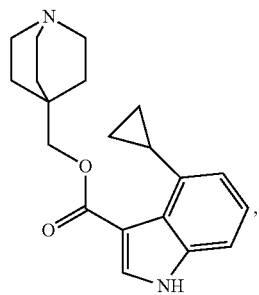 [SMILES: O=C(OCC12CCN(CC1)CC2)c1c[nH]c2cccc(C3CC3)c12] |
| 67 | 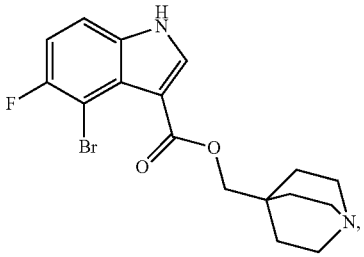 [SMILES: O=C(OCC12CCN(CC1)CC2)c1c[nH]c2ccc(F)c(Br)c12] |
| 68 | 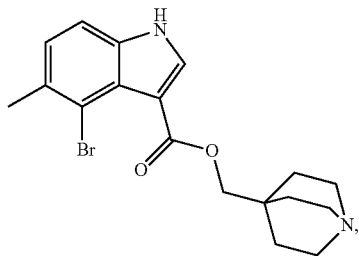 [SMILES: Cc1ccc2[nH]cc(C(=O)OCC34CCN(CC3)CC4)c2c1Br] |
| Compound No. | Structure |
|---|---|
| 70 | 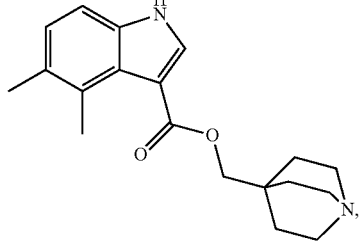 |
| 75 | 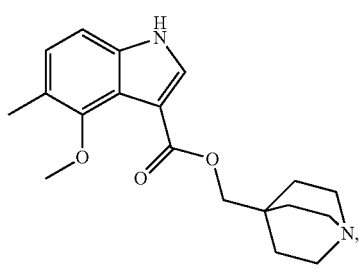 [SMILES: COc1c(C)ccc2[nH]cc(C(=O)OCC34CCN(CC3)CC4)c12] |
| 80 | 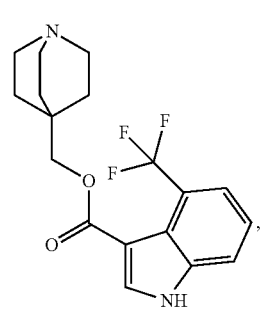 [SMILES: O=C(OCC12CCN(CC1)CC2)c1c[nH]c2cccc(C(F)(F)F)c12] |
| 83 | 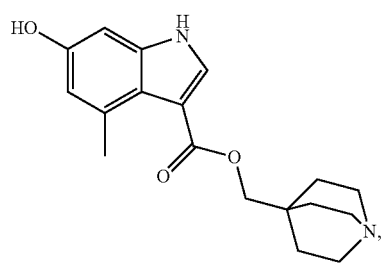 [SMILES: Cc1cc(O)cc2[nH]cc(C(=O)OCC34CCN(CC3)CC4)c12] |
| 88 | 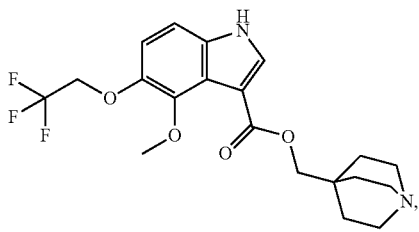 [SMILES: COc1c(OCC(F)(F)F)ccc2[nH]cc(C(=O)OCC34CCN(CC3)CC4)c12] |

| Compound No. | Structure |
|---|---|
| 89 | 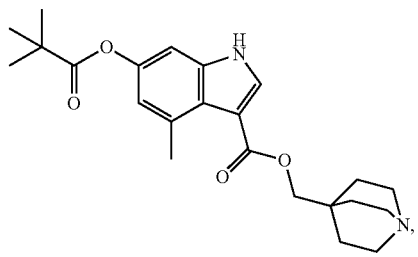 [SMILES: Cc1cc(OC(=O)C(C)(C)C)cc2[nH]cc(C(=O)OCC34CCN(CC3)CC4)c12] |
| 91 | 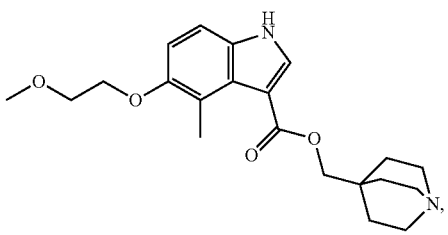 [SMILES: COCCOc1ccc2[nH]cc(C(=O)OCC34CCN(CC3)CC4)c2c1C] |
| 92 | 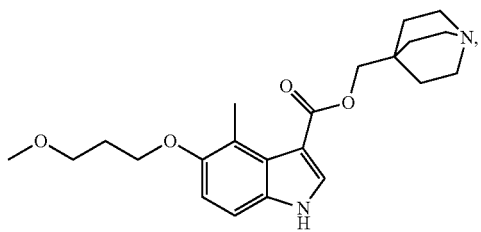 [SMILES: COCCCOc1ccc2[nH]cc(C(=O)OCC34CCN(CC3)CC4)c2c1C] |
| 93 | 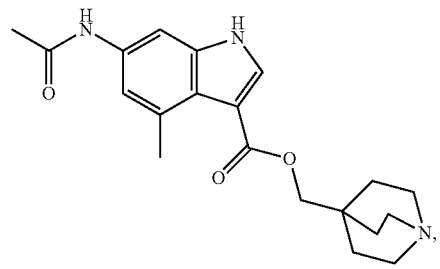 [SMILES: CC(=O)Nc1cc(C)c2c(C(=O)OCC34CCN(CC3)CC4)c[nH]c2c1] |
| 94 | 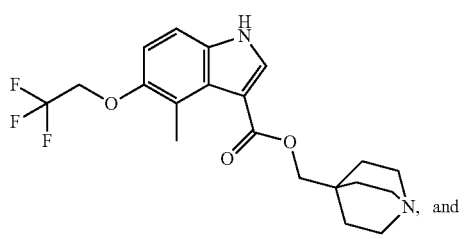 [SMILES: Cc1c(OCC(F)(F)F)ccc2[nH]cc(C(=O)OCC34CCN(CC3)CC4)c12], and |
| 95 | 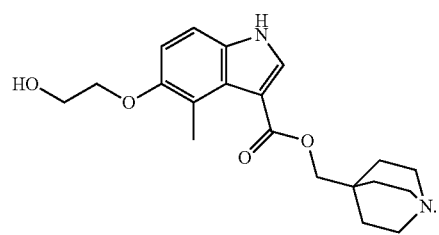 [SMILES: Cc1c(OCCO)ccc2[nH]cc(C(=O)OCC34CCN(CC3)CC4)c12]. |
Embodiment 27
A compound, or a salt thereof, selected from the group consisting of:
| Compound No. | Structure |
|---|---|
| 35 | 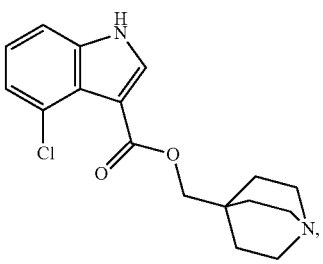 [SMILES: O=C(OCC12CCN(CC1)CC2)c1c[nH]c2cccc(Cl)c12] |
| 38 | 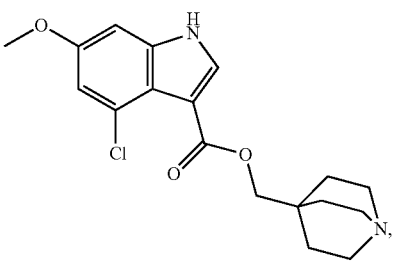 [SMILES: COc1cc(Cl)c2c(C(=O)OCC34CCN(CC3)CC4)c[nH]c2c1] |
| 46 | 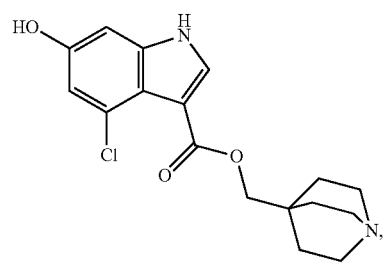 [SMILES: O=C(OCC12CCN(CC1)CC2)c1c[nH]c2cc(O)cc(Cl)c12] |
| 62 | 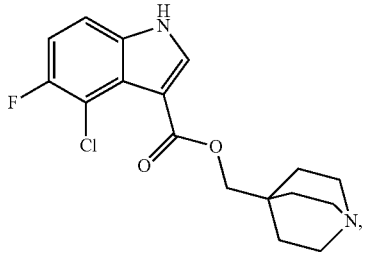 [SMILES: O=C(OCC12CCN(CC1)CC2)c1c[nH]c2ccc(F)c(Cl)c12] |
| 63 | 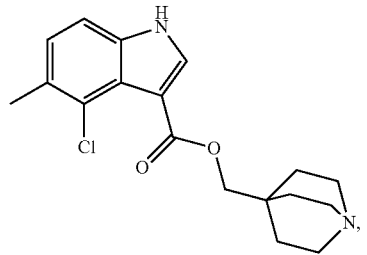 [SMILES: Cc1ccc2[nH]cc(C(=O)OCC34CCN(CC3)CC4)c2c1Cl] |

| Compound No. | Structure |
|---|---|
| 64 | 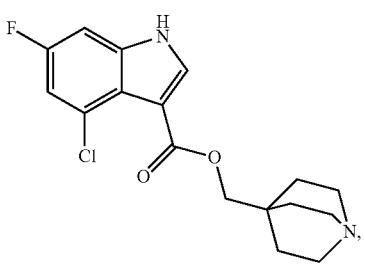 [SMILES: O=C(OCC12CCN(CC1)CC2)c1c[nH]c2cc(F)cc(Cl)c12] |
| 65 | 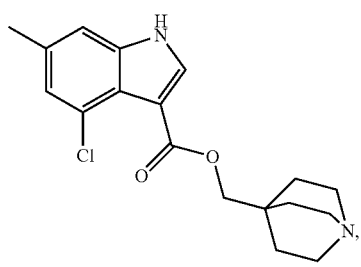 [SMILES: Cc1cc(Cl)c2c(C(=O)OCC34CCN(CC3)CC4)c[nH]c2c1] |
| 71 | 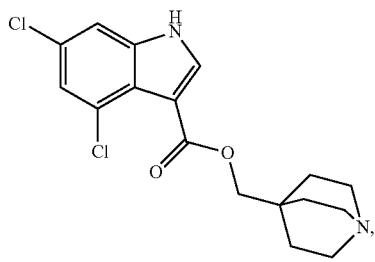 [SMILES: O=C(OCC12CCN(CC1)CC2)c1c[nH]c2cc(Cl)cc(Cl)c12] |
| 74 | 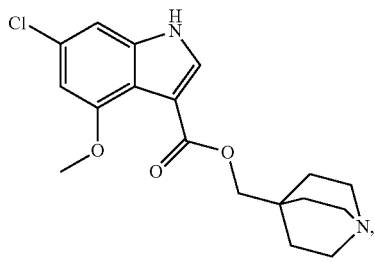 [SMILES: COc1cc(Cl)cc2[nH]cc(C(=O)OCC34CCN(CC3)CC4)c12] |
| 77 | 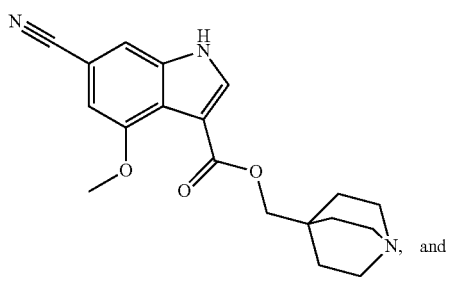 [SMILES: COc1cc(C#N)cc2[nH]cc(C(=O)OCC34CCN(CC3)CC4)c12] and |

| Compound No. | Structure |
|---|---|
| 82 | 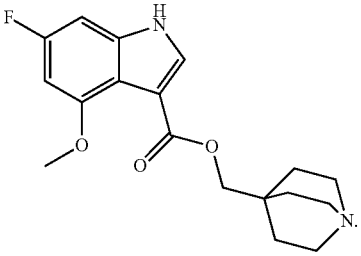 [SMILES: COc1cc(F)cc2[nH]cc(C(=O)OCC34CCN(CC3)CC4)c12] |

Embodiment 28

A pharmaceutical composition comprising a compound of any one of embodiments 1-27, or a pharmaceutically acceptable salt thereof, and a pharmaceutically acceptable carrier.

Embodiment 29

A method for treating or preventing a condition mediated by the α7 nicotinic acetylcholine receptor (α7 NAChR), comprising administering to an individual in need thereof an effective amount of a compound of any one of embodiments 1-27, or a pharmaceutically acceptable salt thereof.

Embodiment 30

The method of embodiment 29, wherein the condition is selected from the group consisting of schizophrenia, cognitive symptoms of schizophrenia, attention deficit symptoms of schizophrenia, cognitive deficits associated with schizophrenia, Alzheimer's disease, neurodegeneration associated with Alzheimer's disease, pre-senile dementia (mild cognitive impairment), senile dementia, Parkinson's disease, psychosis, cognitive deficits associated with psychosis, attention deficit disorder, attention deficit hyperactivity disorder (ADHD), a mood disorder, depression anxiety, post-traumatic stress disorder, cognitive deficits associated with a mood disorder, an affective disorder, pain, symptoms associated with pain, inflammation, traumatic brain injury, and Huntington's disease.

Embodiment 31

The method of embodiment 29, wherein the condition is selected from the group consisting of schizophrenia, cognitive symptoms of schizophrenia, attention deficit symptoms of schizophrenia, cognitive deficits associated with schizophrenia, Alzheimer's disease, neurodegeneration associated with Alzheimer's disease, and Parkinson's disease.

Embodiment 32

The method of any one of embodiments 29-31, wherein said compound is administered once per day.

Embodiment 33

The method of any one of embodiments 29-32, wherein said compound is administered orally.

Embodiment 34

The method of any one of embodiments 29-33, further comprising administering to the individual in need thereof an additional pharmaceutical agent, treatment modality, or combination thereof.

Embodiment 35

The method of embodiment 34, wherein the additional pharmaceutical agent, treatment modality, or combination thereof is selected from the group consisting of an acetylcholinesterase inhibitor, an antipsychotic agent, and an NMDA antagonist.

Embodiment 36

A composition comprising an effective amount of a compound of any one of embodiments 1-27, or a pharmaceutically acceptable salt thereof, for use in treating or preventing a condition mediated by the α7 nicotinic acetylcholine receptor (α7 NAChR). The conditions mediated by the α7-nicotinic acetylcholine receptor (α7 NAChR) include those described herein.

Embodiment 37

Use of a composition comprising an effective amount of a compound of any one of embodiments 1-27, or a pharmaceutically acceptable salt thereof, in the manufacture of a medicament for treating or preventing a condition mediated by the α7 nicotinic acetylcholine receptor (α7 NAChR).

Embodiment 38

Use of a composition comprising an effective amount of a compound of any one of embodiments 1-27, or a pharmaceutically acceptable salt thereof, for treating or preventing a condition mediated by the α7 nicotinic acetylcholine receptor (α7 NAChR).

Embodiment 39

A kit comprising a composition comprising an effective amount of a compound of any one of embodiments 1-27, or a pharmaceutically acceptable salt thereof, and instructions for use.

All documents, including patents, patent application and publications cited herein, including all documents cited therein, tables, and drawings, are hereby expressly incorporated by reference in their entirety for all purposes.

While the foregoing written description of the compounds, uses, and methods described herein enables one of ordinary skill in the art to make and use the compounds, uses, and methods described herein, those of ordinary skill in the art will understand and appreciate the existence of variations, combinations, and equivalents of the specific embodiment, method, and examples herein. The compounds, uses, and methods provided herein should therefore not be limited by the above-described embodiments, methods, or examples, but rather encompasses all embodiments and methods within the scope and spirit of the compounds, uses, and methods provided herein.

What is claimed is:

1. A compound having the formula (I):

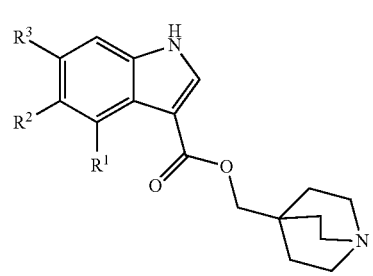

wherein
R$^1$ is C$_1$-C$_6$ alkyl, C$_1$-C$_6$ alkoxy, C$_3$-C$_6$ cycloalkyl, or bromo, wherein the C$_1$-C$_6$ alkyl, C$_1$-C$_6$ alkoxy, or C$_3$-C$_6$ cycloalkyl is unsubstituted or substituted with 1 to 5 halo substituents;
R$^2$ and R$^3$ are each independently hydrogen, C$_1$-C$_6$ alkyl, C$_3$-C$_6$ cycloalkyl, halo, cyano, —NR$^a$R$^b$, —NHC(O)R$^c$, —OR$^d$, or —OC(O)R$^e$;
R$^a$, R$^b$, and R$^c$ are each independently hydrogen, unsubstituted C$_1$-C$_6$ alkyl, or unsubstituted C$_3$-C$_6$ cycloalkyl;
R$^d$ is hydrogen, C$_1$-C$_6$ alkyl, or C$_3$-C$_6$ cycloalkyl, wherein the C$_1$-C$_6$ alkyl or C$_3$-C$_6$ cycloalkyl is unsubstituted or substituted with 1 to 5 substituents independently selected from the group consisting of hydroxyl, C$_1$-C$_6$ alkoxy, and halo; and
R$^e$ is unsubstituted C$_1$-C$_6$ alkyl or unsubstituted C$_3$-C$_6$ cycloalkyl;
provided that 1) at least one of R$^2$ and R$^3$ is hydrogen, and 2) when R$^1$ is C$_1$-C$_6$ alkoxy, R$^2$ is other than hydrogen,
or a salt thereof.

2. The compound of claim 1, or a salt thereof, wherein R$^1$ is C$_1$-C$_6$ alkyl or C$_3$-C$_6$ cycloalkyl, wherein the C$_1$-C$_6$ alkyl or C$_3$-C$_6$ cycloalkyl is unsubstituted or substituted with 1 to 5 halo substituents.

3. The compound of claim 1, or a salt thereof, wherein R$^1$ is unsubstituted C$_1$-C$_6$ alkyl.

4. The compound of claim 1, or a salt thereof, wherein R$^1$ is —CH$_3$.

5. The compound of claim 1, or a salt thereof, wherein R$^1$ is C$_1$-C$_6$ alkoxy, which is unsubstituted or substituted with 1 to 5 halo substituents.

6. The compound of claim 1, or a salt thereof, wherein R$^1$ is —OCH$_3$.

7. The compound of claim 1, or a salt thereof, wherein R$^1$ is bromo.

8. The compound of claim 1, or a salt thereof, wherein R$^2$ is hydrogen.

9. The compound of claim 1, or a salt thereof, wherein R$^2$ is C$_1$-C$_6$ alkyl or C$_3$-C$_6$ cycloalkyl.

10. The compound of claim 1, or a salt thereof, wherein R$^2$ is —CH$_3$.

11. The compound of claim 1, or a salt thereof, wherein R$^2$ is halo.

12. The compound of claim 1, or a salt thereof, wherein R$^2$ is fluoro or chloro.

13. The compound of claim 1, or a salt thereof, wherein R$^2$ is cyano.

14. The compound of claim 1, or a salt thereof, wherein $R^2$ is —$OR^d$, and $R^d$ is hydrogen or unsubstituted $C_1$-$C_6$ alkyl.

15. The compound of claim 14, or a salt thereof, wherein $R^d$ is —$CH_3$.

16. The compound of claim 1, or a salt thereof, wherein $R^2$ is $OR^d$, and $R^d$ is $C_1$-$C_6$ alkyl substituted with $C_1$-$C_6$ alkoxy.

17. The compound of claim 1, or a salt thereof, wherein $R^3$ is hydrogen.

18. The compound of claim 1, or a salt thereof, wherein $R^3$ is $C_1$-$C_6$ alkyl or $C_3$-$C_6$ cycloalkyl.

19. The compound of claim 1, or a salt thereof, wherein $R^3$ is —$CH_3$.

20. The compound of claim 1, or a salt thereof, wherein $R^3$ is halo.

21. The compound of claim 1, or a salt thereof, wherein $R^3$ is fluoro or chloro.

22. The compound of claim 1, or a salt thereof, wherein $R^3$ is cyano.

23. The compound of claim 1, or a salt thereof, wherein $R^3$ is —$OR^d$, and $R^d$ is hydrogen or unsubstituted $C_1$-$C_6$ alkyl.

24. The compound of claim 23, or a salt thereof, wherein $R^d$ is —$CH_3$.

25. The compound of claim 1, wherein
   $R^1$ is $C_1$-$C_4$ alkyl, $C_1$-$C_4$ alkoxy, $C_3$-$C_4$ cycloalkyl, or bromo, wherein the $C_1$-$C_4$ alkyl is unsubstituted or substituted with 1 to 5 fluoro substituents;
   $R^2$ and $R^3$ are each independently hydrogen, $C_1$-$C_6$ alkyl, fluoro, chloro, cyano, —NHC(O)$R^c$, —$OR^d$, or —OC(O)$R^e$;
   $R^c$ is hydrogen or unsubstituted $C_1$-$C_6$ alkyl;
   $R^d$ is hydrogen or $C_1$-$C_6$ alkyl, wherein the $C_1$-$C_6$ alkyl is unsubstituted or substituted with 1 to 5 substituents independently selected from the group consisting of hydroxyl, $C_1$-$C_6$ alkoxy, and halo; and
   $R^e$ is unsubstituted $C_1$-$C_6$ alkyl;
   provided that 1) at least one of $R^2$ and $R^3$ is hydrogen, and 2) when $R^1$ is $C_1$-$C_4$ alkoxy, $R^2$ is other than hydrogen, or a salt thereof.

26. The compound of claim 1, or a salt thereof, wherein the compound is selected from the group consisting of:

| Compound No. | Structure |
|---|---|
| 21 | |
| 24 | |
| 34 | 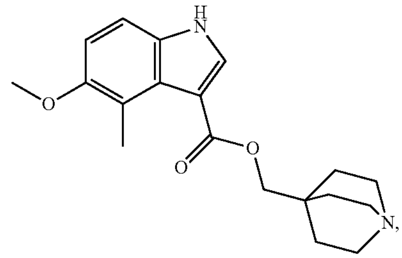 [SMILES: COc1ccc2[nH]cc(C(=O)OCC34CCN(CC3)CC4)c2c1C] |
| 37 | 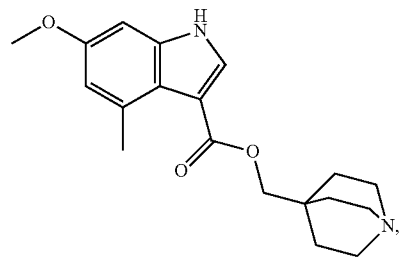 [SMILES: COc1cc(C)c2c(C(=O)OCC34CCN(CC3)CC4)c[nH]c2c1] |
| 40 | 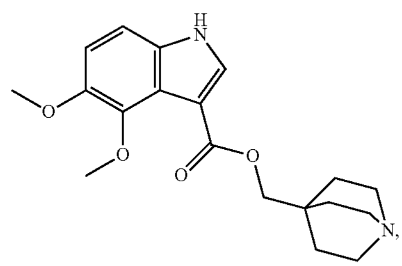 [SMILES: COc1ccc2[nH]cc(C(=O)OCC34CCN(CC3)CC4)c2c1OC] |
| 41 | 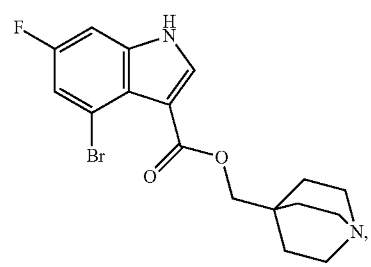 [SMILES: O=C(OCC12CCN(CC1)CC2)c1c[nH]c2cc(F)cc(Br)c12] |
| 42 | 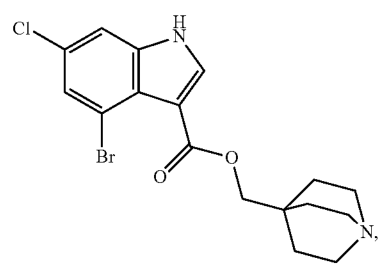 [SMILES: O=C(OCC12CCN(CC1)CC2)c1c[nH]c2cc(Cl)cc(Br)c12] |
| 43 | 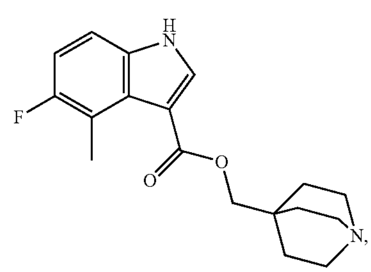 [SMILES: Cc1c(F)ccc2[nH]cc(C(=O)OCC34CCN(CC3)CC4)c12] |

-continued
| Compound No. | Structure |
|---|---|
| 44 | 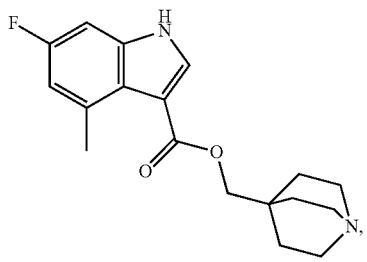 [SMILES: Cc1cc(F)cc2[nH]cc(C(=O)OCC34CCN(CC3)CC4)c12] |
| 47 | 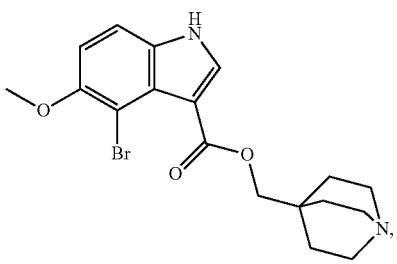 |
| 48 | 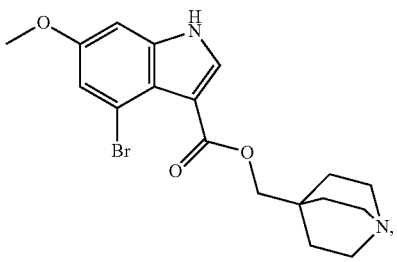 [SMILES: COc1cc(Br)c2c(C(=O)OCC34CCN(CC3)CC4)c[nH]c2c1] |
| 49 | 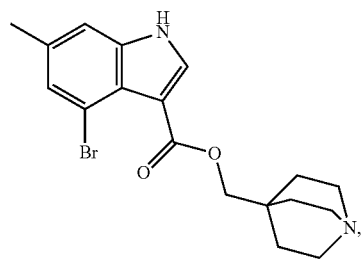 [SMILES: Cc1cc(Br)c2c(C(=O)OCC34CCN(CC3)CC4)c[nH]c2c1] |
| 50 | 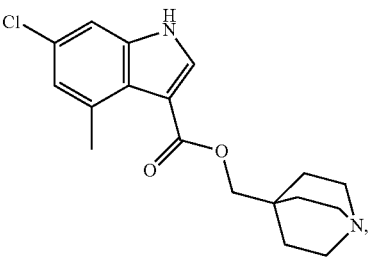 [SMILES: Cc1cc(Cl)cc2[nH]cc(C(=O)OCC34CCN(CC3)CC4)c12] |
-continued
| Compound No. | Structure |
|---|---|
| 53 | 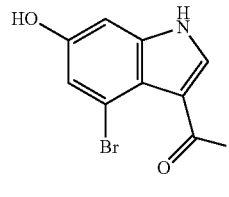 |
| 54 | 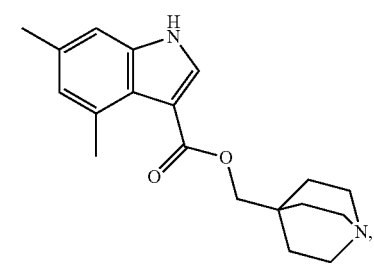 [SMILES: Cc1cc(C)c2c(C(=O)OCC34CCN(CC3)CC4)c[nH]c2c1] |
| 60 | 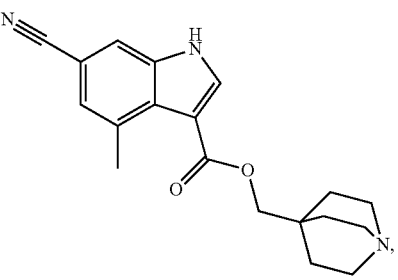 [SMILES: Cc1cc(C#N)cc2[nH]cc(C(=O)OCC34CCN(CC3)CC4)c12] |
| 61 | 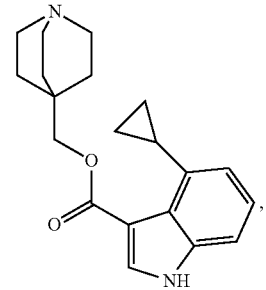 [SMILES: O=C(OCC12CCN(CC1)CC2)c1c[nH]c2cccc(C3CC3)c12] |
| 67 | 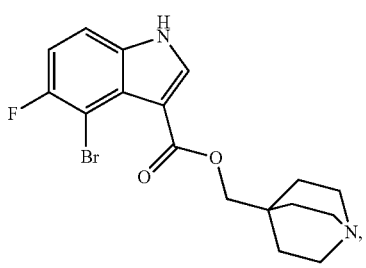 [SMILES: O=C(OCC12CCN(CC1)CC2)c1c[nH]c2ccc(F)c(Br)c12] |

27. A compound, or a salt thereof, selected from the group consisting of:

| Compound No. | Structure |
|---|---|
| 35 | 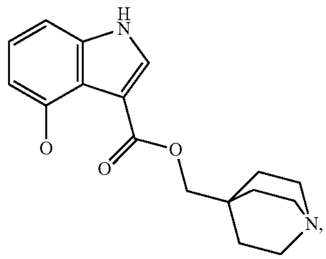 [SMILES: O=C(OCC12CCN(CC1)CC2)c1c[nH]c2cccc(O)c12] |
| 38 | 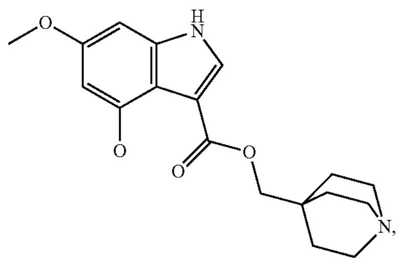 [SMILES: COc1cc(O)c2c(C(=O)OCC34CCN(CC3)CC4)c[nH]c2c1] |
| 46 | 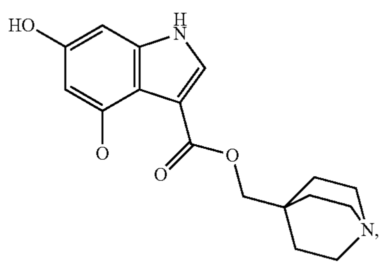 [SMILES: O=C(OCC12CCN(CC1)CC2)c1c[nH]c2cc(O)cc(O)c12] |
| 62 | 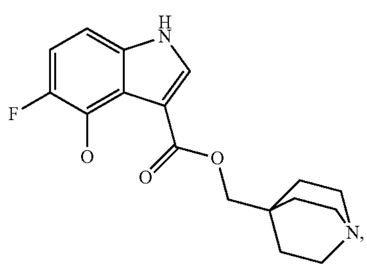 [SMILES: O=C(OCC12CCN(CC1)CC2)c1c[nH]c2ccc(F)c(O)c12] |
| 63 | 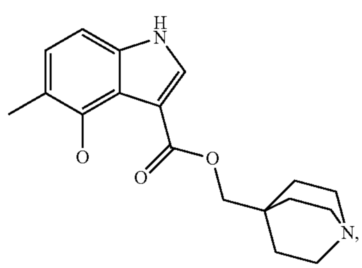 [SMILES: Cc1ccc2[nH]cc(C(=O)OCC34CCN(CC3)CC4)c2c1O] |
| 64 | 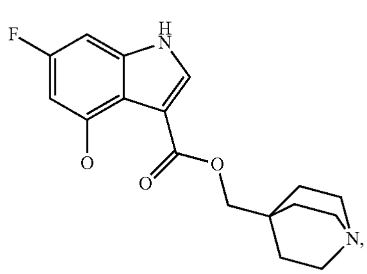 [SMILES: O=C(OCC12CCN(CC1)CC2)c1c[nH]c2cc(F)cc(O)c12] |

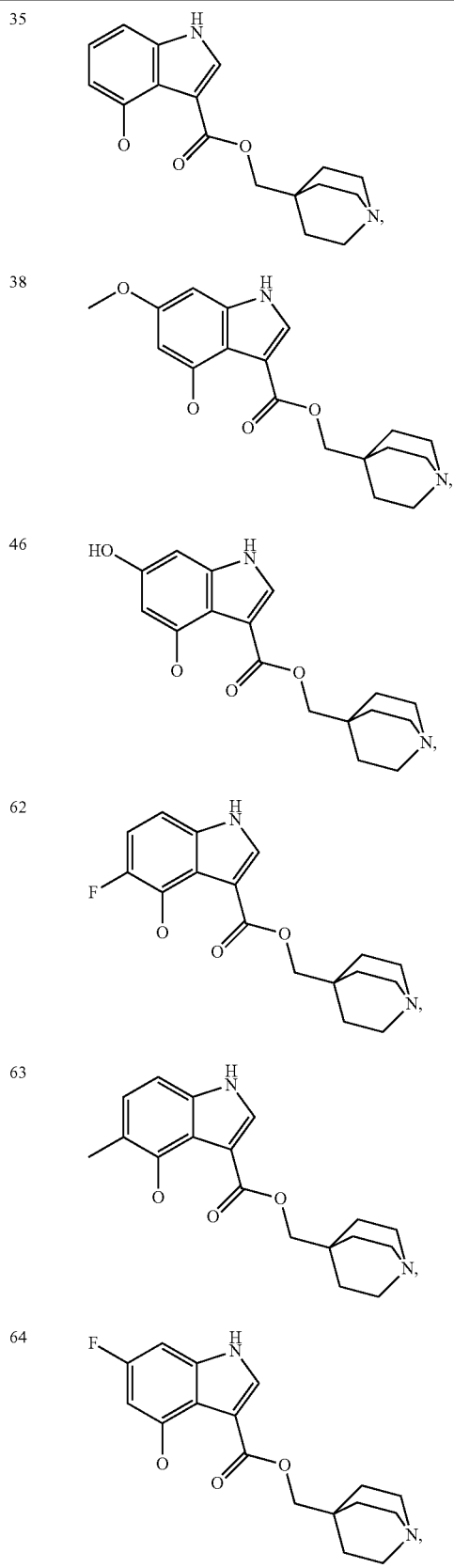

-continued

| Compound No. | Structure |
|---|---|
| 65 | 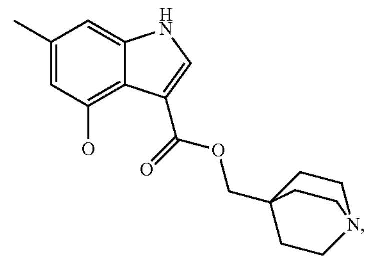 [SMILES: Cc1cc(O)c2c(C(=O)OCC34CCN(CC3)CC4)c[nH]c2c1] |
| 71 | 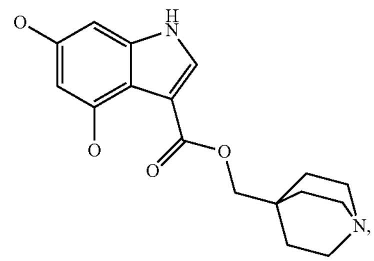 [SMILES: O=C(OCC12CCN(CC1)CC2)c1c[nH]c2cc(O)cc(O)c12] |
| 74 | 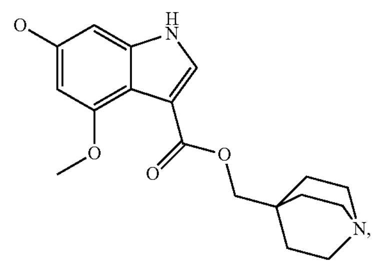 [SMILES: COc1cc(O)cc2[nH]cc(C(=O)OCC34CCN(CC3)CC4)c12] |
| 77 | 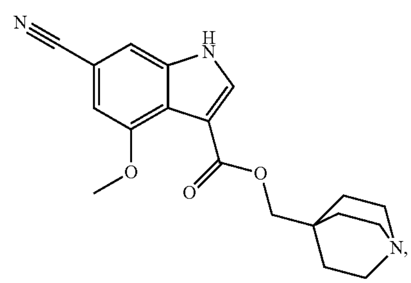 |
| and | |
| 82 | 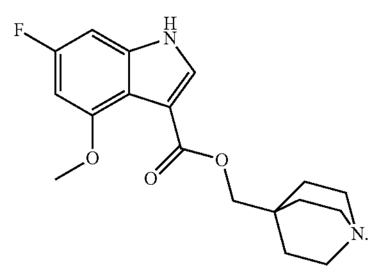 [SMILES: COc1cc(F)cc2[nH]cc(C(=O)OCC34CCN(CC3)CC4)c12] |

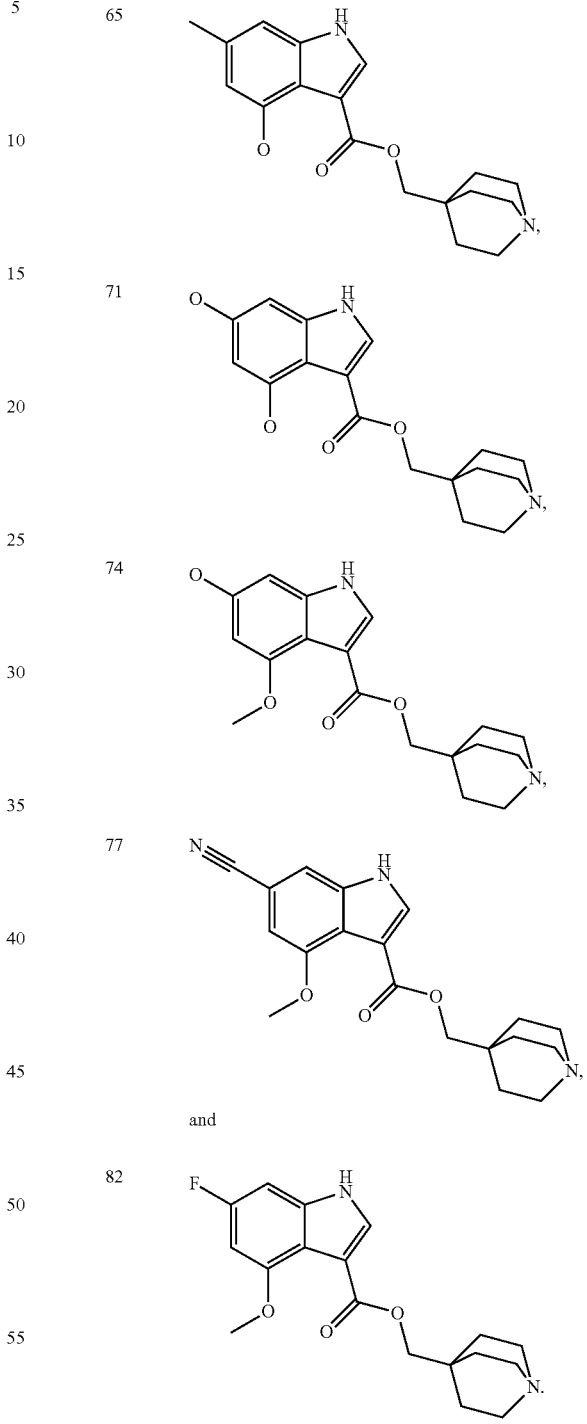

28. A pharmaceutical composition comprising a compound of claim 1, or a pharmaceutically acceptable salt thereof, and a pharmaceutically acceptable carrier.

29. A method for modulating an α7-nicotinic acetylcholine receptor (α7 NAChR), comprising contacting the α7 NAChR with an effective amount of a compound of claim 1, or a pharmaceutically acceptable salt thereof.

30. A pharmaceutical composition comprising a compound of claim 27, or a pharmaceutically acceptable salt thereof, and a pharmaceutically acceptable carrier.

31. A method for modulating an α7-nicotinic acetylcholine receptor (α7 NAChR), comprising contacting the α7 NAChR with an effective amount of a compound of claim 27, or a pharmaceutically acceptable salt thereof.

32. A pharmaceutical composition comprising a compound of claim 26, or a pharmaceutically acceptable salt thereof, and a pharmaceutically acceptable carrier.

33. A method for modulating an α7-nicotinic acetylcholine receptor (α7 NAChR), comprising contacting the α7 NAChR with an effective amount of a compound of claim 26, or a pharmaceutically acceptable salt thereof.

* * * * *